United States Patent
Bartberger et al.

(10) Patent No.: US 7,666,888 B2
(45) Date of Patent: Feb. 23, 2010

(54) SUBSTITUTED AZOLE AROMATIC HETEROCYCLES AS INHIBITORS OF 11β-HSD-1

(75) Inventors: Michael D. Bartberger, Sherman Oaks, CA (US); Christopher H. Fotsch, Thousands Oaks, CA (US); Martin Haraldsson, Taby (SE); David St. Jean, Camarillo, CA (US); Lars Johansson, Bromma (SE); Marianne Nilsson, Rimbo (SE); Lori Sutin, Danderyd (SE); Katrina Flyrén, Solna (SE)

(73) Assignees: Amgen Inc., Thousand Oaks, CA (US); Biovitrum AB, Stockholm (SE)

( * ) Notice: Subject to any disclaimer, the term of this patent is extended or adjusted under 35 U.S.C. 154(b) by 0 days.

(21) Appl. No.: 11/779,599

(22) Filed: Jul. 18, 2007

(65) Prior Publication Data

US 2008/0021022 A1  Jan. 24, 2008

Related U.S. Application Data

(60) Provisional application No. 60/831,961, filed on Jul. 20, 2006, provisional application No. 60/924,520, filed on May 18, 2007.

(51) Int. Cl.
*A61K 31/422* (2006.01)
*A61K 31/4155* (2006.01)
*C07D 261/06* (2006.01)
*C07D 231/10* (2006.01)

(52) U.S. Cl. .................. 514/378; 514/406; 548/248; 548/364.1

(58) Field of Classification Search .......... 544/137, 544/367, 405, 60; 546/17, 208, 272.1; 548/248; 514/227.8, 236.8, 254.04, 255.05, 326, 340, 514/378
See application file for complete search history.

(56) References Cited

U.S. PATENT DOCUMENTS

| | | | |
|---|---|---|---|
| 4,765,539 A | 8/1988 | Noakes et al. | |
| 4,962,885 A | 10/1990 | Coffee | |
| 5,112,598 A | 5/1992 | Biesalski | |
| 5,494,911 A | 2/1996 | Bartlett et al. | |
| 5,532,259 A | 7/1996 | Bartlett et al. | |
| 5,556,611 A | 9/1996 | Biesalski | |
| 5,912,114 A | 6/1999 | Hutchinson et al. | |
| 5,950,619 A | 9/1999 | van der Linden et al. | |
| 5,954,047 A | 9/1999 | Armer et al. | |
| 5,970,974 A | 10/1999 | van der Linden et al. | |
| 6,096,770 A | 8/2000 | Lennox et al. | |
| 6,180,796 B1 | 1/2001 | Morohashi et al. | |
| 6,262,098 B1 | 7/2001 | Huebner et al. | |
| 6,387,920 B2 | 5/2002 | Huebner et al. | |
| 6,458,960 B1 | 10/2002 | Morohashi et al. | |
| 6,727,273 B2 | 4/2004 | Huebner et al. | |
| 6,743,815 B2 | 6/2004 | Huebner et al. | |
| 6,869,953 B2 | 3/2005 | Haag et al. | |
| 6,869,969 B2 | 3/2005 | Huebner et al. | |
| 6,946,462 B2 | 9/2005 | Haag et al. | |

(Continued)

FOREIGN PATENT DOCUMENTS

| | | |
|---|---|---|
| EP | 0 558 258 | 9/1993 |
| EP | 0 569 193 | 11/1993 |
| EP | 0 902 288 | 3/1999 |
| EP | 1 069 114 | 1/2001 |
| EP | 1 236 726 | 9/2002 |
| WO | WO 94/12285 | 6/1994 |
| WO | WO 94/14543 | 7/1994 |
| WO | WO 95/26234 | 10/1995 |
| WO | WO 95/26235 | 10/1995 |
| WO | WO 95/32807 | 12/1995 |
| WO | WO 97/39745 | 10/1997 |
| WO | WO 99/07670 | 2/1999 |

(Continued)

OTHER PUBLICATIONS

Vippagunta et al., Crystalline solids, 2001, Advanced Drug Delivery Reviews, 48, pp. 3 and 18.*

(Continued)

*Primary Examiner*—Kamal A Saeed
*Assistant Examiner*—Kristin Bianchi
(74) *Attorney, Agent, or Firm*—Foley & Lardner LLP

(57) ABSTRACT

Compounds of formula I and IV are described and have therapeutic utility, particularly in the treatment of diabetes, obesity and related conditions and disorder:

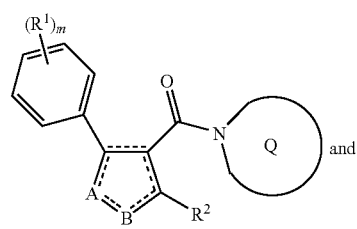

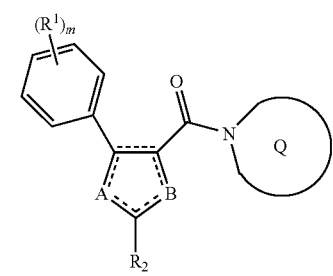

wherein the variables A-B, $R^1$, $R^2$, m, and Q are described herein.

14 Claims, No Drawings

U.S. PATENT DOCUMENTS

| | | | |
|---|---|---|---|
| 2002/0137769 A1* | 9/2002 | Lee et al. | 514/326 |
| 2004/0010005 A1 | 1/2004 | Barnett et al. | |
| 2004/0097734 A1* | 5/2004 | Gerlach et al. | 544/323 |
| 2004/0180881 A1 | 9/2004 | Berta et al. | |
| 2005/0096376 A1* | 5/2005 | Sundermann et al. | 514/414 |
| 2006/0223852 A1* | 10/2006 | Gillespie et al. | 514/314 |
| 2006/0241121 A1* | 10/2006 | Greenlee et al. | 514/253.12 |
| 2007/0249631 A1* | 10/2007 | Oberboersch et al. | 514/257 |

FOREIGN PATENT DOCUMENTS

| | | |
|---|---|---|
| WO | WO 99/47196 | 9/1999 |
| WO | WO 00/56729 | 9/2000 |
| WO | WO 01/16116 | 3/2001 |
| WO | WO 03/015780 | 2/2003 |
| WO | WO 03/088908 | 10/2003 |
| WO | WO 2004/050087 | 6/2004 |
| WO | WO 2004/054974 | 7/2004 |
| WO | WO 94/24095 | 10/2004 |
| WO | WO 2004/100946 | 11/2004 |
| WO | WO 2005/105759 A1 * | 11/2005 |

OTHER PUBLICATIONS

Alberola, Angel, et al., Comparative Reactivity of 3-Methyl-5-Penysisoxazole and 3-Methyl-a5- Penylisothiazole Against Electrophilic Compounds, *Journal of Heterocyclic Chemistry*, 1995, 32(2), pp. 537-541.

Albiston, A.L., et al., "Cloning and tissue distribution of the human 11 beta-hydroxysteroid dehydrogenase type 2 enzyme", *Mol Cell Endocrinol*, 1994, 105(2):R11-7.

Anstead, G.M, "Steroids, retinoids, and wound healing", *Adv Wound Care*, 1998, 11(6), pp. 277-285.

Basu, U., et al., "Search for New Analeptic. I. Synthesis of Cyclotetra-Methyleneisoxazole", *J. Indian Chem. Soc.*, 1946, 23, pp. 189-192.

Beer, H.D., et al., "Glucocorticoid-regulated gene expression during cutaneous wound repair" *Vitam Horm*, 2000, 59, pp. 217-239.

Bellows, C.G., et al., *Bone* 23. 1998, : pp. 119-125.

Betti, M., et al., "The Isomerizm of Isoxazolecarboxylic Acids", *Gazzeta Chimica Italiana*, 1921, 51(II), pp. 229-239.

Billaudel, B. and B.C.J. Sutter (1979) Horm. Metab. Res. 11: pp. 555-560.

Brough, Paul A. et al., *Bioorganic & Medicinal Chemistry Letters*, 2005, 15(23), pp. 5197-5201.

Bujalska, I.J., S. Kumar, and P.M. Stewart (1997) Lancet 349: pp. 1210-1213.

*Burger's Medicinal Chemistry and Drug Discovery* 6th ed. (Donald J. Abraham ed., 2001, Wiley).

Cardonna, C., et al., "Synthesis and Bacteriostatic Activity of Hydroxamic Acid Derivative of Isoxazole", *Farmaco, Edizione Scientifica*, 1960, 15, pp. 647-654.

Carenzi, A., et al., "New Isoxazole Derivatives Provided With Antihypertensive Activity", *Arzneimittel-Forschung*, 1989, 39(6), pp. 642-646.

Cheng, Y.C.; Prushoff, W.H. *Biochem. Pharmacol.* 1973, 22, pp. 3099-3108.

Cooper, M.S. et al., *Bone* 27, 2000, pp. 375-381.

Cooper, M.S., et al., "11beta-hydroxysteroid dehydrogenase in human fibroblasts: expression and regulation depends on tissue of origin", *ENDO 2003 Abstracts* 2003.

Dahl et al., Poster 524 at *American Association of Cancer Research*, San Francisco, Calif., Apr. 1-5, 2000.

Dains, F.B. et al, *Journal of the American Chemical Society*, 1921, 43, pp. 1200-1202.

Dains, F.B., et al., "Reactions of the Formamidines. III. Synthesis of Isoxazolone, Isoxazole, Cuampacetoc and Benzoylacetic Acid Derivatives", *Journal of the American Chemical Society*, 1913, 35, pp. 959-970.

Davani, B. et al. (2000) J. Biol. Chem. Nov. 10, 2000; 275(45): pp. 34841-34844.

de Quervain, D.J. et al., *Nature*, 1998, 394: pp. 787-790.

*Design and Application of Prodrugs* (H. Bundgaard ed., 1985, Harwood Academic Publishers Gmfh).

Diethelm, A.G., "Surgical management of complications of steroid therapy", *Ann Surg*, 1977, 185(3): pp. 251-263.

During et al., *Ann. Neurol.*, 1989,25, p. 351.

Engelke et al., Poster 342 at *American Association of Cancer Research*, San Francisco, Calif., Apr. 1-5, 2000.

English et al., J. Clin. Endocrinol. Metab. 1999, 84: pp. 2080-2085.

Fossa, Paola, et al., "5-Substituted 4-Isoxazolecarboxamides with Platelet Antiaggregating and Other Activities", *Ist, Sci. Farm., Univ. Genova*, Genoa, I-16132, Italy Farmaco, 1991, 46(6), pp. 789-802.

Fraser, R. et al. (1999) Hypertension 33: pp. 1364-1368.

Frey, F.J., et al, "Pharmacology of 11 beta-hydroxysteroid dehydrogenase", *Steroids*, 1994, 59(2):, pp. 74-79.

Ganong, W.F. Review of Medical Physiology. Eighteenth edition ed. Stamford, Connecticut: Appleton & Lange; 1997.

Ge et al., Biology of Reproduction 1999, 60: pp. 855-860.

Geissler et al., Nat. Genet. 1994, 7: pp. 34-39.

Goodson, in Medical Applications of Controlled Release, supra, vol. 2, pp. 115 (1984).

Halleux, C.M. et al. (1999) J. Clin. Endocrinol. Metab. 84: pp. 4097-4105.

Hammami, M.M., et al., "Regulation of 11 beta-hydroxysteroid dehydrogenase activity in human skin fibroblasts: enzymatic modulation of glucocorticoid action", *J Clin Endocrinol Metab*, 1991, 73(2), pp. 326-334.

Hamon, G.A., Hunt, T.K., Spencer, E.M. "In vivo effects of systemic insulin-like growth factor-I alone and complexed with insulin-like growth factor binding protein-3 on corticosteroid suppressed wounds", *Growth Regul* ,1993, 3(1), pp. 53-56.

Hanson, J.C. et al., "Derivatives of 6-Aminopenicillanic Acid", *Journal of the Chemical Society*, 1965, November, pp. 5976-5983.

Houssay, B.A. (1942) Endocrinology 30: 884-892.

Howard et al., 1989, *J. Neurosurg.* 71, p. 105.

Introduction to Pharmaceutical Dosage Forms, 4th ed., Lea & Febiger, Philadelphia (1985).

J. Zhang, et al. *Biochemistry*, 44, 2005, pp. 6948-6957.

Jamieson et al. (2000) J. Endocrinol. 165: pp. 685-692.

Jens T. Carstensen, Drug Stability: Principles & Practice, 2d. Ed., Marcel Dekker, NY, NY, 1995, pp. 379-380.

Kang, K.H., et al., "Solution-phase Combinatorial Synthesis of Isoxazolines and Isoxazoles Using [2+3] Cycloaddition Reaction of Nitrile Oxides", *Tetrahedron Letters*, 2001, 42(6), pp. 1057-1060.

Kim, C.H., et al., *J. Endocrinol.* 162, 1999, pp. 371-379.

Kitawaki et al., J. Clin. Endocrin. Metab., 2000, 85: pp. 1371-3292-3296.

Kotelevtsev, Y. et al., (1997) Proc. Natl. Acad. Sci. USA 94: pp. 14924-14929.

Laato, M., et al., "Epidermal growth factor (EGF) prevents methylprednisolone-induced inhibition of wound healing", *J Surg Res*, 1989, 47(4):pp. 354-359.

Labrie et al., Mol. Cell. Endocrinol. 1991, 78: pp. C113-C118.

Langer, *Science*, 1990, 249, p. 1527.

Leszczynska, Barbara, et al., "Synthesis of 1-acyl-4-(5-Nitrofurfurylidenamino) Piperazines", *Acta Poloniae Pharmaceutica*, 1981, 38(5), pp. 539-543.

Levy et al., *Science*, 1985, 228, p. 190.

Long, C.D. and Leukins, F.D.W. (1936) J. Exp. Med. 63: pp. 465-549.

Mason, D., *Immunology Today*, 1991, 12: 57-60; Rook et al., *supra*.

Medical Applications of Controlled Release, Langer and Wise (eds.), CRC Pres., Boca Raton, Fla. (1974).

Mercado, A.M., et al., "Restraint stress alters the expression of interleukin-1 and keratinocyte growth factor at the wound site: an in situ hybridization study", *J Neuroimmunol*, 2002, 129(1-2), pp. 74-83.

Monder C, et al., "11 beta-hydroxysteroid dehydrogenase", *Vitam Horm*, 1993, 47, pp. 187-271.

Montague & O'Rahilly, Diabetes 49:, 2000, pp. 883-888.

Nio, Chorng Shyr, et al., "Synthesis, Metalation and Elecrophilic Quencing of Alkylisoxazole-4-Tertiary Carboxamides", Heterocycles, 1986, 24(2), pp. 401-412.

Nobel et al., Eur. J. Biochem. 2001, 268: pp. 4113-4125.

O'Callaghan, C.N., *Journal of the Chemical Society*, Perkin Transactions 1: Organic and Bio-Organic Chemistry (1972-1999) (1972), (11), pp. 1416-1419.

Oishi, Y., et al., "Molecular basis of the alteration in skin collagen metabolism in response to in vivo dexamethasone treatment: effects on the synthesis of collagen type I and III, collagenase, and tissue inhibitors of metalloproteinases". *Br J Dermatol*, 2002, 147(5):pp. 859-868.

Peltoketo, et al., J. Mol. Endocrinol. 1999, 23: pp. 1-11.

Penning et al., Biochem. J. 2000, 351: pp. 67-77.

Pierce, G.F., et al., "Transforming growth factor beta reverses the glucocorticoid-induced wound-healing deficit in rats: possible regulation in macrophages by platelet-derived growth factor", *Proc Natl Acad Sci U S A*, 1989, 86(7): pp. 2229-2233.

Quattropani, C., et al., "Reduced activity of 11beta-hydroxysteroid dehydrogenase in patients with cholestasis", *J Clin Invest.*, 2001, Nov: 108 (9), pp. 1299-1305.

Rajan, V., et al., *Neuroscience*, 1996, 16: pp. 65-70.

Raleigh et al., *Proc. Amer. Assoc. Cancer Research Annual Meeting*, 1999, 40, p. 397.

Langer and Peppas, *J Macromol. Sci Rev. Macromol. Chem.*, 1983, 23, p. 61.

Remington's Pharmaceutical Sciences, 18th ed., Mack Publishing, Easton PA (1990).

Rojas, I.G., et al., "Stress-induced susceptibility to bacterial infection during cutaneous wound healing" *Brain Behav Immun*, 2002, 16(1), pp. 74-84.

Rook, G.A.W., *Baillièr's Clin. Endocrinol. Metab.*, 1999, 13: pp. 576-581.

Saudek et al., *N. Engl. J Med*, 1989, 321, p. 574.

Seckl, et al., Endocrinology, 2001, 142: pp. 1371-1376.

Seckl, J.R., Front. (2000) *Neuroendocrinol.* 18: pp. 49-99.

Sefton, *CRC Crit. Ref Biomed Eng.*, 1987, 14, 201.

Slight, S.H., et al., "Inhibition of tissue repair by spironolactone: role of mineralocorticoids in fibrous tissue formation", *Mol Cell Biochem*, 1998, 189(1-2), pp. 47-54.

Stewart, P.M., et al., "11 beta-Hydroxysteroid dehydrogenase", *Vitam Horm*, 1999, 57, pp. 249-324.

Stokes, J., Noble, et al. "Distribution of glucocorticoid and mineralocorticoid receptors and 11beta-hydroxysteroid dehydrogenases in human and rat ocular tissues", *Invest Ophthalmol Vis Sci 2000*;41(7): pp. 1629-1638.

Teelucksingh, S., et al., "Potentiation of hydrocortisone activity in skin by glycyrrhetinic acid", *Lancet*, 1990, 335(8697), pp. 1060-1063.

*The Practice of Medicinal Chemistry*; Wermuth, C.G., Ed.; Academic Press: New York, 1996; p. 203.

Tronche, F. et al., *Nature Genetics*, 1999 23: pp. 99-103.

S.M. Raleigh et al., *British J Cancer*, 1999, 80, Suppl 2, p. 96.

Walker E. A. et al, poster P3-698 at the Endocrine society meeting Jun. 12-15, 1999, San Diego.

Walker, B.R. et al. (1995) J. Clin. Endocrinol. Metab. 80: pp. 3155-3159.

Walker, B.R. et al. (1998) Hypertension 31: pp. 891-895.

Woods, S.C. et al. (1998) Science, 280: pp. 1378-1383.

Buchwald et al., Surgery, 1980, 88, p. 507.

* cited by examiner

SUBSTITUTED AZOLE AROMATIC HETEROCYCLES AS INHIBITORS OF 11β-HSD-1

This application claims the benefit of priority of U.S. Provisional Patent Application No. 60/831,961, which was filed on Jul. 20, 2006, and of U.S. Provisional Patent Application No. 60/924,520, which was filed on May 18, 2007.

BACKGROUND OF THE INVENTION

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11 β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identified in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal development leads to male pseudohermaphroditism. Geissler et al., Nat. Genet. 1994, 7:34-39. Both 17β-HSD3 and various 3α-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α,17β-diol and the interconversion of the androgens DHEA and androstenedione and therefore play an important role in androgen metabolism. Ge et al., Biology of Reproduction 1999, 60:855-860.

Glucorticoids, Diabetes and Hepatic Glucose Production

It has been known for more than half a century that glucocorticoids have a central role in diabetes. For example, the removal of the pituitary gland or the adrenal gland from a diabetic animal alleviates the most severe symptoms of diabetes and lowers the concentration of glucose in the blood (Long, C. D. and Leukins, F. D. W. (1936) J. Exp. Med. 63: 465-490; Houssay, B. A. (1942) Endocrinology 30: 884-892). It is also well established that glucocorticoids enable the effect of glucagon on the liver.

The role of 11βHSD1 as an important regulator of local glucocorticoid effect and thus of hepatic glucose production is well substantiated (see, e.g., Jamieson et al. (2000) J. Endocrinol. 165: 685-692). Hepatic insulin sensitivity was improved in healthy human volunteers treated with the non-specific 11βHSD1 inhibitor carbenoxolone (Walker, B. R. et al. (1995) J. Clin. Endocrinol. Metab. 80: 3155-3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6 Pase) the enzyme catalyzing the last common step of gluconeogenesis and glycogenolysis. Finally, blood glucose levels and hepatic glucose production are reduced in mice in which the 11βHSD1 gene is knocked-out. Data from this model also confirm that inhibition of 11βHSD1 will not cause hypoglycemia, as predicted since the basal levels of PEPCK and G6 Pase are regulated independently of glucocorticoids (Kotelevtsev, Y. et al., (1997) Proc. Natl. Acad. Sci. USA 94: 14924-14929).

FR 2,384,498 discloses compounds having a high hypoglycemic effect. Therefore, treatment of hyperglycemia with these compounds may lead to hypoglycemia.

Reduction of Obesity and Obesity Related Cardiovascular Risk Factors

Obesity is an important factor in syndrome X as well as in the majority (>80%) of type 2 diabetes, and omental fat appears to be of central importance. Abdominal obesity is closely associated with glucose intolerance, hyperinsulinemia, hypertriglyceridemia, and other factors of the so-called syndrome X (e.g. increased blood pressure, decreased levels of HDL and increased levels of VLDL) (Montague & O'Rahilly, Diabetes 49: 883-888, 2000). Inhibition of the 11βHSD1 enzyme in pre-adipocytes (stromal cells) has been shown to decrease the rate of differentiation into adipocytes. This is predicted to result in diminished expansion (possibly reduction) of the omental fat depot, i.e., reduced central obesity (Bujalska, I. J., S. Kumar, and P. M. Stewart (1997) Lancet 349: 1210-1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097-

4105). Furthermore, there is a clear correlation between glucocorticoid "activity" and cardiovascular risk factor suggesting that a reduction of the glucocorticoid effects would be beneficial (Walker, B. R. et al. (1998) Hypertension 31: 891-895; Fraser, R. et al. (1999) Hypertension 33: 1364-1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378-1383).

Beneficial Effect on the Pancreas

Inhibition of 11βHSD1 in isolated murine pancreatic β-cells improves glucose-stimulated insulin secretion (Davani, B. et al. (2000) J. Biol. Chem. 2000 Nov. 10; 275(45): 34841-4). Glucocorticoids were previously known to reduce pancreatic insulin release in vivo (Billaudel, B. and B. C. J. Sutter (1979) Horm. Metab. Res. 11: 555-560). Thus, inhibition of 11βHSD1 is predicted to yield other beneficial effects for diabetes treatment, besides the effects on liver and fat.

Beneficial Effects on Cognition and Dementia

Stress and glucocorticoids influence cognitive function (de Quervain, D. J.-F., B. Roozendaal, and J. L. McGaugh (1998) Nature 394: 787-790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65-70; Seckl, J. R., Front. (2000) Neuroendocrinol. 18: 49-99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99-103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite.

Use of Immuno-Modulation Using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillièr's Clin. Endocrinol. Metab. 13: 576-581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normally biased towards a humoral response when in fact the appropriate response would be cell based. Temporal inhibition of 11βHSD1, local or systemic, might be used to push the immune system into the appropriate response (Mason, D. (1991) Immunology Today 12: 57-60; Rook et al., supra).

An analogous use of 11βHSD1 inhibition, in this case temporal, would be to booster the immune response in association with immunization to ensure that a cell based response would be obtained, when desired.

Reduction of Intraocular Pressure

Recent data suggest that the levels of the glucocorticoid target receptors and the 11βHSD enzymes determines the susceptibility to glaucoma (Stokes, J. et al. (2000) Invest. Opthalmol. 41: 1629-1638). Further, inhibition of 11βHSD1 was recently presented as a novel approach to lower the intraocular pressure (Walker E. A. et al, poster P3-698 at the Endocrine society meeting Jun. 12-15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithelialium of the cornea (the site of aqueous production), to ciliary muscle and to the sphincter and dilator muscles of the iris. In contrast, the distant isoenzyme 11βHSD2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., Cheng, S. L. and Kim, G. S. (1999) J. Endocrinol. 162: 371-379). The negative effect on bone nodule formation could be blocked by the non-specific inhibitor carbenoxolone suggesting an important role of 11βHSD1 in the glucocorticoid effect (Bellows, C. G., Ciaccia, A. and Heersche, J. N. M. (1998) Bone 23: 119-125). Other data suggest a role of 11βHSD1 in providing sufficiently high levels of active glucocorticoid in osteoclasts, and thus in augmenting bone resorption (Cooper, M. S. et al. (2000) Bone 27: 375-381). Taken together, these different data suggest that inhibition of 11βHSD1 may have beneficial effects against osteoporosis by more than one mechanism working in parallel.

Reduction of Hypertension

Bile acids inhibit 11β-hydroxysteroid dehydrogenase type 2. This results in a shift in the overall body balance in favour of cortisol over cortisone, as shown by studying the ratio of the urinary metabolites (Quattropani, C., Vogt, B., Odermatt, A., Dick, B., Frey, B. M., Frey, F. J. (2001) J Clin Invest. November; 108(9):1299-305. "Reduced activity of 11beta-hydroxysteroid dehydrogenase in patients with cholestasis".). Reducing the activity of 11β-HSD1 in the liver by a selective inhibitor is predicted to reverse this imbalance, and acutely counter the symptoms such as hypertension, while awaiting surgical treatment removing the biliary obstruction.

Wound Healing

Cortisol performs a broad range of metabolic functions and other functions. The multitude of glucocorticoid action is exemplified in patients with prolonged increase in plasma glucocorticoids, so called "Cushing's syndrome". Patients with Cushing's syndrome have prolonged increase in plasma glucocorticoids and exhibit impaired glucose tolerance, type 2 diabetes, central obesity, and osteoporosis. These patients also have impaired wound healing and brittle skin (Ganong, W. F. Review of Medical Physiology. Eighteenth edition ed. Stamford, Conn.: Appleton & Lange; 1997).

Glucocorticoids have been shown to increase risk of infection and delay healing of open wounds (Anstead, G. M. Steroids, retinoids, and wound healing. Adv Wound Care 1998; 11(6):277-85). Patients treated with glucocorticoids have 2-5-fold increased risk of complications when undergoing surgery (Diethelm, A. G. Surgical management of complications of steroid therapy. Ann Surg 1977; 185(3):251-63).

The European patent application No. EP 0902288 discloses a method for diagnosing the status of wound healing in a patient, comprising detecting cortisol levels in said wound. The authors suggest that elevated levels of cortisol in wound fluid, relative to normal plasma levels in healthy individuals, correlates with large, non-healing wounds (Hutchinson, T. C., Swaniker, H. P., Wound diagnosis by quantitating cortisol in wound fluids. European patent application No. EP 0 902 288, published Mar. 17, 1999).

In humans, the 11β-HSD catalyzes the conversion of cortisol to cortisone, and vice versa. The parallel function of 11β-HSD in rodents is the interconversion of corticosterone and 11-dehydrocorticosterone (Frey, F. J., Escher, G., Frey, B. M. Pharmacology of 11 beta-hydroxysteroid dehydrogenase. Steroids 1994; 59(2):74-9). Two isoenzymes of 11β-HSD, 11β-HSD1 and 11β-HSD2, have been characterized, and differ from each other in function and tissue distribution (Albiston, A. L., Obeyesekere, V. R., Smith, R. E., Krozowski, Z. S. Cloning and tissue distribution of the human 11 beta-hydroxysteroid dehydrogenase type 2 enzyme. Mol Cell Endocrinol 1994; 105(2):R11-7). Like GR, 11β-HSD1 is expressed in numerous tissues like liver, adipose tissue, adrenal cortex, gonads, lung, pituitary, brain, eye etc (Monder C, White P C. 11 beta-hydroxysteroid dehydrogenase. Vitam Horm 1993; 47:187-271; Stewart, P. M., Krozowski, Z. S. 11 beta-Hydroxysteroid dehydrogenase. Vitam Horm 1999; 57:249-324; Stokes, J., Noble, J., Brett, L., Phillips, C., Seckl, J. R., O'Brien, C., et al. Distribution of glucocorticoid and mineralocorticoid receptors and 11beta-hydroxysteroid dehydrogenases in human and rat ocular tissues. Invest Opthalmol Vis Sci 2000; 41(7):1629-38). The function of 11β-HSD1 is to fine-tune local glucocorticoid action. 11β-HSD activity has been shown in the skin of humans and rodents, in human fibroblasts and in rat skin pouch tissue (Hammami, M. M., Siiteri, P. K. Regulation of 11 beta-hydroxysteroid dehydrogenase activity in human skin fibroblasts: enzymatic modulation of glucocorticoid action. J Clin Endocrinol Metab 1991; 73(2):326-34); Cooper, M. S., Moore, J., Filer, A., Buckley, C. D., Hewison, M., Stewart, P. M. 11beta-hydroxysteroid dehydrogenase in human fibroblasts: expression and regulation depends on tissue of origin. ENDO 2003 Abstracts 2003; Teelucksingh, S., Mackie, A. D., Burt, D., McIntyre, M. A., Brett, L., Edwards, C. R. Potentiation of hydrocortisone activity in skin by glycyrrhetinic acid. Lancet 1990; 335 (8697): 1060-3; Slight, S. H., Chilakamarri, V. K., Nasr, S., Dhalla, A. K., Ramires, F. J., Sun, Y., et al. Inhibition of tissue repair by spironolactone: role of mineralocorticoids in fibrous tissue formation. Mol Cell Biochem 1998; 189(1-2):47-54).

Wound healing consists of serial events including inflammation, fibroblast proliferation, secretion of ground substances, collagen production, angiogenesis, wound contraction and epithelialization. It can be divided in three phases; inflammatory, proliferative and remodeling phase (reviewed in Anstead et al., supra).

In surgical patients, treatment with glucocorticoids increases risk of wound infection and delay healing of open wounds. It has been shown in animal models that restraint stress slows down cutaneous wound healing and increases susceptibility to bacterial infection during wound healing. These effects were reversed by treatment with the glucocorticoid receptor antagonist RU486 (Mercado, A. M., Quan, N., Padgett, D. A., Sheridan, J. F., Marucha, P. T. Restraint stress alters the expression of interleukin-1 and keratinocyte growth factor at the wound site: an in situ hybridization study. J Neuroimmunol 2002; 129(1-2):74-83; Rojas, I. G., Padgett, D. A., Sheridan, J. F., Marucha, P. T. Stress-induced susceptibility to bacterial infection during cutaneous wound healing. Brain Behav Immun 2002; 16(1):74-84). Glucocorticoids produce these effects by suppressing inflammation, decrease wound strength, inhibit wound contracture and delay epithelialization (Anstead et al., supra). Glucocorticoids influence wound healing by interfering with production or action of cytokines and growth factors like IGF, TGF-β, EGF, KGF and PDGF (Beer, H. D., Fassler, R., Werner, S. Glucocorticoid-regulated gene expression during cutaneous wound repair. Vitam Horm 2000; 59:217-39; Hamon, G. A., Hunt, T. K., Spencer, E. M. In vivo effects of systemic insulin-like growth factor-I alone and complexed with insulin-like growth factor binding protein-3 on corticosteroid suppressed wounds. Growth Regul 1993; 3(1):53-6; Laato, M., Heino, J., Kahari, V. M., Niinikoski, J., Gerdin, B. Epidermal growth factor (EGF) prevents methylprednisolone-induced inhibition of wound healing. J Surg Res 1989; 47(4):354-9; Pierce, G. F., Mustoe, T. A., Lingelbach, J., Masakowski, V. R., Gramates, P., Deuel, T. F. Transforming growth factor beta reverses the glucocorticoid-induced wound-healing deficit in rats: possible regulation in macrophages by platelet-derived growth factor. Proc Natl Acad Sci USA 1989; 86(7):2229-33). It has also been shown that glucocorticoids decrease collagen synthesis in rat and mouse skin in vivo and in rat and human fibroblasts (Oishi, Y., Fu, Z. W., Ohnuki, Y., Kato, H., Noguchi, T. Molecular basis of the alteration in skin collagen metabolism in response to in vivo dexamethasone treatment: effects on the synthesis of collagen type I and III, collagenase, and tissue inhibitors of metalloproteinases. Br J Dermatol 2002; 147(5):859-68).

EP 0 558 258, EP 0 569 193, and EP 1 069 114 disclose isoxazole derivatives as endothelin agonists and antagonists. These publications do not address the activity of the compounds on 11β-HSD1.

SUMMARY OF THE INVENTION

The present invention relates to novel compounds, compositions thereof and methods for modulating the activity of hydroxysteroid dehydrogenases (HSDs), such as 11β-hydroxysteroid dehydrogenases, 17β-hydroxysteroid dehydrogenases, 20α-hydroxysteroid dehydrogenases, and 3α-hydroxysteroid dehydrogenases, including all isoforms thereof, including but not limited to 11β-hydroxysteroid dehydrogenase type 1 (hereinafter "11β-HSD1"), 11β-hydroxysteroid dehydrogenase type 2 (hereinafter "11β-HSD2"), and 17β-hydroxysteroid dehydrogenase type 3 (hereinafter "17β-HSD3"). In one embodiment, the compounds of the invention inhibit HSD activity.

The present invention also relates to methods for treating or preventing diseases or disorders associated with the action of hydroxysteroid dehydrogenases, comprising administering to a patient in need thereof a therapeutically effective amount of an azole aromatic heterocycle derivative or a pharmaceutically acceptable salt, solvate, stereoisomer, or prodrug thereof. The invention encompasses both selective and non-selective inhibitors of hydroxysteroid dehydrogenases.

It should be understood that selective and non-selective inhibitors of hydroxysteroid dehydrogenases each have benefits in the treatment or prevention of diseases associated with, for example, abnormal glucose levels or hypothalmic function. The invention also encompasses selective inhibitors of HSDs. Two types of selectivity are contemplated, that with respect to selectivity for HSDs as a class over other types of receptors or gene targets related to glucose metabolism, or those which are selective for various HSDs or specific isoforms thereof compared to other HSDs or specific isoforms thereof.

In one embodiment, the azole aromatic heterocycle derivatives can act as selective or non-selective 11β-HSD inhibitors. The compounds may inhibit the interconversion of inactive 11-keto steroids with their active hydroxy equivalents. The present invention provides methods by which the conversion of the inactive to the active form may be controlled, and to useful therapeutic effects which may be obtained as a result of such control. More specifically, but not exclusively, the invention is concerned with interconversion between cortisone and cortisol in humans.

In another embodiment, the azole aromatic heterocycle derivatives of the present invention may be orally active.

The azole aromatic heterocycle derivatives are also useful for modulation of numerous metabolic functions including, but not limited to, one or more of: (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

The azole aromatic heterocycle derivatives may also be useful for inhibiting hepatic gluconeogenesis, and may also be effective to relieve the effects of endogenous glucocorticoids in diabetes mellitus, obesity (including entripetal obesity), neuronal loss and/or the cognitive impairment of old age. Thus, in a further embodiment, the invention provides the use of an inhibitor of HSDs in methods directed to producing one or more therapeutic effects in a patient to whom the azole aromatic heterocycle derivative is administered, said therapeutic effects selected from the group consisting of inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

The invention further provides methods for treating a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the methods comprising administering to a patient in need thereof a therapeutically effective amount of an azole aromatic heterocycle.

The azole aromatic heterocycles of the invention are compounds having Formula (I) or Formula (IV). In one embodiment, compounds of the invention have

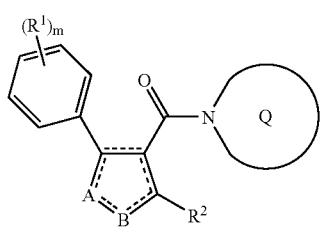

I or a stereoisomer, tautomer, solvate, or pharmaceutically acceptable salt thereof.

A-B represents N—O, O—N, or N(H)—N.

Each ≡≡≡ represents a single or double bond such that only two double bonds are simultaneously present in the ring containing A and B.

$R^1$ is selected from the group consisting of H, $C_{1-8}$-alkyl, $OC_{1-8}$-alkyl, $C_{1-3}$-haloalkyl, OH, CN, $NO_2$, F, Cl, Br, and I.

$R^2$ is selected from the group consisting of H, aryl, heteroaryl, $C_{1-6}$-alkyl, and $C_{1-6}$-haloalkyl.

Ring Q, together with the nitrogen atom it contains, is a cyclic moiety according to formula IIa or IIb:

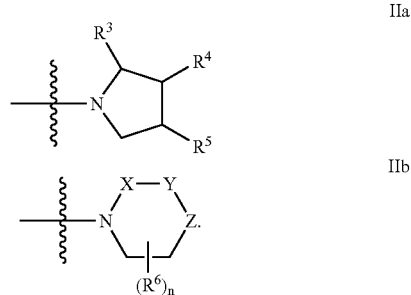

$R^3$, $R^4$, and $R^5$ are independently selected from the group consisting of H, aryl, heteroaryl, $C_{1-8}$-alkyl, $C_{1-8}$-alkyl-aryl, $C_{1-8}$-alkyl-heteroaryl, $C_{1-8}$-alkyl-$C_{1-8}$-alkoxy, $C_3$-$C_{10}$-cycloalkyl, $C_3$-$C_{10}$-heterocycloalkyl, $N(R')_2$, —C(O)N(R')$_2$, —N(R')C(O)OR'.

$R^6$ is selected from the group consisting of H, aryl, heteroaryl, heteroaryloxy, —N(R')$_2$, —C(O)N(R')$_2$, OH, CN, $C_3$-$C_{10}$-cycloalkyl, —C(O)R'.

Any two of $R^3$, $R^4$, $R^5$, and $R^6$, together with the atoms to which they are attached, optionally can combine to form a fused, and optionally further fused, saturated, partially saturated, or unsaturated polycycle containing from 5 to 20 atoms selected from C, N, O, and S.

X, Y, and Z are independently selected from O, NR', and CR'$_2$.

Any cycloalkyl, heterocycloalkyl, aryl, heteroaryl, or fused polycycle is optionally substituted with from one to four members selected from the group consisting of oxo, halogen, —CN, —NO$_2$, $C_{1-8}$-alkyl, $C_{2-8}$-alkenyl, $C_{2-8}$-alkynyl, $C_{1-8}$-alkoxy, $C_{1-8}$-haloalkyl, $C_{2-8}$-hydroxyalkyl, aryloxy, heteroaryl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$ and —NR'C(O)R'.

Each occurrence of R' is independently selected from the group consisting of H, $C_{1-8}$-alkyl, $C_{2-8}$-alkenyl, $C_{2-8}$-alkynyl, $C_{1-14}$-alkoxy, $C_{1-8}$-haloalkyl, $C_{1-8}$-hydroxyalkyl, $C_{1-8}$-hydroxy-diaryl-alkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl.

Each occurrence of R" is independently an unsubstituted member selected from the group consisting of $C_{1-8}$-alkyl, $C_{2-8}$-alkenyl, $C_{2-8}$-alkynyl, $C_{1-4}$-alkoxy, $C_{1-8}$-haloalkyl, $C_{1-8}$-hydroxyalkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl.

The integers m and n are independently selected from 0, 1, 2, and 3.

It should be understood that the invention does not encompass the following compounds:

4-[[3-methyl-5-(2,3,4,5-tetrafluoro-6-hydroxyphenyl)-4-isoxazolyl]carbonyl]-morpholine;

1-[(5-phenyl-4-isoxazolyl)carbonyl]-piperidine;

4-[(5-phenyl-4-isoxazolyl)carbonyl]-morpholine;

1-[[3-(5-chloro-2,4-dihydroxyphenyl)-1H-pyrazol-4-yl]carbonyl]-4-phenyl-piperazine;
4-[[3-(5-chloro-2,4-dihydroxyphenyl)-1H-pyrazol-4-yl]carbonyl]-morpholine;
1-[[3-(5-chloro-2,4-dihydroxyphenyl)-1H-pyrazol-4-yl]carbonyl]-4-methyl-piperazine;
4-[[3-(3,4-dimethoxyphenyl)-1H-pyrazol-4-yl]carbonyl]-morpholine;
1-[[3-(4-fluorophenyl)-4-isoxazolyl]carbonyl]-4-phenyl-piperazine;
1-[(5-methyl-3-phenyl-4-isoxazolyl)carbonyl]-piperazine;
1-[[5-(methyl-d)-3-phenyl-4-isoxazolyl]carbonyl]-pyrrolidine;
1-[(5-ethyl-3-phenyl-4-isoxazolyl)carbonyl]-pyrrolidine;
4-[[5-(methyl-d)-3-phenyl-4-isoxazolyl]carbonyl]-morpholine;
4-[(5-ethyl-3-phenyl-4-isoxazolyl)carbonyl]-morpholine;
4-[(5-methyl-3-phenyl-4-isoxazolyl)carbonyl]-morpholine;
1-[(5-methyl-3-phenyl-4-isoxazolyl)carbonyl]-pyrrolidine;
(S)-2-(methoxymethyl)-1-[(5-methyl-3-phenyl-4-isoxazolyl)carbonyl]-pyrrolidine; and
4-[[3-(2-chlorophenyl)-5-methyl-4-isoxazolyl]carbonyl]-1-piperazinamine.

In another embodiment, compounds of the invention have Formula (IV)

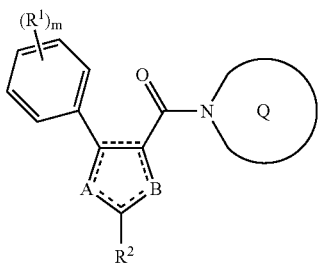

IV or a stereoisomer, tautomer, solvate, or pharmaceutically acceptable salt thereof.

A and B are respectively —N= and —O— or —O— and —N=.

Each ⸗ represents a single or double bond such that only two double bonds are simultaneously present in the ring containing A and B.

$R^1$ is selected from the group consisting of H, $C_{1-8}$-alkyl, $OC_{1-8}$-alkyl, $C_{1-3}$-haloalkyl, OH, CN, $NO_2$, F, Cl, Br, and I.

$R^2$ is selected from the group consisting of H, aryl, heteroaryl, $C_{1-6}$-alkyl, and $C_{1-6}$-haloalkyl.

Ring Q, together with the nitrogen atom it contains, is a cyclic moiety according to formula IIa or IIb:

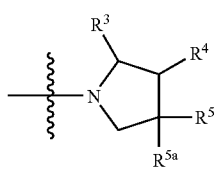

IIa

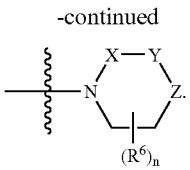

IIb $R^3$, $R^4$, and $R^5$ are independently selected from the group consisting of H, aryl, heteroaryl, $C_{1-8}$-alkyl, $C_{1-8}$-alkyl-aryl, $C_{1-8}$-alkyl-heteroaryl, $C_{1-8}$-alkyl-$C_{1-8}$-alkoxy, $C_3$-$C_{10}$-cycloalkyl, $C_3$-$C_{10}$-heterocycloalkyl, $N(R')_2$, —$C(O)N(R')_2$, and —$N(R')C(O)OR'$.

$R^{5a}$ is H, OH, CN, or $CONH_2$.

$R^6$ is selected from the group consisting of H, aryl, heteroaryl, heteroaryloxy, —$N(R')_2$, —$C(O)N(R')_2$, OH, CN, $C_3$-$C_{10}$-cycloalkyl, and —$C(O)R'$.

Any two of $R^3$, $R^4$, $R^5$, and $R^6$, together with the atoms to which they are attached, optionally can combine to form a fused, and optionally further fused, saturated, partially saturated, or unsaturated polycycle containing from 5 to 20 atoms selected from C, N, O, and S.

X, Y, and Z are independently selected from O, NR', and $CR'_2$.

Any cycloalkyl, heterocycloalkyl, aryl, heteroaryl, or fused polycycle is optionally substituted with from one to four members selected from the group consisting of oxo, halogen, —CN, —$NO_2$, $C_{1-8}$-alkyl, $C_{2-8}$-alkenyl, $C_{2-8}$-alkynyl, $C_{1-8}$-alkoxy, $C_{1-8}$-haloalkyl, $C_{2-8}$-hydroxyalkyl, aryloxy, heteroaryl, —C(O)R', —C(O)OR', —NR'C(O)OR'', —OR', —SR', —OC(O)R', —$C(O)N(R')_2$, —S(O)R'', —$SO_2R''$, —$SO_2N(R')_2$, —$N(R')_2$ and —NR'C(O)R'.

Each occurrence of R' is independently selected from the group consisting of H, $C_{1-8}$-alkyl, $C_{2-8}$-alkenyl, $C_{2-8}$-alkynyl, $C_{1-14}$-alkoxy, $C_{1-8}$-haloalkyl, $C_{1-8}$-hydroxyalkyl, $C_{1-8}$-hydroxy-diaryl-alkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl.

Each occurrence of R'' is independently an unsubstituted member selected from the group consisting of $C_{1-8}$-alkyl, $C_{2-8}$-alkenyl, $C_{2-8}$-alkynyl, $C_{1-4}$-alkoxy, $C_{1-8}$-haloalkyl, $C_{1-8}$-hydroxyalkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-16}$-alkyl, heteroaryl-$C_{1-6}$-alkyl, and aryl-$C_{1-6}$-alkyl.

The variables m and n are integers independently selected from 0, 1, 2, and 3.

In one embodiment, the invention provides pharmaceutical compositions comprising at least one azole aromatic heterocycle derivative and a pharmaceutically acceptable vehicle, carrier, excipient or diluent.

In another embodiment, the invention provides methods for treating insulin-dependent diabetes mellitus comprising administering to a patient in need thereof a therapeutically effective amount of an azole aromatic heterocycle derivative of Formula (I) or Formula (IV).

In another embodiment, the invention provides methods for treating non-insulin-dependent diabetes mellitus comprising administering to a patient in need thereof a therapeutically effective amount of an azole aromatic heterocycle derivative of Formula (I) or Formula (IV).

In another embodiment, the invention provides methods for treating insulin resistance comprising administering to a patient in need thereof a therapeutically effective amount of an azole aromatic heterocycle derivative of Formula (I) or Formula (IV).

In another embodiment, the invention provides methods for treating obesity comprising administering to a patient in need thereof a therapeutically effective amount of an azole aromatic heterocycle derivative of Formula (I) or Formula (IV).

In another embodiment, the invention provides methods for modulating cortisol production comprising administering to a patient in need thereof a therapeutically effective amount of an azole aromatic heterocycle derivative of Formula (I) or Formula (IV).

In another embodiment, the invention provides methods for modulating hepatic glucose production comprising administering to a patient in need thereof a therapeutically effective amount of an azole aromatic heterocycle derivative of Formula (I) or Formula (IV).

In another embodiment, the invention provides methods for modulating hypothalamic function comprising administering to a patient in need thereof a therapeutically effective amount of an azole aromatic heterocycle derivative of Formula (I) or Formula (IV).

In one embodiment, the invention provides methods for treating a hydroxysteroid dehydrogenase-mediated condition or disorder comprising administering to a patient in need thereof a therapeutically effective amount of an azole aromatic heterocycle derivative of Formula (I) or Formula (IV).

In a further embodiment, the invention provides methods for modulating a hydroxysteroid dehydrogenase, comprising administering to a patient in need thereof a therapeutically effective amount of an azole aromatic heterocycle derivative of Formula (I) or Formula (IV).

In still another embodiment, the invention provides methods for treating an 11β-HSD1-mediated condition or disorder comprising administering to a patient in need thereof a therapeutically effective amount of an azole aromatic heterocycle derivative of Formula (I) or Formula (IV).

In yet another embodiment, the invention provides method for modulating the function of 11β-HSD1 in a cell comprising administering to a patient in need thereof a therapeutically effective amount of an azole aromatic heterocycle derivative of Formula (I) or Formula (IV).

In a further embodiment, the invention provides methods for modulating 11β-HSD1, comprising administering to a patient in need thereof a therapeutically effective amount of an azole aromatic heterocycle derivative of Formula (I) or Formula (IV).

In one embodiment, the invention provides methods for treating an 11-HSD2-mediated condition or disorder comprising administering to a patient in need thereof a therapeutically effective amount of an azole aromatic heterocycle derivative of Formula (I) or Formula (IV).

In another embodiment, the invention provides method for modulating the function of 11β-HSD2 in a cell comprising administering to a patient in need thereof a therapeutically effective amount of an azole aromatic heterocycle derivative of Formula (I) or Formula (IV).

In a further embodiment, the invention provides methods for modulating 11β-HSD2, comprising administering to a patient in need thereof a therapeutically effective amount of an azole aromatic heterocycle derivative of Formula (I) or Formula (IV).

In one embodiment, the invention provides methods for treating an 17β-HSD3-mediated condition or disorder comprising administering to a patient in need thereof a therapeu- tically effective amount of an azole aromatic heterocycle derivative of Formula (I) or Formula (IV).

In another embodiment, the invention provides method for modulating the function of 17β-HSD3 in a cell comprising administering to a patient in need thereof a therapeutically effective amount of an azole aromatic heterocycle derivative of Formula (I) or Formula (IV).

In a further embodiment, the invention provides methods for modulating 17β-HSD3, comprising administering to a patient in need thereof a therapeutically effective amount of an azole aromatic heterocycle derivative of Formula (I) or Formula (IV).

These and other embodiments of this invention will be evident upon reference to the following detailed description. To that end, certain patent and other documents are cited herein to more specifically set forth various embodiments of this invention. Each of these documents are hereby incorporated by reference in their entirety.

DETAILED DESCRIPTION

As used herein, the terms have the following meanings:

The term "alkyl" as used herein refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms and at least one double bond. Examples of a ($C_2$-$C_8$)alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent alkyl group (e.g., an alkyl group attached to two other moieties, typically as a linking group). Examples of a ($C_1$-$C_7$)alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. An alkylene group can be unsubstituted or optionally substituted with one or more substituents as described herein below.

The term "alkoxy" as used herein refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the $C_1$-$C_6$ alkyl group's hydrogen atoms is replaced with an amine of formula —N($R^a$)$_2$, wherein each occurrence of $R^a$ is independently —H or ($C_1$-$C_6$)alkyl. Examples of aminoalkyl groups include, but are not limited to, —CH$_2$NH$_2$, —CH$_2$CH$_2$NH$_2$—, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N(CH$_3$)$_2$, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. The bicyclic or tricyclic hydrocarbon ring systems may be spiro-fused. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, spiro[5,4]decane, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The term "halo" as used herein refers to —F, —Cl, —Br or —I.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzthiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" or "heterocycloalkyl" as used herein refers to 5- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "hydroxyalkyl," as used herein, refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

Substituents for the groups referred to as alkyl, heteroalkyl, alkylene, alkenyl, alkynyl, cycloalkyl, heterocycloalkyl, cycloalkenyl and heterocycloalkenyl can be a variety of groups selected from: —OR', =O, =NR', =N—OR', —NR'R", —SR', -halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being exemplary. R', R" and R'" each independently refer to hydrogen, unsubstituted ($C_1$-$C_8$)alkyl, unsubstituted hetero($C_1$-$C_8$)alkyl, unsubstituted aryl and aryl substituted with one to three substituents selected from -halo, unsubstituted alkyl, unsubstituted alkoxy, unsubstituted thioalkoxy and unsubstituted aryl($C_1$-$C_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. An alkyl or heteroalkyl group will have from zero to three substituents, with those groups having two or fewer substituents being exemplary in the present invention. In some embodiments, an alkyl or heteroalkyl radical will be unsubstituted or monosubstituted. An alkyl or heteroalkyl radical can be unsubstituted. From the above discussion of substituents, one of skill in the art will understand that the term "alkyl" is meant to include groups such as trihaloalkyl (e.g., —CF$_3$ and —CH$_2$CF$_3$).

Exemplary substituents for the alkyl and heteroalkyl radicals are selected from: —OR', =O, —NR'R", —SR', -halo, —SiR'R"R'", —OC(O)R', —C(O)R', —CO$_2$R', —C(O)NR'R", —OC(O)NR'R", —NR"C(O)R', —NR"CO$_2$R', —NR'"SO$_2$NR'R", —S(O)R', —SO$_2$R', —SO$_2$NR'R", —NR"SO$_2$R', —CN and —NO$_2$, where R', R" and R'" are as defined above. Typical substituents are selected from: —OR', =O, —NR'R", -halo, —OC(O)R', —CO₂R', —C(O)NR'R", —OC(O)NR'R", —NR"C(O)R', —NR"CO₂R', —NR'''SO₂NR'R", —SO₂R', —SO₂NR'R", —NR"SO₂R'— CN and —NO₂.

Similarly, substituents for the aryl and heteroaryl groups are varied and selected from: -halo, —OR', —OC(O)R', —NR'R", —SR', —R', —CN, —NO₂, —CO₂R', —C(O) NR'R", —C(O)R', —OC(O)NR'R", —NR"C(O)R', —NR"CO₂R', —NR'''C(O)NR'R", —NR'''SO₂NR'R", —NHC(NH₂)=NH, —NR'C(NH₂)=NH, —NH—C(NH₂) =NR', —S(O)R', —SO₂R', —SO₂NR'R", —NR"SO₂R', —N₃, —CH(Ph)₂, perfluoroalkoxy and perfluoro(C₁-C₄) alkyl, in a number ranging from zero to the total number of open valences on the aromatic ring system; and where R', R" and R''' are independently selected from hydrogen, unsubstituted (C₁-C₈)alkyl, unsubstituted hetero(C₁-C₈)alkyl, unsubstituted aryl, unsubstituted heteroaryl, unsubstituted aryl(C₁-C₄)alkyl and unsubstituted aryloxy(C₁-C₄)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Exemplary substituents for aryl and heteroaryl groups are selected from: -halo, —OR', —OC(O)R', —NR'R", —SR', —R', —CN, —NO₂, —CO₂R', —CONR'R", —C(O)R', —OC(O)NR'R", —NR"C(O)R', —S(O)R', —SO₂R', —SO₂NR'R", —NR"SO₂R', —N₃, —CH(Ph)₂, perfluoroalkoxy and perfluoro(C₁-C₄)alkyl, where R' and R" are as defined above. Typically, substituents are selected from: -halo, —OR', —OC(O)R', —NR'R", —R', —CN, —NO₂, —CO₂R', —CONR'R", —NR"C(O)R', —SO₂R', —SO₂NR'R", —NR"SO₂R', perfluoroalkoxy and perfluoro (C₁-C₄)alkyl.

Two of the substituents on adjacent atoms of the aryl or heteroaryl ring may optionally be replaced with a substituent of the formula -T-C(O)—(CH₂)_q—U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH₂)_r—B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)_s—X—(CH₂)_t—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted (C₁-C₆)alkyl.

It is to be understood that the substituent —CO₂H, as used herein, may be optionally replaced with bioisosteric replacements such as:

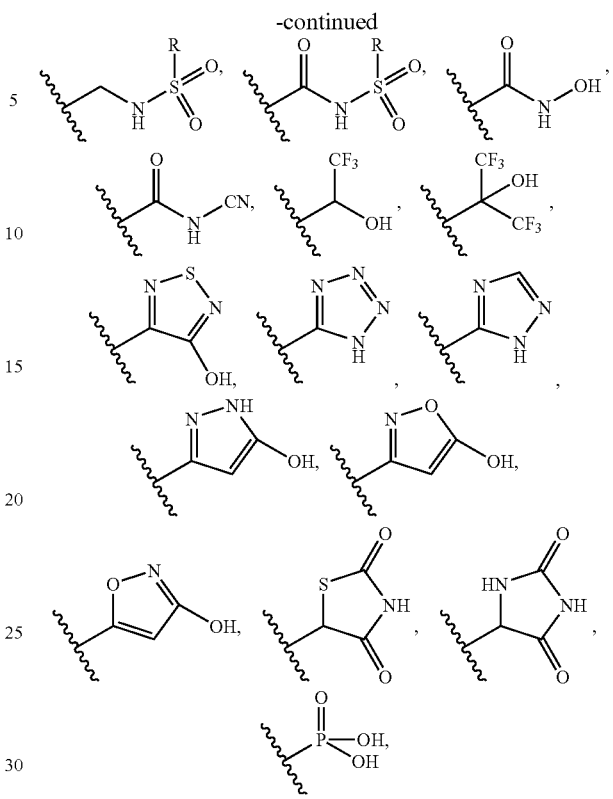

and the like. See, e.g., *The Practice of Medicinal Chemistry*; Wermuth, C. G., Ed.; Academic Press: New York, 1996; p. 203.

The azole aromatic heterocycle derivative can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of an azole aromatic heterocycle derivative, including tautomeric forms of the compound.

Certain azole aromatic heterocycle derivatives may have asymmetric centers and therefore exist in different enantiomeric and diastereomeric forms. An azole aromatic heterocycle derivative can be in the form of an optical isomer or a diastereomer. Accordingly, the invention encompasses azole aromatic heterocycle derivatives and their uses as described herein in the form of their optical isomers, diasteriomers and mixtures thereof, including a racemic mixture. Optical isomers of the azole aromatic heterocycle derivatives can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" or means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example, greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

An azole aromatic heterocycle derivative can be in the form of a pharmaceutically acceptable salt. Depending on its structure, the phrase "pharmaceutically acceptable salt," as used herein, refers to a pharmaceutically acceptable organic or inorganic acid or base salt of an azole aromatic heterocycle derivative. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "isolated and purified form" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of an azole aromatic heterocycle derivative by weight of the isolate. In one embodiment, the isolate contains at least 95% of an azole aromatic heterocycle derivative by weight of the isolate.

As used herein, the term "prodrug" means a derivative of a compound that can hydrolyze, oxidize, or otherwise react under biological conditions (in vitro or in vivo) to provide an active compound, particularly an azole aromatic heterocycle derivative. Examples of prodrugs include, but are not limited to, derivatives and metabolites of an azole aromatic heterocycle derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). Prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* $6^{th}$ ed. (Donald J. Abraham ed., 2001, Wiley) and *Design and Application of Prodrugs* (H. Bundgaard ed., 1985, Harwood Academic Publishers Gmfh).

As used herein, the terms "treat", "treating" and "treatment" refer to the eradication or amelioration of a disease or symptoms associated with a disease. In certain embodiments, such terms refer to minimizing the spread or worsening of the disease resulting from the administration of one or more prophylactic or therapeutic agents to a patient with such a disease.

As used herein, the terms "prevent", "preventing" and "prevention" refer to the prevention of the onset, recurrence or spread of the disease in a patient resulting from the administration of a prophylactic or therapeutic agent.

The term "effective amount" as used herein refers to an amount of an azole aromatic heterocycle derivative or other active ingredient sufficient to provide a therapeutic or prophylactic benefit in the treatment or prevention of a disease or to delay or minimize symptoms associated with a disease. Further, a therapeutically effective amount with respect to an azole aromatic heterocycle derivative means that amount of therapeutic agent alone, or in combination with other therapies, that provides a therapeutic benefit in the treatment or prevention of a disease. Used in connection with an azole aromatic heterocycle derivative, the term can encompass an amount that improves overall therapy, reduces or avoids symptoms or causes of disease, or enhances the therapeutic efficacy of or synergies with another therapeutic agent.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

The terms "modulate", "modulation" and the like refer to the ability of a compound to increase or decrease the function, or activity of, for example, 11β-HSD1. "Modulation", as used herein in its various forms, is intended to encompass inhibition, antagonism, partial antagonism, activation, agonism and/or partial agonism of the activity associated with 11β-HSD1. 11β-HSD1 inhibitors are compounds that, e.g., bind to, partially or totally block stimulation, decrease, prevent, delay activation, inactivate, desensitize, or down regulate signal transduction. 11β-HSD1 activators are compounds that, e.g., bind to, stimulate, increase, open, activate, facilitate, enhance activation, sensitize or up regulate signal transduction. The ability of a compound to modulate 11β-HSD1 can be demonstrated in an enzymatic assay or a cell-based assay. For example, the inhibition of 11β-HSD1 may decrease cortisol levels in a patient and/or increase cortisone levels in a patient by blocking the conversion of cortisone to cortisol. Alternatively, the inhibition of 11β-HSD2 can increase cortisol levels in a patient and/or decrease cortisone levels in a patient by blocking the conversion of cortisol to cortisone.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

The term "HSD" as used herein, refers to hydroxysteroid dehydrogenase enzymes in general, including, but not limited to, 11-beta-hydroxysteroid dehydrogenases (11β-HSDs), 17-beta-hydroxysteroid dehydrogenases (17β-HSDs), 20-alpha-hydroxysteroid dehydrogenases (20α-HSDs), 3-alpha-hydroxysteroid dehydrogenases (3α-HSDs), and all isoforms thereof.

The term "11β-HSD1" as used herein, refers to the 11-beta-hydroxysteroid dehydrogenase type 1 enzyme, variant, or isoform thereof. 11β-HSD1 variants include proteins substantially homologous to native 11β-HSD1, i.e., proteins having one or more naturally or non-naturally occurring amino acid deletions, insertions or substitutions (e.g., 11β-HSD1 derivatives, homologs and fragments). The amino acid sequence of a 11β-HSD1 variant can be at least about 80% identical to a native 11β-HSD1, or at least about 90% identical, or at least about 95% identical.

The term "11β-HSD2" as used herein, refers to the 11-beta-hydroxysteroid dehydrogenase type 2 enzyme, variant, or isoform thereof. 11β-HSD2 variants include proteins substantially homologous to native 11β-HSD2, i.e., proteins having one or more naturally or non-naturally occurring amino acid deletions, insertions or substitutions (e.g., 11β-HSD2 derivatives, homologs and fragments). The amino acid sequence of a 11β-HSD2 variant can be at least about 80% identical to a native 11β-HSD2, or at least about 90% identical, or at least about 95% identical. (see Bart et al., *J. Med. Chem.*, 2002, 45:3813-3815).

The term "17β-HSD3" as used herein, refers to the 17-beta-hydroxysteroid dehydrogenase type 3 enzyme, variant, or isoform thereof. 17β-HSD3 variants include proteins substantially homologous to native 17β-HSD3, i.e., proteins having one or more naturally or non-naturally occurring amino acid deletions, insertions or substitutions (e.g., 17β-HSD3 derivatives, homologs and fragments). The amino acid sequence of a 17β-HSD3 variant can be at least about 80% identical to a native 17β-HSD3, or at least about 90% identical, or at least about 95% identical.

As used herein, the term "HSD-responsive condition or disorder" and related terms and phrases refer to a condition or disorder that responds favorably to modulation of a hydroxysteroid dehydrogenase enzyme (HSD). Favorable responses to HSD modulation include alleviation or abrogation of the disease and/or its attendant symptoms, inhibition of the disease, i.e., arrest or reduction of the development of the disease, or its clinical symptoms, and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and at least partially responsive to or affected by HSD modulation (e.g., an HSD inhibitor results in some improvement in patient well-being in at least some patients). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11β-HSD1-responsive condition or disorder" and related terms and phrases refer to a condition or disorder that responds favorably to modulation of 11β-HSD1 activity. Favorable responses to 11β-HSD1 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD1-responsive condition or disease may be completely or partially responsive to 11β-HSD1 modulation. An 11β-HSD1-responsive condition or disorder may be associated with inappropriate, e.g., less than or greater than normal, 11β-HSD1 activity and at least partially responsive to or affected by 11β-HSD1 modulation (e.g., a 11β-HSD1 inhibitor results in some improvement in patient well-being in at least some patients). Inappropriate 11β-HSD1 functional activity might arise as the result of 11β-HSD1 expression in cells which normally do not express 11β-HSD1, decreased 11β-HSD1 expression or increased 11β-HSD1 expression. A 11β-HSD1-responsive condition or disorder may include a 11β-HSD1-mediated condition or disorder.

As used herein, the term "11β-HSD2-responsive condition or disorder" and related terms and phrases refer to a condition or disorder that responds favorably to modulation of 11β-HSD2 activity. Favorable responses to 11β-HSD2 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD2-responsive condition or disease may be completely or partially responsive to 11β-HSD2 modulation. An 11β-HSD2-responsive condition or disorder may be associated with inappropriate, e.g., less than or greater than normal, 11β-HSD2 activity and at least partially responsive to or affected by 11β-HSD2 modulation (e.g., a 11β-HSD2 inhibitor results in some improvement in patient well-being in at least some patients).

As used herein, the term "17β-HSD3-responsive condition or disorder" and related terms and phrases refer to a condition or disorder that responds favorably to modulation of 17β-HSD3 activity. Favorable responses to 17β-HSD3 modulation include alleviation or abrogation of the disease and/or its attendant symptoms, inhibition of the disease, i.e., arrest or reduction of the development of the disease, or its clinical symptoms, and regression of the disease or its clinical symptoms. An 17β-HSD3-responsive condition or disease may be completely or partially responsive to 17β-HSD3 modulation. An 17β-HSD3-responsive condition or disorder may be associated with inappropriate, e.g., less than or greater than normal, 17β-HSD3 activity and at least partially responsive to or affected by 17β-HSD3 modulation (e.g., a 17β-HSD3 inhibitor results in some improvement in patient well-being in at least some patients). Inappropriate 17β-HSD3 functional activity might arise as the result of 17β-HSD3 expression in cells which normally do not express 17β-HSD3, decreased 17β-HSD3 expression or increased 17β-HSD3 expression. A 17β-HSD3-responsive condition or disorder may include a 17β-HSD3-mediated condition or disorder.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11β-HSD1-mediated condition or disorder" and related terms and phrases refer to a condition or disorder characterized by inappropriate, e.g., less than or greater than normal, 11β-HSD1 activity. A 11β-HSD1-mediated condition or disorder may be completely or partially characterized by inappropriate 11β-HSD1 activity. However, a 11β-HSD1-mediated condition or disorder is one in which modulation of 11β-HSD1 results in some effect on the underlying condition or disease (e.g., a 11β-HSD1 inhibitor results in some improvement in patient well-being in at least some patients).

As used herein, the term "11β-HSD2-mediated condition or disorder" and related terms and phrases refer to a condition or disorder characterized by inappropriate, e.g., less than or greater than normal, 11β-HSD2 activity. A 11β-HSD2-mediated condition or disorder may be completely or partially characterized by inappropriate 11β-HSD2 activity. However, a 11β-HSD2-mediated condition or disorder is one in which modulation of 11β-HSD2 results in some effect on the underlying condition or disease (e.g., a 11β-HSD2 inhibitor results in some improvement in patient well-being in at least some patients).

As used herein, the term "17β-HSD3-mediated condition or disorder" and related terms and phrases refer to a condition or disorder characterized by inappropriate, e.g., less than or greater than normal, 17β-HSD3 activity. A 17β-HSD3-mediated condition or disorder may be completely or partially characterized by inappropriate 17β-HSD3 activity. However, a 17β-HSD3-mediated condition or disorder is one in which modulation of 17β-HSD3 results in some effect on the underlying condition or disease (e.g., a 17β-HSD3 inhibitor results in some improvement in patient well-being in at least some patients).

The following abbreviations are used herein and have the indicated definitions: DMEM is Dulbecco's Modified Eagle Medium; Et$_3$N is triethylamine; EtOAc is ethyl acetate; MeOH is methanol; MS is mass spectrometry; NMR is nuclear magnetic resonance; PBS is phosphate-buffered saline; SPA is scintillation proximity assay; THF is tetrahydrofuran; and TMS is trimethylsilyl.

Compounds of the Invention

The present invention provides compounds of Formula (I) and Formula (IV) as well as their pharmaceutically acceptable salts, solvates, stereoisomers, or prodrugs thereof, or mixtures thereof, collectively referred to as the "azole aromatic heterocycle derivatives."

In one embodiment, compounds of the invention have Formula (I)

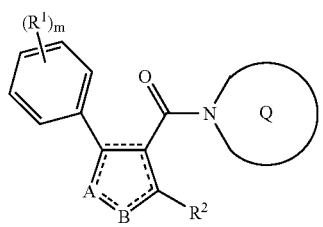

I where the variables are as defined above.

In one embodiment, the invention provides for a compound of formula I, or a stereoisomer, tautomer, solvate, or pharmaceutically acceptable salt thereof, where $R^2$ is selected from the group consisting of $C_{1-8}$-alkyl, particularly $CH_3$; $C_{1-6}$-haloalkyl, particularly $CF_3$; and aryl, particularly optionally substituted phenyl.

In yet another embodiment, the invention provides for a compound of formula I, or a stereoisomer, tautomer, solvate, or pharmaceutically acceptable salt thereof, where ring Q is formula IIa:

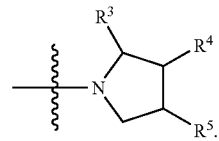

I-IIa

In one embodiment, the invention provides a compound of formula I-IIa, or a stereoisomer, tautomer, solvate, or pharmaceutically acceptable salt thereof, where $R^1$ is selected from the group consisting of H, F, Cl, Br, NO$_2$, and CH$_3$; $R^3$ is H; $R^4$ is selected from the group consisting of aryl and heteroaryl; $R^5$ is H; and m is 1. In another embodiment, in addition to the variables described herein, $R^2$ is selected from the group consisting of optionally substituted phenyl, 2-pyridyl, 3-pyridyl, and 4-pyridyl.

In another embodiment, the invention provides for a compound of formula I, or a stereoisomer, tautomer, solvate, or pharmaceutically acceptable salt thereof, where the compound is of the formula I-IIb:

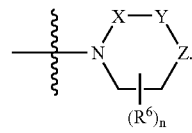

I-IIb

In one embodiment, the invention provides for a compound of formula I-IIb, or a stereoisomer, tautomer, solvate, or pharmaceutically acceptable salt thereof, wherein each of X, Y, and Z is C(R')$_2$. In another embodiment, in the compound of formula I-IIb, n is 0 and $R^2$ is H. In yet another embodiment, in the compound of formula I-IIb, each of X and Y is C(R')$_2$ and Z is O. In still another embodiment, in the compound of formula I-IIb, each of X and Y is C(R')$_2$ and Z is NR'.

In one embodiment, the invention provides for a compound of formula I, where A-B represents N—O. In another embodiment, for the compound of formula I, A-B represents N—O and ring Q is formula IIa.

In one embodiment, the invention provides for a compound of formula I, where A-B represents O—N. In another embodiment, for the compound of formula I, A-B represents O—N and ring Q is formula IIa.

In another embodiment, the invention provides for a compound of formula I, where A-B represents N(H)—N. In yet another embodiment, for the compound of formula I, A-B represents N(H)—N and ring Q is formula IIa.

In another embodiment, compounds of the invention have Formula (IV)

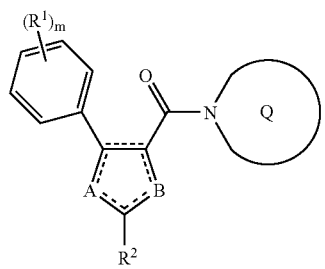

IV where the variables are as defined above.

In one embodiment, the invention provides for a compound of formula IV, or a stereoisomer, tautomer, solvate, or pharmaceutically acceptable salt thereof, where $R^2$ is selected from the group consisting of $C_{1-8}$-alkyl, particularly $CH_3$; $C_{1-6}$-haloalkyl, particularly $CF_3$; and aryl, particularly optionally substituted phenyl.

In yet another embodiment, the invention provides for a compound of formula IV, or a stereoisomer, tautomer, solvate, or pharmaceutically acceptable salt thereof, where ring Q is formula IIa:

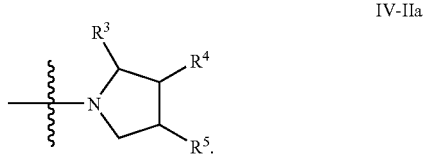

IV-IIa

In one embodiment, the invention provides a compound of formula IV-IIa, or a stereoisomer, tautomer, solvate, or pharmaceutically acceptable salt thereof, where $R^1$ is selected from the group consisting of H, F, Cl, Br, $NO_2$, and $CH_3$; $R^3$ is H; $R^4$ is selected from the group consisting of aryl and heteroaryl; $R^5$ is H; and m is 1. In another embodiment, in addition to the variables described herein, $R^2$ is selected from the group consisting of optionally substituted phenyl, 2-pyridyl, 3-pyridyl, and 4-pyridyl.

In another embodiment, the invention provides for a compound of formula IV, or a stereoisomer, tautomer, solvate, or pharmaceutically acceptable salt thereof, where the compound is of the formula IV-IIb:

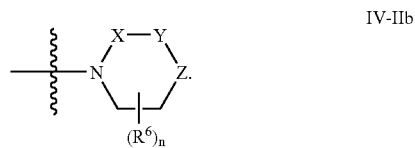

IV-IIb

In one embodiment, the invention provides for a compound of formula IV-IIb, or a stereoisomer, tautomer, solvate, or pharmaceutically acceptable salt thereof, wherein each of X, Y, and Z is $C(R')_2$. In another embodiment, in the compound of formula IV-IIb, n is 0 and $R^2$ is H. In yet another embodiment, in the compound of formula IV-IIb, each of X and Y is $C(R')_2$ and Z is O. In still another embodiment, in the compound of formula IV-IIb, each of X and Y is $C(R')_2$ and Z is NR'.

In one embodiment, the invention provides for a compound of formula IV, where A and B are respectively —N= and —O—. In another embodiment, for the compound of formula IV, A and B are respectively —N= and —O— and ring Q is formula IIa.

In yet another embodiment, the invention provides for a compound of formula IV, where A and B are respectively —O— and —N=. In another embodiment, for the compound of formula IV, A and B are respectively —O— and —N= and ring Q is formula IIa.

The invention provides a pharmaceutical composition comprising a therapeutically effective amount of at least one compound of formula I or Formula (IV), or a stereoisomer, tautomer, solvate, or pharmaceutically acceptable salt thereof, and a pharmaceutically acceptable carrier.

The invention provides a method of inhibiting 11-β-hydroxysteroid dehydrogenase type 1 enzyme in a patient in need thereof comprising administering to the patient a therapeutically effective amount of a compound of formula I or Formula (IV) or a stereoisomer, tautomer, solvate, or pharmaceutically acceptable salt thereof.

The invention provides a method of treating a disease or condition selected from the group consisting of diabetes, obesity, dyslipidemia, hyperinsulinemia, glaucoma, osteoporosis, cognitive disorders, atherosclerosis, immune disorders, hypertension and wound healing in a patient in need thereof comprising administering to the patient a therapeutically effective amount of the compound of formula I or Formula (IV) or a stereoisomer, tautomer, solvate, or pharmaceutically acceptable salt thereof.

The invention further provides a method where the disease or condition is diabetes, obesity, hyperlipidemia, hypercholesterolemia, hypertriglyceridemia, low level of high-density lipoprotein, hyperinsulinemia, or atherosclerosis.

The azole aromatic heterocycle derivatives can have asymmetric centers and therefore exist in different enantiomeric and diastereomeric forms. This invention relates to the use of all optical isomers and stereoisomers of the azole aromatic heterocycle derivatives, and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above are all encompassed.

Specific examples of the compounds of Formula (I) and additional compounds are provided in Table A below.

TABLE A

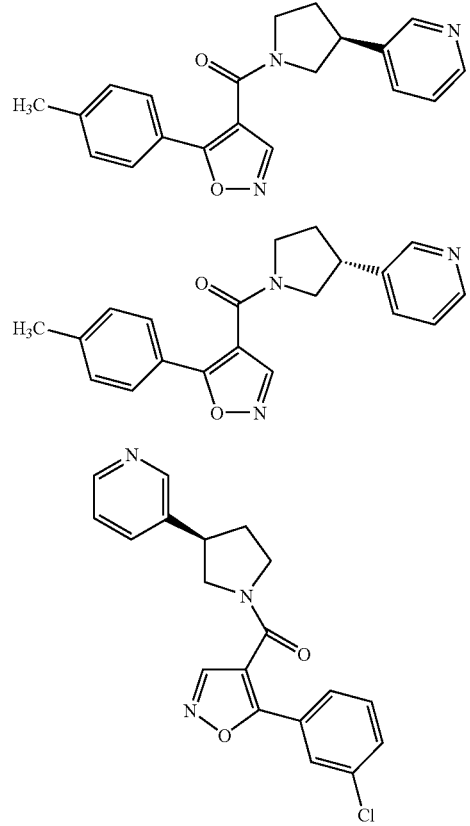

TABLE A-continued
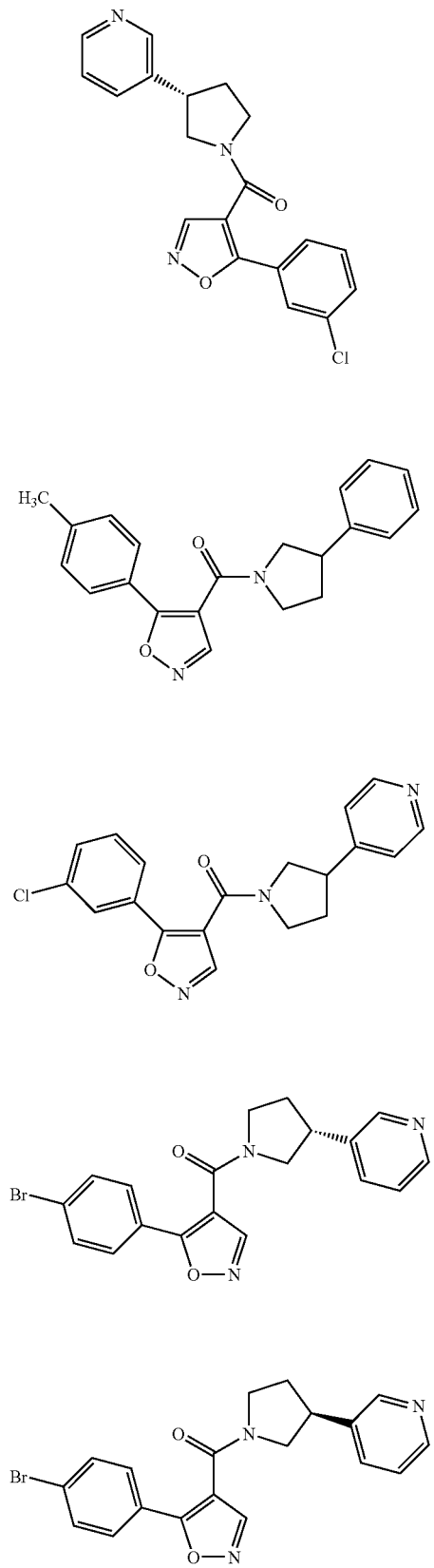
TABLE A-continued
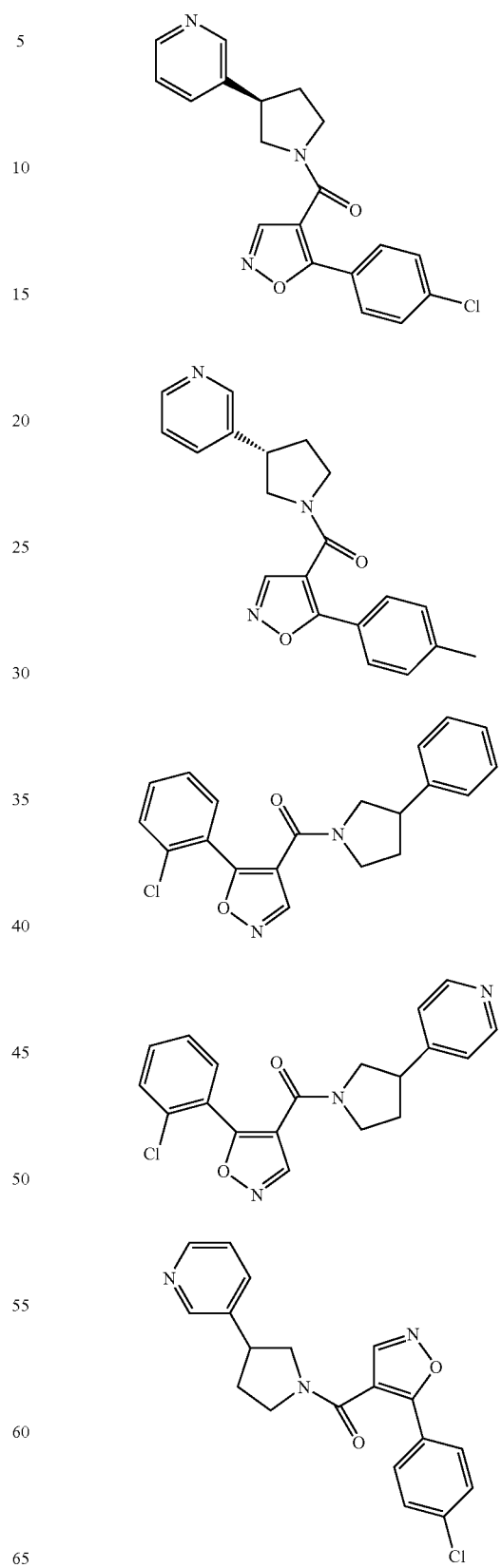

TABLE A-continued
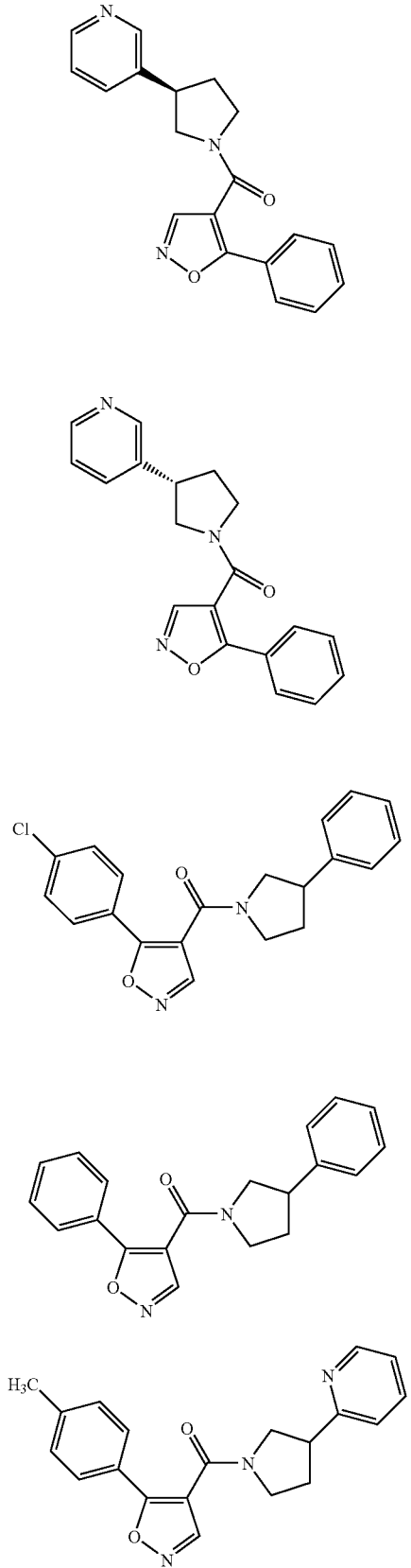
TABLE A-continued
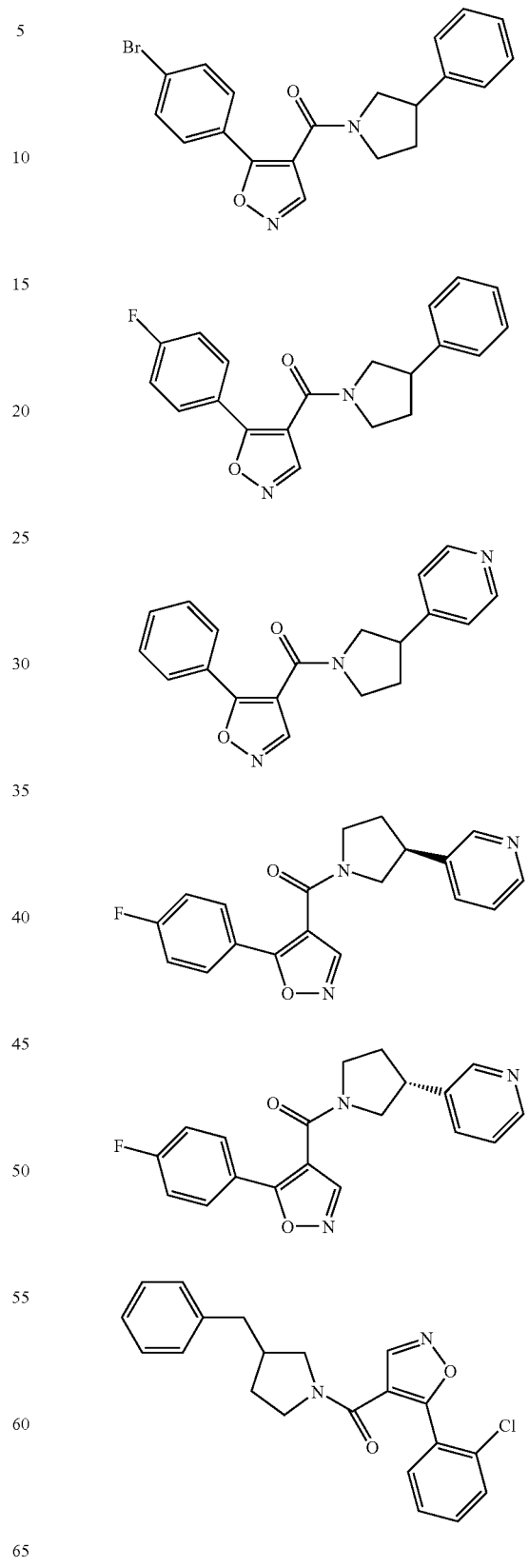

TABLE A-continued
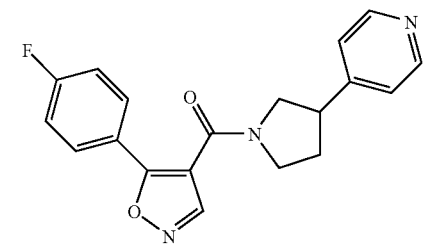
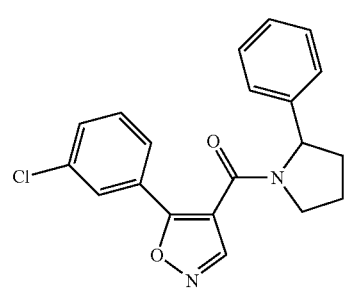
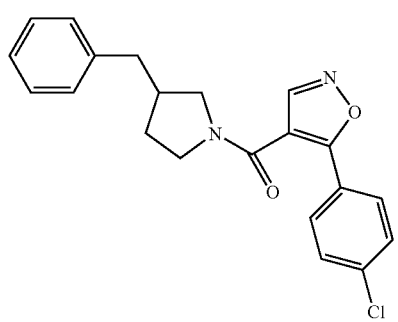
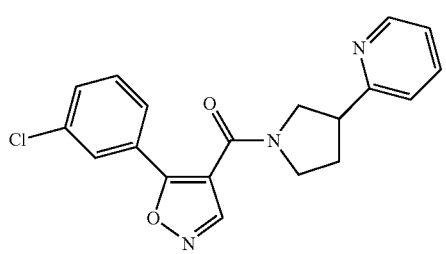
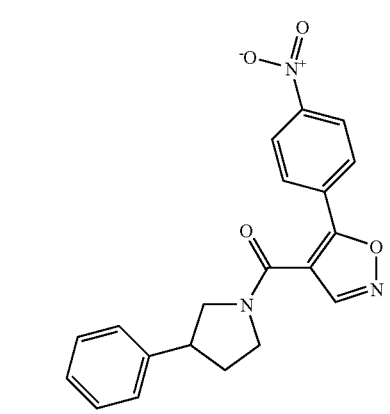
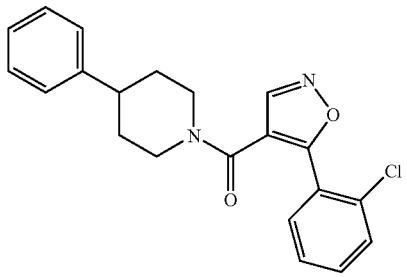
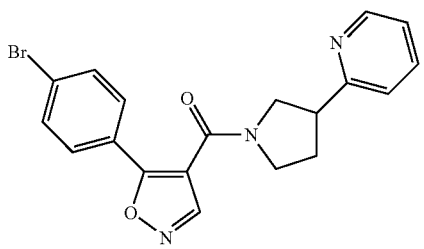
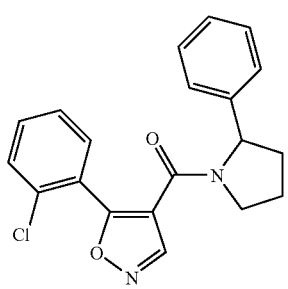
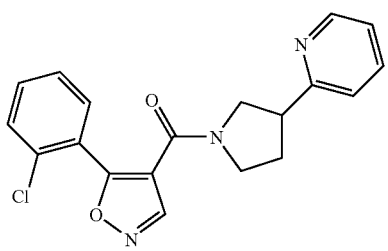
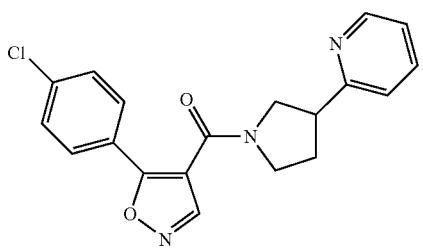
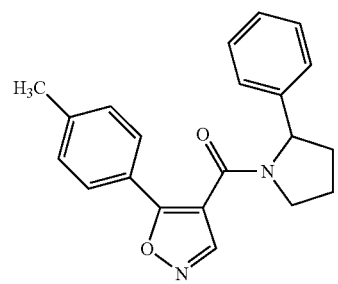

TABLE A-continued
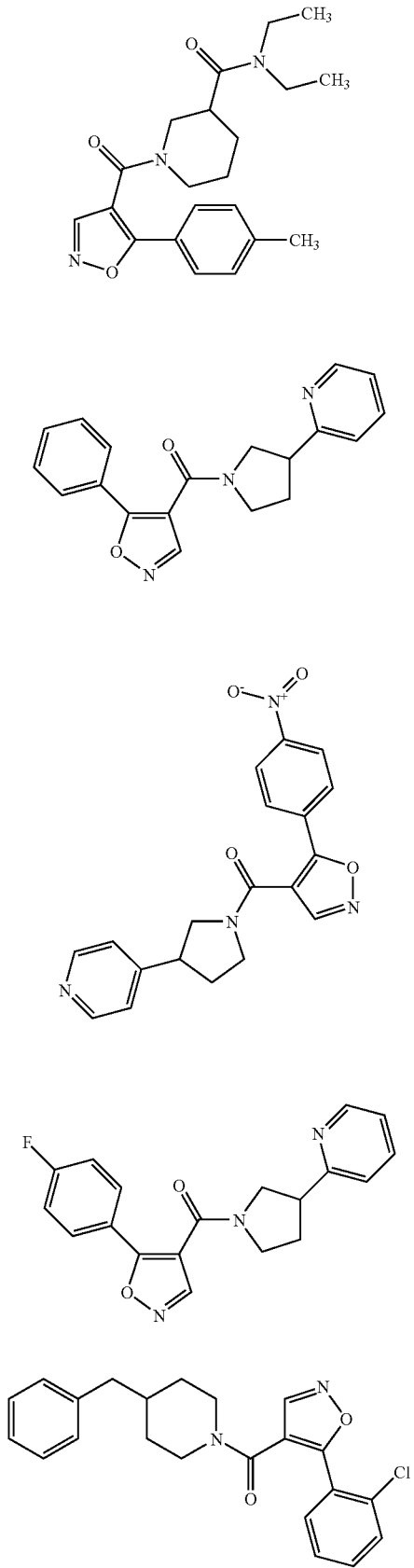
TABLE A-continued
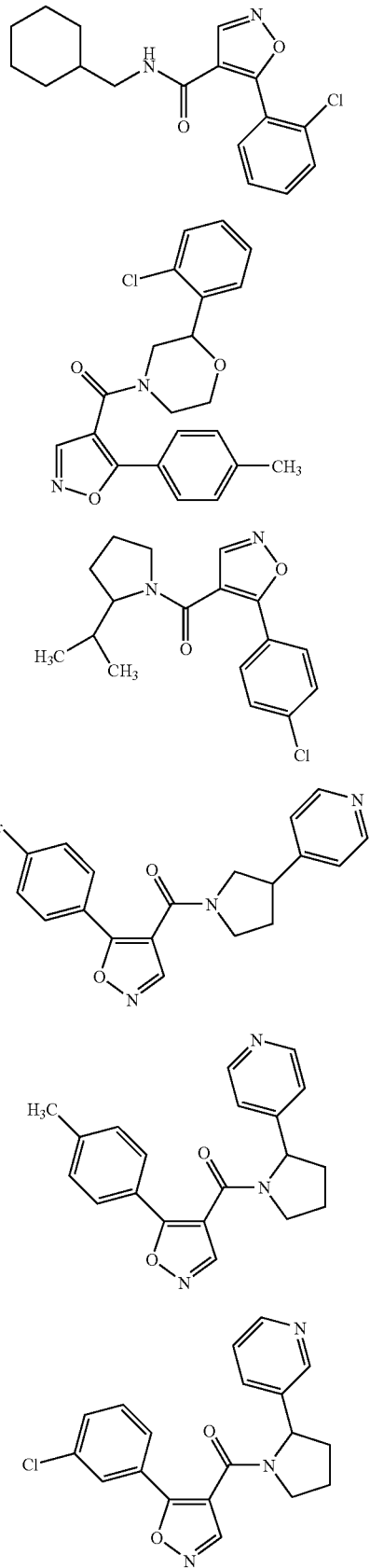

TABLE A-continued
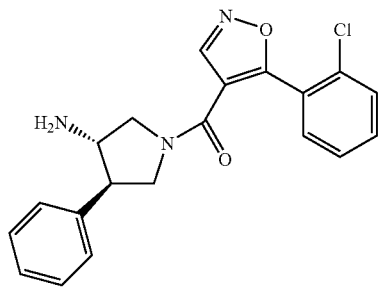
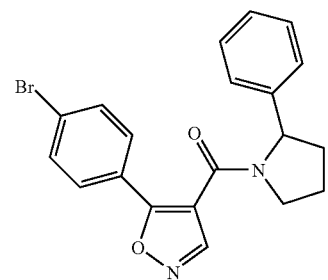
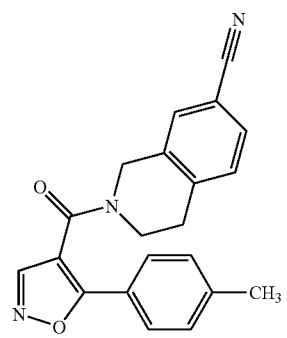
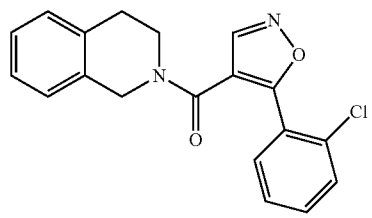
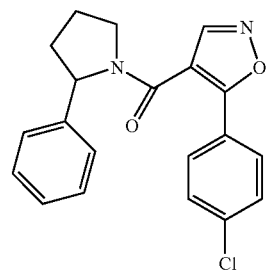
TABLE A-continued
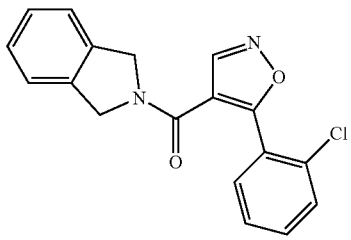
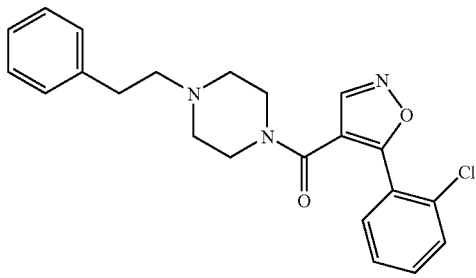
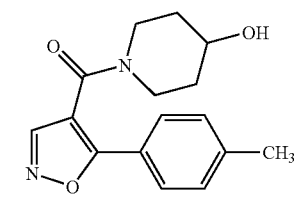
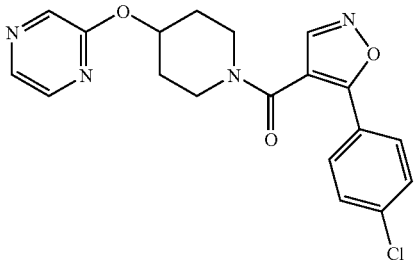
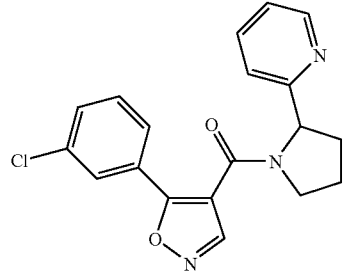
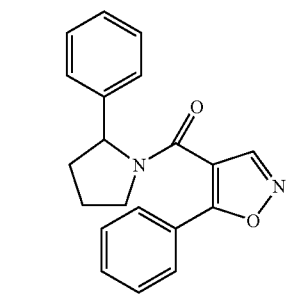

TABLE A-continued
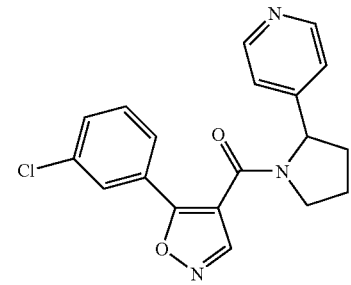
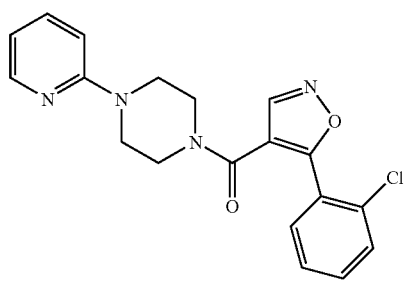
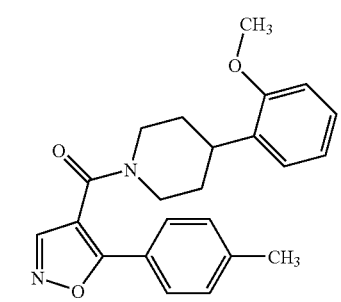
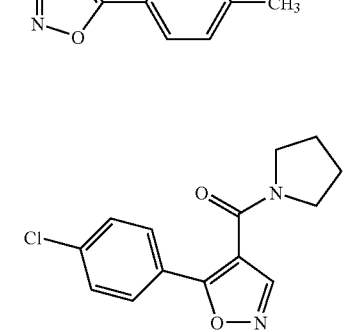
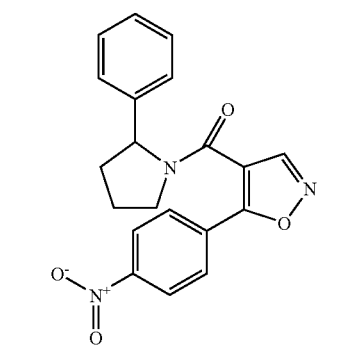
TABLE A-continued
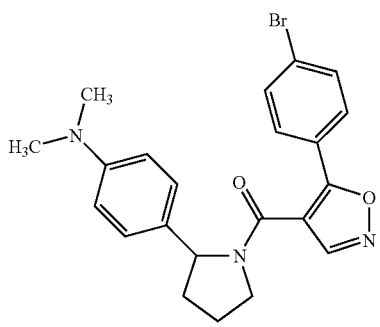
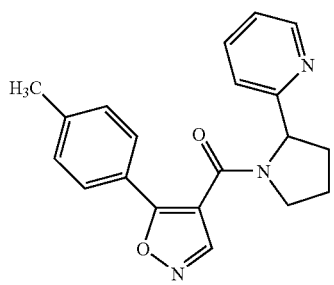
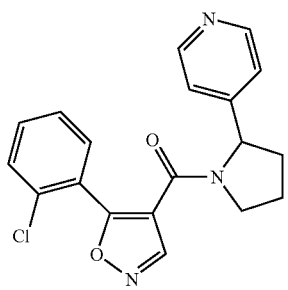
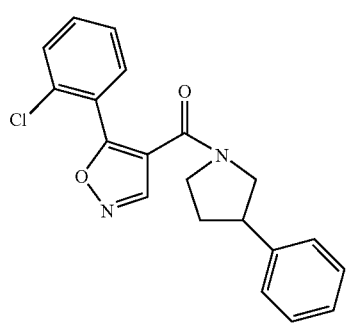
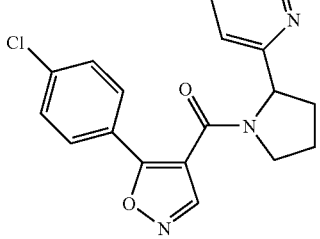

TABLE A-continued
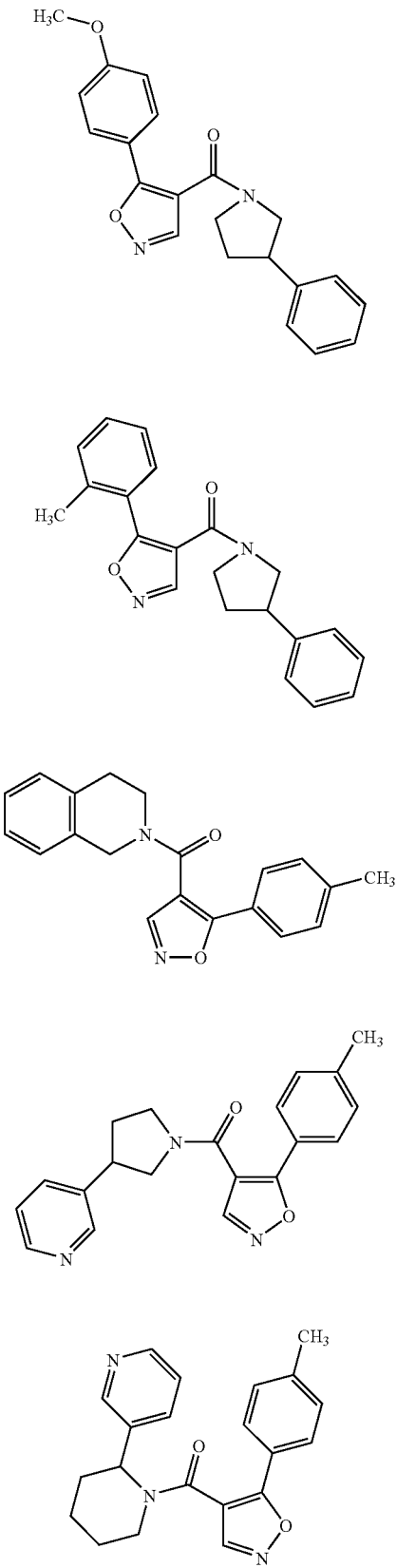
TABLE A-continued
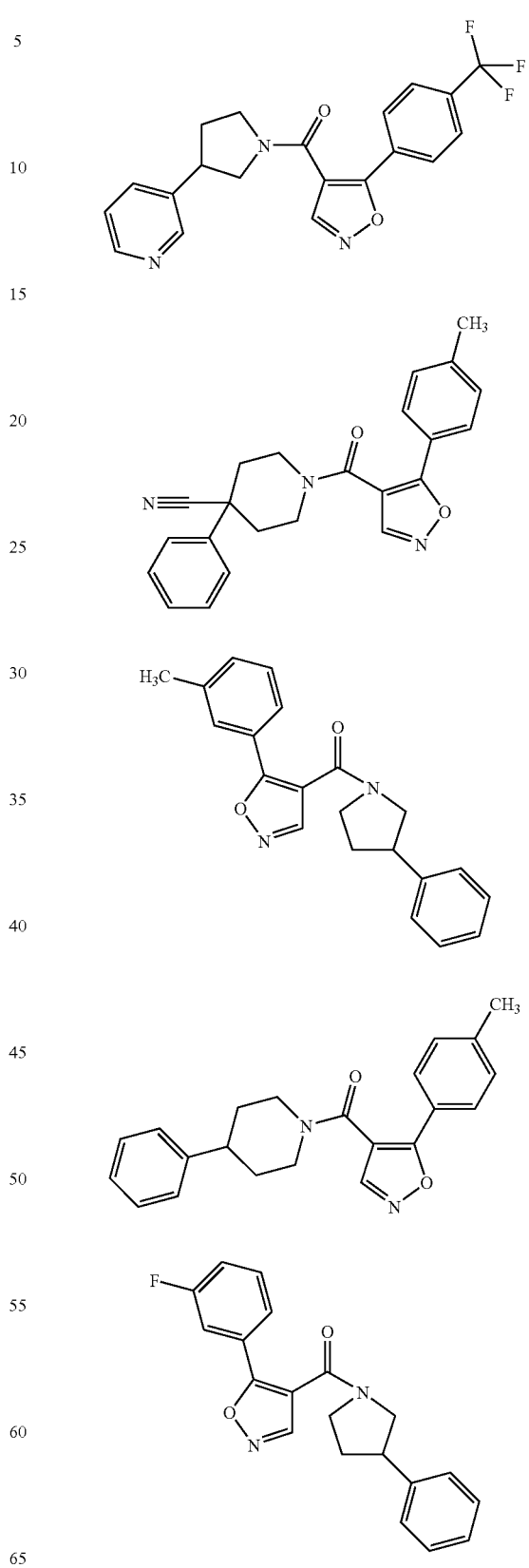

TABLE A-continued
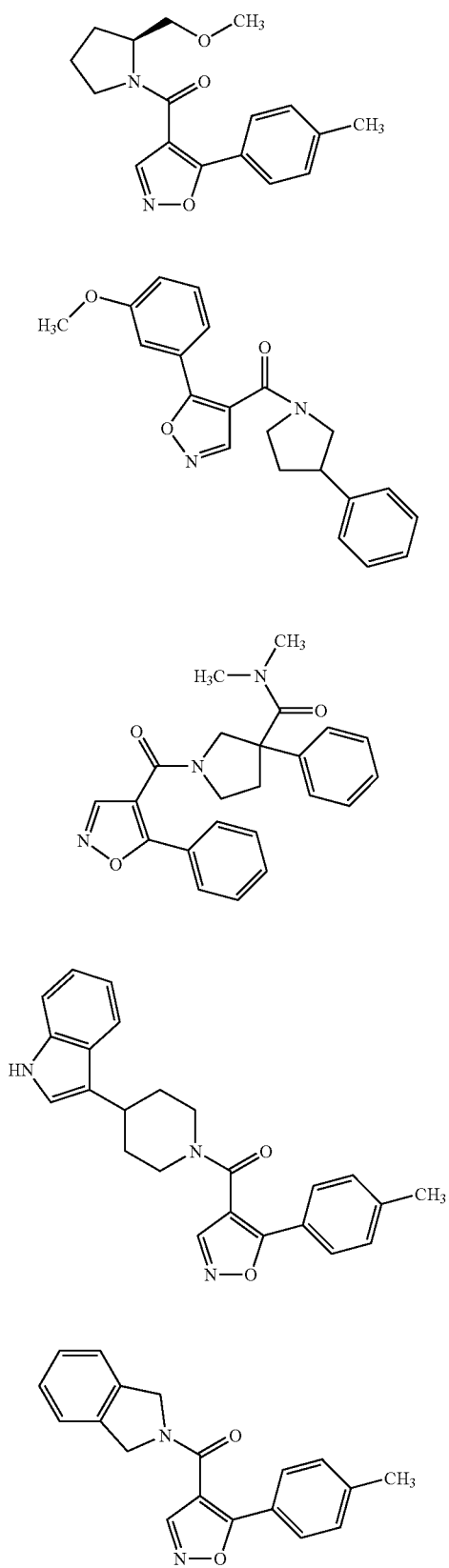
TABLE A-continued
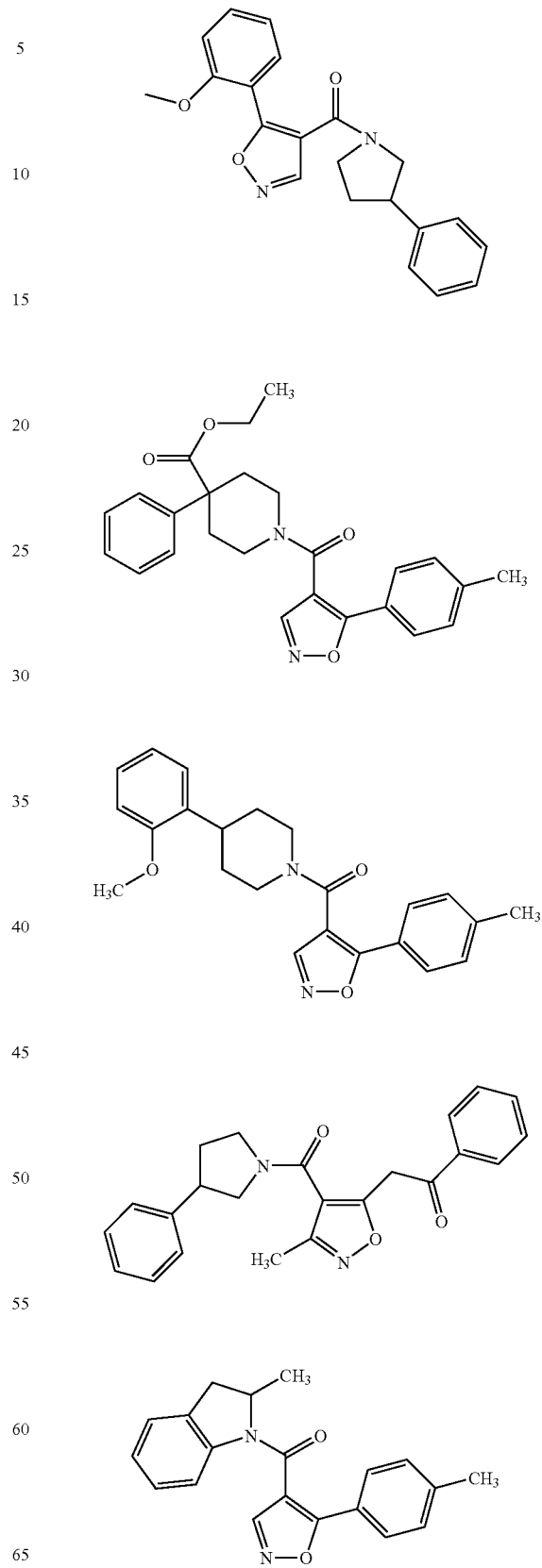

TABLE A-continued
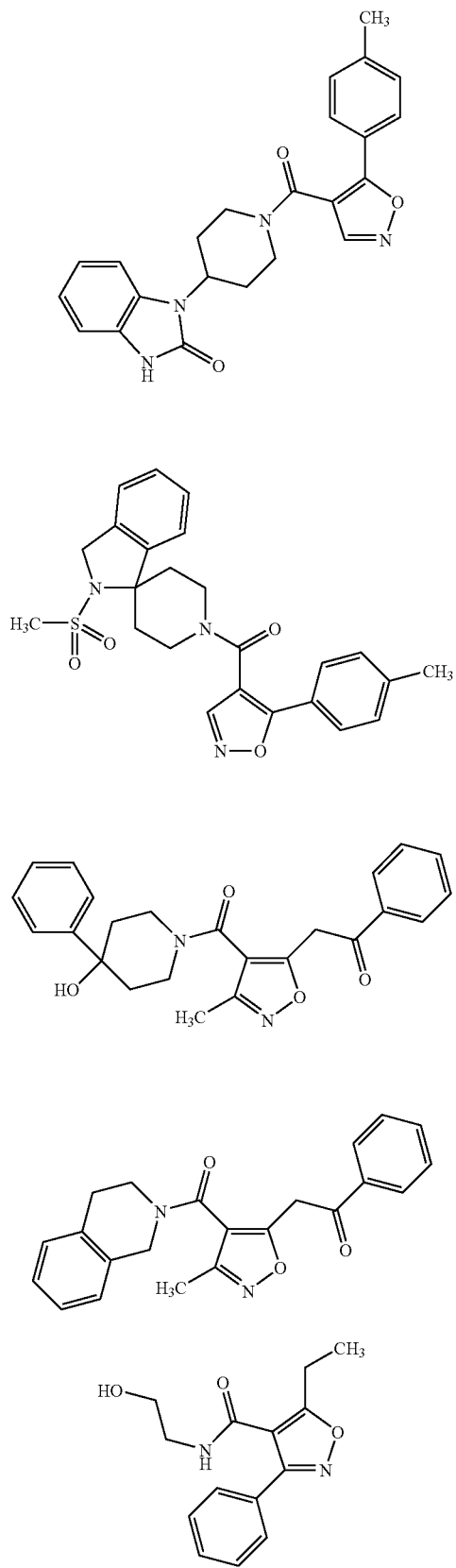
TABLE A-continued
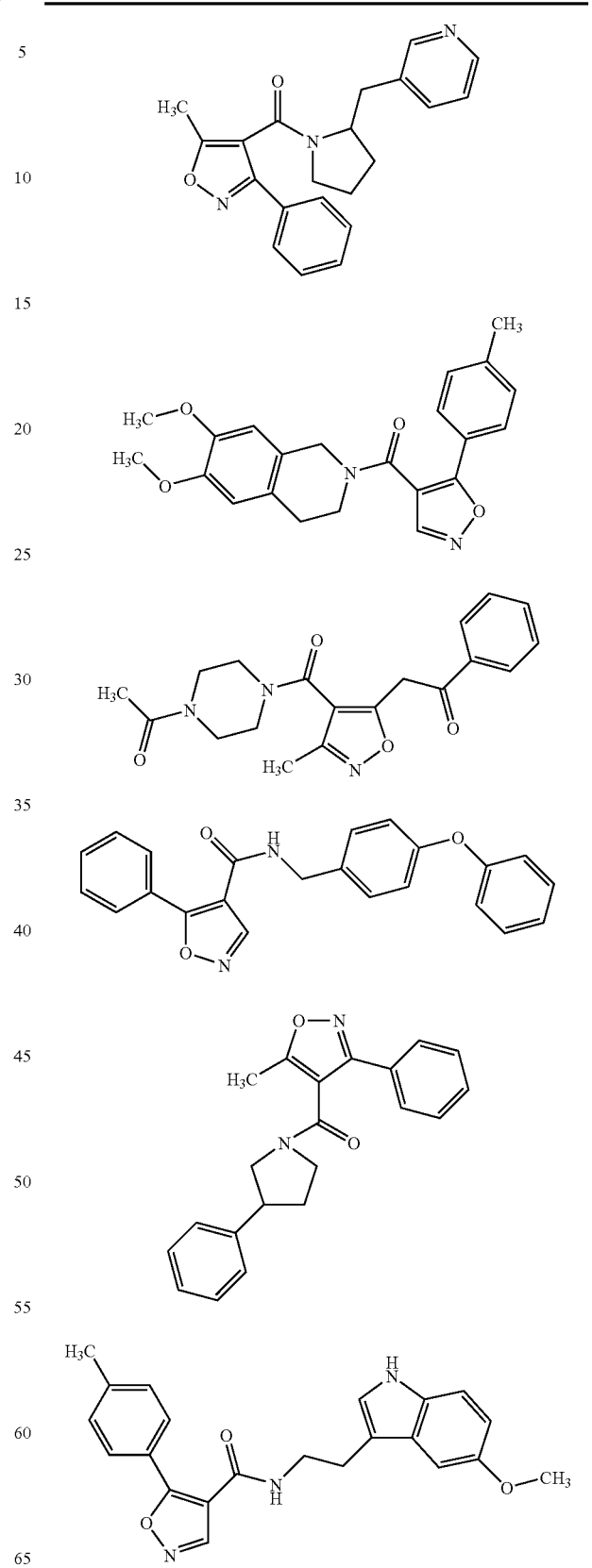

TABLE A-continued
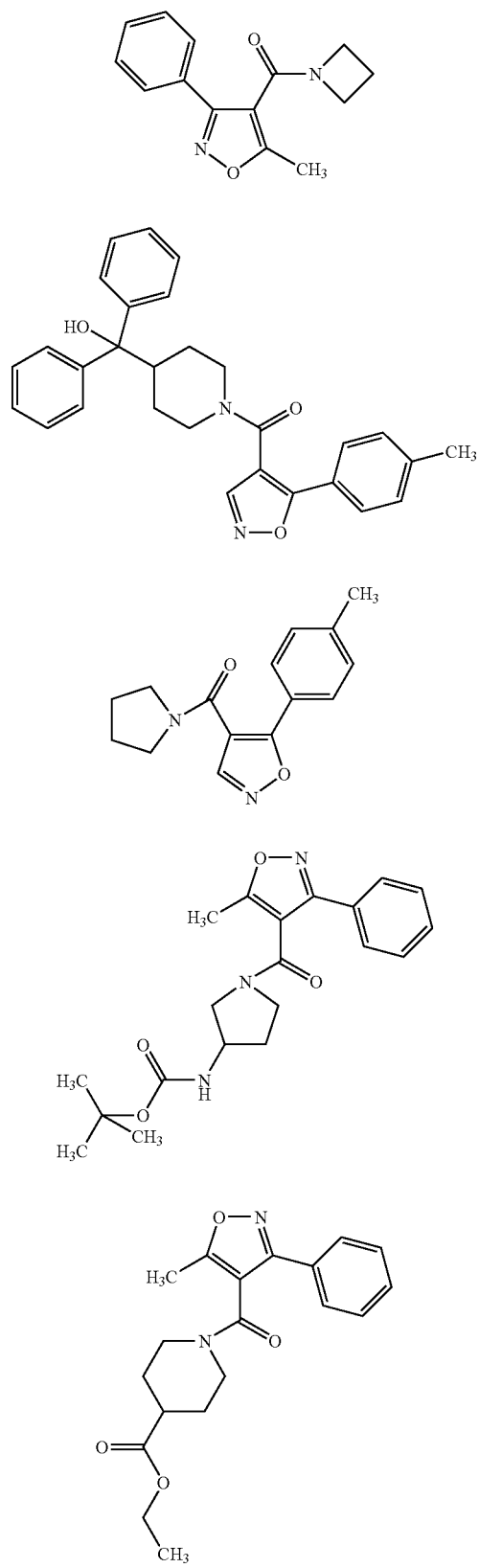
TABLE A-continued
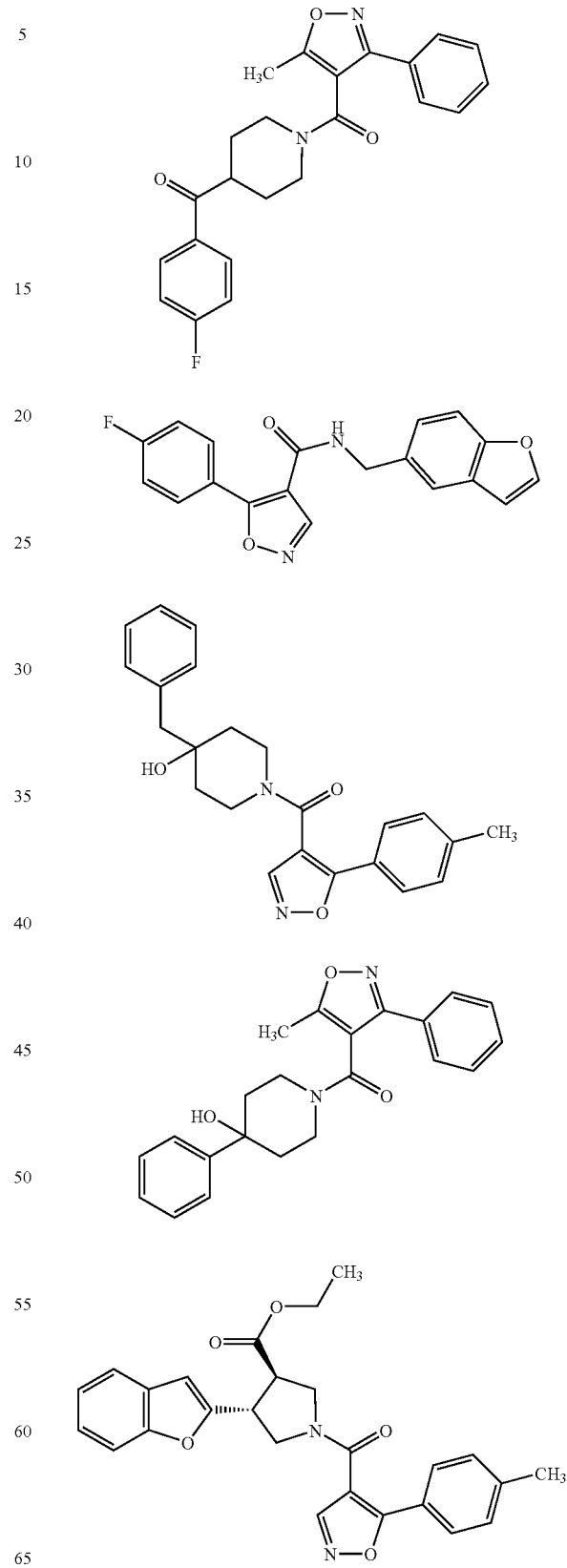

TABLE A-continued
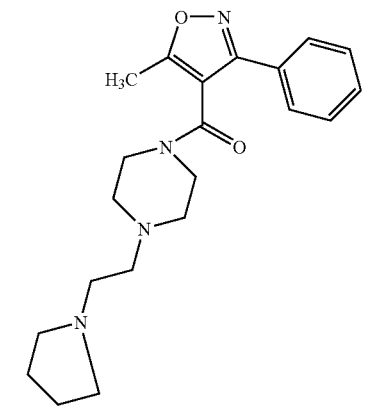
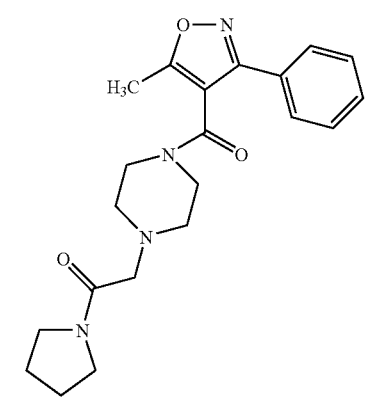
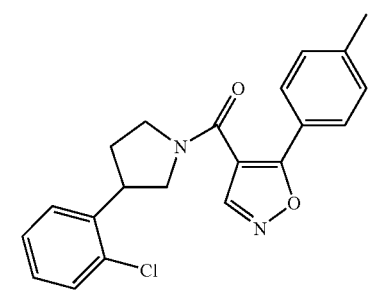
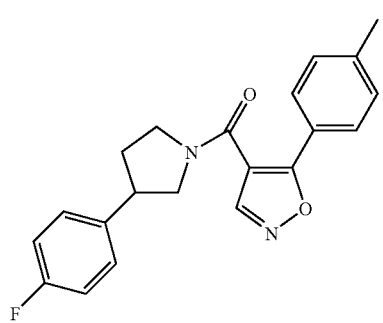
TABLE A-continued
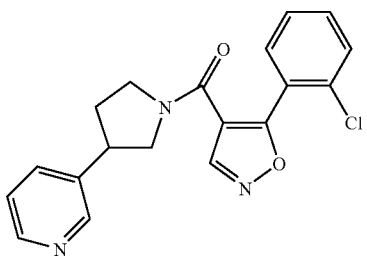
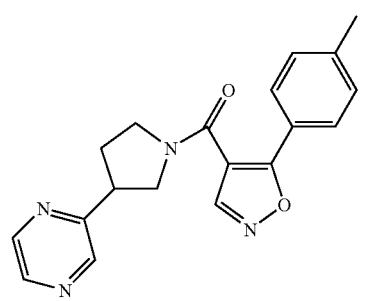
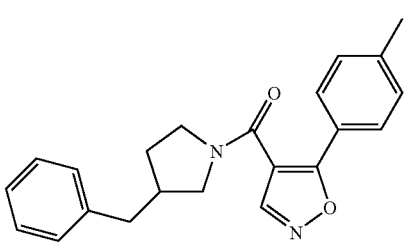
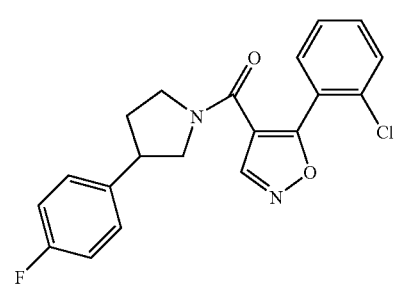
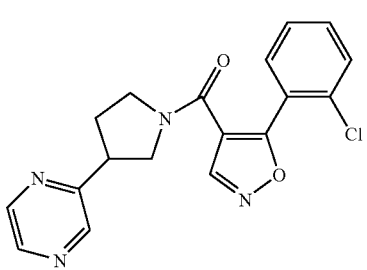

TABLE A-continued
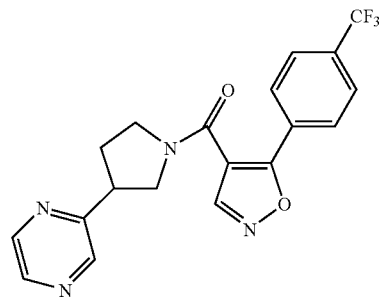
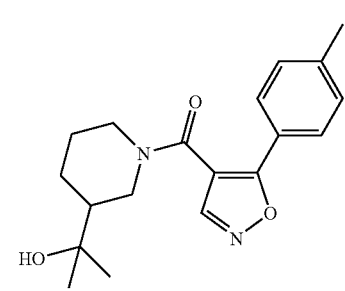
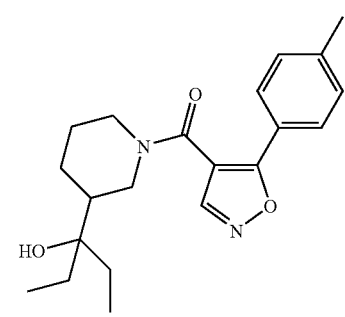
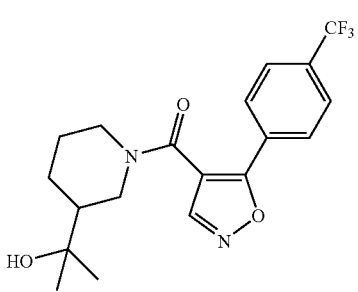
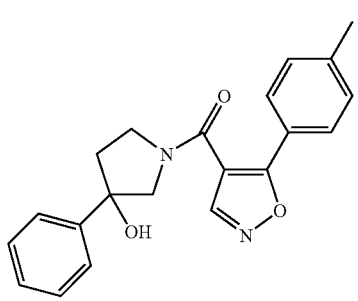
TABLE A-continued
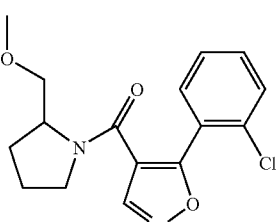
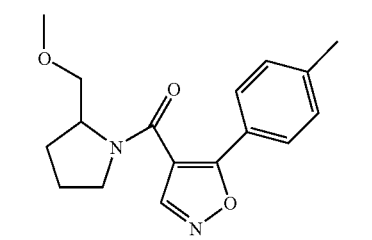
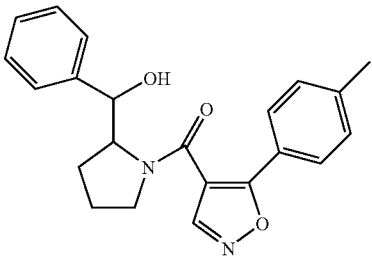
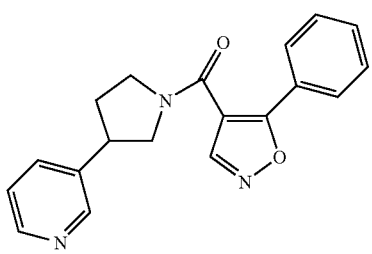
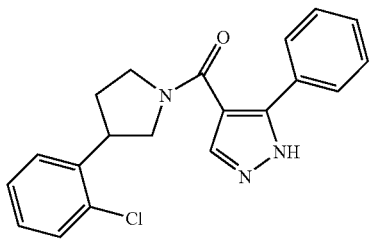
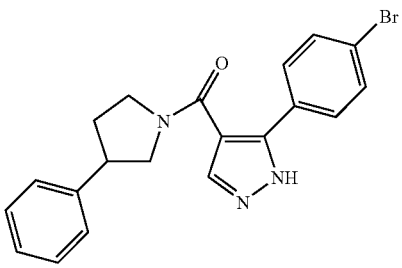

TABLE A-continued
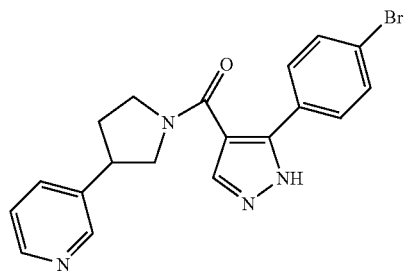
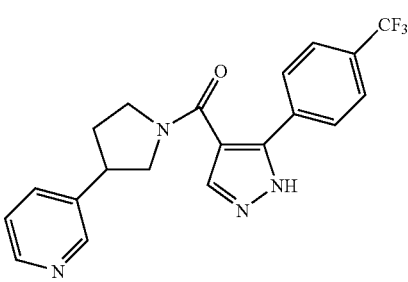
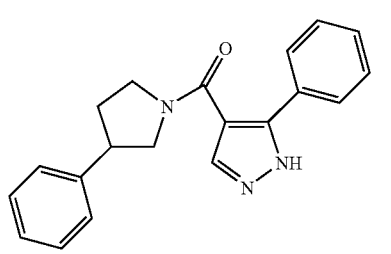
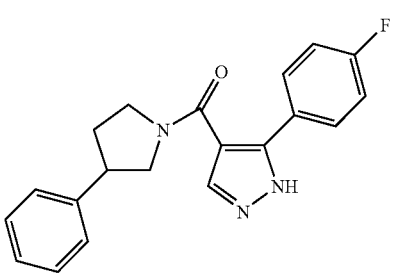
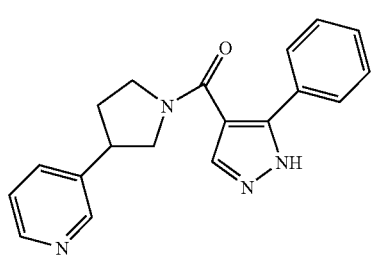
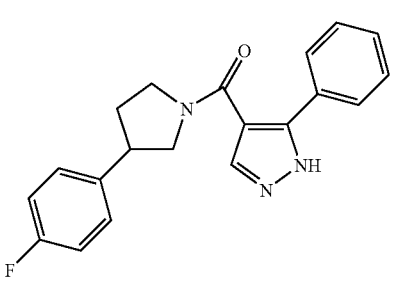
TABLE A-continued
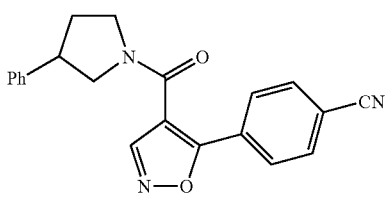
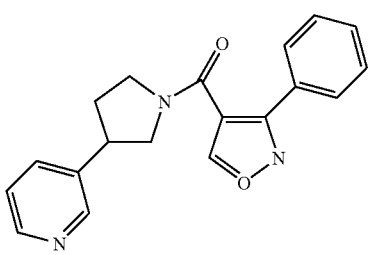
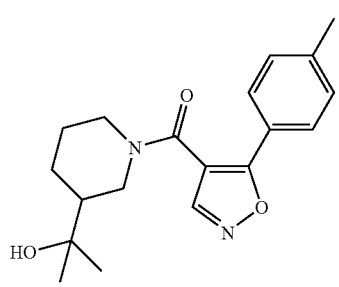
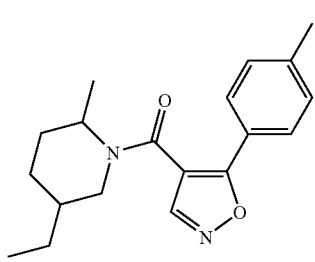
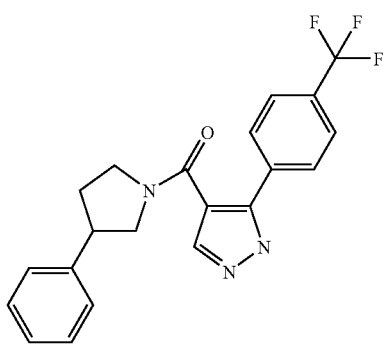

TABLE A-continued
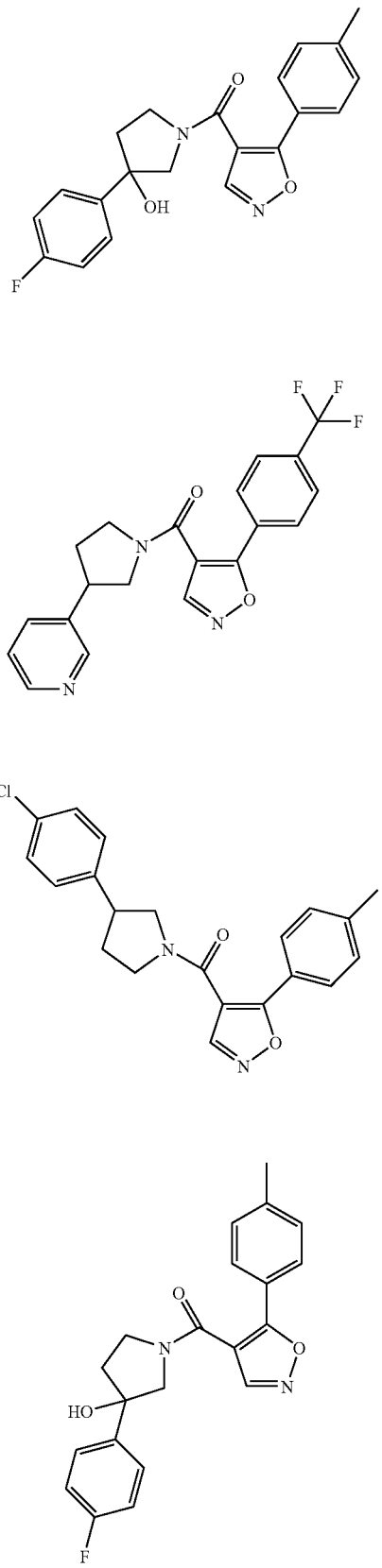
TABLE A-continued
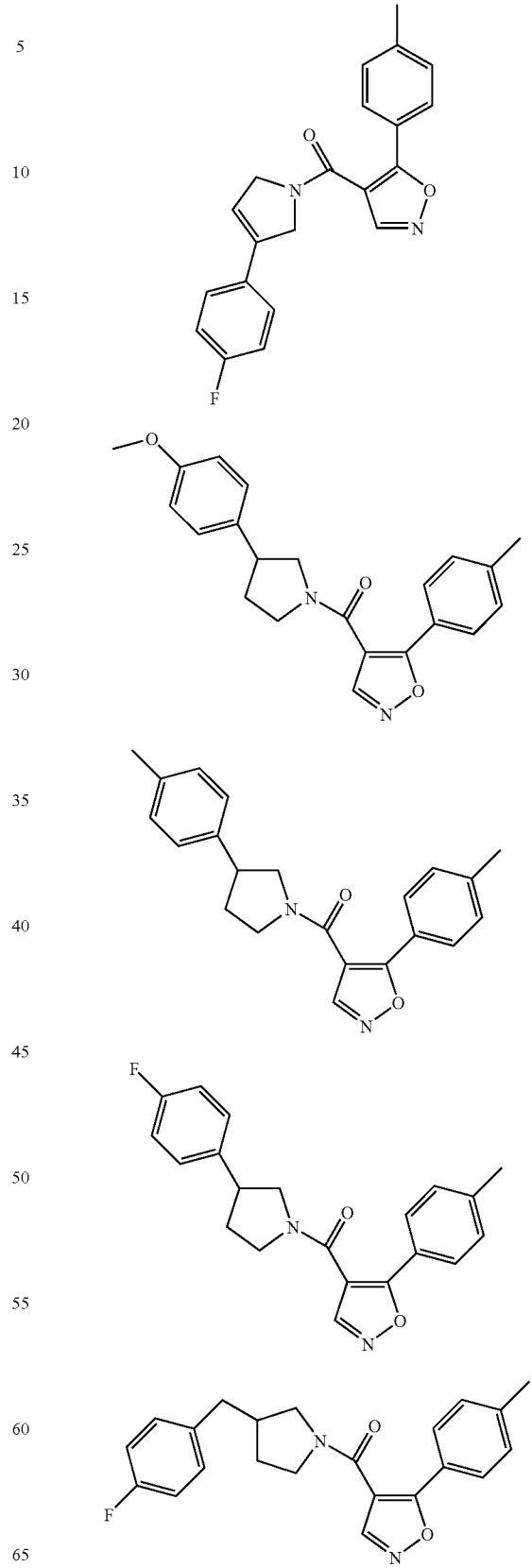

TABLE A-continued
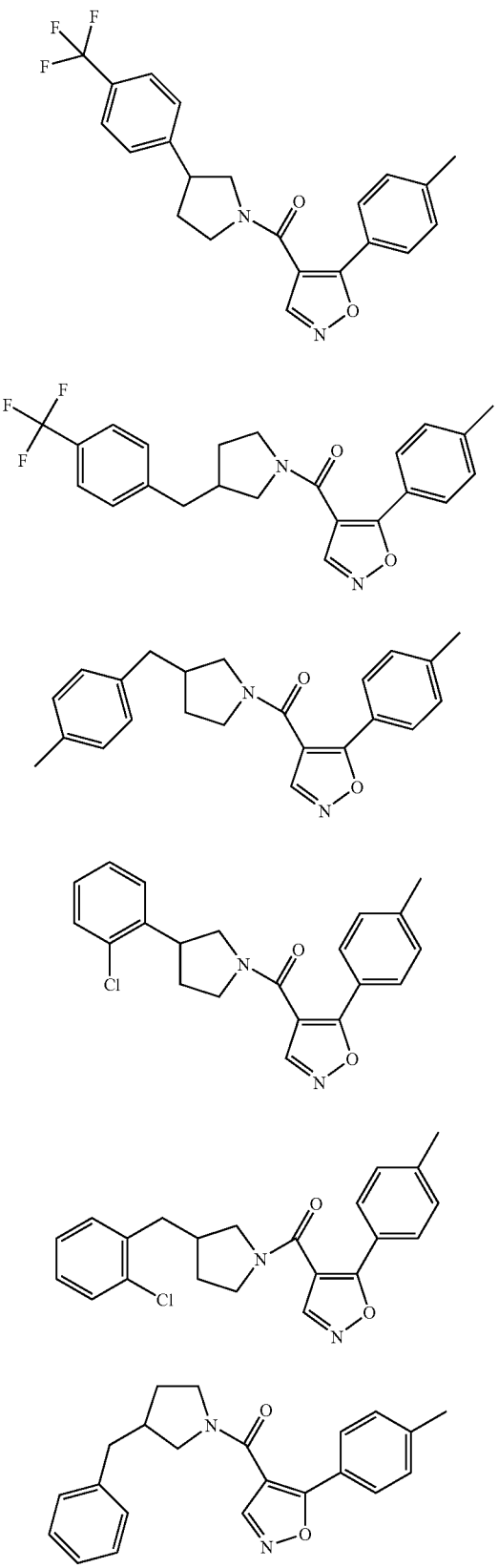
TABLE A-continued
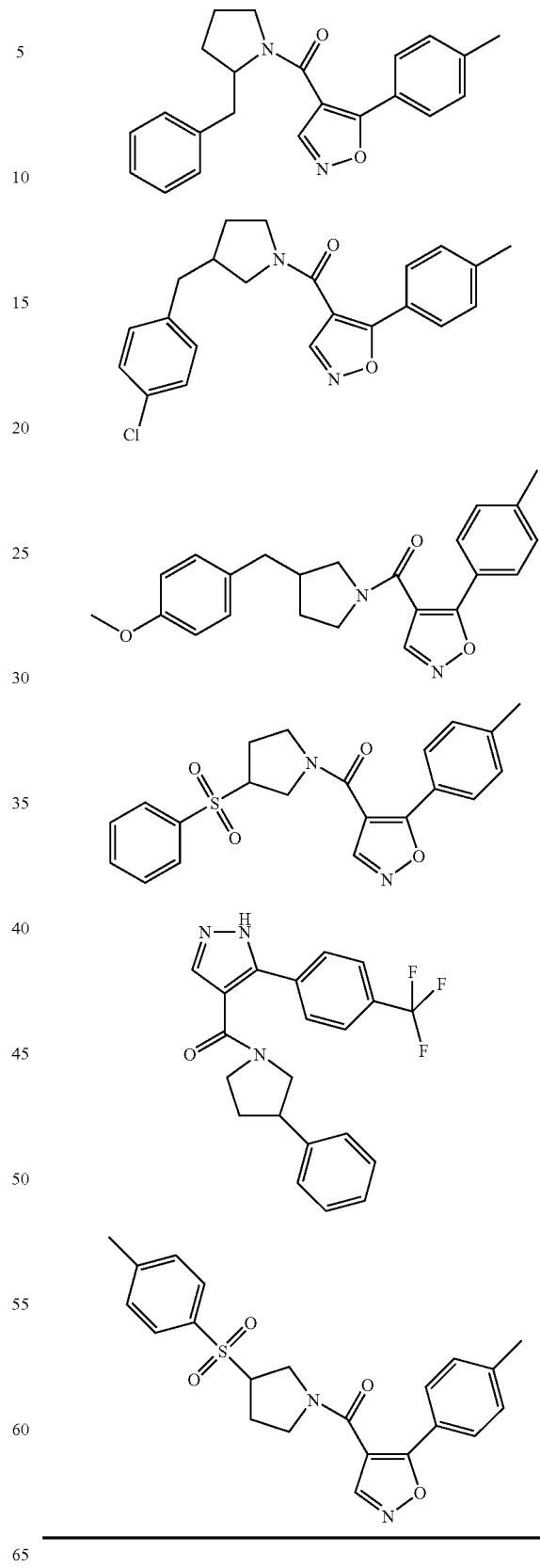
Further specific examples of compounds of the invention are provided in Table B below.

TABLE B
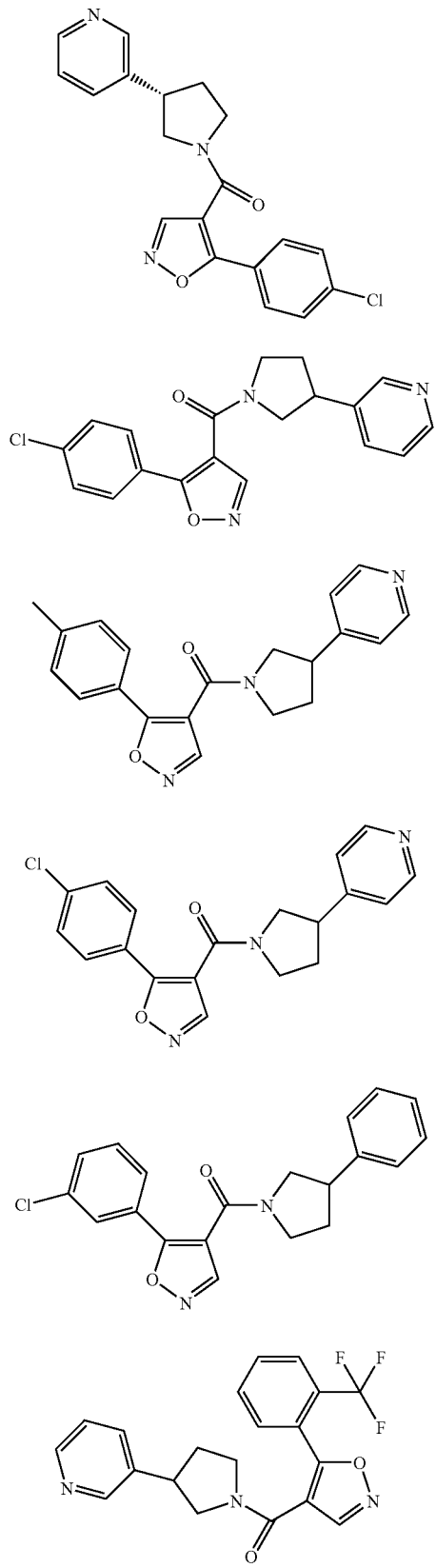
TABLE B-continued
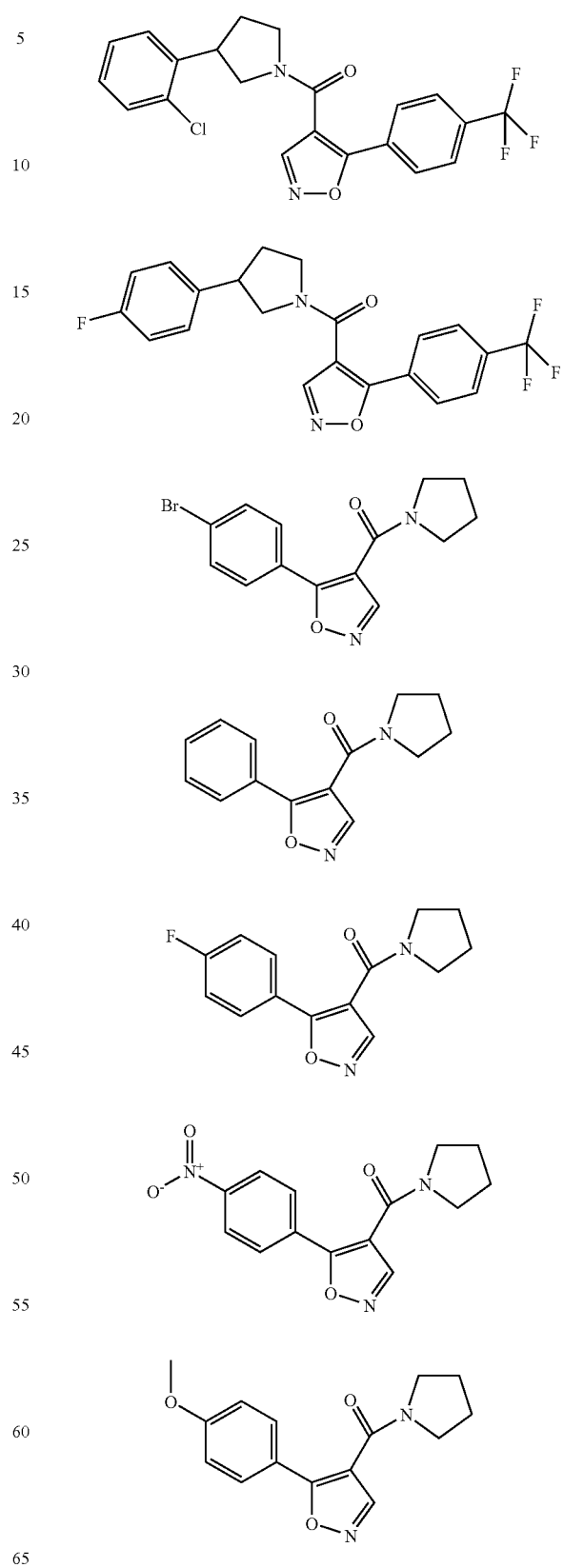

TABLE B-continued
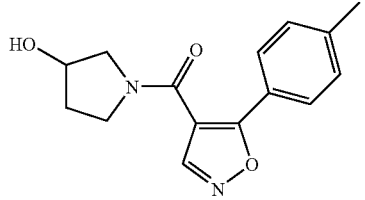
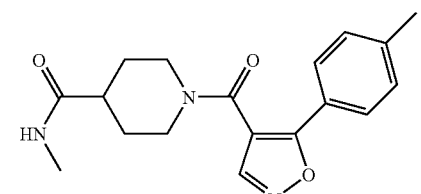
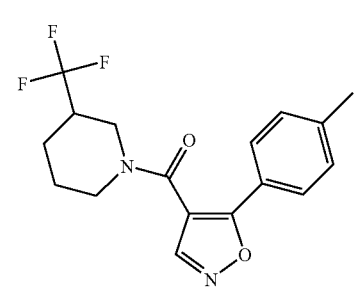
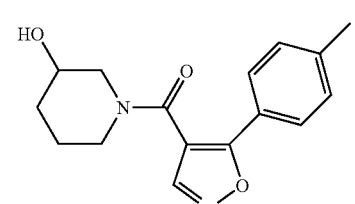
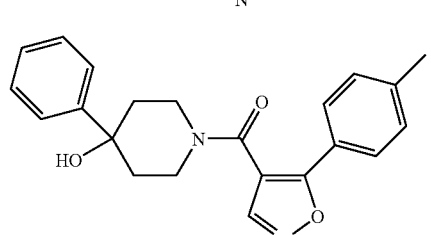
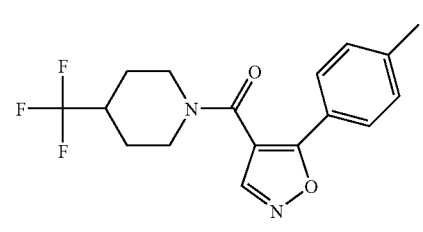
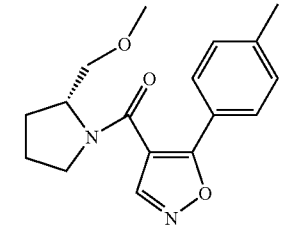
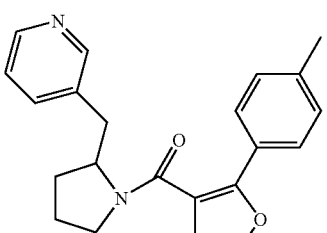
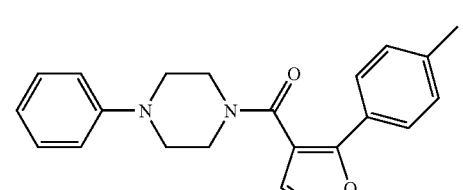
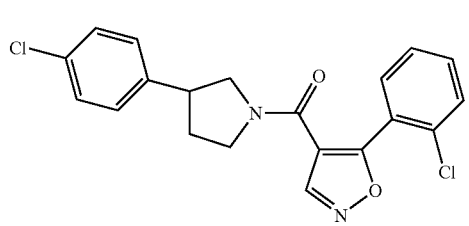
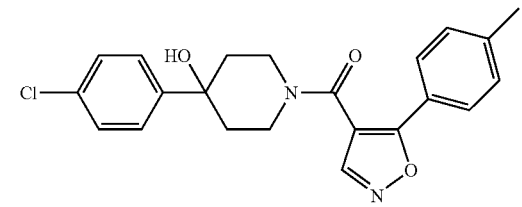
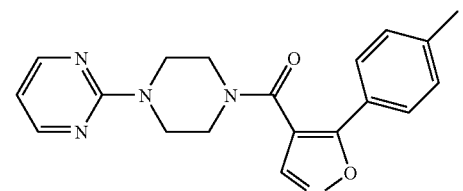
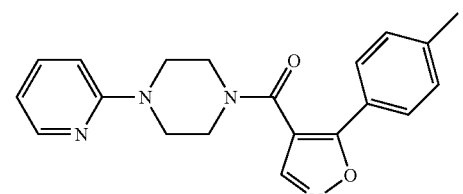
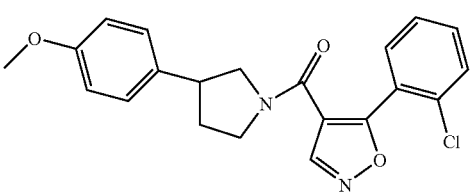

TABLE B-continued
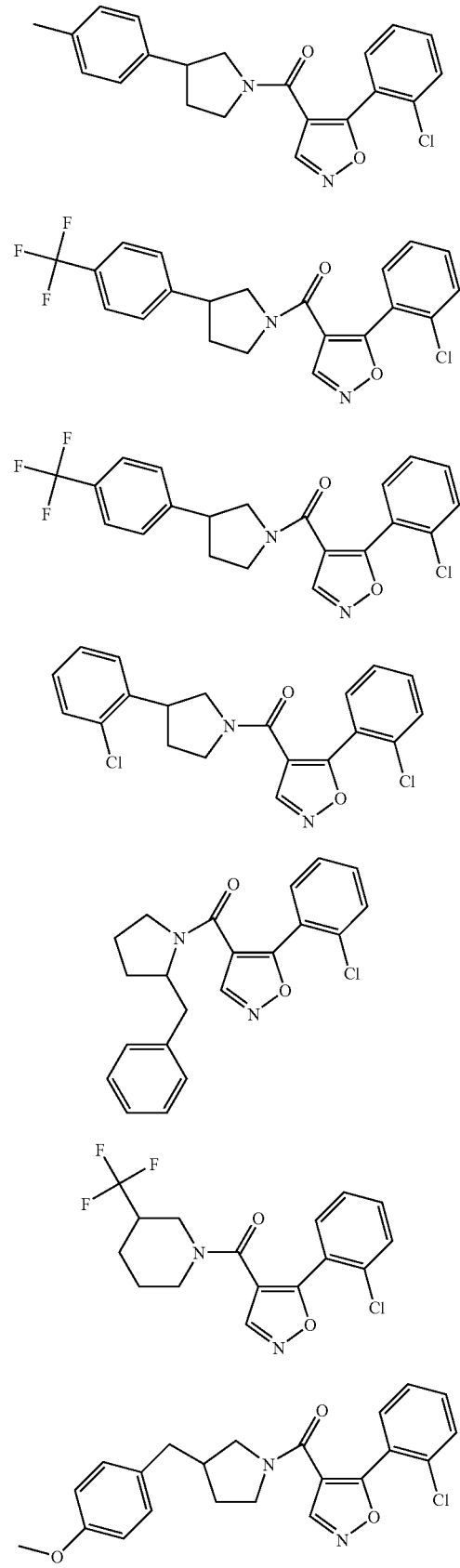
TABLE B-continued
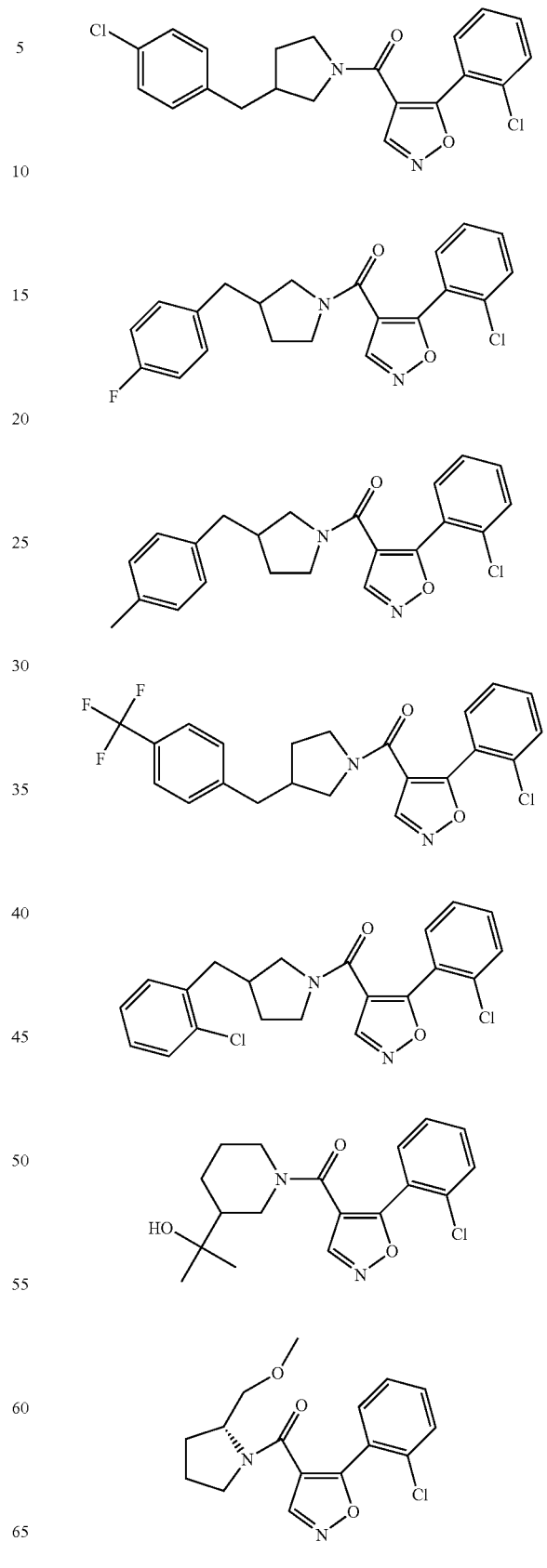

TABLE B-continued
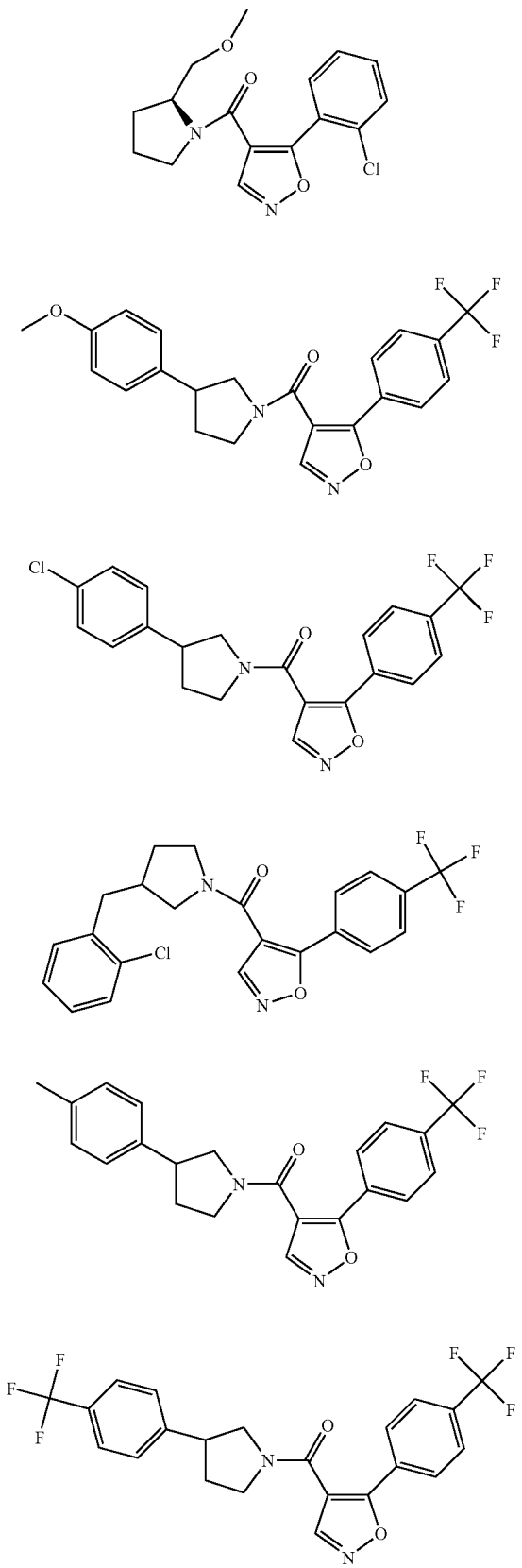
TABLE B-continued
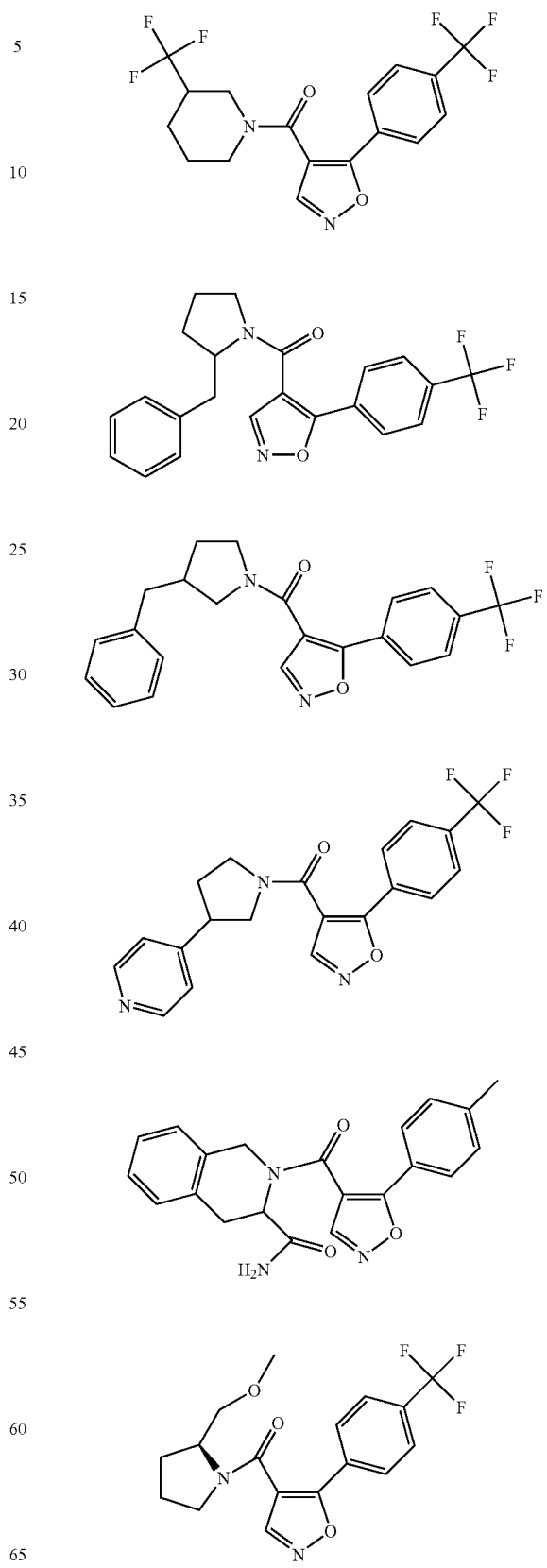

TABLE B-continued
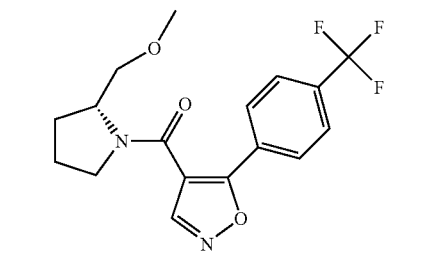
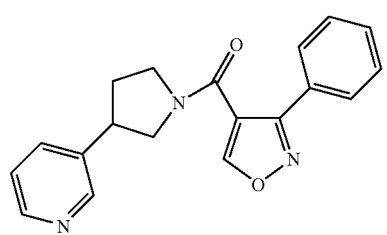
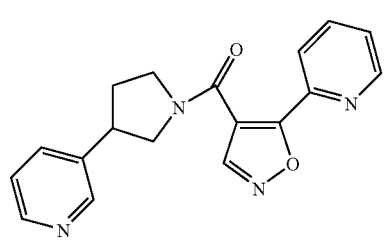
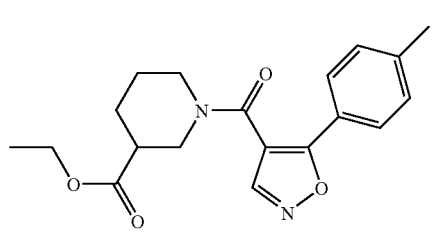
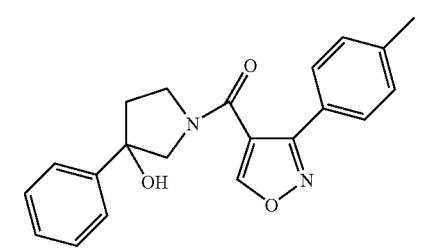
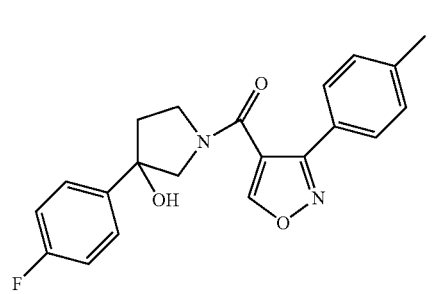
TABLE B-continued
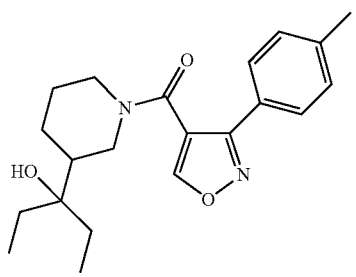
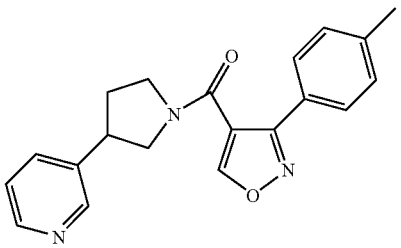
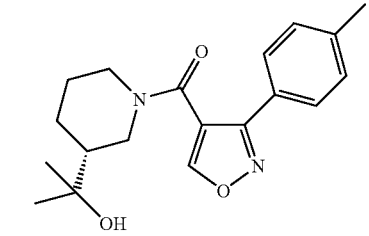
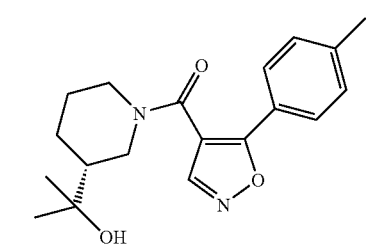
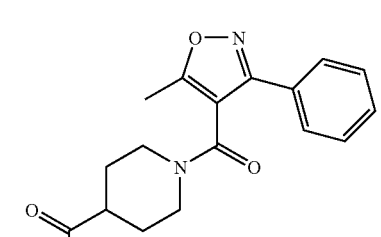
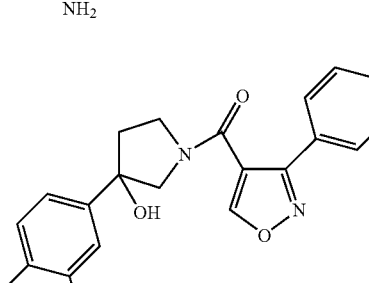

TABLE B-continued
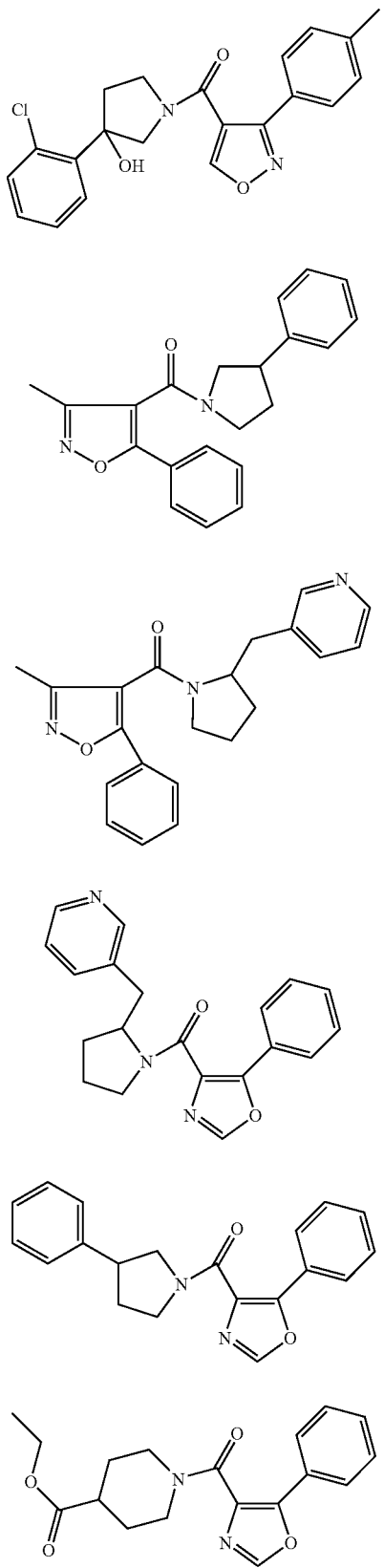
TABLE B-continued
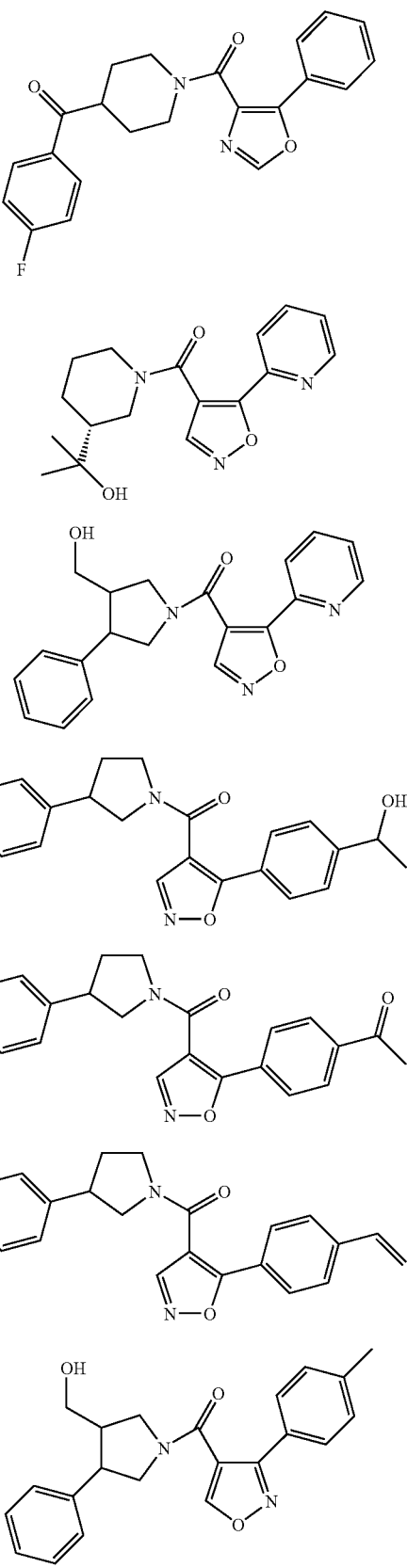

TABLE B-continued
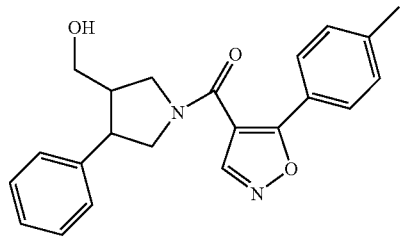
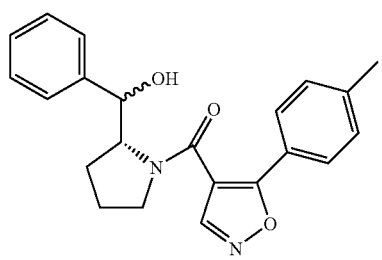
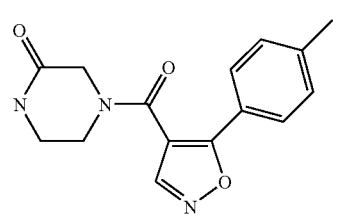
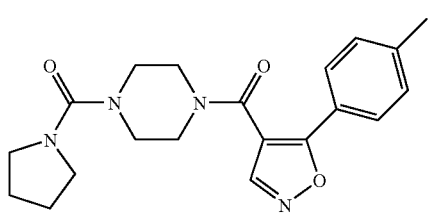
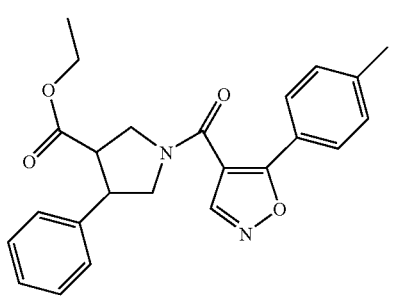
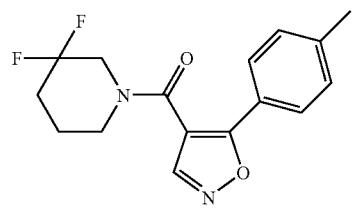
TABLE B-continued
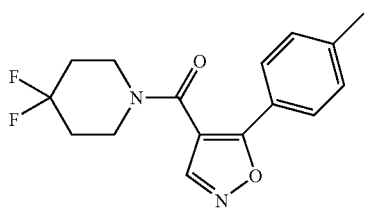
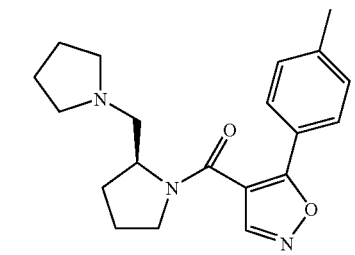
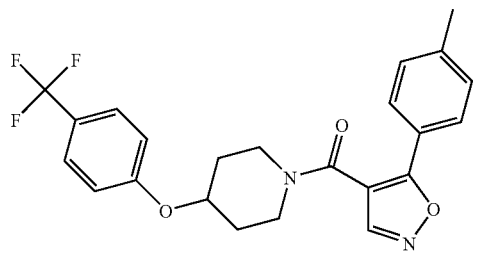
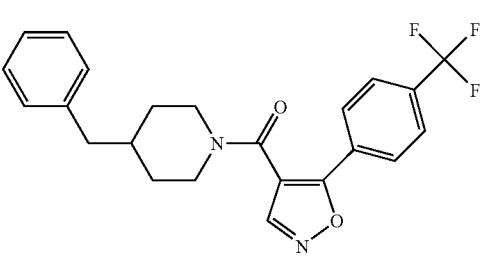
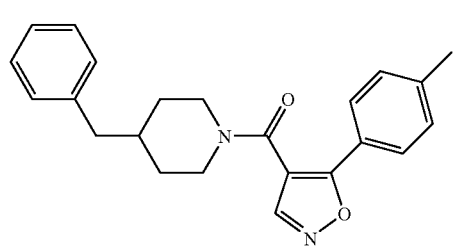
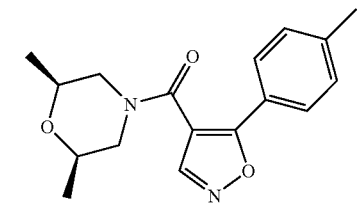

TABLE B-continued
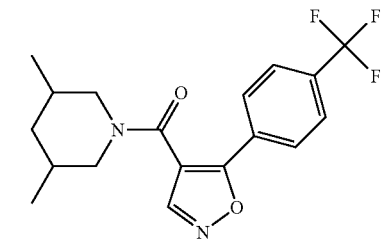
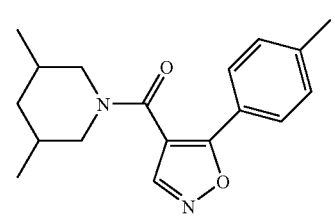
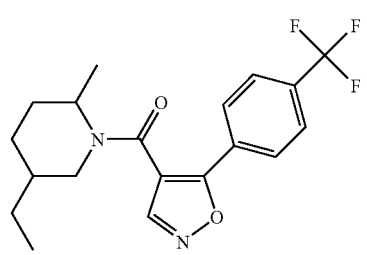
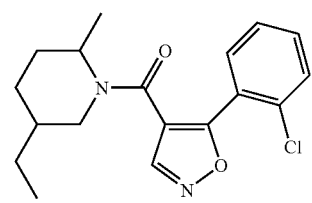
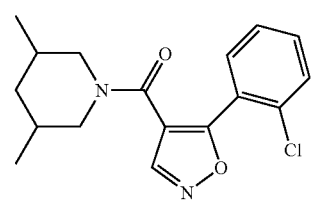
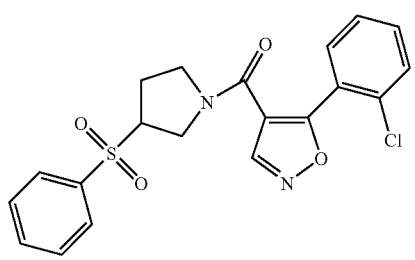
TABLE B-continued
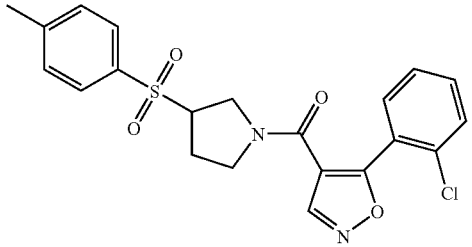
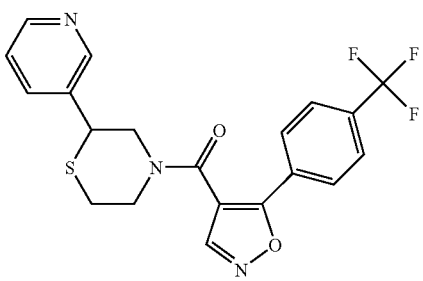
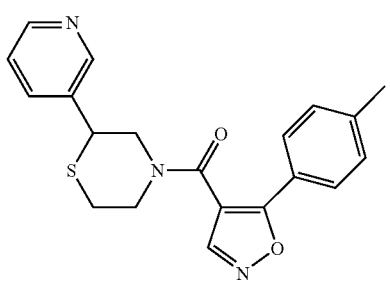
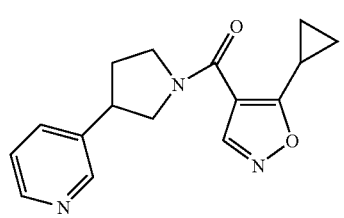
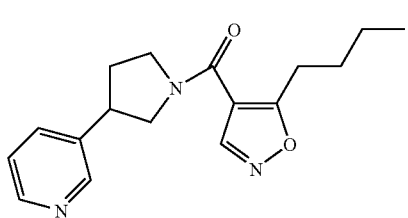
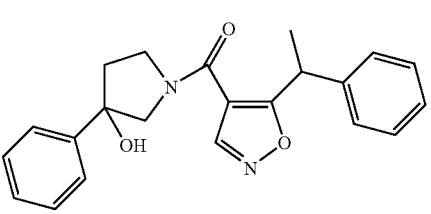

TABLE B-continued
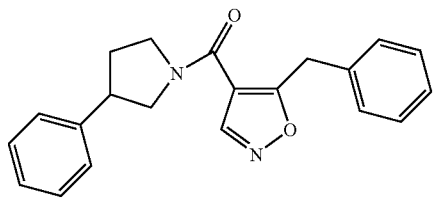
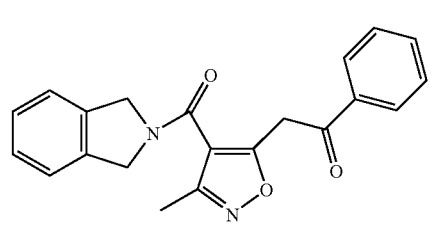
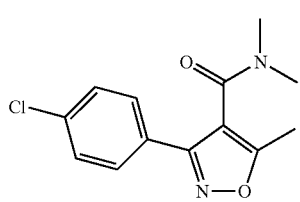
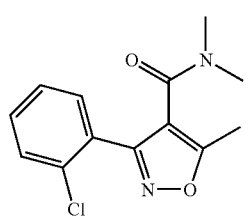
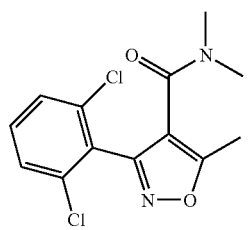
TABLE B-continued
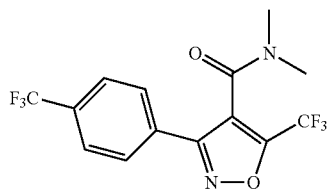
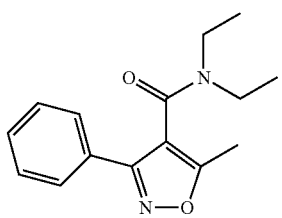
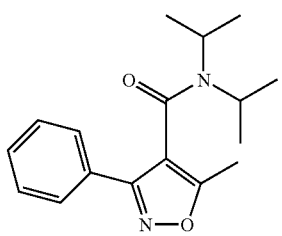
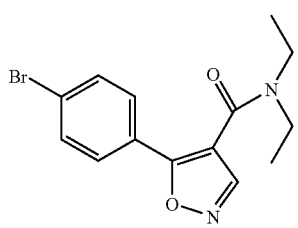
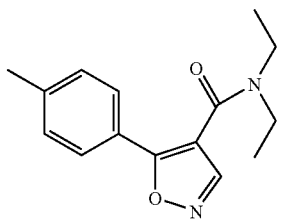
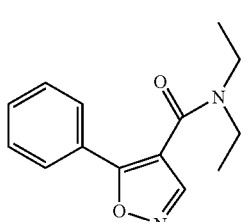
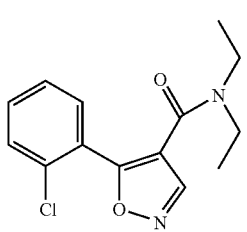

TABLE B-continued
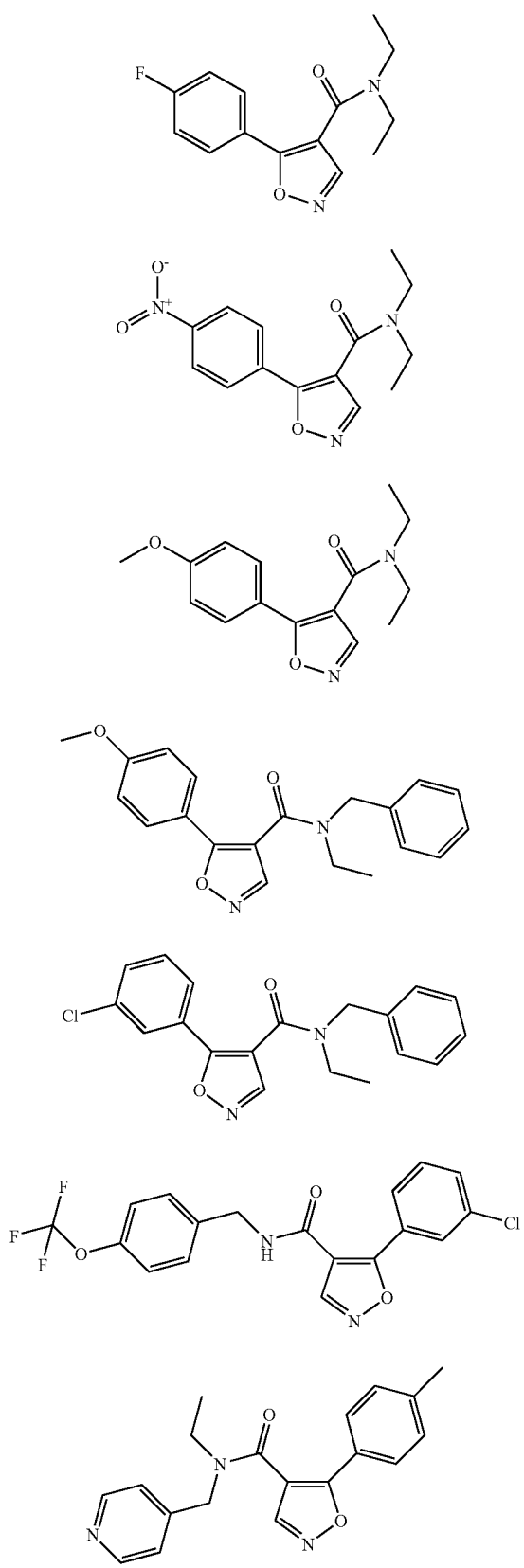
TABLE B-continued
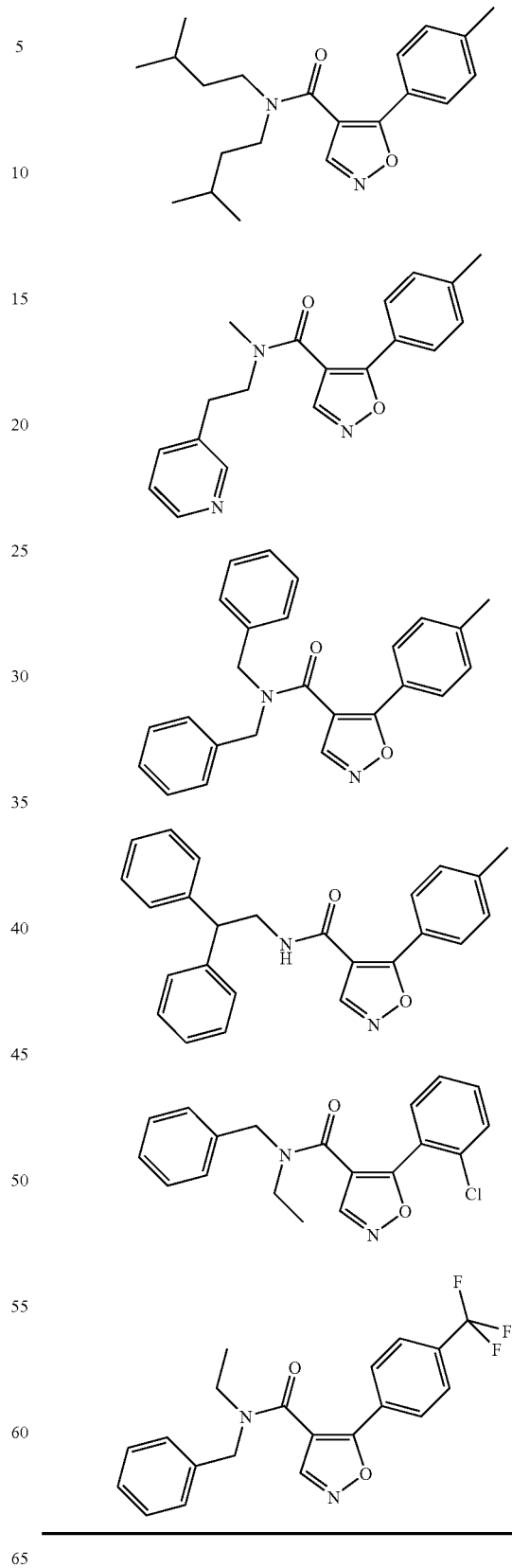
Additional specific examples of compounds of the invention are provided in Table C below.

TABLE C
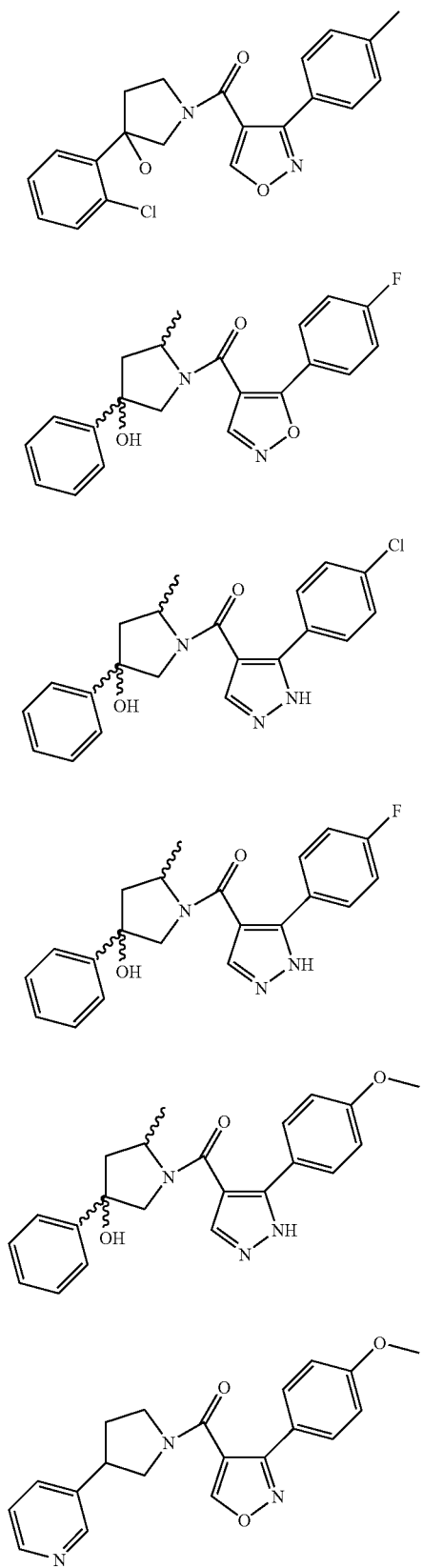
TABLE C-continued
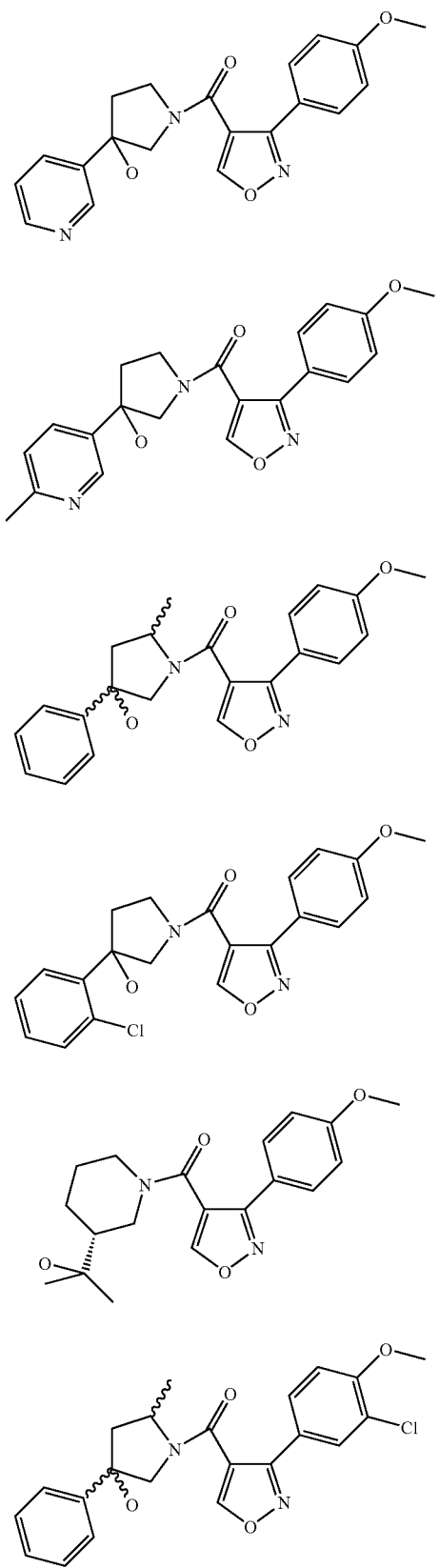

TABLE C-continued
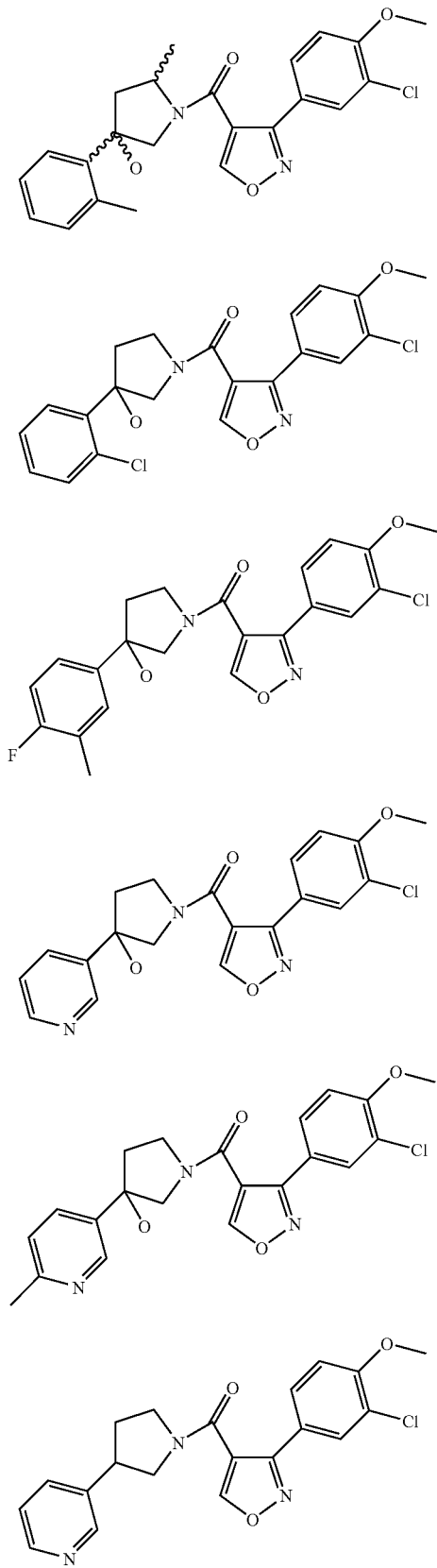
TABLE C-continued
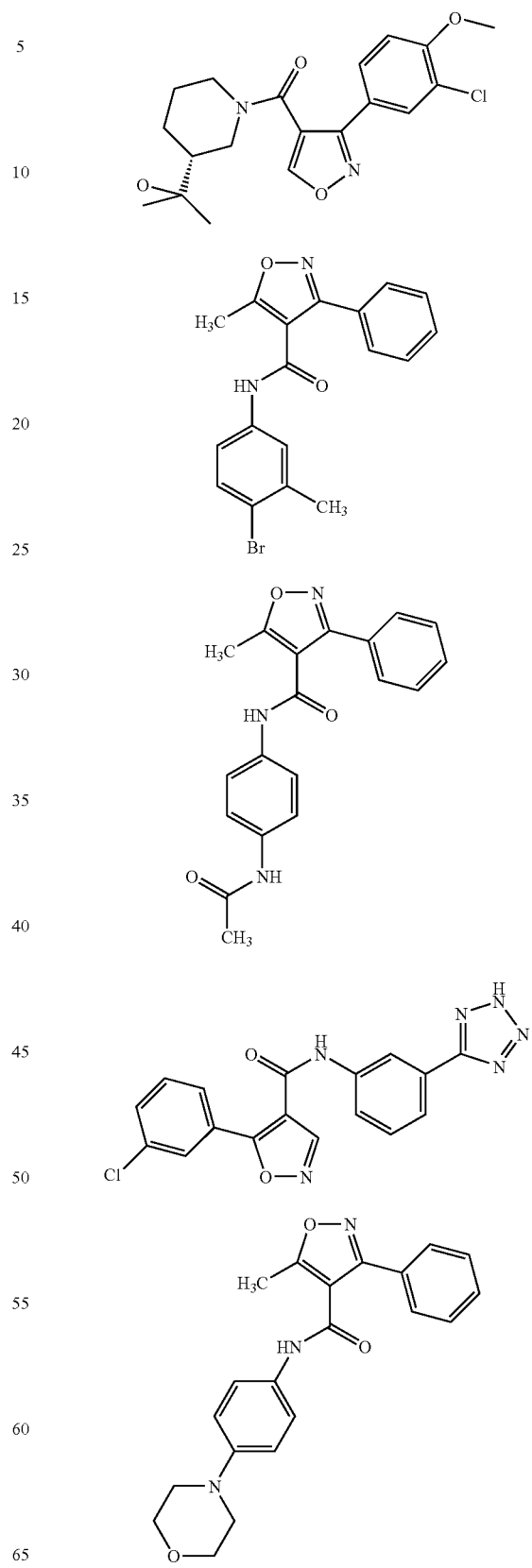

TABLE C-continued
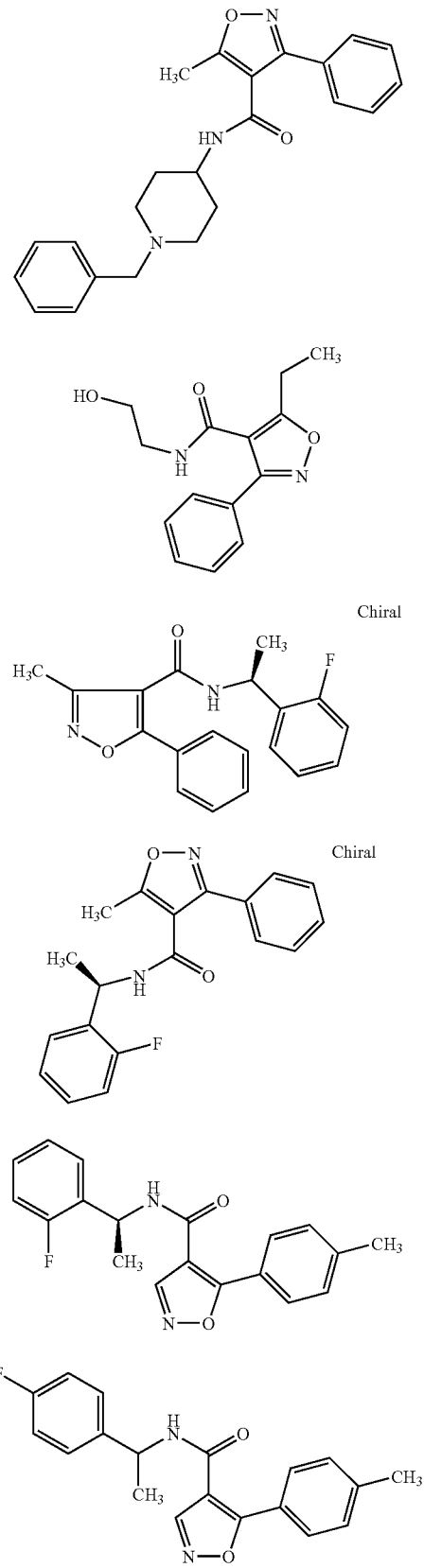
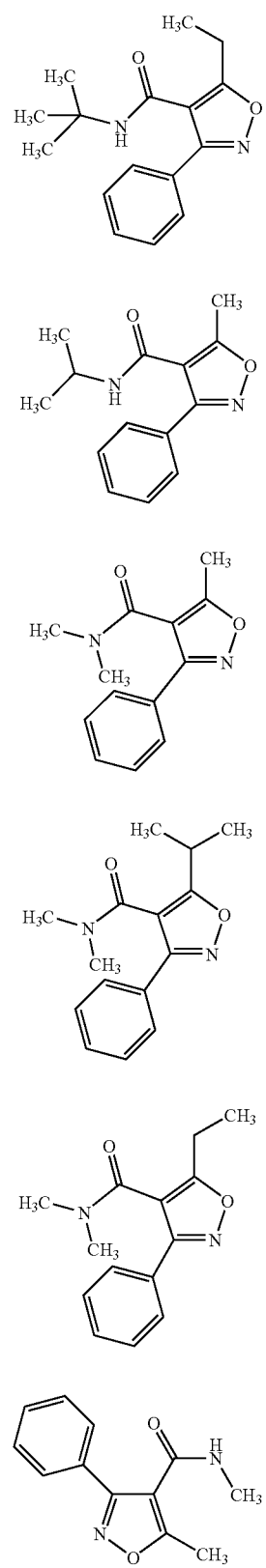

TABLE C-continued
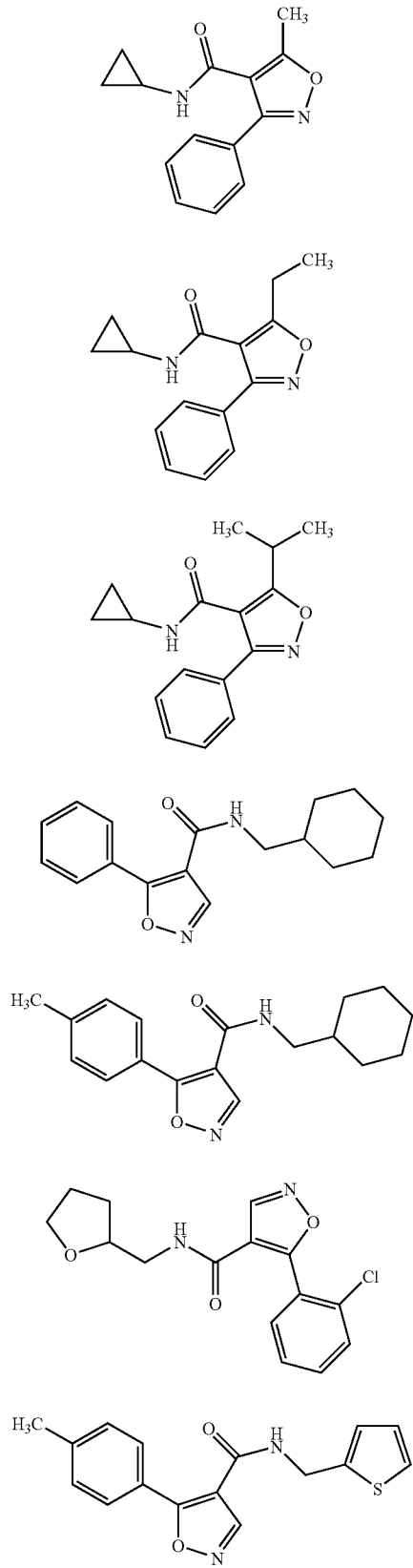
TABLE C-continued
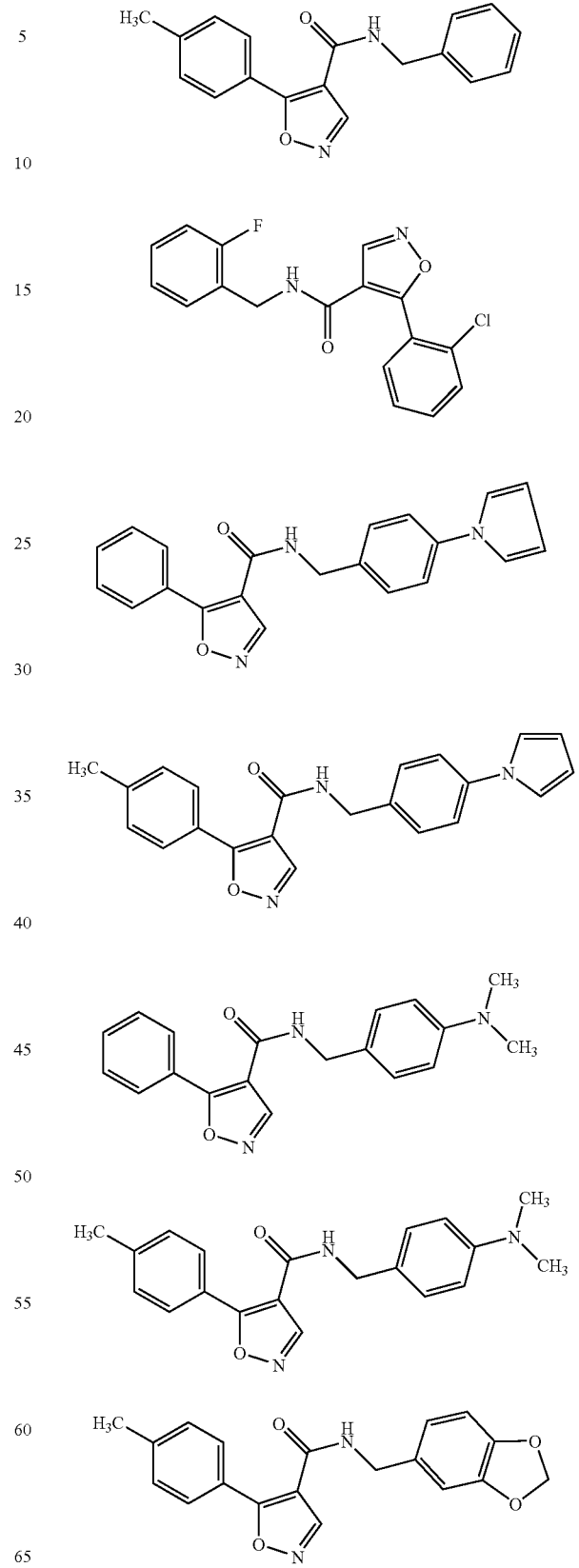

TABLE C-continued
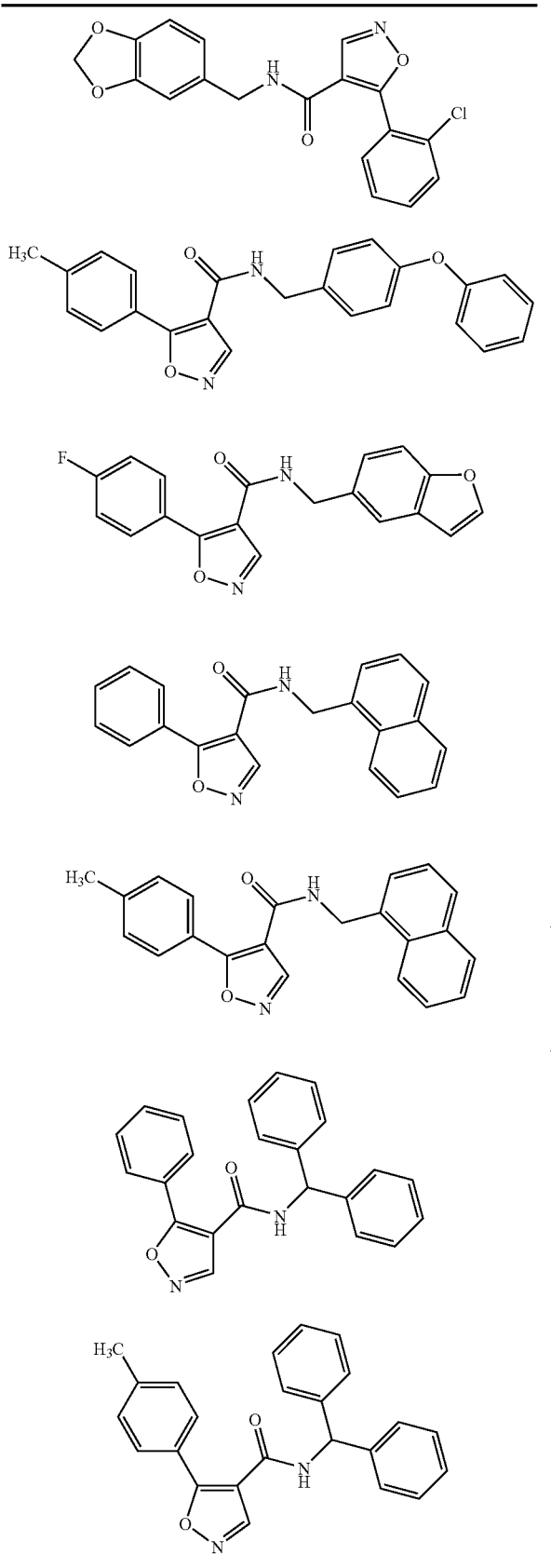
TABLE C-continued
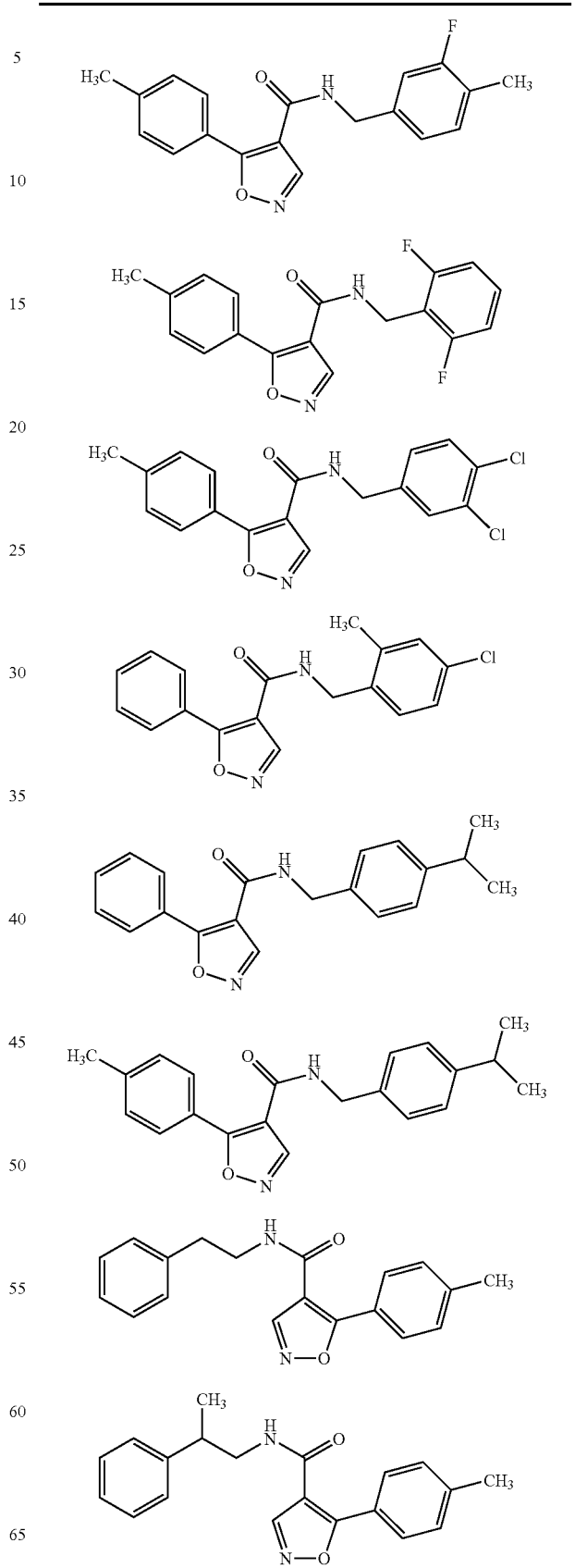

TABLE C-continued

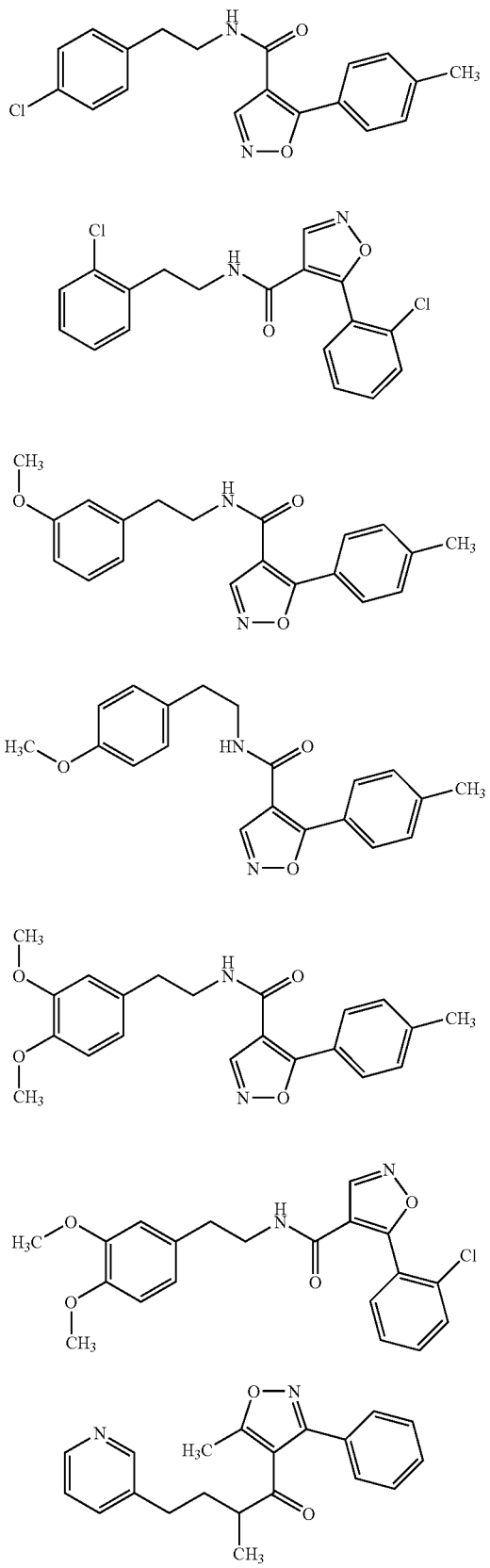

TABLE C-continued

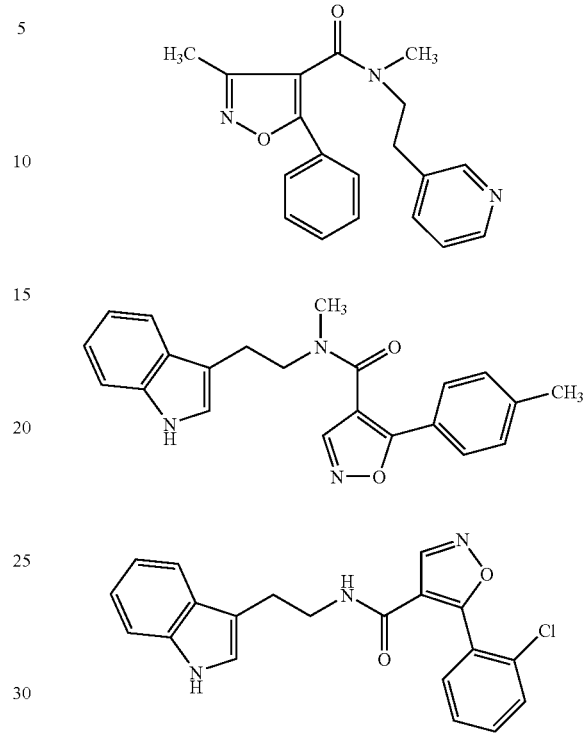

The invention provides a pharmaceutical composition comprising a therapeutically effective amount of a compound in Table A or a stereoisomer, tautomer, solvate, or pharmaceutically acceptable salt thereof, and a pharmaceutically acceptable carrier.

The invention provides a method of inhibiting 11-β-hydroxysteroid dehydrogenase type 1 enzyme in a patient in need thereof comprising administering to the patient a therapeutically effective amount of a compound in Table A or a stereoisomer, tautomer, solvate, or pharmaceutically acceptable salt thereof.

The invention provides a method of treating a disease or condition selected from the group consisting of diabetes, obesity, dyslipidemia, hyperinsulinemia, glaucoma, osteoporosis, cognitive disorders, atherosclerosis, immune disorders, hypertension and wound healing in a patient in need thereof comprising administering to the patient a therapeutically effective amount of the compound in Table A or a stereoisomer, tautomer, solvate, or pharmaceutically acceptable salt thereof. In particular, the invention provides a method where the disease or condition is diabetes, obesity, hyperlipidemia, hypercholesterolemia, hypertriglyceridemia, low level of high-density lipoprotein, hyperinsulinemia, or atherosclerosis.

All publications mentioned herein are hereby incorporated by reference. By the expression "comprising" means "including but not limited to." Thus, other non-mentioned substances, additives or carriers may be present.

The invention will now be described in reference to the following examples. These examples are not to be regarded as limiting the scope of the present invention, but shall only serve in an illustrative manner.

EXAMPLES

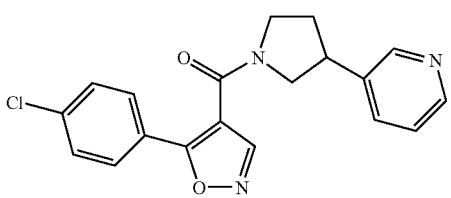

Example 1

(5-(4-Chlorophenyl)isoxazol-4-yl)(3-(pyridin-3-yl)pyrrolidin-1-yl)methanone

To a 150 mL round-bottomed flask equipped with magnetic stirring was added 3-(pyrrolidin-3-yl)pyridine (1.0 g, 6.7 mmol, source: ASDI Inc.) in 25 mL of N-methylpyrrolidinone (NMP). To this solution was added 5-(4-chlorophenyl)isoxazole-4-carboxylic acid (1.6 g, 7.1 mmol, source: CiVentiChem), 1-hydroxybenzotriazole (1.0 g, 7.4 mmol), and 1-ethyl-3-(3-dimethylaminopropyl) carbodiimide hydrochloride (1.6 g, 8.1 mmol), and the mixture was stirred at ambient temp. After ca. 4 days, water was added (ca. 150 mL) and the aqueous layer was extracted with EtOAc (3×75 mL). The organic extracts were combined, washed with water, sat'd NaHCO$_3$, and brine. The organic layers were combined and dried over MgSO$_4$, filtered and concentrated in vacuo. The crude material was absorbed onto silica gel and purified on a 120 g Isco Redi-sep® silica gel column using CH$_2$Cl$_2$ with 3% (2M NH$_3$ in CH$_3$OH) as the eluant to give the desired product. Mass Spec. m/z+ion=354.1, m/z negative ion=352.1.

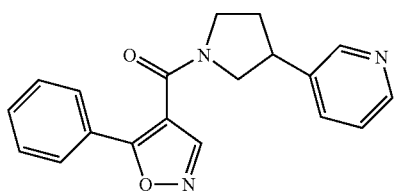

Example 2

(5-Phenylisoxazol-4-yl)(3-(pyridin-3-yl)pyrrolidin-1-yl)methanone

To a 15 mL round-bottomed flask equipped with magnetic stirring was added 3-(pyrrolidin-3-yl)pyridine (250 mg, 1700 µmol, source: ASDI Inc.) and 4 mL of N-methylpyrrolidinone (NMP). 5-Phenylisoxazole-4-carboxylic acid (300 mg, 1600 µmol, source: CiVentiChem) was added followed by 1-hydroxybenzotriazole (250 mg, 1800 µmol) and 1-ethyl-3-(3-dimethylaminopropyl)carbodiimide hydrochloride (380 mg, 2000 µmol). Added 2 mL more NMP, and the reaction mixture was stirred at ambient temp. After 3 days, added 30 mL of water and extracted with EtOAc (3×15 mL). The organic layers were combined, washed with sat'd NaHCO$_3$ and brine. The organic layers were then dried over MgSO$_4$, filtered and concentrated in vacuo. The sample was absorbed onto silica gel and purified on a 40 g Isco Redi-sep® silica gel column that had been pre-equilibrated with CH$_2$Cl$_2$+2% MeOH. The product was eluted sample with CH$_2$Cl$_2$+2% (2M NH$_3$ in MeOH). A viscous yellow oil was isolated as desired product (mass=260 mg). Mass Spec. m/z+ion=320.1.

The next four compounds were prepared in a manner similar to that described for the preparation of (5-phenylisoxazol-4-yl)(3-(pyridin-3-yl)pyrrolidin-1-yl)methanone.

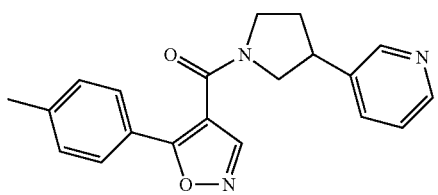

Example 3

(3-(Pyridin-3-yl)pyrrolidin-1-yl)(5-p-tolylisoxazol-4-yl)methanone

Mass=260 mg. Mass Spec. m/z+ ion=334.1.

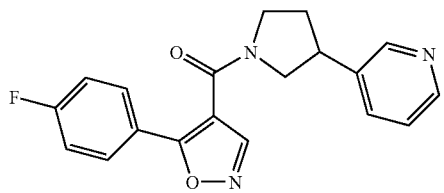

Example 4

(5-(4-Fluorophenyl)isoxazol-4-yl)(3-(pyridin-3-yl)pyrrolidin-1-yl)methanone

Mass=265 mg. Mass Spec. m/z+ ion=338.1.

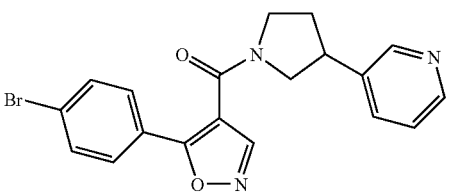

Example 5

(5-(4-Bromophenyl)isoxazol-4-yl)(3-(pyridin-3-yl)pyrrolidin-1-yl)methanone

Mass=100 mg. Mass Spec. m/z+ ion=400.0.

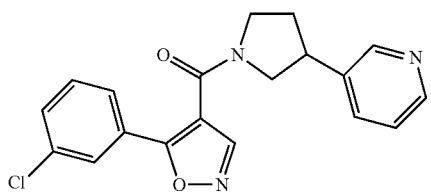

Example 6

(5-(3-Chlorophenyl)isoxazol-4-yl)(3-(pyridin-3-yl)pyrrolidin-1-yl)methanone

Mass=80 mg. Mass Spec. m/z+ ion=354.1.

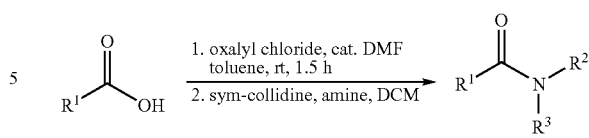

General Procedure for compounds made in Table 1: To a solution of the carboxylic acid (0.5 mmol) in dry toluene (1.5 ml) at 0° C. was added oxalyl chloride (0.65 mmol) and DMF (2011). The reaction mixture was stirred at ambient temp. for 1.5 h, concentrated, and then dissolved in $CH_2Cl_2$. To this was added sym-collidine (1.5 mmol) and the amine were then added. The reaction mixture was stirred at ambient temp. for 18 h, and then diluted with $CH_2Cl_2$ and water. The aqueous layer was extracted with $CH_2Cl_2$ and the combined organic extracts were dried over $Na_2SO_4$, filtered, and concentrated. The crude product was purified by preparative HPLC to give the corresponding amide.

TABLE 1

| Structure | MW | MS | Name |
|---|---|---|---|
| 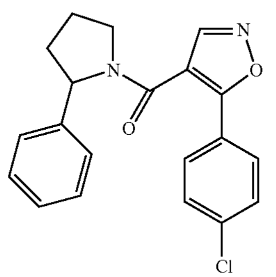 | 352.8 | 353.0 | (5-(4-chlorophenyl)isoxazol-4-yl)(2-phenylpyrrolidin-1-yl)methanone |
|  | 353.8 | 354.1 | (5-(4-chlorophenyl)isoxazol-4-yl)(3-(pyridin-2-yl)pyrrolidin-1-yl)methanone |
|  | 353.8 | 354.1 | (5-(4-chlorophenyl)isoxazol-4-yl)(2-(pyridin-2-yl)pyrrolidin-1-yl)methanone |
| 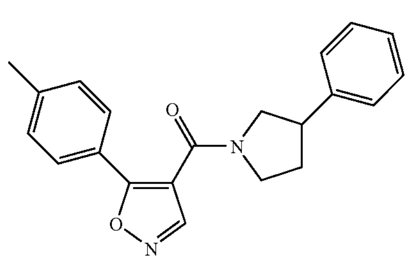 | 332.4 | 333.1 | (3-phenylpyrrolidin-1-yl)(5-p-tolylisoxazol-4-yl)methanone |

TABLE 1-continued
| Structure | MW | MS | Name |
|---|---|---|---|
| 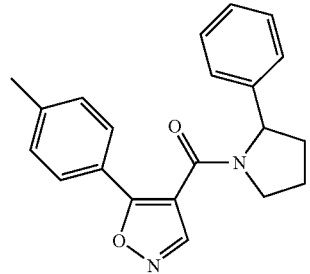 | 332.4 | 333.1 | (2-phenylpyrrolidin-1-yl)(5-p-tolylisoxazol-4-yl)methanone |
| 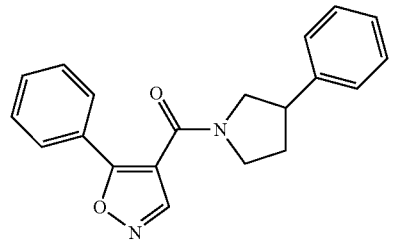 | 318.4 | 319.1 | (5-phenylisoxazol-4-yl)(3-phenylpyrrolidin-1-yl)methanone |
| 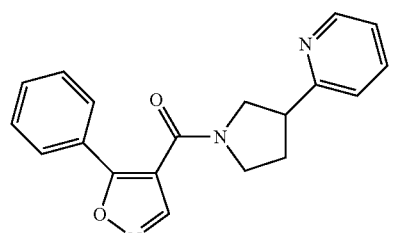 | 319.4 | 320.1 | (5-phenylisoxazol-4-yl)(3-(pyridin-2-yl)pyrrolidin-1-yl)methanone |
| 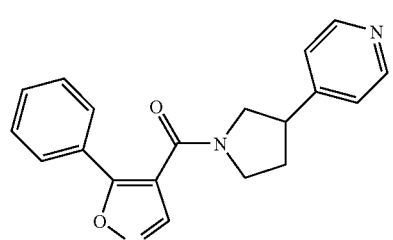 | 319.4 | 320.1 | (5-phenylisoxazol-4-yl)(3-(pyridin-4-yl)pyrrolidin-1-yl)methanone |
| 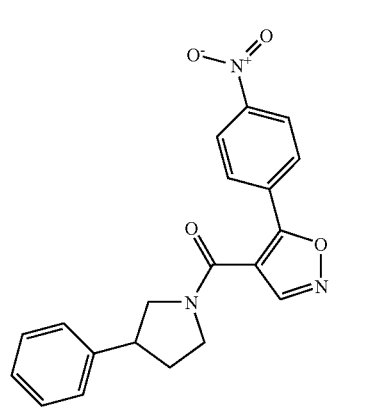 | 363.4 | 364.1 | (5-(4-nitrophenyl)isoxazol-4-yl)(3-phenylpyrrolidin-1-yl)methanone |

TABLE 1-continued

| Structure | MW | MS | Name |
|---|---|---|---|
| 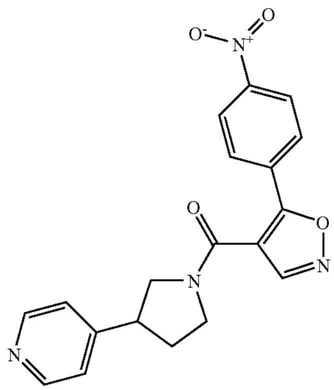 | 364.4 | 365.3 | (5-(4-nitrophenyl)isoxazol-4-yl)(3-(pyridin-4-yl)pyrrolidin-1-yl)methanone |
| 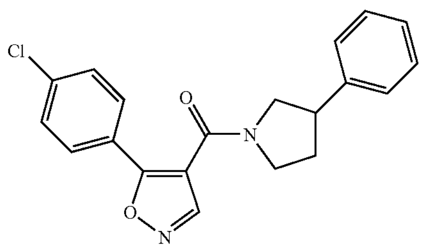 | 352.8 | 353.1 | (5-(4-chlorophenyl)isoxazol-4-yl)(3-phenylpyrrolidin-1-yl)methanone |
| 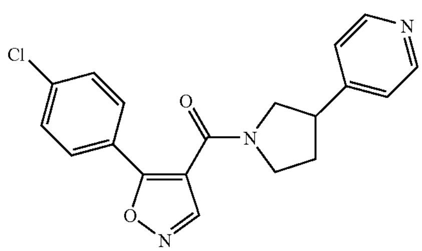 | 353.8 | 354.3 | (5-(4-chlorophenyl)isoxazol-4-yl)(3-(pyridin-4-yl)pyrrolidin-1-yl)methanone |
| | 333.4 | 334.3 | (3-(pyridin-2-yl)pyrrolidin-1-yl)(5-p-tolylisoxazol-4-yl)methanone |
| | 333.4 | 334.3 | (3-(pyridin-4-yl)pyrrolidin-1-yl)(5-p-tolylisoxazol-4-yl)methanone |

TABLE 1-continued

| Structure | MW | MS | Name |
|---|---|---|---|
| 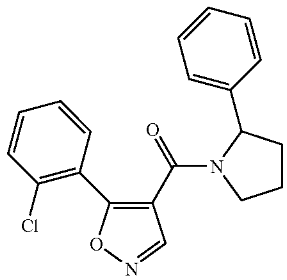 | 352.8 | 353.1 | (5-(2-chlorophenyl)isoxazol-4-yl)(2-phenylpyrrolidin-1-yl)methanone |
| 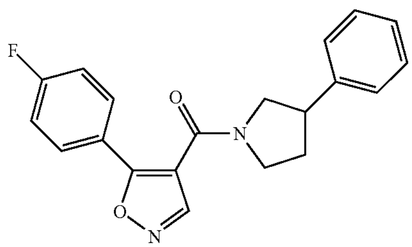 | 336.4 | 337.1 | (5-(4-fluorophenyl)isoxazol-4-yl)(3-phenylpyrrolidin-1-yl)methanone |
| | 337.4 | 338.1 | (5-(4-fluorophenyl)isoxazol-4-yl)(3-(pyridin-2-yl)pyrrolidin-1-yl)methanone |
| | 337.4 | 338.1 | (5-(4-fluorophenyl)isoxazol-4-yl)(3-(pyridin-4-yl)pyrrolidin-1-yl)methanone |
| | 397.3 | 397.0 | (5-(4-bromophenyl)isoxazol-4-yl)(3-phenylpyrrolidin-1-yl)methanone |
| | 397.3 | 397.0 | (5-(4-bromophenyl)isoxazol-4-yl)(2-phenylpyrrolidin-1-yl)methanone |

TABLE 1-continued

| Structure | MW | MS | Name |
|---|---|---|---|
| | 398.3 | 398.0 | (5-(4-bromophenyl)isoxazol-4-yl)(3-(pyridin-2-yl)pyrrolidin-1-yl)methanone |
| | 398.3 | 398.0 | (5-(4-bromophenyl)isoxazol-4-yl)(3-(pyridin-4-yl)pyrrolidin-1-yl)methanone |
| | 352.8 | 353.1 | (5-(3-chlorophenyl)isoxazol-4-yl)(3-phenylpyrrolidin-1-yl)methanone |
| | 352.8 | 353.1 | (5-(3-chlorophenyl)isoxazol-4-yl)(2-phenylpyrrolidin-1-yl)methanone |
| | 353.8 | 354.1 | (5-(3-chlorophenyl)isoxazol-4-yl)(3-(pyridin-2-yl)pyrrolidin-1-yl)methanone |
| | 353.8 | 354.1 | (5-(3-chlorophenyl)isoxazol-4-yl)(3-(pyridin-4-yl)pyrrolidin-1-yl)methanone |

TABLE 1-continued

| Structure | MW | MS | Name |
|---|---|---|---|
| | 353.8 | 354.3 | (5-(3-chlorophenyl)isoxazol-4-yl)(2-(pyridin-3-yl)pyrrolidin-1-yl)methanone |
| 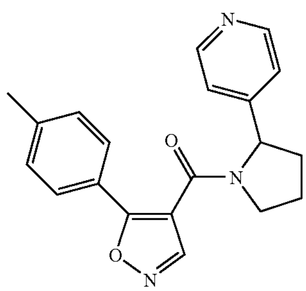 | 333.4 | 334.1 | (2-(pyridin-4-yl)pyrrolidin-1-yl)(5-p-tolylisoxazol-4-yl)methanone |
| 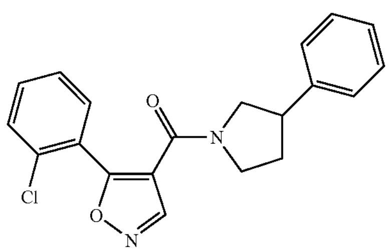 | 352.8 | 353.0 | (5-(2-chlorophenyl)isoxazol-4-yl)(3-phenylpyrrolidin-1-yl)methanone |
| | 353.8 | 354.0 | (5-(2-chlorophenyl)isoxazol-4-yl)(3-(pyridin-2-yl)pyrrolidin-1-yl)methanone |
| | 353.8 | 354.0 | (5-(2-chlorophenyl)isoxazol-4-yl)(3-(pyridin-4-yl)pyrrolidin-1-yl)methanone |

TABLE 1-continued

| Structure | MW | MS | Name |
|---|---|---|---|
| 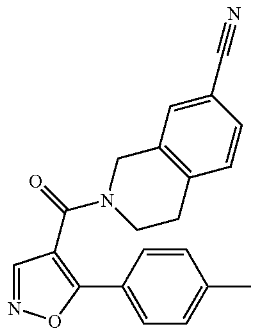 | 343.4 | 344.0 | 2-(5-p-tolylisoxazole-4-carbonyl)-1,2,3,4-tetrahydroisoquinoline-7-carbonitrile |
| 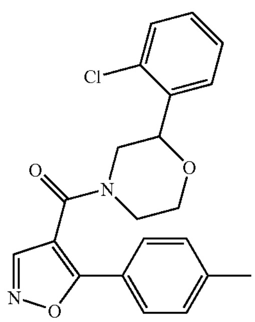 | 382.8 | 383.1 | (2-(2-chlorophenyl)morpholino)(5-p-tolylisoxazol-4-yl)methanone |
| 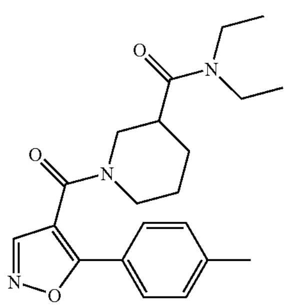 | 369.5 | 370.2 | N,N-diethyl-1-(5-p-tolylisoxazole-4-carbonyl)piperidine-3-carboxamide |

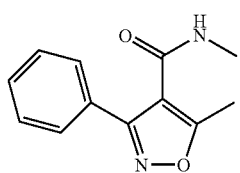

Example 7

N,5-Dimethyl-3-phenylisoxazole-4-carboxamide

N,5-Dimethyl-3-phenylisoxazole-4-carboxamide is commercially available as a white solid.

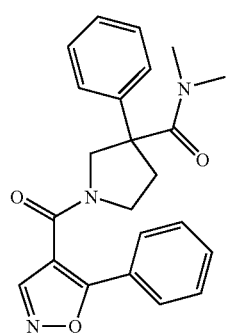

Example 8

N,N-Dimethyl-3-phenyl-1-[(5-phenylisoxazol-4-yl)carbonyl]pyrrolidine-3-carboxamide To a solution of 5-phenylisoxazol-4-carboxylic acid (15 mg, 0.08 mmol) in dichloromethane (2 mL) was added 1-ethyl-3-(3-dimethylaminopropyl)carbodiimide hydrochloride (EDC) (15 mg, 0.08 mol), triethylamine (33 μL, 0.24 mmol) and finally N,N-dimethyl-3-phenylpyrrolidine-3-carboxamide hydrochloride (15 mg, 0.06 mmol) and allowed to stir at ambient temperature overnight. The residue was purified using straight phaseHPLC (1:1 hexane/ethyl acetate) to afford the title compound (4 mg). HRMS (ESI, pos. ion) m/z calcd for $C_{23}H_{23}N_3O_3$: 389.1739, found 389.1744.

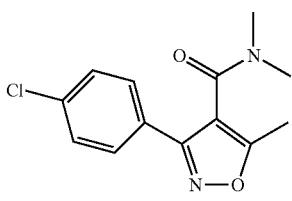

Example 9

3-(4-Chlorophenyl)-N,N,5-trimethylisoxazole-4-carboxamide

To 3-(4-chlorophenyl)-5-methylisoxazol-4-carboxylic acid (25 mg, 0.10 mmol) was added thionyl chloride (1 mL) and the neat solution allowed to stir 60° C. After 30 min, excess thionyl chloride was evaporated and dimethyl amine (40 μL, 0.08 mmol, 2 M in THF) was added and allowed to stir overnight at ambient temperature. The residue was purified using reversed phase HPLC to afford the title compound (5 mg). HRMS (ESI, pos. ion) m/z calcd for $C_{13}H_{13}ClN_2O_2$: 264.0666, found 264.0671.

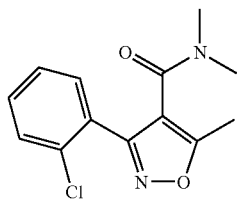

Example 10

3-(2-Chlorophenyl)-N,N,5-trimethylisoxazole-4-carboxamide

To 3-(2-chlorophenyl)-5-methylisoxazol-4-carboxylic acid (25 mg, 0.10 mmol) was added thionyl chloride (1 mL) and the neat solution allowed to stir 60° C. After 30 min, excess thionyl chloride was evaporated and dimethyl amine (40 μL, 0.08 mmol, 2M in tetrahydrofuran) was added and allowed to stir overnight at ambient temperature. The residue was purified using reversed phase HPLC to afford the title compound (5 mg). HRMS (ESI, pos. ion) m/z calcd for $C_{13}H_{13}ClN_2O_2$: 264.0666, found 264.0669.

Example 11

3-(2,6-Dichlorophenyl)-N,N,5-trimethylisoxazole-4-carboxamide

To 3-(2,6-dichlorophenyl)-5-methylisoxazol-4-carboxylic acid (25 mg, 0.10 mmol) was added thionyl chloride (1 mL) and the neat solution allowed to stir 60° C. After 30 min, excess thionyl chloride was evaporated and dimethyl amine (40 μL, 0.08 mmol, 2M in tetrahydrofuran) was added and allowed to stir overnight at ambient temperature. The residue was purified using reversed phase HPLC to afford the title compound (10 mg). HRMS (ESI, pos. ion) m/z calcd for $C_{13}H_{12}Cl_2N_2O_2$: 298.0276, found 298.0276.

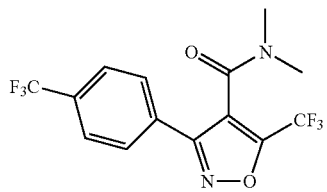

Example 12

N,N-Dimethyl-5-(trifluoromethyl)-3-[4-(trifluoromethyl)phenyl]isoxazole-4-carboxamide To 3-(4-trifluorophenyl)-5-trifluoromethylisoxazol-4-carboxylic acid (25 mg, 0.10 mmol) was added thionyl chloride (1 mL) and the neat solution allowed to stir 60° C. After 30 min, excess thionyl chloride was evaporated and dimethyl amine (40 μL, 0.08 mmol, 2M in tetrahydrofuran) was added and allowed to stir overnight at ambient temperature. The residue was purified using reversed phase HPLC to afford the title compound (10 mg). HRMS (ESI, pos. ion) m/z calcd for $C_{14}H_{10}F_6N_2O_2$: 352.0647, found 352.0653.

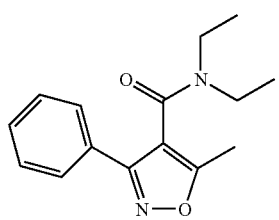

Example 13

N,N-Diethyl-5-methyl-3-phenylisoxazole-4-carboxamide

To 3-phenyl-5-methylisoxazol-4-carboxylic acid (25 mg, 0.10 mmol) was added thionyl chloride (1 mL) and the neat solution allowed to stir 60° C. After 30 min, excess thionyl chloride was evaporated and neat diethylamine was added and allowed to stir overnight at ambient temperature. The residue was purified using reversed phase HPLC to afford the title compound (20 mg). HRMS (ESI, pos. ion) m/z calcd for $C_{15}H_{18}N_2O_2$: 258.1368, found 258.1378.

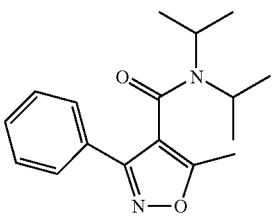

Example 14

N,N-Diisopropyl-5-methyl-3-phenylisoxazole-4-carboxamide

To 3-phenyl-5-methylisoxazol-4-carboxylic acid (25 mg, 0.10 mmol) was added thionyl chloride (1 mL) and the neat solution allowed to stir 60° C. After 30 min, excess thionyl chloride was evaporated and neat diisopropylamine was added and allowed to stir overnight at ambient temperature. The residue was purified using reversed phase HPLC to afford the title compound (15 mg). HRMS (ESI, pos. ion) m/z calcd for $C_{17}H_{22}N_2O_2$: 286.1681, found 286.1678.

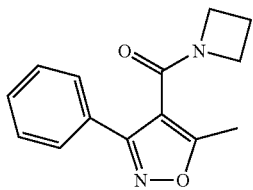

Example 15

4-(Azetidin-1-ylcarbonyl)-5-methyl-3-phenylisoxazole

To 3-phenyl-5-methylisoxazol-4-carboxylic acid (25 mg, 0.10 mmol) was added thionyl chloride (1 mL) and the neat solution allowed to stir 60° C. After 30 min, excess thionyl chloride was evaporated and neat trimethylene imine was added and allowed to stir overnight at ambient temperature. The residue was purified using reversed phase HPLC to afford the title compound (18 mg). HRMS (ESI, pos. ion) m/z calcd for $C_{14}H_{14}N_2O_2$: 242.1055, found 242.1063.

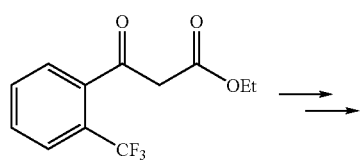

-continued

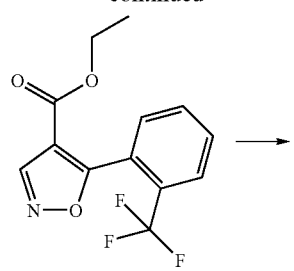

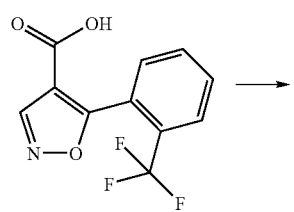

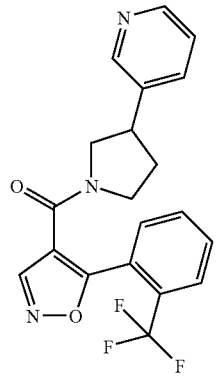

Example 16

3-[1-({5-[2-(Trifluoromethyl)phenyl]isoxazol-4-yl}carbonyl)pyrrolidin-3-yl]pyridine A mixture of methyl 2-trifluoromethylbenzoyl acetate (0.51 g, 2 mmol) and N,N-dimethylformamide dimethylacetal (275 µL, 2 mmol) was heated at 60° C. for 30 min. The resulting yellow oil was cooled and a mixture of methanol (2 mL), water (1 mL) and hydroxylamine hydrochloride (140 mg, 2 mmol) was added and warmed to 60° C. 1 h. The solution was concentrated to yield the intermediate ester. Hydrolysis was effected by dissolving the ester (122 mg, 0.45 mmol) in 2 mL conc hydrochloric acid/acetic acid (1:1) and warmed in the microwave oven 170° C. for 5 min. Concentration gave 5-[2-(trifluoromethyl)phenyl]isoxazole-4-carboxylic acid as an orange solid (80 mg). This acid (30 mg, 0.1 mmol) was dissolved in dimethylformamide (200 µL) followed by the addition of o-(benzotriazol-1-yl)-N,N,N',N'-tetramethyluronium tetrafluoroborate (TBTU) (46 mg, 0.14 mmol), pyridine (16 µL, 0.2 mmol), 3-pyrrolidine-3-ylpyridine (17 mg, 0.11 mmol) and stirred at ambient temperature for 2 h. Half the residue was purified on reversed phase HPLC to afford the title compound (5 mg). HRMS (ESI, pos. ion) m/z calcd for $C_{20}H_{16}F_3N_3O_2$: 387.1195, found 387.1190.

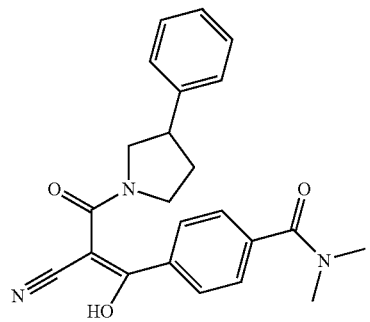

Example 17

4-[(1E)-2-Cyano-1-hydroxy-3-oxo-3-(3-phenylpyrrolidin-1-yl)prop-1-en-1-yl]-N,N-dimethylbenzamide A mixture of 3-[1-({5-[4-(iodophenyl]isoxazol-4-yl}carbonyl)3-phenylpyrrolidin-1-yl] (20 mg, 0.06 mmol), molybdenum hexacarbonyl (8 mg, 0.03 mmol), trans-di(μ-aceto)bis[o-(di-o-tolylphosphino)benzyl]dipalladium(II) (Herrmanns catalyst) (2 mg, 0.002 mmol), potassium carbonate (28 mg, 0.2 mmol) and dimethyl amine (2 M in tetrahydrofuran, 150 μL, 0.3 mmol) in diglyme (1 mL) was warmed in the microwave oven at 150° C. for 2 min. The residue was purified on reversed phase HPLC to yield the title compound (1 mg). HRMS (ESI, pos. ion) m/z calcd for $C_{23}H_{23}N_3O_3$: 389.1739, found 389.1730.

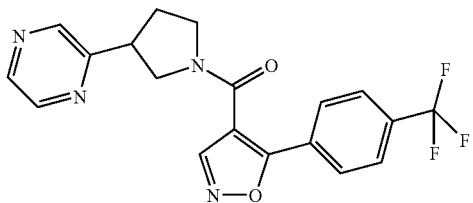

Example 18

2-[1-({5-[4-(Trifluoromethyl)phenyl]isoxazol-4-yl}carbonyl)pyrrolidin-3-yl]pyrazine 5-[4-(Trifluoromethyl)phenyl]isoxazole-4-carboxylic acid (30 mg, 0.12 mmol) was dissolved in acetonitrile (1.5 mL) followed by the addition of o-(benzotriazol-1-yl)-N,N,N',N'-tetramethyluronium tetrafluoroborate (TBTU) (52 mg, 0.16 mmol), pyridine (60 μL, 0.72 mmol) and 2-pyrrolidin-3-yl-pyrazine trihydrochloride (36 mg, 0.14 mmol), and stirred at 60° C. for 30 min. The residue was purified on reversed phase HPLC to yield the title compound (26 mg). HRMS (ESI, pos. ion) m/z calcd for $C_{19}H_{15}F_3N_4O_2$: 388.1147, found 388.1152.

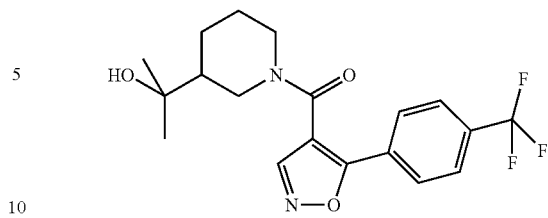

Example 19

2-[1-({5-[4-(Trifluoromethyl)phenyl]isoxazol-4-yl}carbonyl)piperidin-3-yl]propan-2-ol 5-[4-(Trifluoromethyl)phenyl]isoxazole-4-carboxylic acid (30 mg, 0.12 mmol) was dissolved in acetonitrile (1.5 mL) followed by the addition of o-(benzotriazol-1-yl)-N,N,N',N'-tetramethyluronium tetrafluoroborate (TBTU) (52 mg, 0.16 mmol), pyridine (60 μL, 0.72 mmol) and 3-(1-methyl-1-hydroxyethyl)piperidine hydrochloride (25 mg, 0.14 mmol), and stirred at 60° C. for 30 min. The residue was purified on reversed phase HPLC to yield the title compound (23 mg). HRMS (ESI, pos. ion) m/z calcd for $C_{19}H_{21}F_3N_2O_3$: 382.1504, found 382.1502.

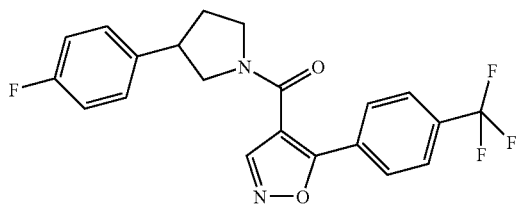

Example 20

4-{[3-(4-Fluorophenyl)pyrrolidin-1-yl]carbonyl}-5-[4-(trifluoromethyl)phenyl] isoxazole 5-[4-(Trifluoromethyl)phenyl]isoxazole-4-carboxylic acid (30 mg, 0.12 mmol) was dissolved in acetonitrile (1.5 mL) followed by the addition of o-(benzotriazol-1-yl)-N,N,N',N'-tetramethyluronium tetrafluoroborate (TBTU) (52 mg, 0.16 mmol), pyridine (60 μL, 0.72 mmol) and 3-(4-fluorophenyl)pyrrolidine oxalate (36 mg, 0.14 mmol), and stirred at 60° C. for 2 h. The residue was purified on reversed phase HPLC to yield the title compound (8 mg). HRMS (ESI, pos. ion) m/z calcd for $C_{21}H_{16}F_4N_2O_2$: 404.1148, found 404.1152.

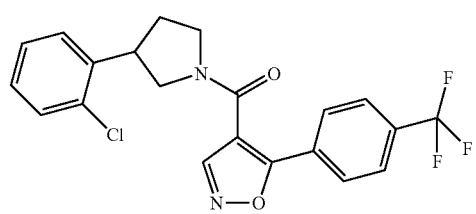

Example 21

4-{[3-(2-Chlorophenyl)pyrrolidin-1-yl]carbonyl}-5-[4-(trifluoromethyl)phenyl] isoxazole 5-[4-(Trifluoromethyl)phenyl]isoxazole-4-carboxylic acid (30 mg, 0.12 mmol) was dissolved in acetonitrile (1.5 mL) followed by the addition of o-(benzotriazol-1-yl)-N,N,N',N'-tetramethyluronium tetrafluoroborate (TBTU) (52 mg, 0.16 mmol), pyridine (60 μL, 0.72 mmol) and 3-(2-chlorophenyl)pyrrolidine oxalate (38 mg, 0.14 mmol), and stirred at 60° C. for 2 h. The residue was purified on reversed phase HPLC to yield the title compound (9 mg). HRMS (ESI, pos. ion) m/z calcd for $C_{21}H_{16}ClF_3N_2O_2$: 420.0852, found 420.0854.

Example 22

4-{4-[(3-Phenylpyrrolidin-1-yl)carbonyl]isoxazol-5-yl}benzonitrile

A mixture of 4-[(3-phenylpyrrolidin-1-yl)carbonyl]-5-(4-iodophenyl)isoxazole (125 mg, 0.28 mmol) and copper(I) cyanide (101 mg, 1.13 mmol) in N-methylpyrrolidinone (5 mL) was stirred 150° C. for 2 h. Some material lost on workup. The residue was purified on reversed phase HPLC to yield the title compound (5 mg). HRMS (ESI, pos. ion) m/z calcd for $C_{21}H_{17}N_3O_2$: 343.1321, found 343.1313.

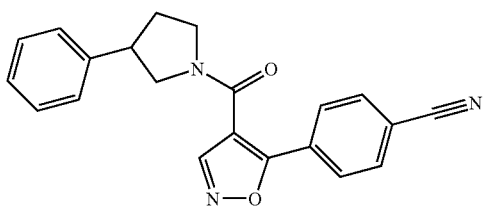

Example 23

4-[(3-Phenylpyrrolidin-1-yl)carbonyl]-5-(4-vinylphenyl)isoxazole

A mixture of 4-[(3-phenylpyrrolidin-1-yl)carbonyl]-5-(4-iodophenyl)isoxazole (50 mg, 0.11 mmol), 4,4,5,5-tetramethyl-2-vinyl-1,3,2-dioxaborolane (50 μL, 0.78 mmol), sodium bicarbonate (20 mg, 0.23 mmol), tris(dibenzylideneacetone)dipalladium(0) (Pd$_2$(dba)$_3$) (2 mg, 0.002 mmol) in 1,2-dimethoxyethane/water (5 mL) was stirred at 60° C. for 1 h. The residue was purified on SiO$_2$ (2:1 hexane/ethyl acetate) to afford the title compound (25 mg). HRMS (ESI, pos. ion) m/z calcd for $C_{22}H_{20}N_2O_2$: 344.1525, found 344.1521.

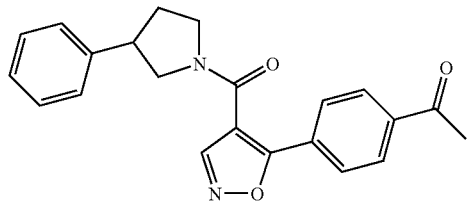

Example 24

1-(4-{4-[(3-Phenylpyrrolidin-1-yl)carbonyl] isoxazol-5-yl}phenyl)ethanone

A mixture of the styrene derivative 4-[(3-phenylpyrrolidin-1-yl)carbonyl]-5-(4-vinylphenyl)isoxazole (100 mg, 0.3 mmol) with palladium(II) dichloride (50 mg, 0.3 mmol) in water was stirred at ambient temperature overnight. Concentration followed by purification on reversed phase HPLC gave the title compound (10 mg). HRMS (ESI, pos. ion) m/z calcd for $C_{22}H_{20}N_2O_3$: 360.1474, found 360.1475.

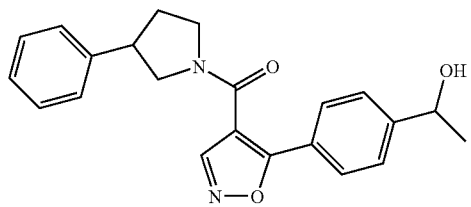

Example 25

1-(4-{4-[(3-Phenylpyrrolidin-1-yl)carbonyl] isoxazol-5-yl}phenyl)ethanol

A mixture of the styrene derivative 4-[(3-phenylpyrrolidin-1-yl)carbonyl]-5-(4-vinylphenyl)isoxazole (20 mg, 0.6 mmol), tetrabutylammonium borohydride (7 mg, 0.03 mmol) and 5,10,15,20-tetraphenyl-21H,23H-porphine cobalt(II) (Co(TPP)) (2 mg, 0.003 mmol) in 2 mL 1/1 mixture 1,2-dimethoxyethane/2-propanol was stirred overnight at ambient temperature. More borohydride was added to effect full conversion. The residue was purified on SiO$_2$ (1:1 hexane/ethyl acetate) to afford the title compound (5 mg). MS (ESI) for $C_{22}H_{22}N_2O_3$ m/z 363 (M+H).

General Methods

Synthetic Method A:

1-Propanephosphonic acid cyclic anhydride (60 μL, 50% solution, 0.10 mmol) was added to the carboxylic acid (0.050 mmol) dissolved in dry DMF (100 μL) immediately followed by a solution of the amine (0.060 mmol) and triethylamine (28 μL, 0.20 mmol) in dry DMF (70 μL). The reaction mixture was shaken over night and was then analyzed by LCMS. If the reaction was not completed more of the coupling reagent (60 μL) was added.

Synthetic Method B:

1-Propanephosphonic acid cyclic anhydride (60-70 μL, 50% solution, ~0.1 mmol) was added to the carboxylic acid (0.050 mmol) dissolved in dry DMF (100 μL) immediately

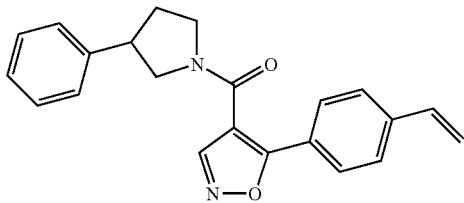

followed by a solution of the amine (0.060 mmol) and pyridine (20 μL, 0.25 mmol) in dry DMF (80 μL). The mixture was shaken at room temperature for 2 h or over night. If the reaction was not completed, after analysis by LCMS, more coupling reagent (30-60 μL) was added.

Synthetic Method C:

1-Propanephosphonic acid cyclic anhydride (90 μL, 50% solution, 0.15 mmol) was added to the carboxylic acid (0.050 mmol) dissolved in dry DMF (100 μL) immediately followed by a solution of the amine (0.060 mmol) and pyridine (30 μL, 0.4 mmol) in dry DMF (70 μL). The mixture was shaken at room temperature for 2 h and was then analyzed by LCMS. More coupling reagent (60 μL) was added if the reaction was not completed.

Preparative HPLC method A: The samples were diluted with methanol and purified by reversed phase preparative HPLC using an XTerra Prep MS C18 OBD column (19 mm×50 mm, 5 μm, cat. no. 186001930) and gradients of $CH_3CN$—$NH_4HCO_3$ buffer (50 mM, pH 10—adjusted with 25% $NH_3$ aq) with a flow of 25 mL/min. The purest product containing fractions were collected, the solvents were evaporated and the materials were dried under vacuum.

Preparative HPLC method B: The samples were diluted with methanol and purified by reversed phase preparative HPLC using an ACE C8 column (21 mm×50 mm, 5 μm, cat. no. ACE-122-0520) and gradients of $CH_3CN$—$NH_4OAc$ buffer (50 mM) with a flow of 25 mL/min. The purest product containing fractions were extracted with DCM and the organic phase was dried with $MgSO_4$. The solvents were evaporated and the materials were dried under vacuum.

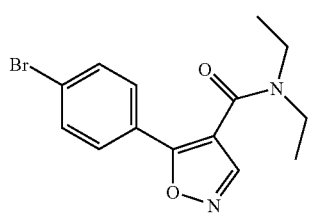

Example 26

5-(4-Bromophenyl)-N,N-diethylisoxazole-4-carboxamide

The title compound was prepared from 5-(4-bromophenyl)isoxazole-4-carboxylic acid (13.4 mg, 0.050 mmol) and diethylamine (4.4 mg, 0.060 mmol) as described in synthetic method A and thereafter purified by preparative HPLC method A to give a solid (3.8 mg). MS (pos) m/z 323.0 and 325.0.

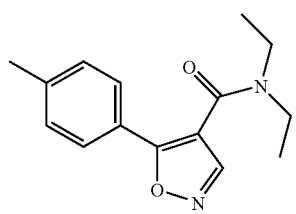

Example 27

N,N-Diethyl-5-(4-methylphenyl)isoxazole-4-carboxamide

The title compound was prepared from 5-(4-methylphenyl)isoxazole-4-carboxylic acid (10.2 mg, 0.050 mmol) and diethylamine (4.4 mg, 0.060 mmol) as described in synthetic method A and thereafter purified by preparative HPLC method A to give a solid (7.0 mg). MS (pos) m/z 259.1 (M+1).

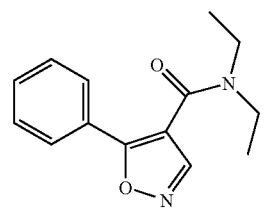

Example 28

N,N-Diethyl-5-phenylisoxazole-4-carboxamide

The title compound was prepared from 5-(phenyl)isoxazole-4-carboxylic acid (9.5 mg, 0.050 mmol) and diethylamine (4.4 mg, 0.060 mmol) as described in synthetic method A and thereafter purified by preparative HPLC method A to give a solid (4.6 mg). MS (pos) m/z 245.2 (M+1).

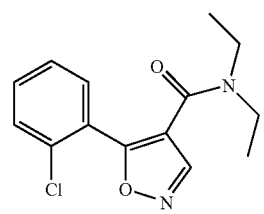

Example 29

5-(2-Chlorophenyl)-N,N-diethylisoxazole-4-carboxamide

The title compound was prepared from 5-(2-chlorophenyl)isoxazole-4-carboxylic acid (11.2 mg, 0.050 mmol) and diethylamine (4.4 mg, 0.060 mmol) as described in synthetic method A and thereafter purified by preparative HPLC method A to give a solid (3.8 mg). MS (pos) m/z 279.1 (M+1).

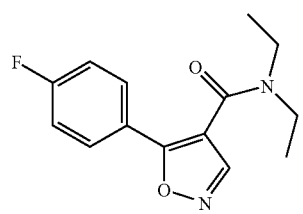

Example 30

N,N-Diethyl-5-(4-fluorophenyl)isoxazole-4-carboxamide

The title compound was prepared from 5-(4-fluorophenyl)isoxazole-4-carboxylic acid (10.4 mg, 0.050 mmol) and diethylamine (4.4 mg, 0.060 mmol) as described in synthetic method A and thereafter purified by preparative HPLC method A to give a solid (11.4 mg). MS (pos) m/z 263.1 (M+1).

Example 31

N,N-Diethyl-5-(4-nitrophenyl)isoxazole-4-carboxamide

The title compound was prepared from 5-(4-nitrophenyl)isoxazole-4-carboxylic acid (11.7 mg, 0.050 mmol) and diethylamine (4.4 mg, 0.060 mmol) as described in synthetic method A and thereafter purified, first by preparative HPLC method A and then by method B, to give a solid (4.3 mg). MS (pos) m/z 290.2 (M+1).

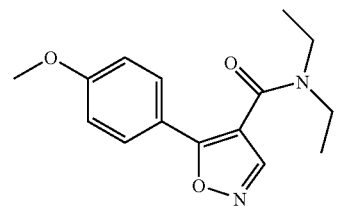

Example 32

N,N-Diethyl-5-(4-methoxyphenyl)isoxazole-4-carboxamide

The title compound was prepared from 5-(4-methoxyphenyl)isoxazole-4-carboxylic acid (11.0 mg, 0.050 mmol) and diethylamine (4.4 mg, 0.060 mmol) as described in synthetic method A and thereafter purified by preparative HPLC method A to give a solid (7.8 mg). MS (pos) m/z 275.2 (M+1).

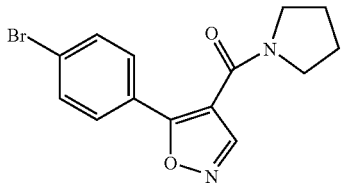

Example 33

5-(4-Bromophenyl)-4-(pyrrolidin-1-ylcarbonyl)isoxazole

The title compound was prepared from 5-(4-bromophenyl)isoxazole-4-carboxylic acid (13.4 mg, 0.050 mmol) and pyrrolidine (4.3 mg, 0.060 mmol) as described in synthetic method A and thereafter purified, first by preparative HPLC method A and then by method B, to give a solid (16.2 mg). MS (pos) m/z 321.0.

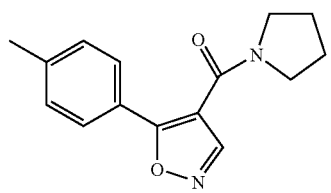

Example 34

5-(4-Methylphenyl)-4-(pyrrolidin-1-ylcarbonyl)isoxazole

The title compound was prepared from 5-(4-methylphenyl)isoxazole-4-carboxylic acid (10.2 mg, 0.050 mmol) and pyrrolidine (4.3 mg, 0.060 mmol) as described in synthetic method A and thereafter purified by preparative HPLC method A to give a solid (7.1 mg). MS (pos) m/z 257.2 (M+H).

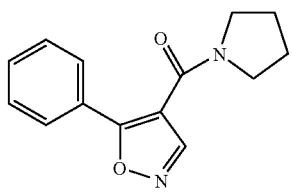

Example 35

5-Phenyl-4-(pyrrolidin-1-ylcarbonyl)isoxazole

The title compound was prepared from 5-(phenyl)isoxazole-4-carboxylic acid (9.5 mg, 0.050 mmol) and pyrrolidine (4.3 mg, 0.060 mmol) as described in synthetic method A and thereafter purified, first by preparative HPLC method A and then by method B, to give a solid (12.9 mg). MS (pos) m/z 243.2 (M+H).

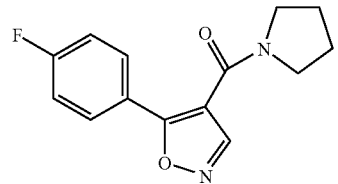

Example 36

5-(4-Fluorophenyl)-4-(pyrrolidin-1-ylcarbonyl)isoxazole

The title compound was prepared from 5-(4-fluorophenyl)isoxazole-4-carboxylic acid (10.4 mg, 0.050 mmol) and pyrrolidine (4.3 mg, 0.060 mmol) as described in synthetic method A and thereafter purified by preparative HPLC method A to give a solid (9.6 mg). MS (pos) m/z 261.1 (M+H).

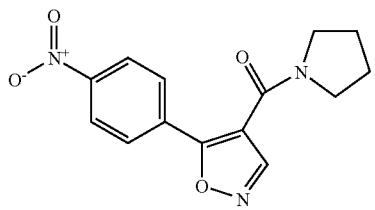

Example 37

5-(4-Nitrophenyl)-4-(pyrrolidin-1-ylcarbonyl)isoxazole

The title compound was prepared from 5-(4-nitrophenyl)isoxazole-4-carboxylic acid (11.7 mg, 0.050 mmol) and pyrrolidine (4.3 mg, 0.060 mmol) as described in synthetic method A and thereafter purified, first by preparative HPLC method A and then by method B, to give a solid (13.4 mg). MS (pos) m/z 288.2 (M+H).

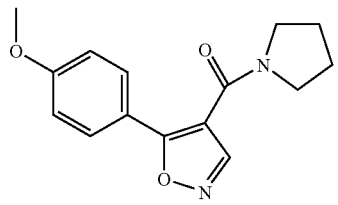

Example 38

5-(4-Methoxyphenyl)-4-(pyrrolidin-1-ylcarbonyl)isoxazole

The title compound was prepared from 5-(4-methoxyphenyl)isoxazole-4-carboxylic acid (11.0 mg, 0.050 mmol) and pyrrolidine (4.3 mg, 0.060 mmol) as described in synthetic method A and thereafter purified, first by preparative HPLC method A and then by method B, to give a solid (15.1 mg). MS (pos) m/z 273.2 (M+H).

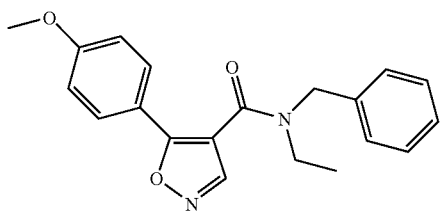

Example 39

N-Benzyl-N-ethyl-5-(4-methoxyphenyl)isoxazole-4-carboxamide

The title compound was prepared from 5-(4-methoxyphenyl)isoxazole-4-carboxylic acid (11.0 mg, 0.050 mmol) and N-ethylbenzylamine (8.1 mg, 0.060 mmol) as described in synthetic method A (using 21 µL of triethylamine and 45 µL of 1-propanephosphonic acid cyclic anhydride) and thereafter purified by preparative HPLC method B (without the extraction step) to give a solid (10.5 mg). MS (pos) m/z 337.2 (M+H).

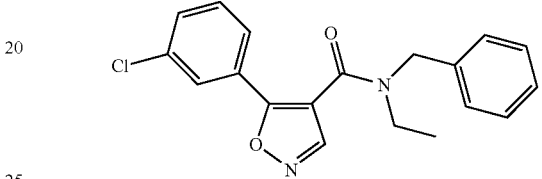

Example 40

N-Benzyl-5-(3-chlorophenyl)-N-ethylisoxazole-4-carboxamide

The title compound was prepared from 5-(3-chlorophenyl)isoxazole-4-carboxylic acid (11.2 mg, 0.050 mmol) and N-ethylbenzylamine (8.1 mg, 0.060 mmol) as described in synthetic method A (using 21 µL of triethylamine and 45 µL of 1-propanephosphonic acid cyclic anhydride) and thereafter purified by preparative HPLC method B (without the extraction step) to give a solid (4.1 mg). MS (pos) m/z 341.2 (M+H).

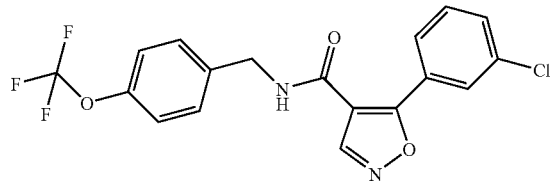

Example 41

5-(3-Chlorophenyl)-N-[4-(trifluoromethoxy)benzyl]isoxazole-4-carboxamide

The title compound was prepared from 5-(3-chlorophenyl)isoxazole-4-carboxylic acid (11.2 mg, 0.050 mmol) and 4-(trifluoromethoxy)benzylamine (11.5 mg, 0.060 mmol) as described in synthetic method A and thereafter purified by preparative HPLC method B to give a solid (4.5 mg). MS (pos) m/z 397.0 (M+H).

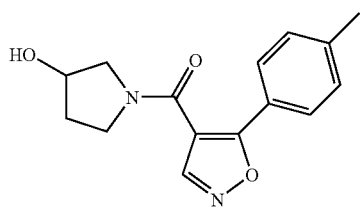

Example 42

1-{[5-(4-Methylphenyl)isoxazol-4-yl]carbonyl}pyrrolidin-3-ol

The title compound was prepared from 5-(4-methylphenyl)isoxazole-4-carboxylic acid (10.2 mg, 0.050 mmol) and 3-pyrrolidinol (5.2 mg, 0.060 mmol) as described in synthetic method B and thereafter purified by preparative HPLC method B to give a solid (4.9 mg). HRMS calcd for C15H16N2O3: 272.1161, found 272.1157.

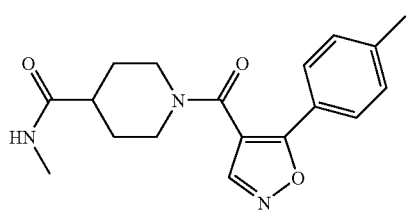

Example 43

N-Methyl-1-{[5-(4-methylphenyl)isoxazol-4-yl]carbonyl}piperidine-4-carboxamide (BVT160878)

The title compound was prepared from 5-(4-methylphenyl)isoxazole-4-carboxylic acid (10.2 mg, 0.050 mmol) and piperidine-4-carboxylic acid methylamide (8.5 mg, 0.060 mmol) as described in synthetic method B and thereafter purified by preparative HPLC method B to give a solid (5.1 mg). HRMS calcd for C18H21N3O3: 327.1583, found 327.1580.

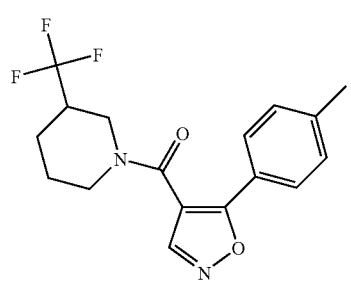

Example 44

1-{[5-(4-Methylphenyl)isoxazol-4-yl]carbonyl}-3-(trifluoromethyl)piperidine

The title compound was prepared from 5-(4-methylphenyl)isoxazole-4-carboxylic acid (10.2 mg, 0.050 mmol) and DL-3-(trifluoromethyl)piperidine (9.2 mg, 0.060 mmol) as described in synthetic method B and thereafter purified by preparative HPLC method B to give a solid (11.2 mg). HRMS calcd for C17H17F3N2O2: 338.1242, found 338.1242.

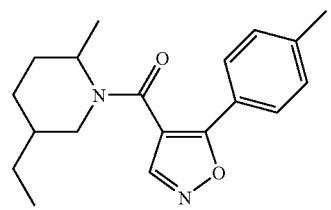

Example 45

5-Ethyl-2-methyl-1-{[5-(4-methylphenyl)isoxazol-4-yl]carbonyl}piperidine

The title compound was prepared from 5-(4-methylphenyl)isoxazole-4-carboxylic acid (10.2 mg, 0.050 mmol) and 5-ethyl-2-methylpiperidine (7.6 mg, 0.060 mmol) as described in synthetic method B and thereafter purified by preparative HPLC method B to give a solid (5.5 mg). HRMS calcd for C19H24N2O2: 312.1838, found 312.1841.

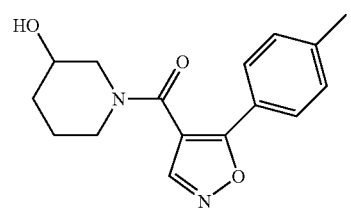

Example 46

1-{[5-(4-Methylphenyl)isoxazol-4-yl]carbonyl}piperidin-3-ol

The title compound was prepared from 5-(4-methylphenyl)isoxazole-4-carboxylic acid (10.2 mg, 0.050 mmol) and 3-hydroxypiperidine (6.1 mg, 0.060 mmol) as described in synthetic method B and thereafter purified by preparative HPLC method B to give a solid (0.6 mg). HRMS calcd for C16H18N2O3: 286.1317, found 286.1315.

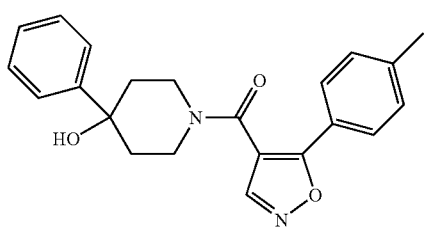

Example 47

1-{[5-(4-Methylphenyl)isoxazol-4-yl]carbonyl}-4-phenylpiperidin-4-ol

The title compound was prepared from 5-(4-methylphenyl)isoxazole-4-carboxylic acid (10.2 mg, 0.050 mmol) and 4-hydroxy-4-phenylpiperidine (10.6 mg, 0.060 mmol) as described in synthetic method B and thereafter purified by preparative HPLC method B to give a solid (3.9 mg). HRMS calcd for C22H22N2O3: 362.1630, found 362.1623.

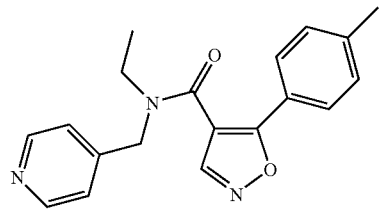

Example 48

N-Ethyl-5-(4-methylphenyl)-N-(pyridin-4-ylmethyl) isoxazole-4-carboxamide

The title compound was prepared from 5-(4-methylphenyl)isoxazole-4-carboxylic acid (10.2 mg, 0.050 mmol) and 4-(ethylaminomethyl)-pyridine (8.2 mg, 0.060 mmol) as described in synthetic method B and thereafter purified by preparative HPLC method B to give a solid (7.8 mg). HRMS calcd for C19H19N3O2: 321.1477, found 321.1485.

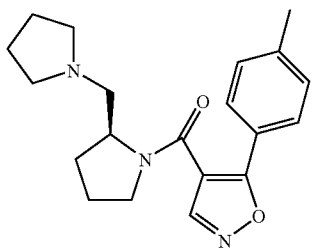

Example 49

5-(4-Methylphenyl)-4-{[(2S)-2-(pyrrolidin-1-ylmethyl)pyrrolidin-1-yl]carbonyl}isoxazole carboxamide The title compound was prepared from 5-(4-methylphenyl)isoxazole-4-carboxylic acid (10.2 mg, 0.050 mmol) and (S)-(+)-1-(2-pyrrolidinylmethyl)-pyrrolidine (9.3 mg, 0.060 mmol) as described in synthetic method B and thereafter purified by preparative HPLC method B to give a solid (6.4 mg). Calcd for C20H25N3O2: 339.1947, found 339.1952.

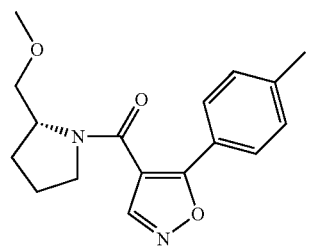

Example 50

4-{[(2R)-2-(Methoxymethyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and (R)-2-methoxymethyl-pyrrolidine (6.9 mg, 0.060 mmol) as described in synthetic method B and thereafter purified by preparative HPLC method B to give a solid (5.9 mg). Calcd for C17H20N2O3: 300.1474, found 300.1478.

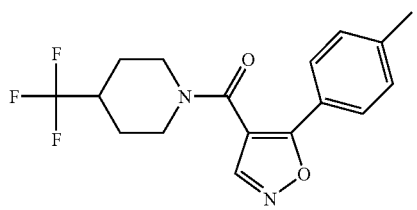

Example 51

1-{[5-(4-Methylphenyl)isoxazol-4-yl]carbonyl}-4-(trifluoromethyl)piperidine

The title compound was prepared from 5-(4-methylphenyl)isoxazole-4-carboxylic acid (10.2 mg, 0.050 mmol) and 4-(trifluoromethyl)piperidine hydrochloride (9.2 mg, 0.060 mmol) as described in synthetic method B and thereafter purified by preparative HPLC method B to give a solid (8.5 mg). Calcd for C17H17F3N2O2: 338.1242, found 338.1238.

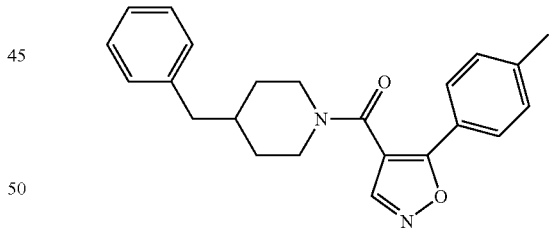

Example 52

4-Benzyl-1-{[5-(4-methylphenyl)isoxazol-4-yl]carbonyl}piperidine

The title compound was prepared from 5-(4-methylphenyl)isoxazole-4-carboxylic acid (10.2 mg, 0.050 mmol) and 4-benzylpiperidine (10.5 mg, 0.060 mmol) as described in synthetic method B and thereafter purified by preparative HPLC method B to give a solid (11.5 mg). Calcd for C23H24N2O2: 360.1838, found 360.1842.

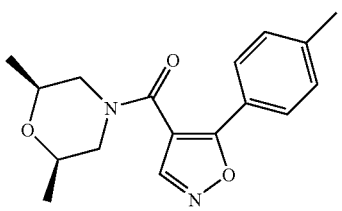

Example 53

(2R,6S)-2,6-Dimethyl-4-{[5-(4-methylphenyl)isoxazol-4-yl]carbonyl}morpholine

The title compound was prepared from 5-(4-methylphenyl)isoxazole-4-carboxylic acid (10.2 mg, 0.050 mmol) and cis-2,6-dimethylmorpholine (6.9 mg, 0.060 mmol) as described in synthetic method B and thereafter purified by preparative HPLC method B to give a solid (9.9 mg). Calcd for C17H20N2O3: 300.1474, found 300.1472.

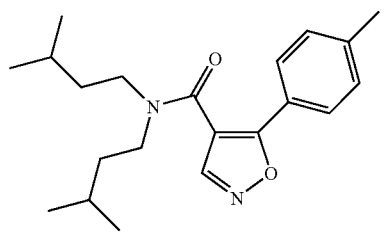

Example 54

N,N-bis(3-Methylbutyl)-5-(4-methylphenyl)isoxazole-4-carboxamide

The title compound was prepared from 5-(4-methylphenyl)isoxazole-4-carboxylic acid (10.2 mg, 0.050 mmol) and diisoamylamine (9.4 mg, 0.060 mmol) as described in synthetic method B and thereafter purified by preparative HPLC method B to give a solid (6.7 mg). Calcd for C21H30N2O2: 342.2307, found 342.2318.

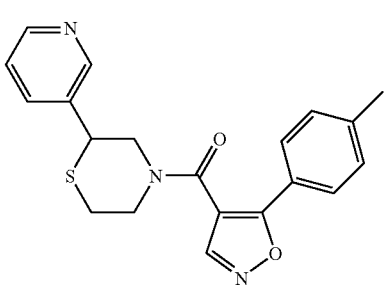

Example 55

4-{[5-(4-Methylphenyl)isoxazol-4-yl]carbonyl}-2-pyridin-3-ylthiomorpholine

The title compound was prepared from 5-(4-methylphenyl)isoxazole-4-carboxylic acid (10.2 mg, 0.050 mmol) and 2-pyridin-3-yl thiomorpholine hydrochloride (13 mg, 0.060 mmol) as described in synthetic method B and thereafter purified by preparative HPLC method B to give a solid (11.5 mg). Calcd for C20H19N3O2S: 365.1198, found 365.1200.

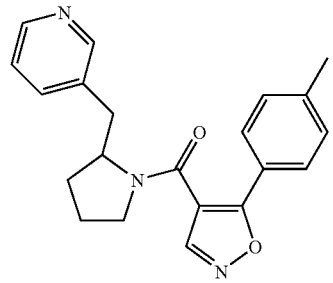

Example 56

3-[(1-{[5-(4-Methylphenyl)isoxazol-4-yl]carbonyl}pyrrolidin-2-yl)methyl]pyridine The title compound was prepared from 5-(4-methylphenyl)isoxazole-4-carboxylic acid (10.2 mg, 0.050 mmol) and 3-pyrrolidin-2-ylmethylpyridine dihydrochloride (14.1 mg, 0.060 mmol) as described in synthetic method B and thereafter purified by preparative HPLC method B to give a solid (4.7 mg). Calcd for C21H21N3O2: 347.1634, found 347.1635.

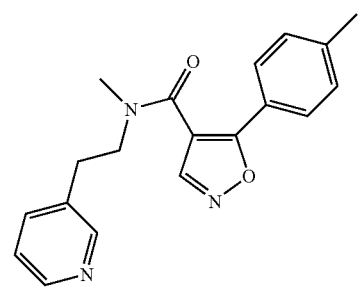

Example 57

N-Methyl-5-(4-methylphenyl)-N-(2-pyridin-3-ylethyl)isoxazole-4-carboxamide

The title compound was prepared from 5-(4-methylphenyl)isoxazole-4-carboxylic acid (10.2 mg, 0.050 mmol) and 3-[2-(methylamino)ethyl]pyridine dihydrochloride (12.5 mg, 0.060 mmol) as described in synthetic method B and thereafter purified by preparative HPLC method B to give a solid (4.6 mg). Calcd for C19H19N3O2: 321.1477, found 321.1491.

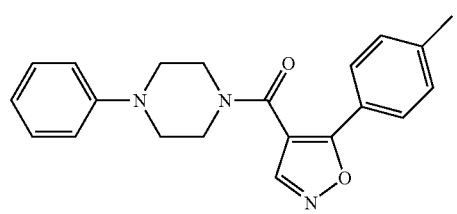

Example 58

1-{[5-(4-Methylphenyl)isoxazol-4-yl]carbonyl}-4-phenylpiperazine

The title compound was prepared from 5-(4-methylphenyl)isoxazole-4-carboxylic acid (10.2 mg, 0.050 mmol) and 1-phenylpiperazine (9.7 mg, 0.060 mmol) as described in synthetic method B and thereafter purified by preparative HPLC method B to give a solid (11.5 mg). Calcd for C21H21N3O2: 347.1634, found 347.1628.

Example 61

3,3-Difluoro-1-{[5-(4-methylphenyl)isoxazol-4-yl]carbonyl}piperidine

The title compound was prepared from 5-(4-methylphenyl)isoxazole-4-carboxylic acid (10.2 mg, 0.050 mmol) and 3,3-difluoropiperidine hydrochloride (9.5 mg, 0.060 mmol) as described in synthetic method B and thereafter purified by preparative HPLC method B to give a solid (4.4 mg). Calcd for C16H16F2N2O2: 306.1180, found 306.1177.

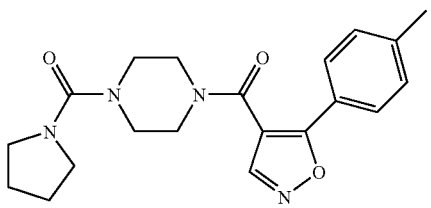

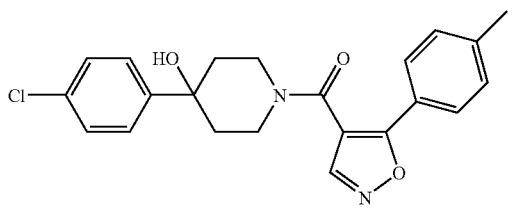

Example 59

1-{[5-(4-Methylphenyl)isoxazol-4-yl]carbonyl}-4-(pyrrolidin-1-ylcarbonyl)piperazine The title compound was prepared from 5-(4-methylphenyl)isoxazole-4-carboxylic acid (10.2 mg, 0.050 mmol) and piperazin-1-yl-pyrrolidin-1-yl-methanone (11.0 mg, 0.060 mmol) as described in synthetic method B and thereafter purified by preparative HPLC method B to give a solid (11.7 mg). Calcd for C20H24N4O3: 368.1848, found 368.1847.

Example 62

4-(4-Chlorophenyl)-1-{[5-(4-methylphenyl)isoxazol-4-yl]carbonyl}piperidin-4-ol

The title compound was prepared from 5-(4-methylphenyl)isoxazole-4-carboxylic acid (10.2 mg, 0.050 mmol) and 4-(4-chlorophenyl)-4-hydroxypiperidine (12.7 mg, 0.060 mmol) as described in synthetic method B and thereafter purified by preparative HPLC method B to give a solid (8.2 mg). Calcd for C22H21ClN2O3: 396.1241, found 396.1239.

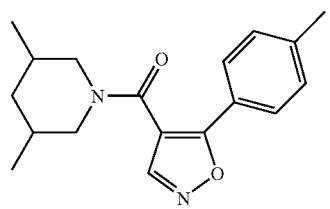

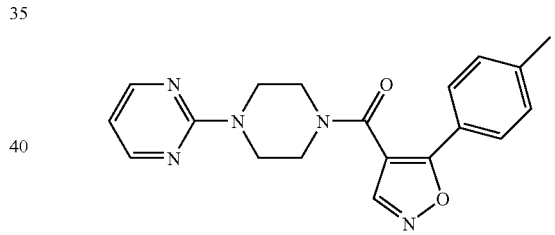

Example 60

3,5-Dimethyl-1-{[5-(4-methylphenyl)isoxazol-4-yl]carbonyl}piperidine

The title compound was prepared from 5-(4-methylphenyl)isoxazole-4-carboxylic acid (10.2 mg, 0.050 mmol) and 3,5-dimethylpiperidine (6.8 mg, 0.060 mmol) as described in synthetic method B and thereafter purified by preparative HPLC method B to give a solid (0.7 mg). Calcd for C18H22N2O2: 298.1681, found 298.1692.

Example 63

2-(4-{[5-(4-Methylphenyl)isoxazol-4-yl]carbonyl}piperazin-1-yl)pyrimidine

The title compound was prepared from 5-(4-methylphenyl)isoxazole-4-carboxylic acid (10.2 mg, 0.050 mmol) and 1-(2-pyrimidyl)piperazine (9.9 mg, 0.060 mmol) as described in synthetic method B and thereafter purified by preparative HPLC method B to give a solid (4.4 mg). Calcd for C19H19N5O2: 349.1539, found 349.1538.

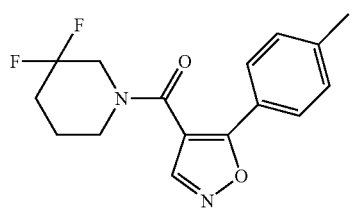

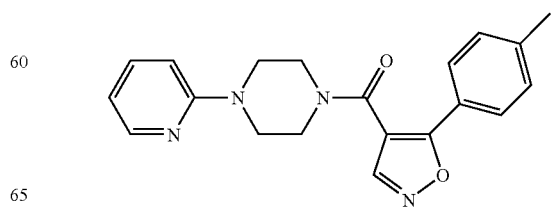

Example 64

1-{[5-(4-Methylphenyl)isoxazol-4-yl]carbonyl}-4-pyridin-2-ylpiperazine

The title compound was prepared from 5-(4-methylphenyl)isoxazole-4-carboxylic acid (10.2 mg, 0.050 mmol) and 1-(2-pyridyl)piperazine (9.8 mg, 0.060 mmol) as described in synthetic method B and thereafter purified by preparative HPLC method B to give a solid (4.4 mg). Calcd for C20H20N4O2: 348.1586, found 348.1593.

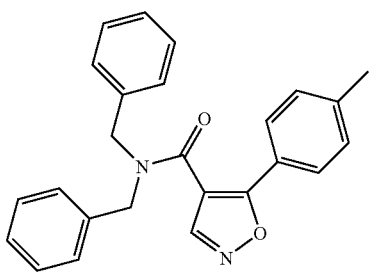

Example 65

N,N-Dibenzyl-5-(4-methylphenyl)isoxazole-4-carboxamide

The title compound was prepared from 5-(4-methylphenyl)isoxazole-4-carboxylic acid (10.2 mg, 0.050 mmol) and dibenzylamine (11.8 mg, 0.060 mmol) as described in synthetic method B and thereafter purified by preparative HPLC method B to give a solid (2.6 mg). Calcd for C25H22N2O2: 382.1681, found 382.1684.

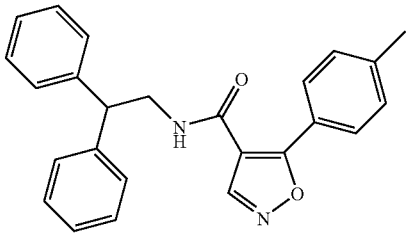

Example 66

N-(2,2-Diphenylethyl)-5-(4-methylphenyl)isoxazole-4-carboxamide

The title compound was prepared from 5-(4-methylphenyl)isoxazole-4-carboxylic acid (10.2 mg, 0.050 mmol) and 2,2-diphenylethylamine (11.8 mg, 0.060 mmol) as described in synthetic method B and thereafter purified by preparative HPLC method B to give a solid (4.0 mg). Calcd for C25H22N2O2: 382.1681, found 382.1682.

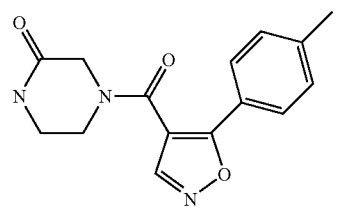

Example 67

4-{[5-(4-Methylphenyl)isoxazol-4-yl]carbonyl}piperazin-2-one

The title compound was prepared from 5-(4-methylphenyl)isoxazole-4-carboxylic acid (10.2 mg, 0.050 mmol) and piperazinone (6.0 mg, 0.060 mmol) as described in synthetic method B and thereafter purified by preparative HPLC method B to give a solid (4.6 mg). Calcd for C15H15N3O3: 285.1113, found 285.1113.

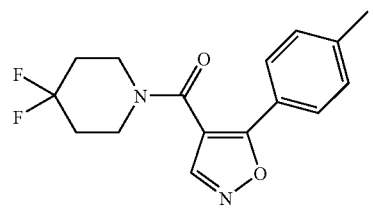

Example 68

4,4-Difluoro-1-{[5-(4-methylphenyl)isoxazol-4-yl]carbonyl}piperidine

The title compound was prepared from 5-(4-methylphenyl)isoxazole-4-carboxylic acid (10.2 mg, 0.050 mmol) and 4,4-difluoropiperidine hydrochloride (9.5 mg, 0.060 mmol) as described in synthetic method B and thereafter purified by preparative HPLC method B to give a solid (3.2 mg). Calcd for C16H16F2N2O2: 306.1180, found 306.1179.

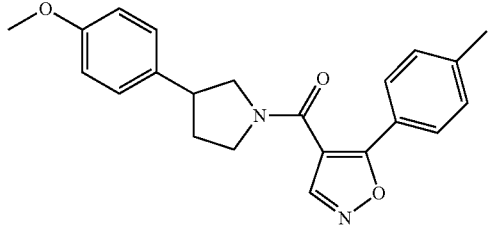

Example 69

4-{[3-(4-Methoxyphenyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-methoxyphenyl)pyrrolidine oxalat (16.0 mg, 0.060 mmol) as described in synthetic method B and thereafter purified by preparative HPLC method B to give a solid (4.3 mg). Calcd for C22H22N2O3: 362.1630, found 362.1636.

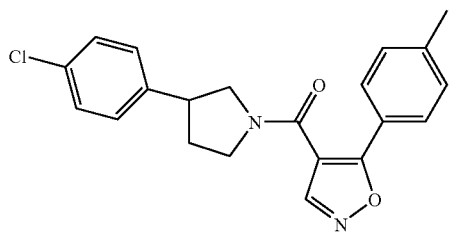

Example 70

4-{[3-(4-Chlorophenyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-chlorophenyl)pyrrolidine oxalate (16.3 mg, 0.060 mmol) as described in synthetic method B and thereafter purified by preparative HPLC method B to give a solid (4.4 mg). Calcd for C21H19ClN2O2: 366.1135, found 366.1138.

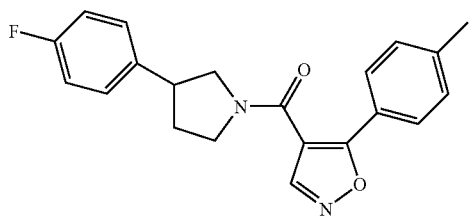

Example 71

4-{[3-(4-Fluorophenyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-fluorophenyl)pyrrolidine oxalate (15.3 mg, 0.060 mmol) as described in synthetic method B and thereafter purified by preparative HPLC method B to give a solid (3.3 mg). Calcd for C21H19FN2O2: 350.1431, found 350.1438.

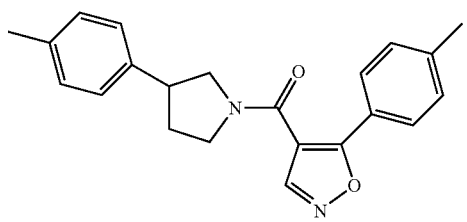

Example 72

5-(4-Methylphenyl)-4-{[3-(4-methylphenyl)pyrrolidin-1-yl]carbonyl}isoxazole

The title compound was prepared from 5-(4-methylphenyl)isoxazole-4-carboxylic acid (10.2 mg, 0.050 mmol) and 3-(4-methylphenyl)pyrrolidine oxalate (15.1 mg, 0.060 mmol) as described in synthetic method B and thereafter purified by preparative HPLC method B to give a solid (2.7 mg). Calcd for C22H22N2O2: 346.1681, found 346.1692.

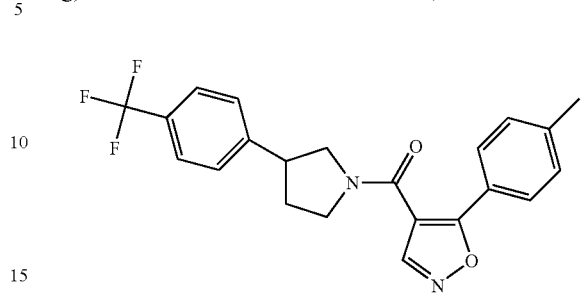

Example 73

5-(4-Methylphenyl)-4-({3-[4-(trifluoromethyl)phenyl]pyrrolidin-1-yl}carbonyl)isoxazole The title compound was prepared from 5-(4-methylphenyl)isoxazole-4-carboxylic acid (10.2 mg, 0.050 mmol) and 3-[4-(trifluoromethyl)phenyl]pyrrolidine oxalate (15.1 mg, 0.050 mmol) as described in synthetic method B and thereafter purified by preparative HPLC method B to give a solid (5.3 mg). Calcd for C22H19F3N2O2: 400.1399, found 400.1403.

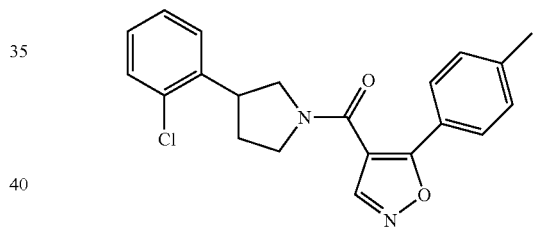

Example 74

4-{[3-(2-Chlorophenyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(2-chlorophenyl)pyrrolidine oxalate (16.3 mg, 0.060 mmol) as described in synthetic method B and thereafter purified by preparative HPLC method B to give a solid (2.5 mg). Calcd for C21H19ClN2O2: 366.1135, found 366.1141.

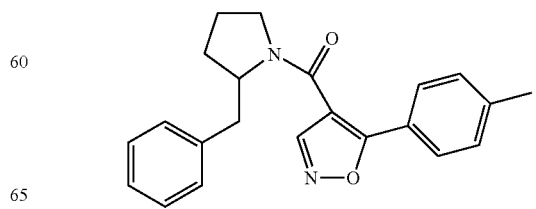

Example 75

4-[(2-Benzylpyrrolidin-1-yl)carbonyl]-5-(4-methylphenyl)isoxazole

The title compound was prepared from 5-(4-methylphenyl)isoxazole-4-carboxylic acid (10.2 mg, 0.050 mmol) and 2-benzylpyrrolidine (9.7 mg, 0.060 mmol) as described in synthetic method B and thereafter purified by preparative HPLC method B to give a solid (6.8 mg). Calcd for C22H22N2O2: 346.1681, found 346.1694.

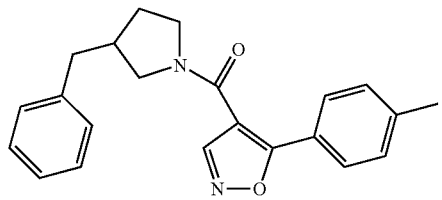

Example 76

4-[(3-Benzylpyrrolidin-1-yl)carbonyl]-5-(4-methylphenyl)isoxazole

The title compound was prepared from 5-(4-methylphenyl)isoxazole-4-carboxylic acid (10.2 mg, 0.050 mmol) and 3-benzylpyrrolidine (9.7 mg, 0.060 mmol) as described in synthetic method B and thereafter purified by preparative HPLC method B to give a solid (5.8 mg). Calcd for C22H22N2O2: 346.1681, found 346.1693.

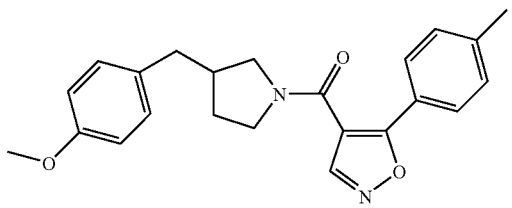

Example 77

4-{[3-(4-Methoxybenzyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-methoxybenzyl)pyrrolidine oxalate (16.9 mg, 0.060 mmol) as described in synthetic method B and thereafter purified by preparative HPLC method B to give a solid (5.5 mg). Calcd for C23H24N2O3: 376.1787, found 376.1801.

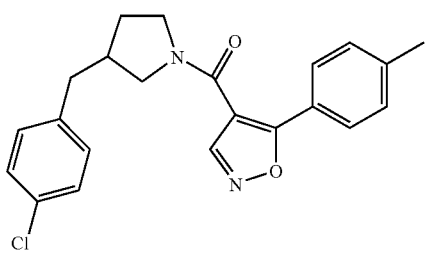

Example 78

4-{[3-(4-Chlorobenzyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-chlorobenzyl)pyrrolidine oxalate (17.1 mg, 0.060 mmol) as described in synthetic method B and thereafter purified by preparative HPLC method B to give a solid (8.1 mg). Calcd for C22H21ClN2O2: 380.1292, found 380.1295.

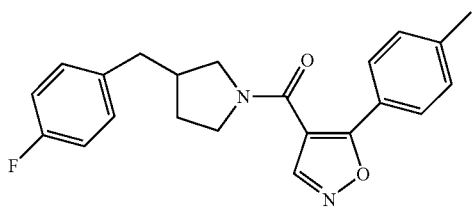

Example 79

4-{[3-(4-Fluorobenzyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-fluorobenzyl)pyrrolidine hydrochloride (12.9 mg, 0.060 mmol) as described in synthetic method B and thereafter purified by preparative HPLC method B to give a solid (6.3 mg). Calcd for C22H21FN2O2: 364.1587, found 364.1604.

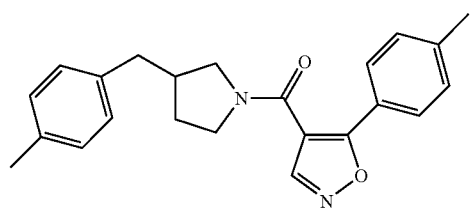

Example 80

4-{[3-(4-Methylbenzyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(4-methylbenzyl)pyrrolidine hydrochloride (12.7 mg, 0.060 mmol) as described in synthetic method B and thereafter purified by preparative HPLC method B to give a solid (5.8 mg). Calcd for C23H24N2O2: 360.1838, found 360.1848.

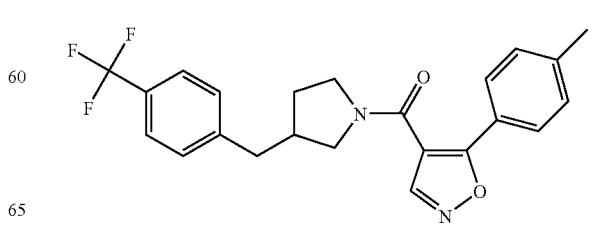

Example 81

5-(4-Methylphenyl)-4-({3-[4-(trifluoromethyl)benzyl]pyrrolidin-1-yl}carbonyl)isoxazole The title compound was prepared from 5-(4-methylphenyl)isoxazole-4-carboxylic acid (10.2 mg, 0.050 mmol) and 3-[4-(trifluoromethyl)benzyl]pyrrolidine oxalate (19.2 mg, 0.060 mmol) as described in synthetic method B and thereafter purified by preparative HPLC method B to give a solid (4.5 mg). Calcd for C23H21F3N2O2: 414.1555, found 414.1562.

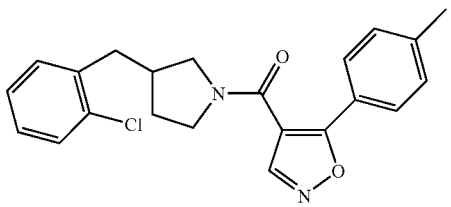

Example 82

4-{[3-(2-Chlorobenzyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and 3-(2-chlorobenzyl)pyrrolidine oxalate (17.1 mg, 0.060 mmol) as described in synthetic method B and thereafter purified by preparative HPLC method B to give a solid (6.4 mg). Calcd for C22H21ClN2O2: 380.1292, found 380.1300.

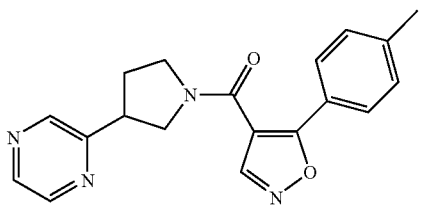

Example 83

2-(1-{[5-(4-Methylphenyl)isoxazol-4-yl]carbonyl}pyrrolidin-3-yl)pyrazine

The title compound was prepared from 5-(4-methylphenyl)isoxazole-4-carboxylic acid (10.2 mg, 0.050 mmol) and 2-pyrrolidin-3-yl-pyrazine trihydrochloride (15.5 mg, 0.060 mmol) as described in synthetic method B and thereafter purified by preparative HPLC method B to give a solid (6.0 mg). Calcd for C19H18N4O2: 334.1430, found 334.1426.

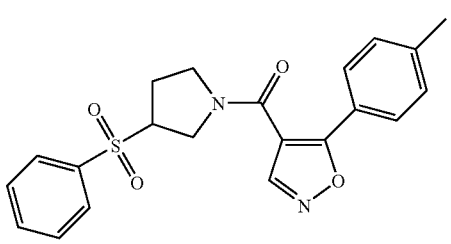

Example 84

5-(4-Methylphenyl)-4-{[3-(phenylsulfonyl)pyrrolidin-1-yl]carbonyl}isoxazole

The title compound was prepared from 5-(4-methylphenyl)isoxazole-4-carboxylic acid (10.2 mg, 0.050 mmol) and 3-(benzenesulfonyl)pyrrolidine hydrochloride (12.7 mg, 0.051 mmol) as described in synthetic method B and thereafter purified by preparative HPLC method B to give a solid (11.5 mg). Calcd for C21H20N2O4S: 396.1144, found 396.1142.

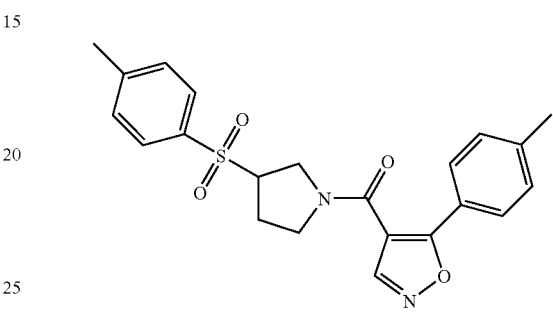

Example 85

5-(4-Methylphenyl)-4-({3-[(4-methylphenyl)sulfonyl]pyrrolidin-1-yl}carbonyl)isoxazole The title compound was prepared from 5-(4-methylphenyl)isoxazole-4-carboxylic acid (10.2 mg, 0.050 mmol) and 3-(4-methylphenylsulfonyl)pyrrolidine hydrochloride (15.7 mg, 0.060 mmol) as described in synthetic method B and thereafter purified by preparative HPLC method B to give a solid (12.1 mg). Calcd for C22H22N2O4S: 410.1300, found 410.1303.

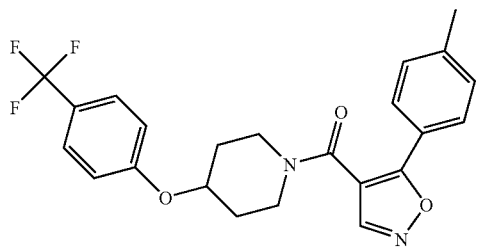

Example 86

1-{[5-(4-Methylphenyl)isoxazol-4-yl]carbonyl}-4-[4-(trifluoromethyl)phenoxy]piperidine The title compound was prepared from 5-(4-methylphenyl)isoxazole-4-carboxylic acid (10.2 mg, 0.050 mmol) and 4-[4-(trifluoromethyl)phenoxy]piperidine (16.9 mg, 0.060 mmol) as described in synthetic method B and thereafter purified by preparative HPLC method B to give a solid (11.6 mg). Calcd for C23H21F3N2O3: 430.1504, found 430.1510.

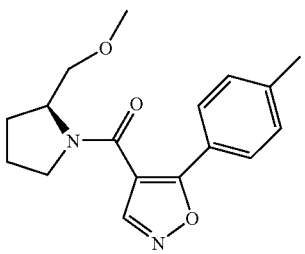

Example 87

4-{[(2S)-2-(Methoxymethyl)pyrrolidin-1-yl]carbonyl}-5-(4-methylphenyl)isoxazole

The title compound was prepared from 5-(4-methylphenyl)isoxazole-4-carboxylic acid (10.2 mg, 0.050 mmol) and (S)-2-methoxymethyl-pyrrolidine (6.9 mg, 0.060 mmol) as described in synthetic method C and thereafter purified by preparative HPLC method B to give a solid (4.6 mg). Calcd for C17H20N2O3: 300.1474, found 300.1474.

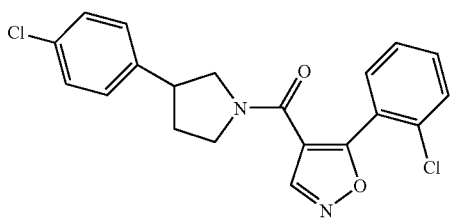

Example 88

5-(2-Chlorophenyl)-4-{[3-(4-methoxyphenyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-methoxyphenyl)pyrrolidine oxalat (16.0 mg, 0.060 mmol) as described in synthetic method C and thereafter purified by preparative HPLC method B to give a solid (5.4 mg). Calcd for C21H19ClN2O3: 382.1084, found 382.1083.

Example 89

5-(2-Chlorophenyl)-4-{[3-(4-chlorophenyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-chlorophenyl)pyrrolidine oxalate (16.3 mg, 0.060 mmol) as described in synthetic method C and thereafter purified by preparative HPLC method B to give a solid (2.5 mg). Calcd for C20H16Cl2 N2O2: 386.0589, found 386.0595.

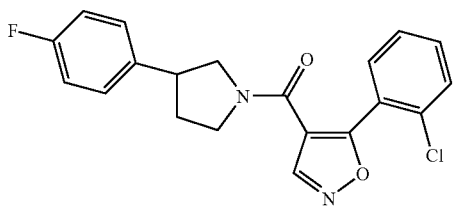

Example 90

5-(2-Chlorophenyl)-4-{[3-(4-fluorophenyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-fluorophenyl)pyrrolidine oxalate (15.3 mg, 0.060 mmol) as described in synthetic method C and thereafter purified by preparative HPLC method B to give a solid (5.2 mg). Calcd for C20H16ClFN2O2: 370.0884, found 370.0890.

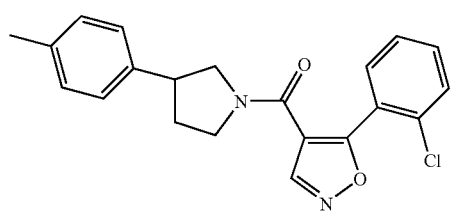

Example 91

5-(2-Chlorophenyl)-4-{[3-(4-methylphenyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-methylphenyl)pyrrolidine oxalate (15.1 mg, 0.060 mmol) as described in synthetic method C and thereafter purified by preparative HPLC method B to give a solid (7.2 mg). Calcd for C21H19ClN2O2: 366.1135, found 366.1133.

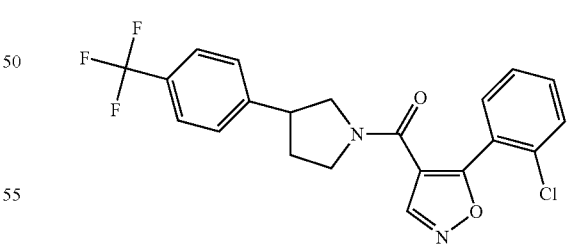

Example 92

5-(2-Chlorophenyl)-4-({3-[4-(trifluoromethyl)phenyl]pyrrolidin-1-yl}carbonyl)isoxazole The title compound was prepared from 5-(2-chlorophenyl)isoxazole-4-carboxylic acid (11.2 mg, 0.050 mmol) and 3-[4-(trifluoromethyl)phenyl]pyrrolidine oxalate (15.1 mg, 0.050 mmol) as described in synthetic method C and thereafter purified by preparative HPLC method B to give a solid (3.8 mg). Calcd for C21H16ClF3N2O2: 420.0852, found 420.0855.

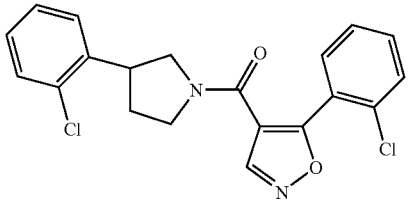

Example 93

5-(2-Chlorophenyl)-4-{[3-(2-chlorophenyl)pyrrolidin-1-yl]carbonyl}isoxazole

The title compound was prepared from 5-(2-chlorophenyl)isoxazole-4-carboxylic acid (11.2 mg, 0.050 mmol) and 3-(2-chlorophenyl)pyrrolidine oxalate (16.3 mg, 0.060 mmol) as described in synthetic method C and thereafter purified by preparative HPLC method B to give a solid (4.0 mg). MS (pos) m/z 387.0 (M+H).

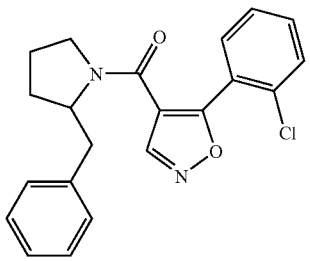

Example 94

4-[(2-Benzylpyrrolidin-1-yl)carbonyl]-5-(2-chlorophenyl)isoxazole

The title compound was prepared from 5-(2-chlorophenyl)isoxazole-4-carboxylic acid (11.2 mg, 0.050 mmol) and 2-benzylpyrrolidine (9.7 mg, 0.060 mmol) as described in synthetic method C and thereafter purified by preparative HPLC method B to give a solid (9.4 mg). Calcd for C21H19ClN2O2: 366.1135, found 366.1136.

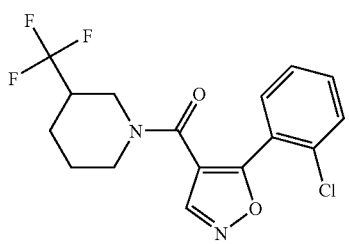

Example 95

1-{[5-(2-Chlorophenyl)isoxazol-4-yl]carbonyl}-3-(trifluoromethyl)piperidine

The title compound was prepared from 5-(2-chlorophenyl)isoxazole-4-carboxylic acid (11.2 mg, 0.050 mmol) and DL-3-(trifluoromethyl)piperidine (9.2 mg, 0.060 mmol) as described in synthetic method C and thereafter purified by preparative HPLC method B to give a solid (11.6 mg). Calcd for C16H14ClF3N2O2: 358.0696, found 358.0702.

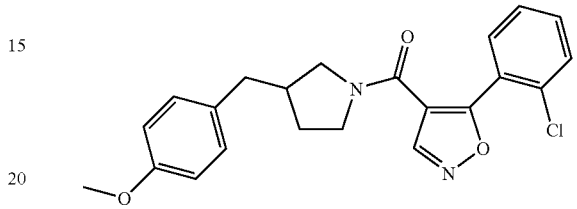

Example 96

5-(2-Chlorophenyl)-4-{[3-(4-methoxybenzyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-methoxybenzyl)pyrrolidine oxalate (16.9 mg, 0.060 mmol) as described in synthetic method C and thereafter purified by preparative HPLC method B to give a solid (8.1 mg). Calcd for C22H21ClN2O3: 396.1241, found 396.1235.

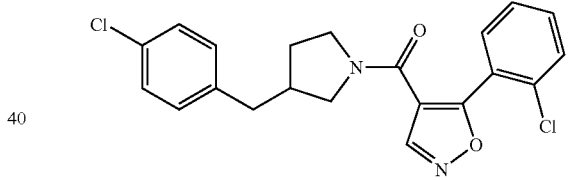

Example 97

4-{[3-(4-Chlorobenzyl)pyrrolidin-1-yl]carbonyl}-5-(2-chlorophenyl)isoxazole

The title compound was prepared from 5-(2-chlorophenyl)isoxazole-4-carboxylic acid (11.2 mg, 0.050 mmol) and 3-(4-chlorobenzyl)pyrrolidine oxalate (17.1 mg, 0.060 mmol) as described in synthetic method C and thereafter purified by preparative HPLC method B to give a solid (8.3 mg). Calcd for C21H18C12 N2O2: 400.0745, found 400.0750.

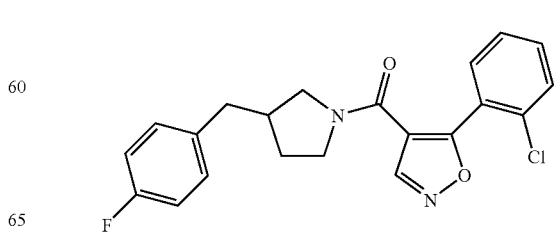

Example 98

5-(2-Chlorophenyl)-4-{[3-(4-fluorobenzyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-fluorobenzyl)pyrrolidine hydrochloride (12.9 mg, 0.060 mmol) as described in synthetic method C and thereafter purified by preparative HPLC method B to give a solid (10.1 mg). Calcd for C21H18ClFN2O2: 384.1041, found 384.1042.

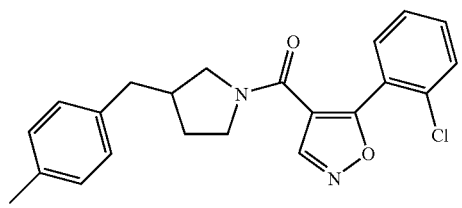

Example 99

5-(2-Chlorophenyl)-4-{[3-(4-methylbenzyl)pyrrolidin-1-yl]carbonyl}isoxazole

The title compound was prepared from 5-(2-chlorophenyl)isoxazole-4-carboxylic acid (11.2 mg, 0.050 mmol) and 3-(4-methylbenzyl)pyrrolidine hydrochloride (12.7 mg, 0.060 mmol) as described in synthetic method C and thereafter purified by preparative HPLC method B to give a solid (8.4 mg). Calcd for C22H21N2O2: 380.1292, found 380.1296.

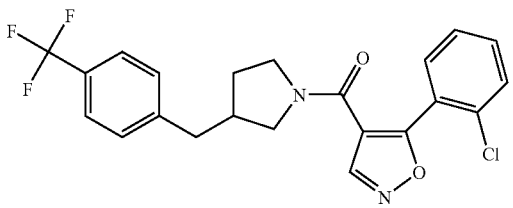

Example 100

5-(2-Chlorophenyl)-4-({3-[4-(trifluoromethyl)benzyl]pyrrolidin-1-yl}carbonyl)isoxazole The title compound was prepared from 5-(2-chlorophenyl)isoxazole-4-carboxylic acid (11.2 mg, 0.050 mmol) and 3-[4-(trifluoromethyl)benzyl]pyrrolidine oxalate (19.2 mg, 0.060 mmol) as described in synthetic method C and thereafter purified by preparative HPLC method B to give a solid (9.2 mg). Calcd for C22H18ClF3N2O2: 434.1009, found 434.1003.

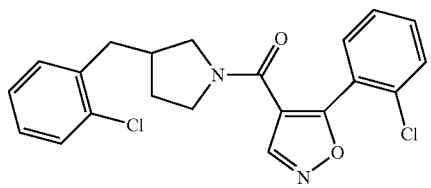

Example 101

4-{[3-(2-Chlorobenzyl)pyrrolidin-1-yl]carbonyl}-5-(2-chlorophenyl)isoxazole

The title compound was prepared from 5-(2-chlorophenyl)isoxazole-4-carboxylic acid (11.2 mg, 0.050 mmol) and 3-(2-chlorobenzyl)pyrrolidine oxalate (17.1 mg, 0.060 mmol) as described in synthetic method C and thereafter purified by preparative HPLC method B to give a solid (6.5 mg). Calcd for C21H18Cl2 N2O2: 400.0745, found 400.0746.

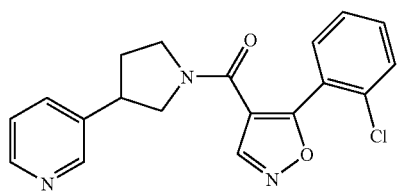

Example 102

3-(1-{[5-(2-Chlorophenyl)isoxazol-4-yl]carbonyl}pyrrolidin-3-yl)pyridine

The title compound was prepared from 5-(2-chlorophenyl)isoxazole-4-carboxylic acid (11.2 mg, 0.050 mmol) and 3-pyrrolidin-3-ylpyridine (8.9 mg, 0.060 mmol) as described in synthetic method C and thereafter purified by preparative HPLC method B to give a solid (8.0 mg). Calcd for C19H16ClN3O2: 353.0931, found 353.0932.

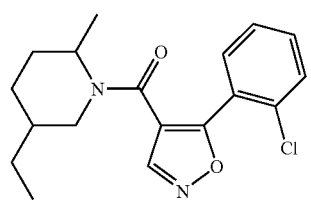

Example 103

1-{[5-(2-Chlorophenyl)isoxazol-4-yl]carbonyl}-5-ethyl-2-methylpiperidine

The title compound was prepared from 5-(2-chlorophenyl)isoxazole-4-carboxylic acid (11.2 mg, 0.050 mmol) and 5-ethyl-2-methylpiperidine (7.6 mg, 0.060 mmol) as described in synthetic method C and thereafter purified by preparative HPLC method B to give a solid (2.8 mg). Calcd for C18H21ClN2O2: 332.1292, found 332.1293.

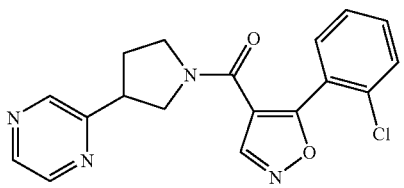

Example 104

2-(1-{[5-(2-Chlorophenyl)isoxazol-4-yl]carbonyl}pyrrolidin-3-yl)pyrazine

The title compound was prepared from 5-(2-chlorophenyl)isoxazole-4-carboxylic acid (11.2 mg, 0.050 mmol) and 2-pyrrolidin-3-yl-pyrazine trihydrochloride (15.5 mg, 0.060 mmol) as described in synthetic method C and thereafter purified by preparative HPLC method B to give a solid (7.0 mg). Calcd for C18H15ClN4O2: 354.0884, found 354.0885.

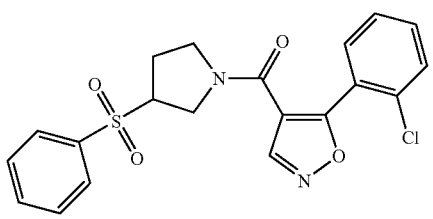

Example 105

5-(2-Chlorophenyl)-4-{[3-(phenylsulfonyl)pyrrolidin-1-yl]carbonyl}isoxazole

The title compound was prepared from 5-(2-chlorophenyl)isoxazole-4-carboxylic acid (11.2 mg, 0.050 mmol) and 3-(benzenesulfonyl)pyrrolidine hydrochloride (12.7 mg, 0.051 mmol) as described in synthetic method C and thereafter purified by preparative HPLC method B to give a solid (13.5 mg). Calcd for C20H17ClN2O4 S: 416.0598, found 416.0591.

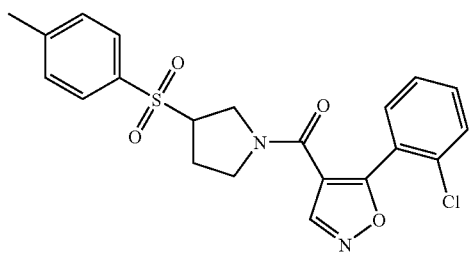

Example 106

5-(2-Chlorophenyl)-4-({3-[(4-methylphenyl)sulfonyl]pyrrolidin-1-yl}carbonyl)isoxazole The title compound was prepared from 5-(2-chlorophenyl)isoxazole-4-carboxylic acid (11.2 mg, 0.050 mmol) and 3-(4-methylphenylsulfonyl)pyrrolidine hydrochloride (15.7 mg, 0.060 mmol) as described in synthetic method C and thereafter purified by preparative HPLC method B to give a solid (13.3 mg). Calcd for C21H19ClN2O4 S: 430.0754, found 430.0753.

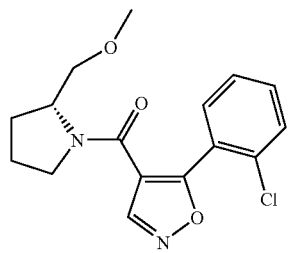

Example 107

5-(2-Chlorophenyl)-4-{[(2R)-2-(methoxymethyl)pyrrolidin-1-yl]carbonyl}isoxazole

The title compound was prepared from 5-(2-chlorophenyl)isoxazole-4-carboxylic acid (11.2 mg, 0.050 mmol) and (R)-2-methoxymethyl-pyrrolidine (6.9 mg, 0.060 mmol) as described in synthetic method C and thereafter purified by preparative HPLC method B to give a solid (8.5 mg). Calcd for C16H17ClN2O3: 320.0928, found 320.0924.

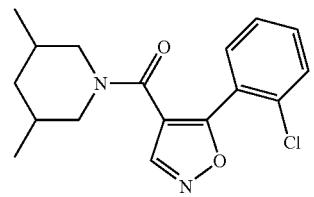

Example 108

1-{[5-(2-Chlorophenyl)isoxazol-4-yl]carbonyl}-3,5-dimethylpiperidine

The title compound was prepared from 5-(2-chlorophenyl)isoxazole-4-carboxylic acid (11.2 mg, 0.050 mmol) and 3,5-dimethylpiperidine (6.8 mg, 0.060 mmol) as described in synthetic method C and thereafter purified by preparative HPLC method B to give a solid (2.1 mg). Calcd for C17H19ClN2O2: 318.1135, found 318.1136.

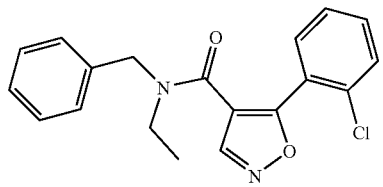

Example 109

N-Benzyl-5-(2-chlorophenyl)-N-ethylisoxazole-4-carboxamide

The title compound was prepared from 5-(2-chlorophenyl)isoxazole-4-carboxylic acid (11.2 mg, 0.050 mmol) and N-ethylbenzylamine (8.1 mg, 0.060 mmol) as described in synthetic method C and thereafter purified by preparative HPLC method B to give a solid (8.4 mg). Calcd for C19H17ClN2O2: 340.0979, found 340.0978.

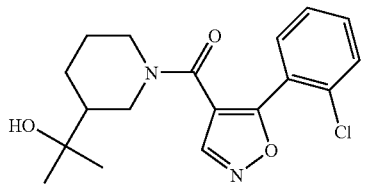

Example 110

2-(1-{[5-(2-Chlorophenyl)isoxazol-4-yl]carbonyl}piperidin-3-yl)propan-2-ol

The title compound was prepared from 5-(2-chlorophenyl)isoxazole-4-carboxylic acid (11.2 mg, 0.050 mmol) and dimethyl-3-piperidylmethanol (10.8 mg, 0.060 mmol) as described in synthetic method C and thereafter purified by preparative HPLC method B to give a solid (5.7 mg). Calcd for C18H21ClN2O3: 348.1241, found 348.1236.

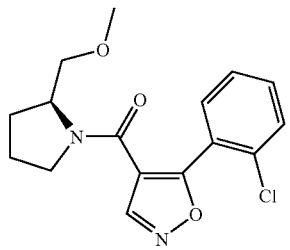

Example 111

5-(2-Chlorophenyl)-4-{[(2S)-2-(methoxymethyl)pyrrolidin-1-yl]carbonyl}isoxazole

The title compound was prepared from 5-(2-chlorophenyl)isoxazole-4-carboxylic acid (11.2 mg, 0.050 mmol) and (S)-2-methoxymethyl-pyrrolidine (6.9 mg, 0.060 mmol) as described in synthetic method C and thereafter purified by preparative HPLC method B to give a solid (11.9 mg). Calcd for C16H17ClN2O3: 320.0928, found 320.0932.

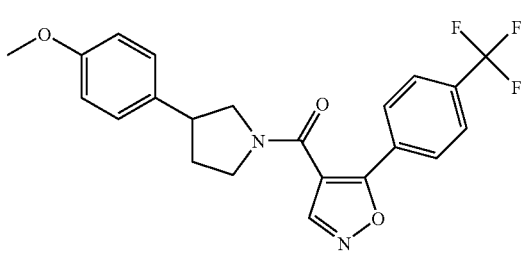

Example 112

4-{[3-(4-methoxyphenyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and 3-(4-methoxyphenyl)pyrrolidine oxalat (16.0 mg, 0.060 mmol) as described in synthetic method C and thereafter purified by preparative HPLC method B to give a solid (6.5 mg). Calcd for C22H19F3N2O3: 416.1348, found 416.1348.

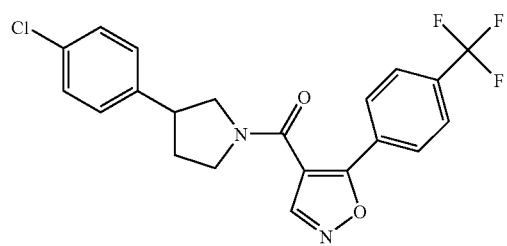

Example 113

4-{[3-(4-Chlorophenyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and 3-(4-chlorophenyl)pyrrolidine oxalate (16.3 mg, 0.060 mmol) as described in synthetic method C and thereafter purified by preparative HPLC method B to give a solid (5.4 mg). Calcd for C21H16ClF3N2O2: 420.0852, found 420.0855.

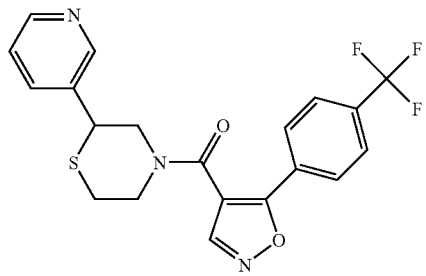

Example 114

2-Pyridin-3-yl-4-({5-[4-(trifluoromethyl)phenyl]isoxazol-4-yl}carbonyl)thiomorpholine The title compound was prepared from 5-(4-trifluoromethylphenyl)isoxazole-4-carboxylic acid (12.9 mg, 0.050 mmol) and 2-pyridin-3-yl thiomorpholine hydrochloride (13.0 mg, 0.060 mmol) as described in synthetic method C and thereafter purified by preparative HPLC method B to give a solid (12.8 mg). Calcd for C20H16F3N3O2S: 419.0915, found 419.0914.

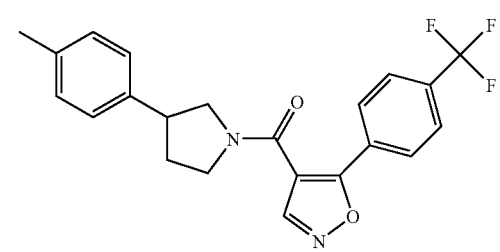

Example 115

4-{[3-(4-Methylphenyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and 3-(4-methylphenyl)pyrrolidine oxalate (15.1 mg, 0.060 mmol) as described in synthetic method C and thereafter purified by preparative HPLC method B to give a solid (6.3 mg). Calcd for C22H19F3N2O2: 400.1399, found 400.1400.

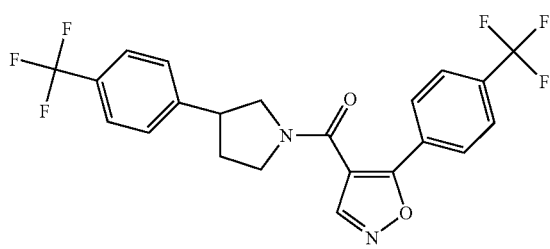

Example 116

5-[4-(Trifluoromethyl)phenyl]-4-({3-[4-(trifluoromethyl)phenyl]pyrrolidin-1-yl}carbonyl)isoxazole The title compound was prepared from 5-(4-trifluoromethylphenyl)isoxazole-4-carboxylic acid (12.9 mg, 0.050 mmol) and 3-[4-(trifluoromethyl)phenyl]pyrrolidine oxalate (18.3 mg, 0.060 mmol) as described in synthetic method C and thereafter purified by preparative HPLC method B to give a solid (5.5 mg). Calcd for C22H16F6N2O2: 454.1116, found 454.1116.

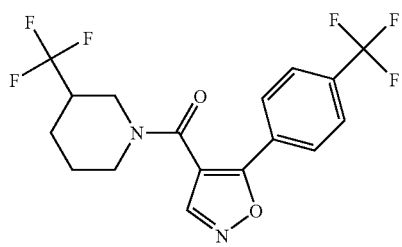

Example 117

3-(Trifluoromethyl)-1-({5-[4-(trifluoromethyl)phenyl]isoxazol-4-yl}carbonyl)piperidine The title compound was prepared from 5-(4-trifluoromethylphenyl)isoxazole-4-carboxylic acid (12.9 mg, 0.050 mmol) and DL-3-(trifluoromethyl)piperidine (9.2 mg, 0.060 mmol) as described in synthetic method C and thereafter purified by preparative HPLC method B to give a solid (11.8 mg). Calcd for C17H14F6N2O2: 392.0959, found 392.0959.

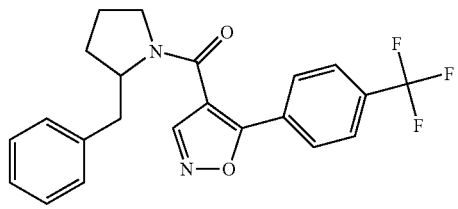

Example 118

4-[(2-Benzylpyrrolidin-1-yl)carbonyl]-5-[4-(trifluoromethyl)phenyl]isoxazole

The title compound was prepared from 5-(4-trifluoromethylphenyl)isoxazole-4-carboxylic acid (12.9 mg, 0.050 mmol) and 2-benzylpyrrolidine (9.7 mg, 0.060 mmol) as described in synthetic method C and thereafter purified by preparative HPLC method B to give a solid (12.5 mg). Calcd for C22H19F3N2O2: 400.1399, found 400.1398.

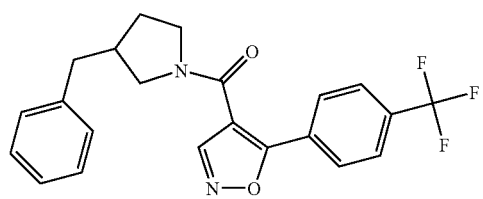

Example 119

4-[(3-Benzylpyrrolidin-1-yl)carbonyl]-5-[4-(trifluoromethyl)phenyl]isoxazole

The title compound was prepared from 5-(4-trifluoromethylphenyl)isoxazole-4-carboxylic acid (12.9 mg, 0.050 mmol) and 3-benzylpyrrolidine (9.7 mg, 0.060 mmol) as described in synthetic method C and thereafter purified by preparative HPLC method B to give a solid (11.3 mg). Calcd for C22H19F3N2O2: 400.1399, found 400.1402.

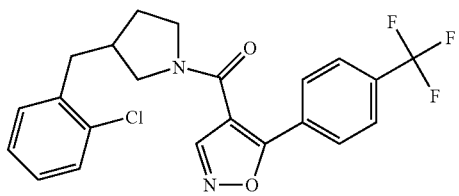

Example 120

4-{[3-(2-Chlorobenzyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and 3-(2-chlorobenzyl)pyrrolidine oxalate (17.1 mg, 0.060 mmol) as described in synthetic method C and thereafter purified by preparative HPLC method B to give a solid (9.2 mg). Calcd for C22H18ClF3N2O2: 434.1009, found 434.1000.

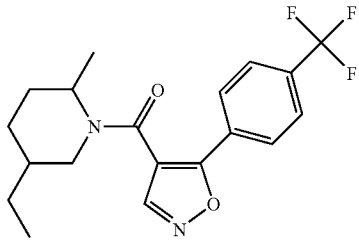

Example 121

5-Ethyl-2-methyl-1-({5-[4-(trifluoromethyl)phenyl]isoxazol-4-yl}carbonyl)piperidine The title compound was prepared from 5-(4-trifluoromethylphenyl)isoxazole-4-carboxylic acid (12.9 mg, 0.050 mmol) and 5-ethyl-2-methylpiperidine (7.6 mg, 0.060 mmol) as described in synthetic method C and thereafter purified by preparative HPLC method B to give a solid (5.3 mg). Calcd for $C19H21F_3N2O2$: 366.1555, found 366.1552.

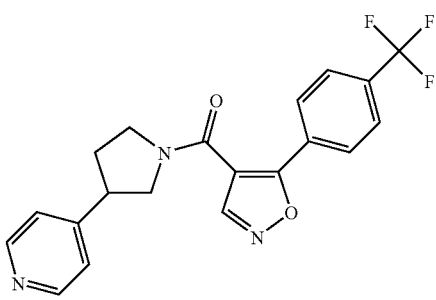

Example 122

4-[1-({5-[4-(Trifluoromethyl)phenyl] isoxazol-4-yl}carbonyl)pyrrolidin-3-yl]pyridine The title compound was prepared from 5-(4-trifluoromethylphenyl)isoxazole-4-carboxylic acid (12.9 mg, 0.050 mmol) and 4-pyrrolidin-3-ylpyridine hydrochloride (11.1 mg, 0.060 mmol) as described in synthetic method C and thereafter purified by preparative HPLC method B to give a solid (11.6 mg). Calcd for C20H16F3N3O2: 387.1195, found 387.1193.

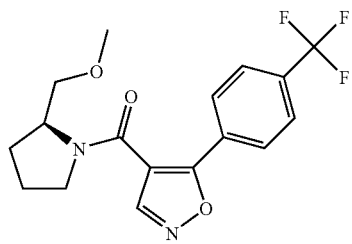

Example 123

4-{[(2S)-2-(Methoxymethyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and (S)-2-methoxymethyl-pyrrolidine (6.9 mg, 0.060 mmol) as described in synthetic method C and thereafter purified by preparative HPLC method B to give a solid (12.8 mg). Calcd for C17H17F3N2O3: 354.1191, found 354.1189.

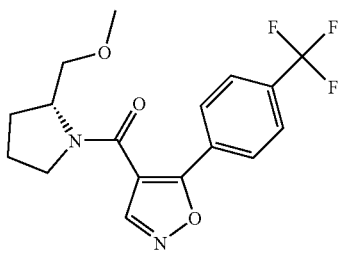

Example 124

4-{[(2R)-2-(Methoxymethyl)pyrrolidin-1-yl]carbonyl}-5-[4-(trifluoromethyl)phenyl]isoxazole The title compound was prepared from 5-(4-trifluoromethylphenyl)isoxazole-4-carboxylic acid (12.9 mg, 0.050 mmol) and (R)-2-methoxymethyl-pyrrolidine (6.9 mg, 0.060 mmol) as described in synthetic method C and thereafter purified by preparative HPLC method B to give a solid (10.1 mg). Calcd for C17H17F3N2O3: 354.1191, found 354.1190.

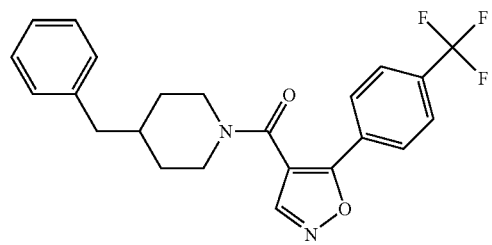

Example 125

4-Benzyl-1-({5-[4-(trifluoromethyl)phenyl]isoxazol-4-yl}carbonyl)piperidine

The title compound was prepared from 5-(4-trifluoromethylphenyl)isoxazole-4-carboxylic acid (12.9 mg, 0.050 mmol) and 4-benzylpiperidine (10.5 mg, 0.060 mmol) as described in synthetic method C and thereafter purified by preparative HPLC method B to give a solid (13.4 mg). Calcd for C23H21F3N2O2: 414.1555, found 414.1544.

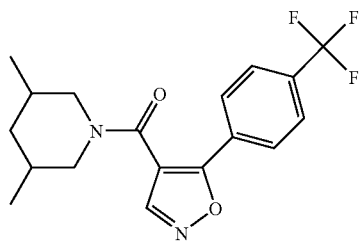

Example 126

3,5-Dimethyl-1-({5-[4-(trifluoromethyl)phenyl]isoxazol-4-yl}carbonyl)piperidine

The title compound was prepared from 5-(4-trifluoromethylphenyl)isoxazole-4-carboxylic acid (12.9 mg, 0.050 mmol) and 3,5-dimethylpiperidine (6.8 mg, 0.060 mmol) as described in synthetic method C and thereafter purified by preparative HPLC method B to give a solid (2.2 mg). Calcd for C18H19F3N2O2: 352.1399, found 352.1399.

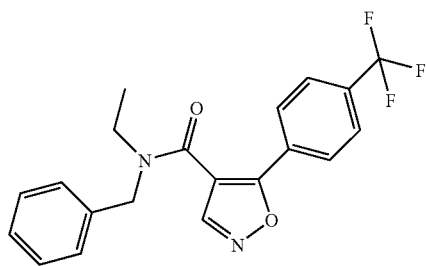

Example 127

N-Benzyl-N-ethyl-5-[4-(trifluoromethyl)phenyl]isoxazole-4-carboxamide

The title compound was prepared from 5-(4-trifluoromethylphenyl)isoxazole-4-carboxylic acid (12.9 mg, 0.050 mmol) and N-ethylbenzylamine (8.1 mg, 0.060 mmol) as described in synthetic method C and thereafter purified by preparative HPLC method B to give a solid (10.7 mg). Calcd for C20H17F3N2O2: 374.1242, found 374.1243.

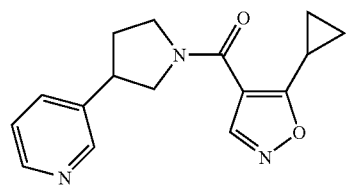

Example 128

3-{1-[(5-cyclopropylisoxazol-4-yl)carbonyl]pyrrolidin-3-yl}pyridine

A solution of 3-pyrrolidin-3-yl-pyridine (15 mg, 0.1 mmol), TBTU (48 mg, 0.15 mmol, 1.5 equ.) and N-ethyl-N-isopropylpropan-2-amine (17 µL, 0.1 mmol) in DMF (0.6 mL) was added to 5-cyclopropylisoxazole-4-carboxylic acid (15 mg, 0.1 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound (12 mg). MS (ESI, pos. ion) m/z calcd for C16H17N3O2: 283.1321, found 283.1316.

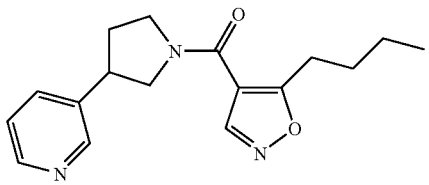

Example 129

3-{1-[(5-butylisoxazol-4-yl)carbonyl]pyrrolidin-3-yl}pyridine

A solution of 3-pyrrolidin-3-yl-pyridine (15 mg, 0.1 mmol), TBTU (48 mg, 0.15 mmol, 1.5 equ.) and N-ethyl-N-isopropylpropan-2-amine (17 µL, 0.1 mmol) in DMF (0.6 mL) was added to 5-butylisoxazole-4-carboxylic acid (17 mg, 0.1 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound (8 mg). MS (ESI, pos. ion) m/z calcd for C17H21N3O2: 299.1634, found 299.1635.

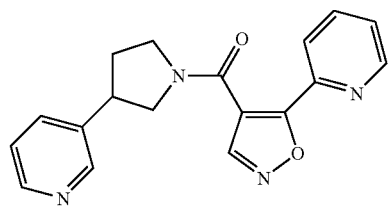

Example 130

2-{4-[(3-pyridin-3-ylpyrrolidin-1-yl)carbonyl]isoxazol-5-yl}pyridine

A solution of 3-pyrrolidin-3-yl-pyridine (15 mg, 0.1 mmol), TBTU (48 mg, 0.15 mmol, 1.5 equ.) and N-ethyl-N-isopropylpropan-2-amine (17 µL, 0.1 mmol) in DMF (0.6 mL) was added to 5-pyridin-2-ylisoxazole-4-carboxylic acid (19 mg, 0.1 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound as (12 mg). MS (ESI, pos. ion) m/z calcd for C18H16N4O2: 320.1273, found 320.1273.

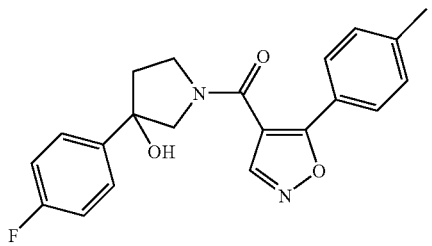

Example 131

3-(4-fluorophenyl)-1-{[5-(4-methylphenyl)isoxazol-4-yl]carbonyl}pyrrolidin-3-ol

A solution of 5-(4-methylphenyl)isoxazole-4-carboxylic acid (20 mg, 0.1 mmol), TBTU (39 mg, 0.12 mmol, 1,2 equ.) and N-ethyl-N-isopropylpropan-2-amine (35 µL, 0.2 mmol, 2 equ) in DMF (1 mL) was added to 3-(4-fluorophenyl)pyrrolidin-3-ol hydrochloride (22 mg, 0.1 mmol) and the reaction mixture was left at rt for 2 h. The solvent was evaporated and the crude product was purified by RP-HPLC. After evaporation of the solvents the product was dried in vacuum to yield the title compound (30 mg). MS (ESI, pos. ion) m/z calcd for C21H19FN2O3: 366.1380, found 366.1380.

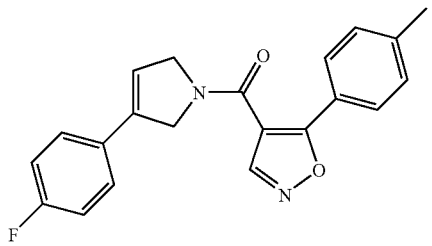

Example 132

4-{[3-(4-fluorophenyl)-2,5-dihydro-1H-pyrrol-1-yl]carbonyl}-5-(4-methylphenyl)isoxazole A solution of 5-(4-methylphenyl)isoxazole-4-carboxylic acid (20 mg, 0.1 mmol), TBTU (39 mg, 0.12 mmol, 1,2 equ.) and N-ethyl-N-isopropylpropan-2-amine (35 µL, 0.2 mmol, 2 equ) in DMF (1 mL) was added to 3-(4-fluorophenyl)-2,5-dihydro-1H-pyrrole hydrochloride (20 mg, 0.1 mmol) and the reaction mixture was left at rt for 2 h. The solvent was evaporated and the crude product was purified by RP-HPLC. After evaporation of the solvents the product was dried in vacuum to yield the title compound (11 mg). MS (ESI, pos. ion) m/z calcd for C21H17F N2O2: 348.1274, found 348.1266.

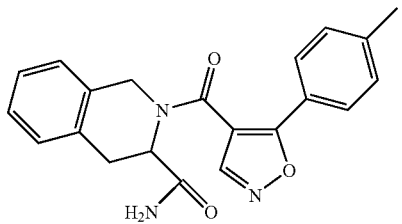

Example 133

2-{[5-(4-methylphenyl)isoxazol-4-yl]carbonyl}-1,2,3,4-tetrahydroisoquinoline-3-carboxamide A solution of 5-(4-methylphenyl)isoxazole-4-carboxylic acid (20 mg, 0.1 mmol), TBTU (39 mg, 0.12 mmol, 1,2 equ.) and N-ethyl-N-isopropylpropan-2-amine (35 µL, 0.2 mmol, 2 equ) in DMF (1 mL) was added to 1,2,3,4-tetrahydroisoquinoline-3-carboxamide (18 mg, 0.1 mmol) and the reaction mixture was left at rt for 2 h. The solvent was evaporated and the crude product was purified by RP-HPLC. After evaporation of the solvents the product was dried in vacuum to yield the title compound (8 mg). MS (ESI, pos. ion) m/z calcd for C21H19N3O3: 361.1426, found 361.1418.

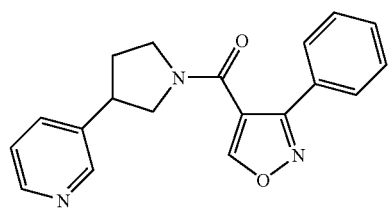

Example 134

3-{1-[(3-phenylisoxazol-4-yl)carbonyl]pyrrolidin-3-yl}pyridine

A solution of 3-pyrrolidin-3-yl-pyridine (8 mg, 0.06 mmol), TBTU (22 mg, 0.12 mmol, 1.2 equ.) and N-ethyl-N-isopropylpropan-2-amine (10 µL, 0.06 mmol) in DMF (0.6 mL) was added to 3-phenylisoxazole-4-carboxylic acid (11 mg, 0.06 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound (12 mg). MS (ESI, pos. ion) m/z calcd for C19H17N3O2: 319.1321, found 319.1326.

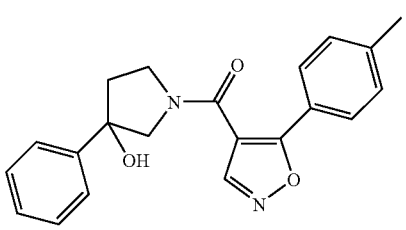

Example 135

1-{[5-(4-methylphenyl)isoxazol-4-yl]carbonyl}-3-phenylpyrrolidin-3-ol

A solution of 5-(4-methylphenyl)isoxazole-4-carboxylic acid (10 mg, 0.05 mmol), TBTU (19 mg, 0.06 mmol, 1,2 equ.) and N-ethyl-N-isopropylpropan-2-amine (26 µL, 0.15 mmol, 3 equ) in DMF (0.3 mL) was added to 3-phenylpyrrolidine hydrochloride (10 mg, 0.05 mmol) and the reaction mixture was left at rt for 2 h. The solvent was evaporated and the crude product was purified by RP-HPLC. After evaporation of the solvents the product was dried in vacuum to yield the title compound (7 mg). MS (ESI, pos. ion) m/z calcd for C21H20N2O3: 348.1474, found 348.1470.

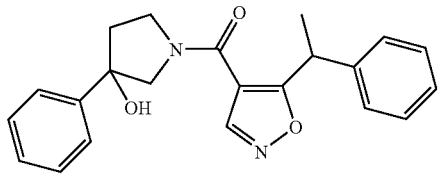

Example 136

3-phenyl-1-{[5-(1-phenylethyl)isoxazol-4-yl]carbonyl}pyrrolidin-3-ol

A solution of 5-(1-phenylethyl)isoxazole-4-carboxylic acid (11 mg, 0.05 mmol) TBTU (19 mg, 0.06 mmol, 1,2 equ.) and N-ethyl-N-isopropylpropan-2-amine (26 μL, 0.15 mmol, 3 equ) in DMF (0.3 mL) was added to 3-phenylpyrrolidine hydrochloride (10 mg, 0.05 mmol) and the reaction mixture was left at rt for 2 h. The solvent was evaporated and the crude product was purified by RP-HPLC. After evaporation of the solvents the product was dried in vacuum to yield the title compound (5 mg). MS (ESI, pos. ion) m/z calcd for C22H22N2O3: 362.1630, found 362.1627.

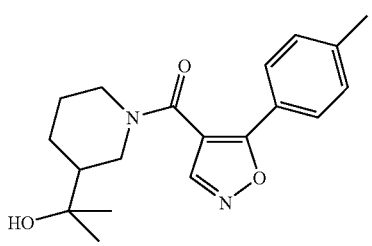

Example 137

2-(1-{[5-(4-methylphenyl)isoxazol-4-yl]carbonyl}piperidin-3-yl)propan-2-ol

A solution of 5-(4-methylphenyl)isoxazole-4-carboxylic acid (10 mg, 0.05 mmol), TBTU (19 mg, 0.06 mmol, 1,2 equ.) and N-ethyl-N-isopropylpropan-2-amine (17 μL, 0.10 mmol, 2 equ) in DMF (0.3 mL) was added to 2-piperidin-3-ylpropan-2-ol hydrochloride (9 mg, 0.05 mmol) and the reaction mixture was left at rt for 2 h. The solvent was evaporated and the crude product was purified by RP-HPLC. After evaporation of the solvents the product was dried in vacuum to yield the title compound (9 mg). MS (ESI, pos. ion) m/z calcd for C19H24N2O3: 328.1787, found 328.1787.

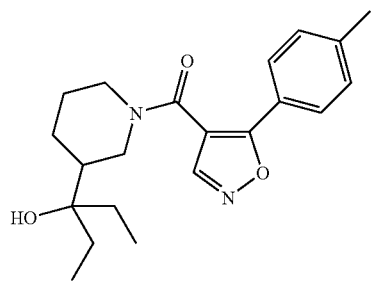

Example 138

3-(1-{[5-(4-methylphenyl)isoxazol-4-yl]carbonyl}piperidin-3-yl)pentan-3-ol

A solution of 5-(4-methylphenyl)isoxazole-4-carboxylic acid (10 mg, 0.05 mmol), TBTU (19 mg, 0.06 mmol, 1,2 equ.) and N-ethyl-N-isopropylpropan-2-amine (17 μL, 0.010 mmol, 2 equ) in DMF (0.3 mL) was added to 3-piperidin-3-ylpentan-3-ol hydrochloride (10 mg, 0.05 mmol) and the reaction mixture was left at rt for 2 h. The solvent was evaporated and the crude product was purified by RP-HPLC. After evaporation of the solvents the product was dried in vacuum to yield the title compound (8 mg). MS (ESI, pos. ion) m/z calcd for C21H28N2O3: 356.2100, found 356.2099.

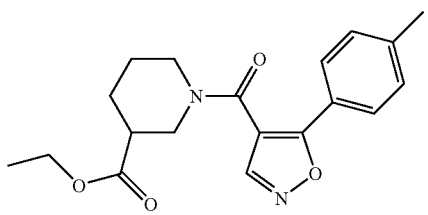

Example 139

Ethyl 1-{[5-(4-methylphenyl)isoxazol-4-yl]carbonyl}piperidine-3-carboxylate

A solution of 5-(4-methylphenyl)isoxazole-4-carboxylic acid (10 mg, 0.05 mmol), TBTU (19 mg, 0.06 mmol, 1,2 equ.) and N-ethyl-N-isopropylpropan-2-amine (17 μL, 0.10 mmol, 2 equ) in DMF (0.3 mL) was added to piperidine-3-carboxylate (8 mg, 0.05 mmol) and the reaction mixture was left at rt for 2 h. The solvent was evaporated and the crude product was purified by RP-HPLC. After evaporation of the solvents the product was dried in vacuum to yield the title compound (10 mg). MS (ESI, pos. ion) m/z calcd for C19H22N2O4: 342.1580, found 342.1585

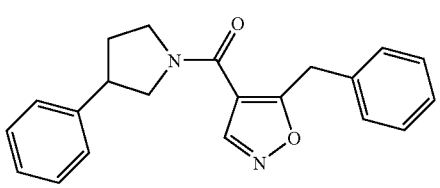

Example 140

5-benzyl-4-[(3-phenylpyrrolidin-1-yl)carbonyl]isoxazole

A solution of 5-benzylisoxazole-4-carboxylic acid (10 mg, 0.05 mmol), TBTU (19 mg, 0.06 mmol, 1,2 equ.) and N-ethyl-N-isopropylpropan-2-amine (17 µL, 0.10 mmol, 2 equ) in DMF (0.3 mL) was added to 3-phenylpyrrolidine (7 mg, 0.05 mmol) and the reaction mixture was left at rt for 2 h. The solvent was evaporated and the crude product was purified by RP-HPLC. After evaporation of the solvents the product was dried in vacuum to yield the title compound (3 mg). MS (ESI, pos. ion) m/z calcd for C21H20N2O2: 332.1525, found 332.1524.

Example 141

1-[(5-benzylisoxazol-4-yl)carbonyl]-3-phenylpyrrolidin-3-ol

A solution of 5-benzylisoxazole-4-carboxylic acid (10 mg, 0.05 mmol), TBTU (19 mg, 0.06 mmol, 1,2 equ.) and N-ethyl-N-isopropylpropan-2-amine (17 µL, 0.10 mmol, 2 equ) in DMF (0.3 mL) was added to 3-phenylpyrrolidin-3-ol hydrochloride (10 mg, 0.05 mmol) and the reaction mixture was left at rt for 2 h. The solvent was evaporated and the crude product was purified by RP-HPLC. After evaporation of the solvents the product was dried in vacuum to yield the title compound (4 mg). MS (ESI, pos. ion) m/z calcd for C21H20N2O3: 348.1474, found 348.1481.

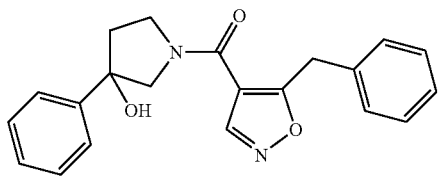

Example 142

3-{1-[(5-benzylisoxazol-4-yl)carbonyl]pyrrolidin-3-yl}pyridine

A solution of 5-benzylisoxazole-4-carboxylic acid (10 mg, 0.05 mmol), TBTU (19 mg, 0.06 mmol, 1,2 equ.) and N-ethyl-N-isopropylpropan-2-amine (17 µL, 0.10 mmol, 2 equ) in DMF (0.3 mL) was added to 3-pyrrolidin-3-yl-pyridine (7 mg, 0.05 mmol) and the reaction mixture was left at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound (3 mg). MS (ESI, pos. ion) m/z calcd for C20H19N3O2: 333.1477, found 333.1477.

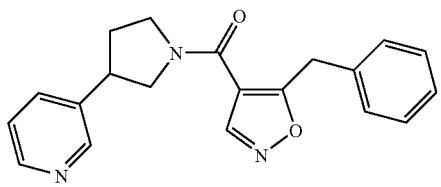

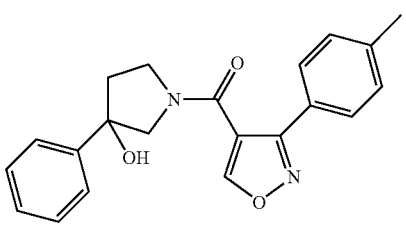

Example 143

1-{[3-(4-methylphenyl)isoxazol-4-yl]carbonyl}-3-phenylpyrrolidin-3-ol

A solution of 3-phenylpyrrolidin-3-ol (8 mg, 0.039 mmol), TBTU (15 mg, 0.047 mmol, 1.2 equ.) and N-ethyl-N-isopropylpropan-2-amine (14 µL, 0,079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (8 mg). MS (ESI, pos. ion) m/z Calcd for C21H20N2O3: 348.1474, found 348.1465.

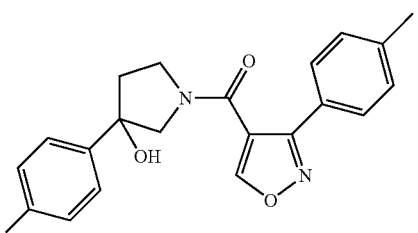

Example 144

3-(4-fluorophenyl)-1-{[3-(4-methylphenyl)isoxazol-4-yl]carbonyl}pyrrolidin-3-ol A solution of 3-(4-fluorophenyl)pyrrolidin-3-ol (9 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (10 mg). MS (ESI, pos. ion) m/z calcd for C21H19FN2O3: 366.1380, found 366.1381.

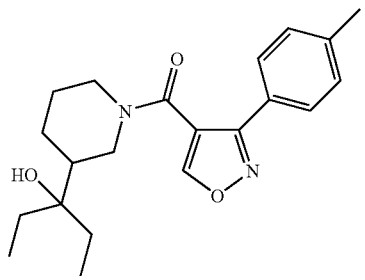

Example 145

3-(1-{[3-(4-methylphenyl)isoxazol-4-yl]carbonyl}piperidin-3-yl)pentan-3-ol

A solution of 3-piperidin-3-ylpentan-3-ol hydrochloride (8 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (8 mg). MS (ESI, pos. ion) m/z calcd for C21H28N2O3: 356.2100, found 356.2098.

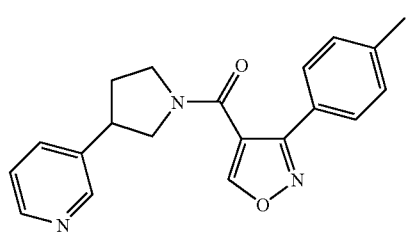

Example 146

3-(1-{[3-(4-methylphenyl)isoxazol-4-yl]carbonyl}pyrrolidin-3-yl)pyridine

A solution of 3-pyrrolidin-3-ylpyridine (6 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na2SO4) and evaporated and dried in vacuum to yield the title compound (8 mg). MS (ESI, pos. ion) m/z calcd for C20H19N3O2: 333.1477, found 333.1479.

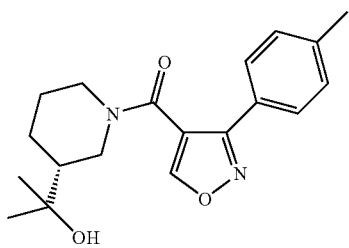

Example 147

2-((3R)-1-{[3-(4-methylphenyl)isoxazol-4-yl]carbonyl}piperidin-3-yl)propan-2-ol

A solution of 2-[(3R)-piperidin-3-yl]propan-2-ol hydrochloride (7 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (10 mg). MS (ESI, pos. ion) m/z calcd for C19H24N2O3: 328.1787, found 328.1783.

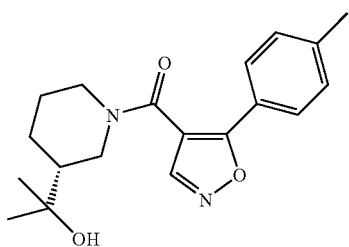

Example 148

2-((3R)-1-{[5-(4-methylphenyl)isoxazol-4-yl]carbonyl}piperidin-3-yl)propan-2-ol

A solution of 2-[(3R)-piperidin-3-yl]propan-2-ol hydrochloride (7 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 5-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (9 mg). MS (ESI, pos. ion) m/z calcd for C19H24N2O3: 328.1787, found 328.1784.

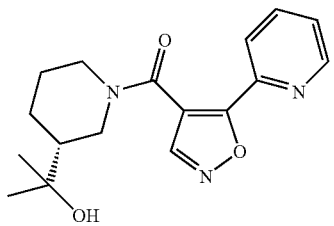

Example 149

2-{(3R)-1-[(3-pyridin-2-ylisoxazol-4-yl)carbonyl]piperidin-3-yl}propan-2-ol

A solution of 2-[(3R)-piperidin-3-yl]propan-2-ol hydrochloride (7 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 5-pyridin-2-ylisoxazole-4-carboxylic acid (7 mg, 0.039 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na$_2$SO$_4$) and evaporated and dried in vacuum to yield the title compound (6 mg). MS (ESI, pos. ion) m/z calcd for C17H21N3O3: 315.1583, found 315.1586.

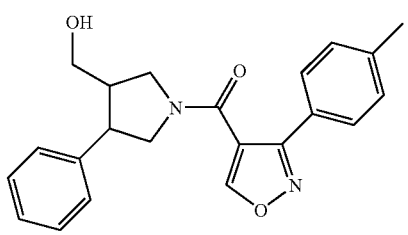

Example 150

((4R)-1-{[3-(4-methylphenyl)isoxazol-4-yl]carbonyl}-4-phenylpyrrolidin-3-yl)methanol A solution of (4-phenylpyrrolidin-3-yl)methanol (7 mg, 0.033 mmol), TBTU (13 mg, 0.039 mmol, 1.2 equ.) and N-ethyl-N-isopropylpropan-2-amine (11 µL, 0.066 mmol, 2 equ.) in DMF (0.3 mL) was added to 3-(4-methylphenyl)isoxazole-4-carboxylic acid (7 mg, 0.033 mmol) and the reaction mixture was stirred at rt for 2 h. The solvent was evaporated and the crude product was purified by RP-HPLC. After evaporation of the solvents the product was dried in vacuum to yield the title compound (5 mg). MS (ESI, pos. ion) m/z calcd for C22H22N2O3: 362.1630, found 362.1624.

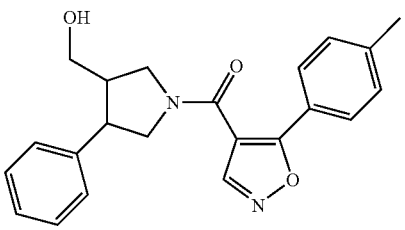

Example 151

((4R)-1-{[5-(4-methylphenyl)isoxazol-4-yl]carbonyl}-4-phenylpyrrolidin-3-yl)methanol A solution of (4-phenylpyrrolidin-3-yl)methanol (7 mg, 0.033 mmol), TBTU (13 mg, 0.039 mmol, 1.2 equ.) and N-ethyl-N-isopropylpropan-2-amine (11 µL, 0.066 mmol, 2 equ.) in DMF (0.3 mL) was added to 5-(4-methylphenyl)isoxazole-4-carboxylic acid (7 mg, 0.033 mmol) and the reaction mixture was stirred at rt for 2 h. The solvent was evaporated and the crude product was purified by RP-HPLC. After evaporation of the solvents the product was dried in vacuum to yield the title compound (4 mg). MS (ESI, pos. ion) m/z calcd for C22H22N2O3: 362.1630, found 362.1629.

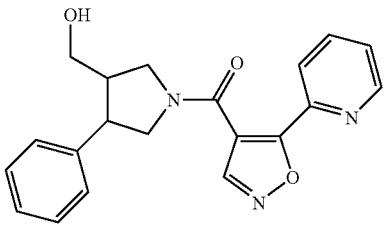

Example 152

{(4R)-4-phenyl-1-[(5-pyridin-2-ylisoxazol-4-yl)carbonyl]pyrrolidin-3-yl}methanol A solution of (4-phenylpyrrolidin-3-yl)methanol (7 mg, 0.033 mmol), TBTU (13 mg, 0.039 mmol, 1.2 equ.) and N-ethyl-N-isopropylpropan-2-amine (11 µL, 0.066 mmol, 2 equ.) in DMF (0.3 mL) was added to 5-pyridin-2-ylisoxazole-4-carboxylic acid (6 mg, 0.033 mmol) and the reaction mixture was stirred at rt for 2 h. The solvent was evaporated and the crude product was purified by RP-HPLC. After evaporation of the solvents from the pure fractions, the residue was dissolved in chloroform and washed with diluted NaOH to provide the neutral compound in the organic phase that was dried (Na$_2$SO$_4$) and evaporated and dried in vacuum to yield the title compound (3 mg). MS (ESI, pos. ion) m/z calcd for C20H19N3O3: 349.1426, found 349.1427.

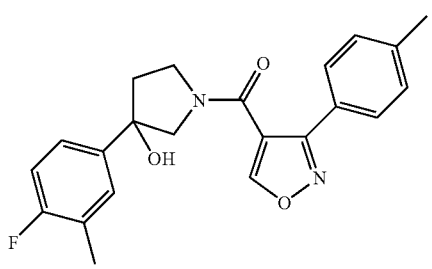

Example 153

3-(4-fluoro-3-methylphenyl)-1-{[3-(4-methylphenyl)isoxazol-4-yl]carbonyl}pyrrolidin-3-ol A solution of 3-(4-fluoro-3-methylphenyl)pyrrolidin-3-ol hydrochloride (9 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (12 mg). MS (ESI, pos. ion) m/z calcd for C22H21FN2O3: 380.1536, found 380.1532.

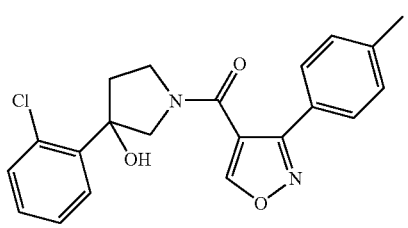

Example 154

3-(2-chlorophenyl)-1-{[3-(4-methylphenyl)isoxazol-4-yl]carbonyl}pyrrolidin-3-ol

A solution of 3-(2-chlorophenyl)pyrrolidin-3-ol hydrochloride (9 mg, 0.039 mmol), TBTU (15 mg, 0.047 mmol, 1.2 equ.) and N-ethyl-N-isopropylpropan-2-amine (14 µL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (11 mg). MS (ESI, pos. ion) m/z calcd for C21H19ClN2O3: 382.1084, found 382.1080.

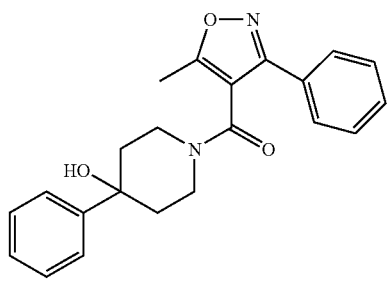

Example 155

1-[(5-Methyl-3-phenylisoxazol-4-yl)carbonyl]-4-phenylpiperidin-4-ol

5-Methyl-3-phenylisooxazole-4-carboxylic acid (40 mg, 0.197 mmol), 4-hydroxy-4-phenylpiperidine (28.8 mg, 0.151 mmol), 1-ethyl-3-(3-dimethylaminopropyl)carbodiimide hydrochloride (37.7 mg, 0.197 mmol) and triethylamine (59.8 mg, 0.591 mmol) were mixed in dichloromethane (2 mL) and stirred at room temperature over night. Solvent was evaporated in vacuo, and the residue was taken up in methanol (1 mL), filtered and purified by preparative chromatography. The combined fractions were partitioned between NaHCO3 (sat) and ethylacetate. The organic layer was washed with water and concentrated in vacuo to afford the title compound. HRMS (ESI, pos. ion) m/z calcd for $C_{22}H_{22}N_2O_3$: 362.1630, found 362.1627.

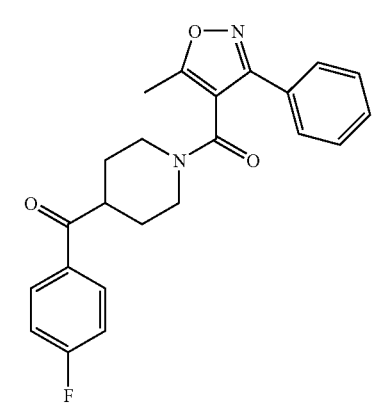

Example 156

(4-Fluorophenyl){1-[(5-methyl-3-phenylisoxazol-4-yl)carbonyl]piperidin-4-yl}methanone 5-Methyl-3-phenylisooxazole-4-carboxylic acid (40 mg, 0.197 mmol), 4-(4-Fluorobenzoyl)piperidine hydrochloride (31.4 mg, 0.151 mmol), 1-ethyl-3-(3-dimethylaminopropyl)carbodiimide hydrochloride (37.7 mg, 0.197 mmol) and triethylamine (59.8 mg, 0.591 mmol) were mixed in dichloromethane (2 ml) and stirred at room temperature over night. Solvent was evaporated in vacuo, and the residue was taken up in methanol (1 mL), filtered and purified by preparative chromatography. The fractions were partitioned between NaHCO3 (sat) and ethylacetate. The organic layer was washed with water and concentrated in vacuo to afford the title compound. HRMS (ESI, pos. ion) m/z calcd for $C_{23}H_{21}FN_2O_3$: 392.1536, found 392.1542.

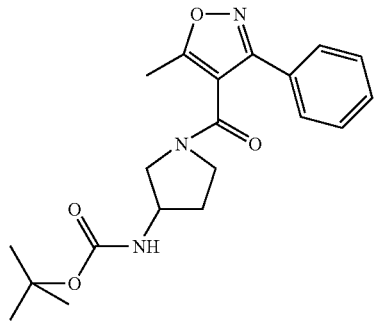

Example 157 tert-butyl {1-[(5-methyl-3-phenylisoxazol-4-yl)carbonyl]pyrrolidin-3-yl}carbamate 5-Methyl-3-phenylisooxazole-4-carboxylic acid (40 mg, 0.197 mmol), 3-(teroom temperature-Butoxycarbonylamino)pyrrolidine (40 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for $C_{20}H_{25}N_3O_4$: 371.1845, found 371.1851.

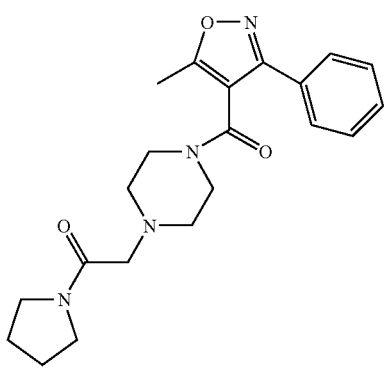

Example 158

1-[(5-Methyl-3-phenylisoxazol-4-yl)carbonyl]-4-(2-oxo-2-pyrrolidin-1-ylethyl)piperazine 5-Methyl-3-phenylisooxazole-4-carboxylic acid (40 mg, 0.197 mmol), piperazine acetic acid pyrrolidid (42.4 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for $C_{21}H_{26}N_4O_3$: 382.2005, found 382.2016.

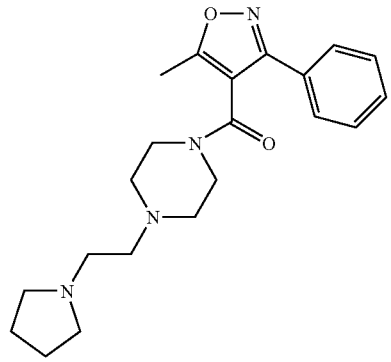

Example 159

1-[(5-Methyl-3-phenylisoxazol-4-yl)carbonyl]-4-(2-pyrrolidin-1-ylethyl)piperazine 5-Methyl-3-phenylisooxazole-4-carboxylic acid (40 mg, 0.197 mmol), 1-(2-(1-Pyrrolidinyl)-ethyl)-piperazine (39.4 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for $C_{21}H_{28}N_4O_2$: 368.2212, found 368.2217.

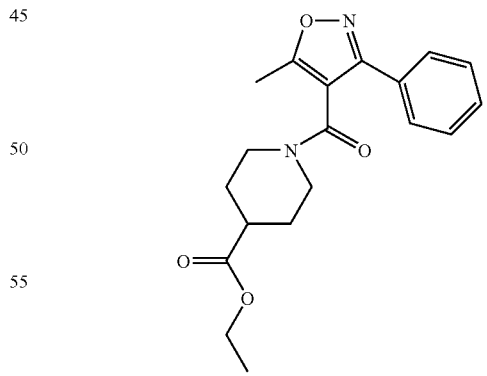

Example 160

Ethyl 1-[(5-methyl-3-phenylisoxazol-4-yl)carbonyl]piperidine-4-carboxylate

5-Methyl-3-phenylisooxazole-4-carboxylic acid (40 mg, 0.197 mmol), ethyl isonipecotate (33.8 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{19}$H$_{22}$N$_2$O$_4$: 342.1580, found 342.1578.

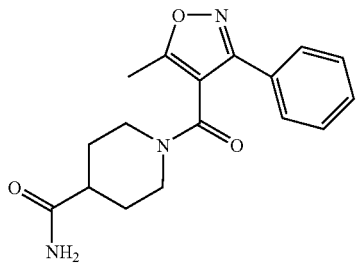

Example 161

1-[(5-Methyl-3-phenylisoxazol-4-yl)carbonyl]piperidine-4-carboxamide

5-Methyl-3-phenylisooxazole-4-carboxylic acid (40 mg, 0.197 mmol), isonipecotamide (27.5 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{17}$H$_{19}$N$_3$O$_3$: 313.1426, found 313.1431.

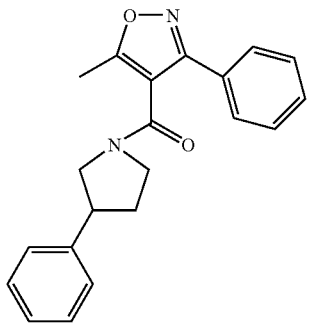

Example 162

5-methyl-3-phenyl-4-[(3-phenylpyrrolidin-1-yl)carbonyl]isoxazole

5-Methyl-3-phenylisooxazole-4-carboxylic acid (40 mg, 0.197 mmol), 3-phenyl-pyrrolidine (31.6 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{21}$H$_{20}$N$_2$O$_2$: 332.1525, found 332.1539.

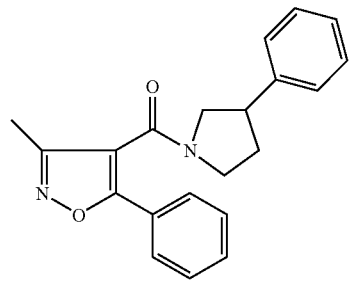

Example 163

3-methyl-5-phenyl-4-[(3-phenylpyrrolidin-1-yl)carbonyl]isoxazole

3-Methyl-5-phenyl-4-isoxazolecarboxylic acid (40 mg, 0.197 mmol), 3-phenyl-pyrrolidine (31.6 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.5 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{21}$H$_{20}$N$_2$O$_2$: 332.1525, found 332.1535.

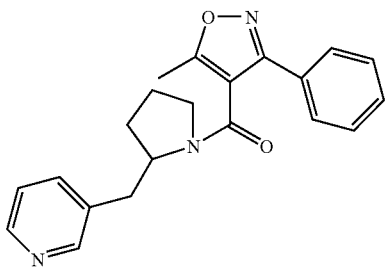

Example 164

3-({1-[(5-Methyl-3-phenylisoxazol-4-yl)carbonyl]pyrrolidin-2-yl}methyl)pyridine

5-Methyl-3-phenylisooxazole-4-carboxylic acid (40 mg, 0.197 mmol), 3-(pyrrolidin-2-ylmethyl)pyridine (50.5 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{21}$H$_{21}$N$_3$O$_2$: 349.1426, found 349.1693.

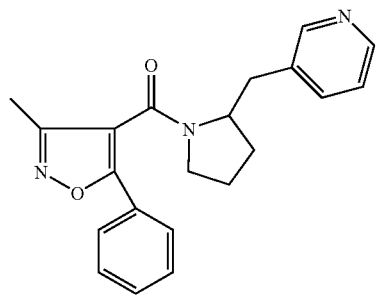

Example 165

3-({1-[(3-methyl-5-phenylisoxazol-4-yl)carbonyl]pyrrolidin-2-yl}methyl)pyridine

3-Methyl-5-phenyl-4-isoxazolecarboxylic acid (40 mg, 0.197 mmol), 3-(pyrrolidin-2-ylmethyl)pyridine (50.5 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{21}$H$_{21}$N$_3$O$_2$: 347.1634, found 347.1642.

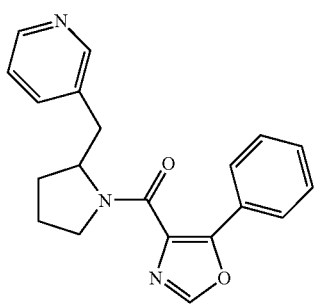

Example 166

3-({1-[(5-Phenyl-1,3-oxazol-4-yl)carbonyl]pyrrolidin-2-yl}methyl)pyridine

5-Phenyl-1,3-oxazole-4-carboxylic acid (40 mg, 0.211 mmol), 3-(pyrrolidin-2-ylmethyl)pyridine (50.5 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{20}$H$_{19}$N$_3$O$_2$: 333.1477, found 333.1484.

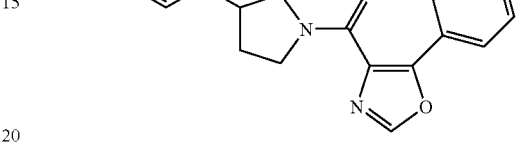

Example 167

5-phenyl-4-[(3-phenylpyrrolidin-1-yl)carbonyl]-1,3-oxazole

5-Phenyl-1,3-oxazole-4-carboxylic acid (40 mg, 0.211 mmol), 3-Phenyl-pyrrolidine (31.6 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for C$_{20}$H$_{18}$N$_2$O$_2$: 318.1368, found 318.1377.

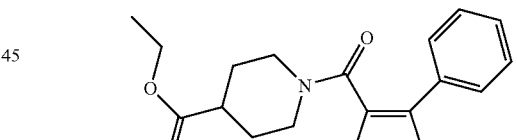

Example 168

Ethyl 1-[(5-phenyl-1,3-oxazol-4-yl)carbonyl]piperidine-4-carboxylate

5-Phenyl-1,3-oxazole-4-carboxylic acid (40 mg, 0.211 mmol), ethyl isonipecotate (36.2 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for $C_{18}H_{20}N_2O_4$: 328.1423, found 328.1430.

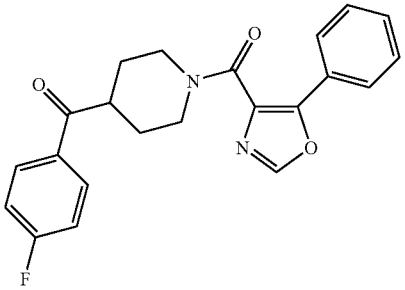

Example 169

(4-Fluorophenyl){1-[(5-phenyl-1,3-oxazol-4-yl)carbonyl]piperidin-4-yl}methanone

5-Phenyl-1,3-oxazole-4-carboxylic acid (40 mg, 0.211 mmol), 4-(4-Fluorobenzoyl)piperidine hydrochloride (56.2 mg, 0.215 mmol), O-(benzotriazol-1-yl)-N,N,N',N'-tetramethyluronium tetrafluoroborate (86.2 mg, 0.268 mmol) and diisopropylethylamine (25.4 mg, 0.197 mmol) were mixed in dimethylformamide (1.0 mL) and stirred at room temperature. Solvent was evaporated in vacuo, and the residue was taken up in methanol (1 mL), filtered and purified by preparative chromatography. The combined fractions were partitioned between NaHCO$_3$ (sat) and ethylacetate. The organic layer was washed with water and concentrated in vacuo to afford the title compound. HRMS (ESI, pos. ion) m/z calcd for $C_{22}H_{19}FN_2O_3$: 378.1380, found 378.1384.

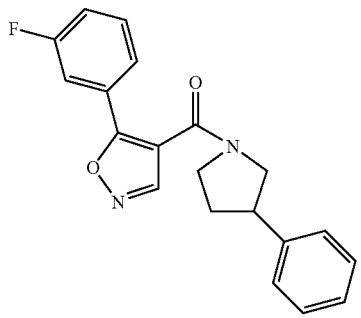

Example 170

5-(3-fluorophenyl)-4-[(3-phenylpyrrolidin-1-yl)carbonyl]isoxazole 5-(3-fluorophenyl)-isoxazole-4-carboxylic acid (47.8 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for $C_{20}H_{17}FN_2O_2$: 336.1274, found 336.1277.

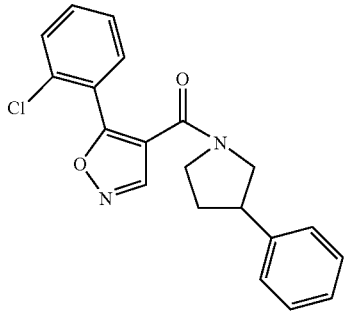

Example 171

5-(2-Chlorophenyl)-4-[(3-phenylpyrrolidin-1-yl)carbonyl]isoxazole 5-(2-chlorophenyl)-isoxazole-4-carboxylic acid (51.6 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/Acetic acid (pH 4) and ethyl acetate. The organic fractions were washed with H$_2$O/brine and concentrated in vacuo to afford the title compound. HRMS (ESI, pos. ion) m/z calcd for $C_{20}H_{17}ClN_2O_2$: 352.0979, found 352.0980.

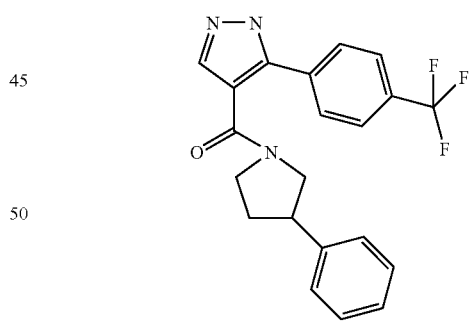

Example 172

4-[(3-phenylpyrrolidin-1-yl)carbonyl]-5-[4-(trifluoromethyl)phenyl]-1H-pyrazole

1-Phenyl-5-(4-trifluoromethyl)phenylpyrazole-4-carboxylic acid (59.1 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{18}$F$_3$N$_3$O: 385.1402, found 385.1402.

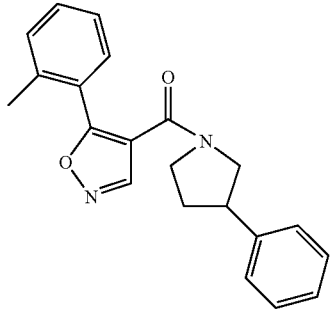

Example 173

5-(2-methylphenyl)-4-[(3-phenylpyrrolidin-1-yl)carbonyl]isoxazole 5-(2-methylphenyl)-isoxazole-4-carboxylic acid (46.9 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{20}$N$_2$O$_2$: 332.1525, found 332.1531.

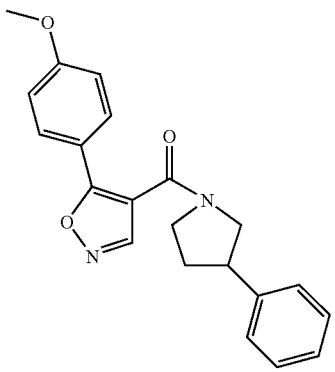

Example 174

5-(4-Methoxyphenyl)-4-[(3-phenylpyrrolidin-1-yl)carbonyl]isoxazole 5-(4-methoxyphenyl)-isoxazole-4-carboxylic acid (50.6 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{20}$N$_2$O$_3$: 348.1474, found 348.1483.

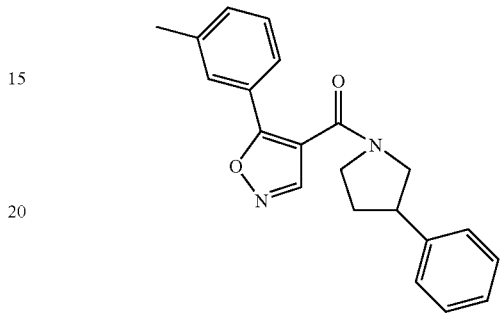

Example 175

5-(3-methylphenyl)-4-[(3-phenylpyrrolidin-1-yl)carbonyl]isoxazole 5-(3-methylphenyl)-isoxazole-4-carboxylic acid (46.9 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{20}$N$_2$O$_2$: 332.1525, found 332.1531.

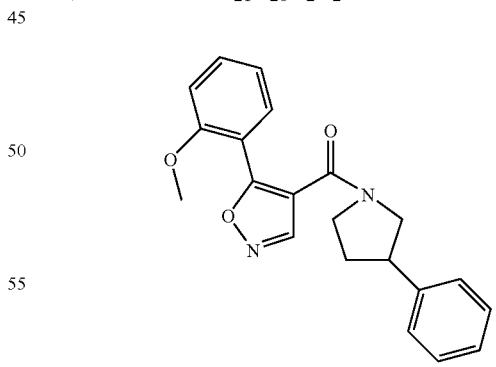

Example 176

5-(2-methoxyphenyl)-4-[(3-phenylpyrrolidin-1-yl)carbonyl]isoxazole 5-(2-methoxyphenyl)-isoxazole-4-carboxylic acid (50.6 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{20}$N$_2$O$_3$: 348.1474, found 348.1479.

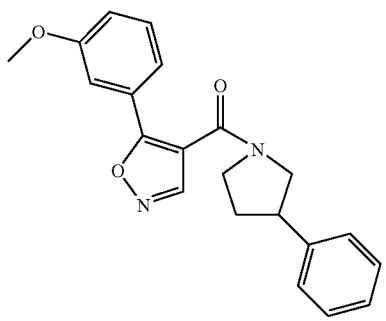

Example 177

5-(3-Methoxyphenyl)-4-[(3-phenylpyrrolidin-1-yl)carbonyl]isoxazole 5-(3-methoxyphenyl)-isoxazole-4-carboxylic acid (50.6 mg, 0.231 mmol), 3-phenylpyrrolidine (40 mg, 0.271 mmol), O-(benzotriazol-1-yl)-N,N,N',N'-tetramethyluronium tetrafluoroborate (92.6 mg, 0.288 mmol) and diisopropylethylamine (49.7 mg, 0.384 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc:petroleum ether). The combined fractions were partitioned between H$_2$O/acetic acid (pH 4) and ethyl acetate. The organic fractions were washed with H$_2$O/brine and concentrated in vacuo to afford the title compound. HRMS (ESI, pos. ion) m/z calcd for C$_{21}$H$_{20}$N$_2$O$_3$: 348.1474, found 348.1482.

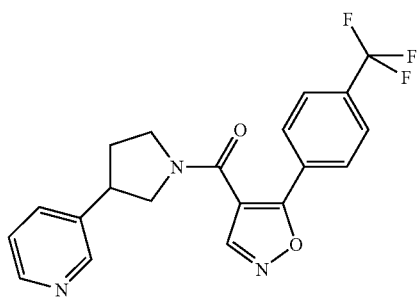

Example 178

3-[1-({5-[4-(trifluoromethyl)phenyl]isoxazol-4-yl}carbonyl)pyrrolidin-3-yl]pyridine Example 179

(a) 2-(3-trifluoromethyl)benzoyl-3-dimethylamino-acrylic acid ethyl ester

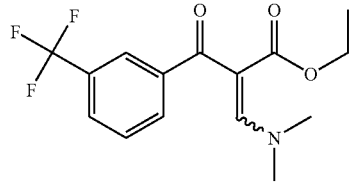

DMF/DMA (0.73 g, 0.004 mol) was added to a solution of ethyl (3-trifluoromethylbenzoyl)acetate (1.0 g, 0.004 mol) in toluene (5 mL). The resulting solution was heated in a sealed tube at 60° C. over night. Removal of solvents gave the crude product, which was used directly to synthesize 5-(3-trifluoromethyl)-isoxazole-4-carboxylic acid ethyl ester in the next step. MS ESI, pos. ion) m/z: 316.

Example 180

(b) 5-(3-trifluoromethyl)-isoxazole-4-carboxylic acid ethyl ester

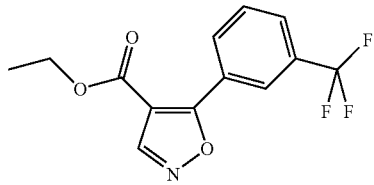

Hydroxylamine HCl (48.5 mg, 0.698 mmol) and sodium carbonate (37.7 mg, 0.355 mmol) were added to a solution of 2-(2-trifluoromethyl)benzoyl-3-dimethylamino-acrylic acid ethyl ester (200.0 mg, 0.634 mmol) in MeOH:H$_2$O (40:20) at ROOM TEMPERATURE. The mixture was acidified to pH 4-5 using glacial acetic acid (8 drops) and heated to reflux for 3 h. The mixture was cooled, basified to pH 8 with ammonium hydroxide solution and extracted with DCM. Removal of the solvent provided a yellow gum, which was used directly in the next step. MS (ESI, pos. ion) m/z: 386.

Example 181

(c) 5-(3-trifluoromethyl)-isoxazole-4-carboxylic acid

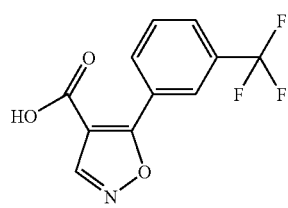

Example 182

5-(3-trifluoromethyl)-isoxazole-4-carboxylic acid ethyl ester (238 mg, 0.834 mmol) was added to HCl (conc):AcOH (1.5 mL of each) and heated in microwave for 600 s at 170° C. The reaction mixture was then added to diethylether and a saturated solution of sodiumhydrocarbonate and the organic layer was washed with $H_2O$/brine. Removal of solvent in vacuo gave the carboxylic acid intermediate. MS (ESI, pos. ion) m/z: 358.

Example 183

(d) 3-[1-({5-[4-(trifluoromethyl)phenyl]isoxazol-4-yl}carbonyl)pyrrolidin-3-yl]pyridine 5-(3-trifluoromethyl)-isoxazole-4-carboxylic acid (60.0 mg, 0.187 mmol), 3-pyrrolidin-3-ylpyridine (30.2 mg, 0.204 mmol), O-(benzotriazol-1-yl)-N,N,N',N'-tetramethyluronium tetrafluoroborate (81.7 mg, 0.255 mmol) and diisopropylethylamine (43.9 mg, 0.339 mmol) were mixed in dimethylformamide (1.5 mL) and stirred at room temperature over night. Solvent was evaporated in vacuo (0.5-1.0 mL) and the residue was taken up in dichloromethane (1 mL), filtered and purified by normal-phase chromatography (20-50% EtOAc: petroleum ether). The combined organic fractions were partitioned between $H_2O$/acetic acid (pH 4) and ethyl acetate. The organic fractions were washed with $H_2O$/brine and concentrated in vacuo to afford the title compound. MS (ESI, pos. ion) m/z: 388.

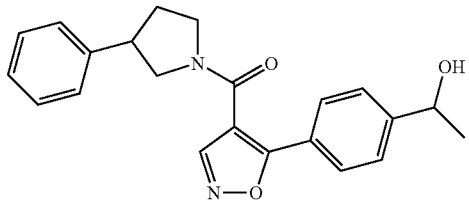

Example 184

1-(4-{4-[(3-Phenylpyrrolidin-1-yl)carbonyl] isoxazol-5-yl}phenyl)ethanol

A mixture of the styrene derivative 4-[(3-phenylpyrrolidin-1-yl)carbonyl]-5-(4-vinylphenyl)isoxazole (20 mg, 0.6 mmol), tetrabutylammonium borohydride (7 mg, 0.03 mmol) and 5,10,15,20-tetraphenyl-21H,23H-porphine cobalt(II) (Co(TPP)) (2 mg, 0.003 mmol) in 2 mL 1/1 mixture 1,2-dimethoxyethane/2-propanol was stirred overnight at ambient temperature. More borohydride was added to effect full conversion. The residue was purified on $SiO_2$ (1:1 hexane/ethyl acetate) to afford the title compound. HRMS (ESI, pos. ion) m/z calcd for $C_{22}H_{22}N_2O_3$: 362.1630, found 362.1628.

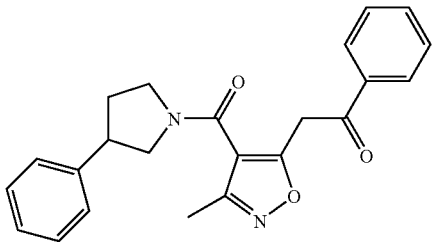

Example 185

2-{3-methyl-4-[(3-phenylpyrrolidin-1-yl)carbonyl]isoxazol-5-yl}-1-phenylethanone

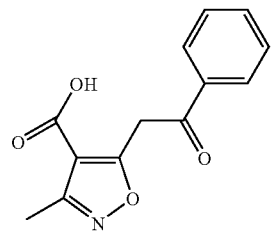

Example 186

(a) 3-methyl-5-(2-oxo-2-phenylethyl)isoxazole-4-carboxylic Acid

A solution of lithium bis(trimethylsilyl)amide (10 g, 60 mmol, 3 eq) in toluene (60 mL) was added drop wise during 15 min to a solution of 3,5-dimethylisoxazole-4-carboxylic acid (2.82 g, 20 mmol) and methyl benzoate (2.5 mL, 1 eq) in THF (20 mL) at a temperature not exceeding 40 deg. After 1 h the reaction was quenched by the addition of a water solution of 0.1M HCl (0.3 L) leaving the water phase still basic and the phases was separated. The water phase was washed with toluene and then reduced in volume by evaporation until most of the residual organic solvents were removed. 1M HCl was added dropwise with stirring. The resulting crystals were filtered and dried in vacuum to yield the title compound. 1H NMR (400 MHz, CHLOROFORM-D) δ ppm 2.45 (s, 3H) 4.75 (s, 2H) 7.43-7.51 (m, 2H) 7.55-7.63 (m, 1H) 7.86-8.12 (m, 2H)

Example 187

(b) 2-{3-methyl-4-[(3-phenylpyrrolidin-1-yl)carbonyl]isoxazol-5-yl}-1-phenylethanone A solution of TBTU (0.48 g, 1.5 mmol, 1.5 eq.) in DMF (2 mL) was added to a mixture of 3-methyl-5-(2-oxo-2-phenylethyl)isoxazole-4-carboxylic acid (0.24 g, 1 mmol, 1 eq), N-ethyl-N-isopropylpropan-2-amine (0.18 mL, 1 eq) and 3-phenylpyrrolidine (0.15 g, 1 eq) in DMF (1 mL). The resulting solution was stirred at room temperature. Chloroform (25 mL) was added and the solution was washed with water and 1 M HCl, dried (Na$_2$SO$_4$) and evaporated. The residue was purified by flash chromatography (SiO$_2$ 1:2 heptane/EtOAc) to afford the title compound. MS (ESI, POS. ION) M/Z Calcd for C$_{23}$H$_{22}$N$_2$O$_3$: 374.1630, found 374.1632.

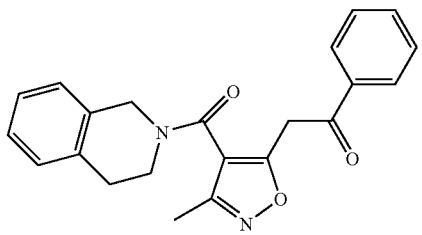

Example 188

2-[4-(3,4-dihydroisoquinolin-2(1H)-ylcarbonyl)-3-methylisoxazol-5-yl]-1-phenylethanone A solution of TBTU (0.48 g, 1.5 mmol, 1.5 eq.) in DMF (2 mL) was added to a mixture of 3-methyl-5-(2-oxo-2-phenylethyl)isoxazole-4-carboxylic acid (0.24 g, 1 mmol, 1 eq), N-ethyl-N-isopropylpropan-2-amine (0.18 mL, 1 eq) and 1,2,3,4-tetrahydroisoquinoline (0.12 mL, 1 eq) in DMF (1 mL). The resulting solution was stirred at room temperature. Chloroform (25 mL) was added and the solution was washed with water and 1 M HCl, dried (Na$_2$SO$_4$) and evaporated. The residue was purified by flash chromatography (SiO$_2$ 1:2 heptane/EtOAc) to afford the title compound. MS (ESI, POS. ION) M/Z Calcd for C$_{22}$H$_{20}$N$_2$O$_3$: 360.1474, found 360.1472.

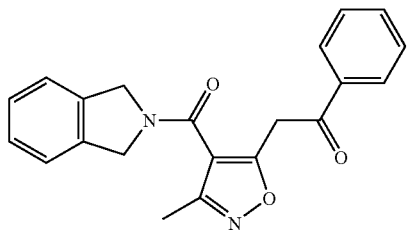

Example 189

2-[4-(1,3-dihydro-2H-isoindol-2-ylcarbonyl)-3-methylisoxazol-5-yl]-1-phenylethanone A solution of TBTU (0.48 g, 1.5 mmol, 1,5 eq.) in DMF (2 mL) was added to a mixture of 3-methyl-5-(2-oxo-2-phenylethyl)isoxazole-4-carboxylic acid (0.24 g, 1 mmol, 1 eq), N-ethyl-N-isopropylpropan-2-amine (0.18 mL, 1 eq) and isoindoline (0.11 mL, 1 eq) in DMF (1 mL). The resulting solution was stirred at room temperature. Chloroform (25 mL) was added and the solution was washed with water and 1 M HCl, dried (Na$_2$SO$_4$) and evaporated. The residue was purified by flash chromatography (SiO$_2$ 1:2 heptane/EtOAc) to afford the title compound. MS (EI) 347 (M+1)

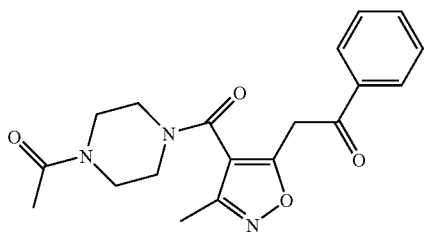

Example 190

2-{4-[(4-acetylpiperazin-1-yl)carbonyl]-3-methylisoxazol-5-yl}-1-phenylethanone

A solution of TBTU (0.48 g, 1.5 mmol, 1,5 eq.) in DMF (2 mL) was added to a mixture of 3-methyl-5-(2-oxo-2-phenylethyl)isoxazole-4-carboxylic acid (0.24 g, 1 mmol, 1 eq), N-ethyl-N-isopropylpropan-2-amine (0.18 mL, 1 eq) and 1-acetylpiperazine (0.13 g, 1 eq) in DMF (1 mL). The resulting solution was stirred at room temperature. Chloroform (25 mL) was added and the solution was washed with water and 1 M HCl, dried (Na$_2$SO$_4$) and evaporated. The residue was purified by flash chromatography (SiO$_2$ 1:2 heptane/EtOAc) to afford the title compound. MS (ESI, POS. ION) M/Z Calcd for C$_{19}$H$_{21}$N$_3$O$_4$: 355.1532, found 355.1538.

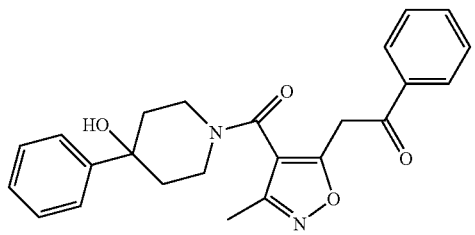

Example 191

2-{4-[(4-hydroxy-4-phenylpiperidin-1-yl)carbonyl]-3-methylisoxazol-5-yl}-1-phenylethanone A solution of TBTU (0.48 g, 1.5 mmol, 1.5 eq.) in DMF (2 mL) was added to a mixture of 3-methyl-5-(2-oxo-2-phenylethyl)isoxazole-4-carboxylic acid (0.24 g, 1 mmol, 1 eq), N-ethyl-N-isopropylpropan-2-amine (0.18 mL, 1 eq) and 4-phenylpiperidin-4-ol (0.18 g, 1 eq) in DMF (1 mL). The resulting solution was stirred at room temperature. Chloroform (25 mL) was added and the solution was washed with water and 1 M HCl, dried (Na$_2$SO$_4$) and evaporated. The residue was purified by flash chromatography (SiO$_2$ 1:2 heptane/EtOAc) to afford the title compound. MS (ESI, POS. ION) M/Z Calcd for C$_{24}$H$_{24}$N$_2$O$_4$: 404.1736, found 404.1732.

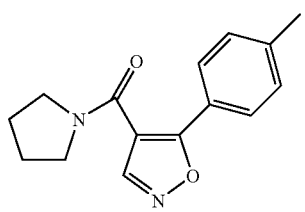

Example 192

5-(4-Methylphenyl)-4-(pyrrolidin-1-ylcarbonyl)isoxazole

To 5-(4-methylphenyl)isoxazole-4-carbonyl chloride (30 mg, 0.14 mmol) in dichloromethane (1 mL) was added pyrrolidine (11 mg, 0.16 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{15}H_{16}N_2O_2$: 256.1212, found 256.1214.

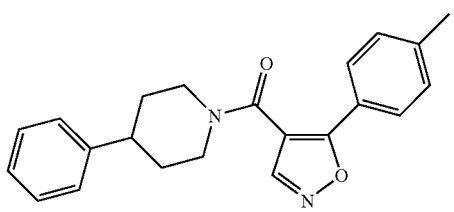

Example 193

1-{[5-(4-Methylphenyl)isoxazol-4-yl]carbonyl}-4-phenylpiperidine

To 5-(4-methylphenyl)isoxazole-4-carbonyl chloride (21 mg, 0.068 mmol) in dichloromethane (1 mL) was added 4-phenylpiperidine (17 mg, 0.068 mmol, 1 eq.), and the reaction mixture was stirred for 1 h. The solvent was removed, and the residue was purified by preparative reverse-phase HPLC to give the title compound. HRMS (ESI, pos. ion) m/z calcd for $C_{22}H_{22}N_2O_2$: 346.1681, found 346.1685.

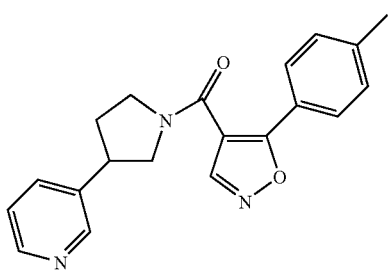

Example 194

3-(1-{[5-(4-Methylphenyl)isoxazol-4-yl]carbonyl}pyrrolidin-3-yl)pyridine

To 5-(4-methylphenyl)isoxazole-4-carbonyl chloride (15 mg, 0.068 mmol) in dichloromethane (1 mL) was added 3-pyrrolidin-3-ylpyridine (11 mg, 0.074 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{20}H_{19}N_3O_2$: 333.1477, found 333.1471.

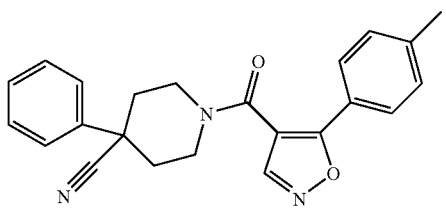

Example 195

1-{[5-(4-Methylphenyl)isoxazol-4-yl]carbonyl}-4-phenylpiperidine-4-carbonitrile

To 5-(4-methylphenyl)isoxazole-4-carbonyl chloride (10 mg, 0.045 mmol) in dichloromethane (1 mL) was added 4-phenylpiperidine-4-carbonitrile (10 mg, 0.054 mmol, 1.2 eq.), and the reaction mixture was stirred for 1 h. The solvent was removed, and the residue was purified by preparative reverse-phase HPLC to give the title compound. HRMS (ESI, pos. ion) m/z calcd for $C_{23}H_{21}N_3O_2$: 371.1634, found 371.1635.

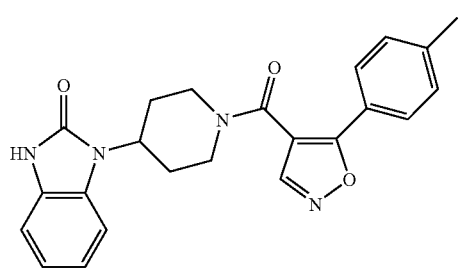

Example 196

1-(1-{[5-(4-Methylphenyl)isoxazol-4-yl]carbonyl}piperidin-4-yl)-1,3-dihydro-2H-benzimidazol-2-one To 5-(4-methylphenyl)isoxazole-4-carbonyl chloride (10 mg, 0.054 mmol) in dichloromethane (1 mL) was added 1-piperidin-4-yl-1,3-dihydro-2H-benzimidazol-2-one (10 mg, 0.046 mmol, 1 eq.), and the reaction mixture was stirred for 1 h. The solvent was removed, and the residue was purified by preparative reverse-phase HPLC to give the title compound. HRMS (ESI, pos. ion) m/z calcd for $C_{23}H_{22}N_4O_3$: 402.1692, found 402.1695.

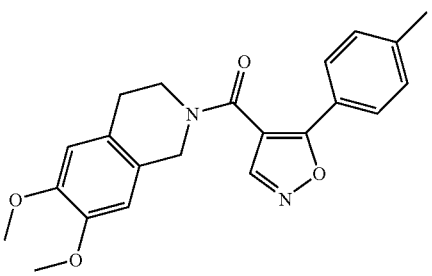

Example 197

6,7-Dimethoxy-2-{[5-(4-methylphenyl)isoxazol-4-yl]carbonyl}-1,2,3,4-tetrahydroisoquinoline

To 5-(4-methylphenyl)isoxazole-4-carbonyl chloride (10 mg, 0.045 mmol) in dichloromethane (1 mL) was added 6,7-dimethoxy-1,2,3,4-tetrahydroisoquinoline (11 mg, 0.052 mmol, 1.2 eq.), and the reaction mixture was stirred for 1 h. The solvent was removed, and the residue was purified by preparative reverse-phase HPLC to give the title compound. HRMS (ESI, pos. ion) m/z calcd for $C_{22}H_{22}N_2O_4$: 378.1580, found 378.1585.

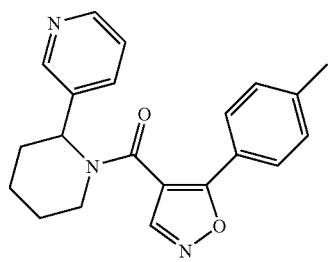

Example 198

3-(1-{[5-(4-Methylphenyl)isoxazol-4-yl]carbonyl}piperidin-2-yl)pyridine

To 5-(4-methylphenyl)isoxazole-4-carbonyl chloride (10 mg, 0.045 mmol) in dichloromethane (1 mL) was added 3-piperidin-2-ylpyridine (11 mg, 0.045 mmol, 1.0 eq), and the reaction mixture was stirred for 1 h. The solvent was removed, and the residue was purified by preparative reverse-phase HPLC to give the title compound. HRMS (ESI, pos. ion) m/z calcd for $C_{21}H_{21}N_3O_2$: 347.1634, found 347.1644.

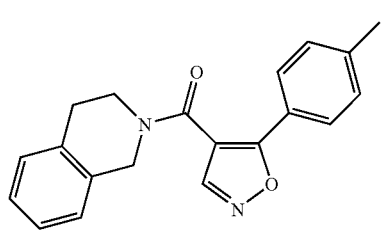

Example 199

2-{[5-(4-Methylphenyl)isoxazol-4-yl]carbonyl}-1,2,3,4-tetrahydroisoquinoline

To 5-(4-methylphenyl)isoxazole-4-carbonyl chloride (10 mg, 0.045 mmol) in dichloromethane (1 mL) was added 1,2,3,4-tetrahydroisoquinoline (6.6 mg, 0.050 mmol, 1.1 eq), and the reaction mixture was stirred for 1 h. The solvent was removed, and the residue was purified by preparative reverse-phase HPLC to give the title compound. HRMS (ESI, pos. ion) m/z calcd for $C_{20}H_{18}N_2O_2$: 318.1368, found 318.1377.

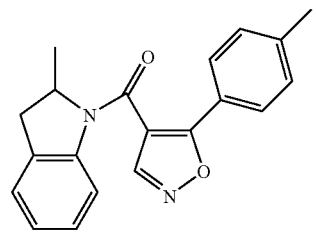

Example 200

2-Methyl-1-{[5-(4-methylphenyl)isoxazol-4-yl]carbonyl}indoline

To 5-(4-methylphenyl)isoxazole-4-carbonyl chloride (10 mg, 0.045 mmol) in dichloromethane (1 mL) was added 2-methylindoline (6.6 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{20}H_{18}N_2O_2$: 318.1368, found 318.1379.

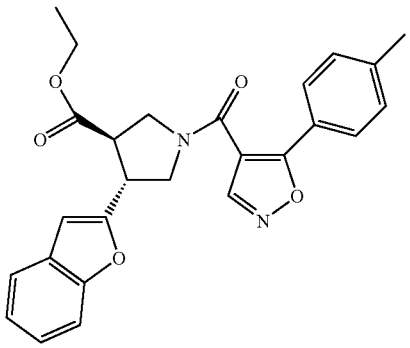

Example 201

Ethyl (±)-trans-4-(1-benzofuran-2-yl)-1-{[5-(4-methylphenyl)isoxazol-4-yl]carbonyl}pyrrolidine-3-carboxylate

To 5-(4-methylphenyl)isoxazole-4-carbonyl chloride (10 mg, 0.045 mmol) in dichloromethane (1 mL) was added ethyl (±)-trans-4-(1-benzofuran-2-yl)pyrrolidine-3-carboxylate (13 mg, 0.050 mmol, 1.1 equ.), and the reaction mixture was stirred for 1 h. The solvent was removed, and the residue was purified by preparative reverse-phase HPLC to give the title compound. HRMS (ESI, pos. ion) m/z calcd for $C_{26}H_{24}N_2O_5$: 444.1685, found 444.1693.

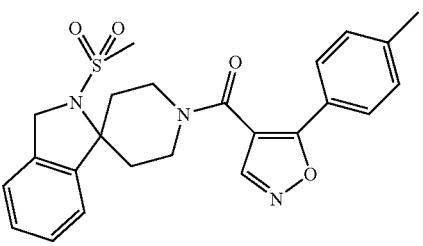

Example 202

1'-{[5-(4-Methylphenyl)isoxazol-4-yl]carbonyl}-2-(methylsulfonyl)-2,3-dihydrospiro[isoindole-1,4'-piperidine]

To 5-(4-methylphenyl)isoxazole-4-carbonyl chloride (10 mg, 0.045 mmol) in dichloromethane (1 mL) was added 2-(methylsulfonyl)-2,3-dihydrospiro[isoindole-1,4'-piperidine] (13.2 mg, 0.050 mmol, 1.1 eq), and the reaction mixture was stirred for 1 h. The solvent was removed, and the residue was purified by preparative reverse-phase HPLC to give the title compound. HRMS (ESI, pos. ion) m/z calcd for $C_{24}H_{25}N_3O_4S$: 451.1566, found 451.1567.

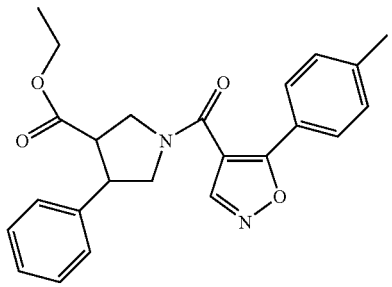

Example 203

Ethyl 1-{[5-(4-methylphenyl)isoxazol-4-yl]carbonyl}-4-phenylpiperidine-4-carboxylate To 5-(4-methylphenyl)isoxazole-4-carbonyl chloride (10 mg, 0.045 mmol) in dichloromethane (1 mL) was added ethyl 4-phenylpyrrolidine-3-carboxylate (11 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{25}H_{26}N_2O_4$: 418.1893, found 418.1893.

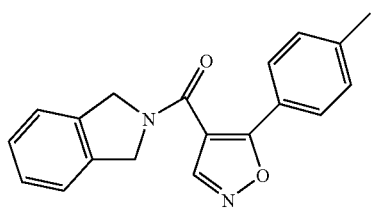

Example 204

2-{[5-(4-Methylphenyl)isoxazol-4-yl]carbonyl}isoindoline

To 5-(4-methylphenyl)isoxazole-4-carbonyl chloride (10 mg, 0.045 mmol) in dichloromethane (1 mL) was added isoindoline (5.9 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{19}H_{16}N_2O_2$: 304.1212, found 304.1222.

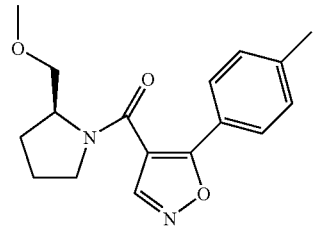

Example 205

4-{[(2S)-2-(Methoxymethyl)pyrrolidin-1-yl]carbonyl}-5-(4-methylphenyl)isoxazole

To 5-(4-methylphenyl)isoxazole-4-carbonyl chloride (10 mg, 0.045 mmol) in dichloromethane (1 mL) was added (2S)-2-(methoxymethyl)pyrrolidine (5.7 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{17}H_{20}N_2O_3$: 300.1474, found 300.1481.

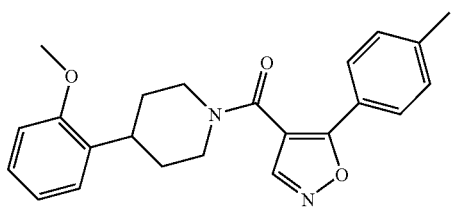

Example 206

4-(2-Methoxyphenyl)-1-{[5-(4-methylphenyl)isoxazol-4-yl]carbonyl}piperidine

To 5-(4-methylphenyl)isoxazole-4-carbonyl chloride (10 mg, 0.045 mmol) in dichloromethane (1 mL) was added 4-(2-methoxyphenyl)piperidine (9.5 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{23}H_{24}N_2O_3$: 376.1787, found 376.1790.

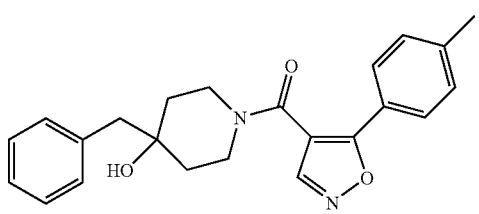

Example 207

4-Benzyl-1-{[5-(4-methylphenyl)isoxazol-4-yl]carbonyl}piperidin-4-ol

To 5-(4-methylphenyl)isoxazole-4-carbonyl chloride (10 mg, 0.045 mmol) in dichloromethane (1 mL) was added 4-benzylpiperidin-4-ol (9.5 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{23}H_{24}N_2O_3$: 376.1787, found 376.1790.

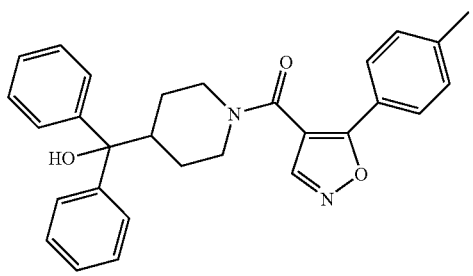

Example 208

(1-{[5-(4-Methylphenyl)isoxazol-4-yl]carbonyl}piperidin-4-yl)(diphenyl)methanol

To 5-(4-methylphenyl)isoxazole-4-carbonyl chloride (10 mg, 0.045 mmol) in dichloromethane (1 mL) was added diphenyl(piperidin-4-yl)methanol (13.3 mg, 0.074 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{29}H_{28}N_2O_3$: 452.2100, found 452.2107.

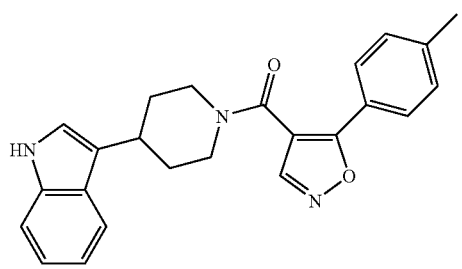

Example 209

3-(1-{[5-(4-Methylphenyl)isoxazol-4-yl]carbonyl}piperidin-4-yl)-1H-indole

To 5-(4-methylphenyl)isoxazole-4-carbonyl chloride (10 mg, 0.045 mmol) in dichloromethane (1 mL) was added 3-piperidin-4-yl-1H-indole (9.9 mg, 0.050 mmol, 1.1 eq.), and the reaction mixture was stirred for 1 h. The solvent was removed, and the residue was purified by preparative reverse-phase HPLC to give the title compound. HRMS (ESI, pos. ion) m/z calcd for $C_{24}H_{23}N_3O_2$: 385.1790, found 385.1797.

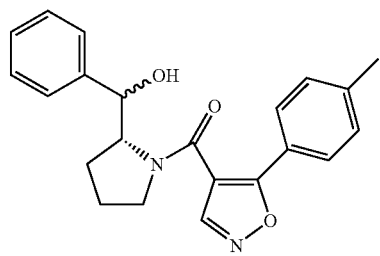

Example 210

((2R)-1-{[5-(4-Methylphenyl)isoxazol-4-yl]carbonyl}pyrrolidin-2-yl)(phenyl)methanol

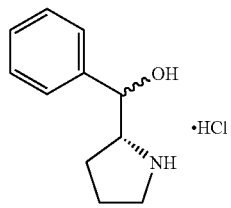

Example 211

(a) phenyl[(2R)-pyrrolidin-2-yl]methanol hydrochloride

To a solution of tert-butyl (2R)-2-formylpyrrolidine-1-carboxylate (500 mg, 2.51 mmol) in dry THF (7 mL) at −78° C. was added 1 M phenylmagnesium bromide solution in THF (7.5 mL, 7.5 mmol, 3 eq.). After stirring the reaction mixture for 2 h, saturated aqueous ammonium chloride (1.5 mL) was added. The mixture was warmed to room temperature, and water (50 mL) and ethyl acetate (25 mL) were added. The phases were separated, and the aqueous layer was extracted with ethyl acetate (25 mL). The combined organic phases were washed with 10% citric acid, brine, saturated aqueous sodium bicarbonate, and dried over $MgSO_4$. The solvent was evaporated and the residue was purified by silica gel chromatography (pentane/ethyl acetate, 7:3) to give tert-butyl (2R)-2-[hydroxy(phenyl)methyl]pyrrolidine-1-carboxylate a colorless oil. Subsequent BOC deprotection was carried out by dissolving the intermediate in ethyl acetate (3 mL) and leading a stream of HCl (g) through the solution for 20 min. The solvent was evaporated to give the title compound as a colorless oil.

Example 212

(b) ((2R)-1-{[5-(4-Methylphenyl)isoxazol-4-yl]carbonyl}pyrrolidin-2-yl)(phenyl)methanol To a solution of 5-(4-methylphenyl)isoxazole-4-carbonyl chloride (22 mg, 0.11 mmol) in acetonitrile (5 mL) was added o-(benzotriazol-1-yl)-N,N,N',N'-tetramethyluronium tetrafluoroborate (TBTU) (45 mg, 0.14 mmol, 1.3 eq.), pyridine (34 μL, 0.42 mmol, 4 eq.), and phenyl[(2R)-pyrrolidin-2-yl]methanol hydrochloride (25 mg, 0.12 mmol, 1.1 eq.). The reaction mixture was stirred at ambient temperature for 20 h and at 40° C. for an additional 2 h. The solvent was removed, and the residue was purified by preparative reverse-phase HPLC to yield the product as a white solid. HRMS (ESI, pos. ion) m/z calcd for $C_{22}H_{22}N_2O_3$: 362.1630, found 362.1625.

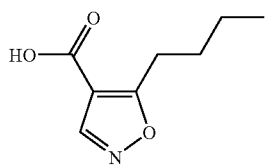

Example 213

5-Butylisoxazole-4-carboxylic acid

Methyl 3-oxoheptanoate (0.16 g, 1 mmol) and 1,1-dimethoxy-N,N-dimethylmethanamine (0.12 g, 1 mmol) was mixed and heated for 1 h at 60° C. The bright yellow oil was dissolved in methanol (2 mL) and water (1 mL) whereby and hydroxylamine hydrochloride (0.07 g, 1 mmol) was added, resulting in a pH of ca 5. The reaction was heated at 60° C. for 3 days. The solvents were evaporated and the residue refluxed in acetic acid: conc. HCL (1+1 mL) for 4 h. The solvents were evaporated to dryness and the residue dissolved in water at ca pH 10, filtered and acidified with HCl and extracted to DCM, dried (Na2SO4) and evaporated to yield the title compound as a light brown solid. 1H NMR (400 MHz, CHLOROFORM-D) δ ppm 0.93 (t, J=7.32 Hz, 3 H) 1.33-1.45 (m, 2 H) 1.69-1.78 (m, 2 H) 3.12 (t, J=7.57 Hz, 2 H) 8.50 (s, 1H)

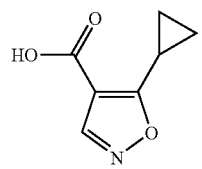

Example 214

5-Cyclopropylisoxazole-4-carboxylic acid

Methyl 3-cyclopropyl-3-oxopropanoate (0.28 g, 2 mmol) and 1,1-dimethoxy-N,N-dimethylmethanamine (0.24 g, 2 mmol) was mixed and heated for 20 h at 60° C. The bright yellow oil was dissolved in methanol (2 mL) and H$_2$O (1 mL) and hydroxylamine hydrochloride (0.14 g, 2 mmol) was added, resulting in a pH of ca 5. The reaction was heated for 90 min at 60° C. The solvents were evaporated and the residue refluxed in acetic acid: conc. HCl (3+3 mL) for 4 h. The mixture was stored at room temperature for 2 days and the solid was filtered off and dried in vacuum to yield the title compound as a grey solid. This compound is also commercially available. 1H NMR (400 MHz, CHLOROFORM-D) δ ppm 1.18-1.28 (m, 2 H) 1.28-1.35 (m, 2 H) 2.78-2.90 (m, 1 H) 8.45 (s, 1 H)

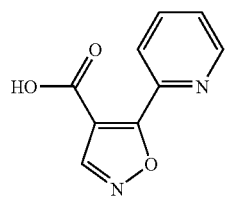

Example 215

5-Pyridin-2-ylisoxazole-4-carboxylic acid

Methyl 3-oxo-3-pyridin-2-ylpropanoate (0.39 g, 2 mmol) and 1,1-dimethoxy-N,N-dimethylmethanamine (0.24 g, 2 mmol) was mixed and heated for 20 h at 60° C. The dark oil was dissolved in methanol (2 mL) and H2O (1 mL) and hydroxylamine hydrochloride (0.14 g, 2 mmol), resulting in a pH of ca 5. The reaction was heated at 60° C. for 90 where after the solvents were evaporated and the residue refluxed in acetic acid: conc. HCL (3+3 mL) for 4 h. The reaction was evaporate to dryness and dissolved in water at ca pH 10, washed with DCM and acidified with HCl and extracted to DCM, dried (Na2SO4) and evaporated to yield the title compound as a dark purple solid. 1H NMR (400 MHz, DMSO-D6) δ ppm 7.70-7.80 (m, 1 H) 8.17-8.29 (m, 2 H) 8.81-8.87 (m, 1 H) 9.07 (s, 1 H)

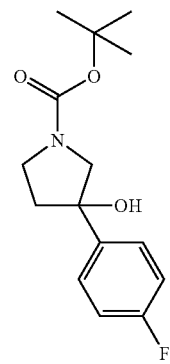

Example 216 tert-Butyl 3-(4-fluorophenyl)-3-hydroxypyrrolidine-1-carboxylate

A solution of 4-fluorophenylmagnesium bromide (1M in THF, 11 mL, 11 mmol) was added gradually to a solution of tert-butyl 3-oxopyrrolidine-1-carboxylate (1.85 g, 10 mmol) in diethyl ether (40 mL) during 5 min at ambient temperature. The mixture was stirred for 30 min and thereafter slowly quenched with NH3Cl (10 mL, 3M). The organic phase was isolated and evaporated. The residue was purified by flash chromatography (SiO$_2$ 2:1 heptane/EtOAc) to afford the title compound, which was used without further purification. MS (EI) 208 (M-tBuO)

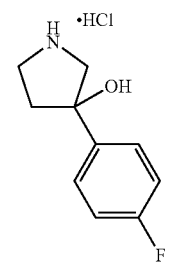

Example 217

3-(4-Fluorophenyl)pyrrolidin-3-ol hydrochloride tert-butyl 3-(4-fluorophenyl)-3-hydroxypyrrolidine-1-carboxylate (0.11 g, 0.39 mmol) was dissolved in EtOAc (11 mL) and HCl (g) was bubbled through the solution in a gentle stream for 15 min. Filtration afforded the title compound, This material was used in the next step without further purification. MS (EI) 182 (M+1).

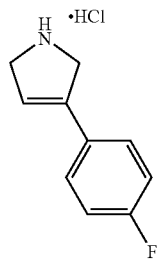

Example 218

3-(4-Fluorophenyl)-2,5-dihydro-1H-pyrrole Hydrochloride tert-butyl 3-(4-fluorophenyl)-3-hydroxypyrrolidine-1-carboxylate (0.22 g, 0.78 mmol) was dissolved in TFA (1 mL) and left at room temperature for 1 h. After evaporation the residue was dissolved in EtOAc and HCl (g) was bubbled through the solution and evaporated. This procedure was repeated one more time in order to isolate the HCl salt rather that the TFA salt. After drying in vacuum the residue was dissolved in a small amount of isopropanol and diethyl ether was added to crystallize the product. Crystallization is mixed with oil formation. Decantation of the solvent and drying left the title compound as a solid.

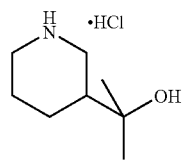

Example 219

2-Piperidin-3-ylpropan-2-ol hydrochloride

Methyl magnesium bromide (5 mL, 3M in diethyl ether, 15 mmol) was added dropwise to a solution of the 1-tert-butyl 3-ethyl piperidine-1,3-dicarboxylate (1.29 g, 5 mmol) in diethyl ether (20 mL) and THF (20 mL) during 10 min. The mixture was stirred for 30 min and thereafter slowly quenched with $NH_3Cl$ solution (10 mL, 3M). The phases were separated and the organic phase was evaporated to yield a yellow oil. The oil was dissolved in DCM (2 mL) and TFA (2 mL) was added and the reaction was left at room temperature for 15 min. The solvents were evaporated and the residue dissolved in EtOAc. HCl was bubbled through the solution in a gentle stream for 10 minutes. The solvent was evaporated and the residue dried in vacuum. Dissolution in EtOAc (100 mL) and stirring for 1 h at room temperature yielded the solid product, which was filtered off and dried in vacuum to produce white crystals. 1H NMR (400 MHz, DMSO-D6) δ ppm 1.01 (d, J=15.87 Hz, 6 H) 1.08-1.26 (m, 1 H) 1.46-1.68 (m, 2 H) 1.74 (d, J=10.99 Hz, 2 H) 2.47-2.56 (m, 1 H) 2.55-2.75 (m, 1 H) 3.11 (d, J=12.45 Hz, 1 H) 3.24 (d, J=12.45 Hz, 1 H) 8.81 (s, 1 H) 9.18 (s, 1 H).

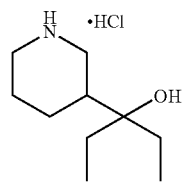

Example 220

3-Piperidin-3-ylpentan-3-ol hydrochloride

Ethyl magnesium bromide (15 mL, 1M in diethyl ether, 15 mmol) was added dropwise to a solution of the 1-tert-butyl 3-ethyl piperidine-1,3-dicarboxylate (1.29 g, 5 mmol) in diethyl ether (20 mL) and THF (20 mL) during 10 min. The mixture was stirred for 30 min and thereafter slowly quenched with $NH_3Cl$ solution (10 mL, 3M). The phases were separated and the organic phase was evaporated to yield a yellow oil. The oil was dissolved in DCM (2 mL) and TFA (2 mL) was added and the reaction was left for left at room temperature for 15 min at room temperature. The solvents were evaporated and the residue dissolved in EtOAc. HCl was bubbled through the solution in a gentle stream for 10 minutes. The solvent was evaporated and the residue dried in vacuum. Dissolvation in EtOAc (10 mL) and addition of diethyl ether (100 mL) and stirring for 1 h at room temperature gave the title compound as white crystals. 1H NMR (400 MHz, CHLOROFORM-D) δ ppm 0.78-0.91 (m, 6 H) 1.27-1.56 (m, 5 H) 1.83 (d, J=13.18 Hz, 1 H) 1.87-1.98 (m, 2 H) 2.02-2.18 (m, 2 H) 2.65-2.91 (m, 2 H) 3.39 (d, J=12.45 Hz, 1 H) 3.53 (d, J=12.70 Hz, 1 H) 9.22 (s, 1 H) 9.49 (s, 1 H).

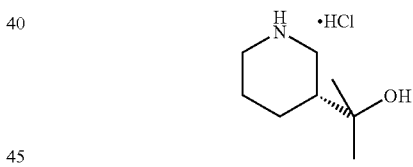

Example 221

2-[(3R)-Piperidin-3-yl]propan-2-ol hydrochloride

Methyl magnesium bromide (2 mL, 3M in diethyl ether, 6 mmol) was added dropwise to a solution of the 1-tert-butyl 3-ethyl (3R)-piperidine-1,3-dicarboxylate (514 mg, 2 mmol) in diethyl ether (20 mL) and THF (20 mL) during 10 min. The mixture was stirred for 30 min and thereafter slowly quenched with $NH_3Cl$ solution (10 mL, 3M). The phases were separated and the organic phase was evaporated to yield an oil. The oil was dissolved in EtOAc (50 mL) and HCl was bubbled through the solution in a gentle stream for 10 minutes and then left at room temperature on. The solvent was evaporated and the residue dissolved in EtOAc (100 mL) and stirring for 3 h at room temperature gave a solid that was filtered off and dried in vacuum to yield the title compound as white crystals.

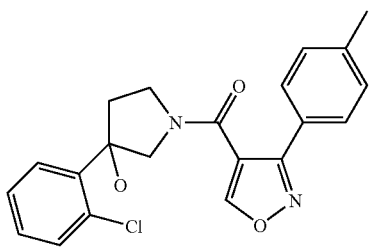

Example 222

3-(2-chlorophenyl)-1-{[3-(4-methylphenyl)isoxazol-4-yl]carbonyl}pyrrolidin-3-ol

A solution of 3-(2-chlorophenyl)pyrrolidin-3-ol hydrochloride (9 mg, 0.039 mmol), TBTU (15 mg, 0.047 mmol, 1.2 equ.) and N-ethyl-N-isopropylpropan-2-amine (14 μL, 0.079 mmol, 2 equ.) in DMF (0.3 mL) was added to 3-(4-methylphenyl)isoxazole-4-carboxylic acid (8 mg, 0.039 mmol) and the reaction mixture was stirred at rt for 2 h. The solvent was evaporated and the crude product was purified by RP-HPLC. After evaporation of the solvents the product was dried in vacuum to yield the title compound (11 mg). MS (ESI, pos. ion) m/z: calcd for $C_{21}H_{19}ClN_2O_3$: 382.1084, found 382.1080.

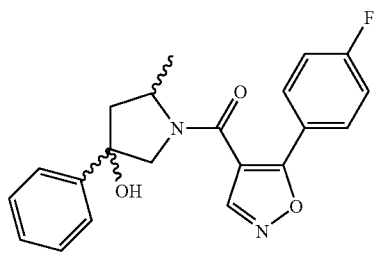

Example 223

1-{[5-(4-fluorophenyl)isoxazol-4-yl]carbonyl}-5-methyl-3-phenylpyrrolidin-3-ol

N-ethyl-N-isopropylpropan-2-amine (14 μL, 0.04 mmol) was added to a solution of 5-(4-fluorophenyl)isoxazole-4-carboxylic acid (8 mg, 0.04 mmol), 5-methyl-3-phenylpyrrolidin-3-ol (7 mg, 0.04 mmol) and TBTU (15 mg, 0.048 mmol, 1.2 equ.) in DMF (0.3 mL) at rt. The reaction mixture was left at rt for 2 h. The crude product was purified by RP-HPLC. After evaporation of the solvents the product was dried in vacuum to yield the title compound (11 mg). MS (ESI, pos. ion) m/z: calcd for $C_{21}H_{19}FN_2O_3$: 366.1380, found 366.1391.

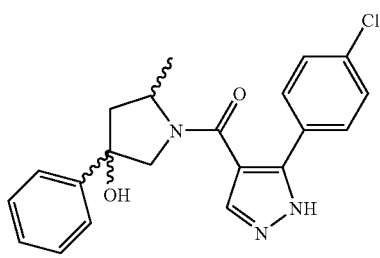

Example 224

1-{[5-(4-chlorophenyl)-1H-pyrazol-4-yl]carbonyl}-5-methyl-3-phenylpyrrolidin-3-ol N-ethyl-N-isopropylpropan-2-amine (14 μL, 0.04 mmol) was added to a solution of 5-(4-chlorophenyl)-1H-pyrazole-4-carboxylic acid (11 mg, 0.048 mmol, 1.2 equ.), 5-methyl-3-phenylpyrrolidin-3-ol (7 mg, 0.04 mmol) and TBTU (15 mg, 0.048 mmol, 1.2 equ.) in DMF (0.3 mL) at rt. The reaction mixture was left at rt for 2 h. The crude product was purified by RP-HPLC. After evaporation of the solvents the product was dried in vacuum to yield the title compound (4 mg). MS (ESI, pos. ion) m/z: calcd for $C_{21}H_{20}ClN_3O_2$: 381.1244, found 381.1243.

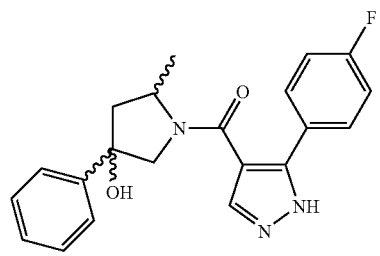

Example 225

1-{[5-(4-fluorophenyl)-1H-pyrazol-4-yl]carbonyl}-5-methyl-3-phenylpyrrolidin-3-ol Pyridine (13 μL, 0.16 mmol, 4 equ.) was added to a solution of 5-(4-fluorophenyl)-1H-pyrazole-4-carboxylic acid (8 mg, 0.04 mmol), 5-methyl-3-phenylpyrrolidin-3-ol (7 mg, 0.04 mmol) and TBTU (15 mg, 0.048 mmol, 1.2 equ.) in DMF (0.3 mL) at rt. The reaction mixture was stirred at 60° C. overnight. The crude product was purified by RP-HPLC. After evaporation of the solvents the product was dried in vacuum to yield the title compound (3 mg). MS (ESI, pos. ion) m/z: calcd for $C_{21}H_{20}FN_3O_2$: 365.1540, found 365.1541.

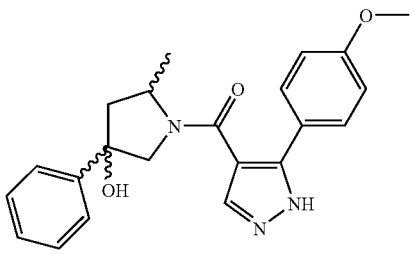

Example 226

1-{[5-(4-methoxyphenyl)-1H-pyrazol-4-yl]carbonyl}-5-methyl-3-phenylpyrrolidin-3-ol A solution of 5-methyl-3-phenylpyrrolidin-3-ol (9 mg, 0.05 mmol) and triethylamine (28 µL, 0.2 mmol, 4 equ.) in DMF (0.2 mL) was added to a solution of 5-(4-methoxyphenyl)-1H-pyrazole-4-carboxylic acid (11 mg, 0.05 mmol, 1.2 equ.) and 1-propanephosphonic acid cyclic anhydride (70 µL, 0.115 mmol, 2.3 equ., 50% solution in ethyl acetate) in DMF (0.1 mL) at rt. The reaction mixture was stirred at 60° C. overnight. The crude product was purified by RP-HPLC. After evaporation of the solvents the product was dried in vacuum to yield the title compound (3 mg). MS (ESI, pos. ion) m/z: calcd for $C_{22}H_{23}N_3O_3$: 377.1739, found 377.1739.

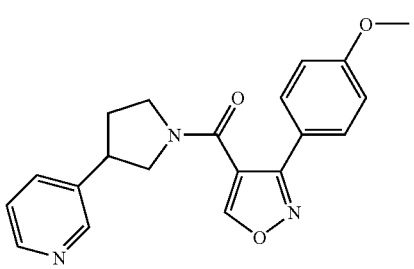

Example 227

3-(1-{[3-(4-methoxyphenyl)isoxazol-4-yl]carbonyl}pyrrolidin-3-yl)pyridine

A solution of 3-(4-methoxyphenyl)isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 3-pyrrolidin-3-ylpyridine (4 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (9 mg). MS (ESI, pos. ion) m/z: calcd for $C_{20}H_{19}N_3O_3$: 349.1426, found 349.1427.

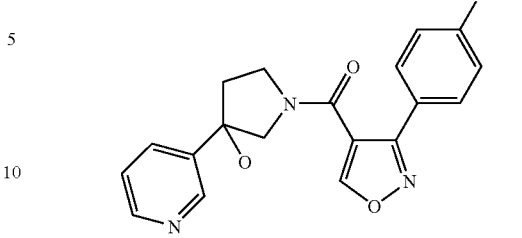

Example 228

1-{[3-(4-methoxyphenyl)isoxazol-4-yl]carbonyl}-3-pyridin-3-ylpyrrolidin-3-ol

A solution of 3-(4-methoxyphenyl)isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 3-pyridin-3-ylpyrrolidin-3-ol dihydrochloride (7 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (6 mg). MS (ESI, pos. ion) m/z: calcd for $C_{20}H_{19}N_3O_4$: 365.1376, found 365.1375.

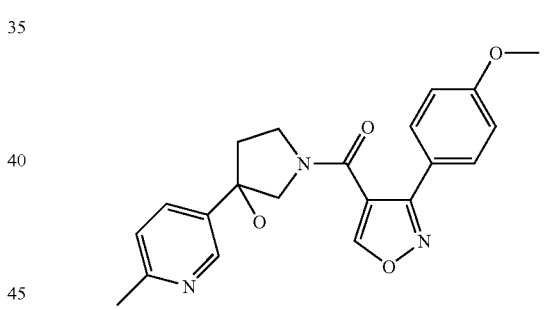

Example 229

1-{[3-(4-methoxyphenyl)isoxazol-4-yl]carbonyl}-3-(6-methylpyridin-3-yl)pyrrolidin-3-ol A solution of 3-(4-methoxyphenyl)isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 3-(6-methylpyridin-3-yl)pyrrolidin-3-ol dihydrochloride (8 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (3 mg). MS (ESI, pos. ion) m/z: calcd for $C_{21}H_{21}N_3O_4$: 379.1532, found 379.1529.

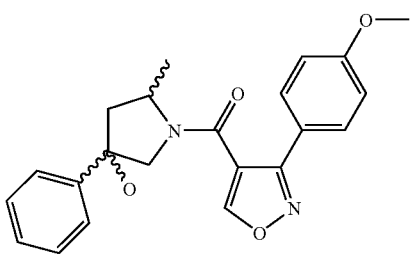

Example 230

1-{[3-(4-methoxyphenyl)isoxazol-4-yl]carbonyl}-5-methyl-3-phenylpyrrolidin-3-ol

A solution of 3-(4-methoxyphenyl)isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 5-methyl-3-phenylpyrrolidin-3-ol (5 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (6 mg). MS (ESI, pos. ion) m/z: calcd for C$_{22}$H$_{22}$N$_2$O$_4$: 378.1580, found 378.1580.

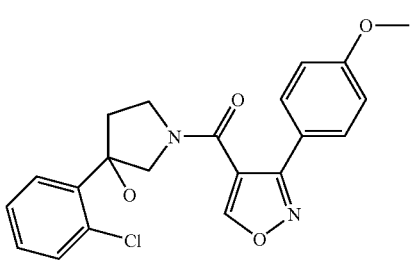

Example 231

3-(2-chlorophenyl)-1-{[3-(4-methoxyphenyl)isoxazol-4-yl]carbonyl}pyrrolidin-3-ol A solution of 3-(4-methoxyphenyl)isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 3-(2-chlorophenyl)pyrrolidin-3-ol hydrochloride (7 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (9 mg). MS (ESI, pos. ion) m/z: calcd for C$_{21}$H$_{19}$ClN$_2$O$_4$: 398.1033, found 398.1036.

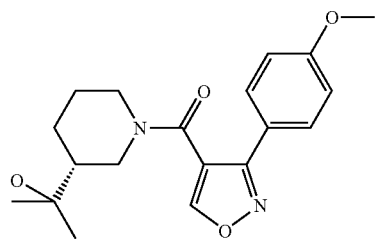

Example 232

2-((3R)-1-{[3-(4-methoxyphenyl)isoxazol-4-yl]carbonyl}piperidin-3-yl)propan-2-ol A solution of 3-(4-methoxyphenyl)-isoxazole-4-carboxylic acid (7 mg, 0.03 mmol), N-ethyl-N-isopropylpropan-2-amine (16 µL, 0.09 mmol, 3 equ.) and TBTU (12 mg, 0.036 mmol, 1.2 equ.) in DMF (0.3 mL) was added to 2-[(3R)-piperidin-3-yl]propan-2-ol hydrochloride (5 mg, 0.03 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (8 mg). MS (ESI, pos. ion) m/z: calcd for C$_{19}$H$_{24}$N$_2$O$_4$: 344.1736, found 344.1737.

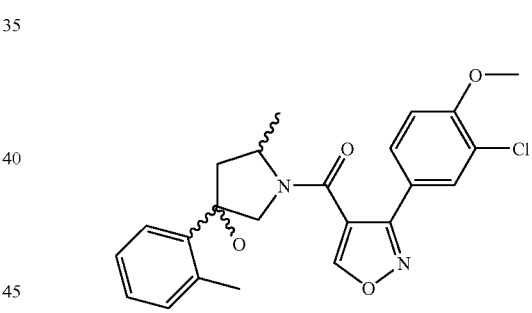

Example 233

1-{[3-(3-chloro-4-methoxyphenyl)isoxazol-4-yl]carbonyl}-5-methyl-3-phenylpyrrolidin-3-ol A solution of 3-(3-chloro-4-methoxyphenyl)-isoxazole-4-carboxylic acid (10 mg, 0.04 mmol), N-ethyl-N-isopropylpropan-2-amine (14 µL, 0.08 mmol, 2 equ.) and TBTU (15 mg, 0.046 mmol, 1.2 equ.) in DMF (0.3 mL) was added to 5-methyl-3-phenylpyrrolidin-3-ol (7 mg, 0.04 mmol). After 1 h at rt the crude product was purified by RP-HPLC, evaporated and dried in vacuum to yield the title compound (12 mg). MS (ESI, pos. ion) m/z: calcd for C$_{22}$H$_{21}$ClN$_2$O$_4$: 412.1190, found 412.1189.

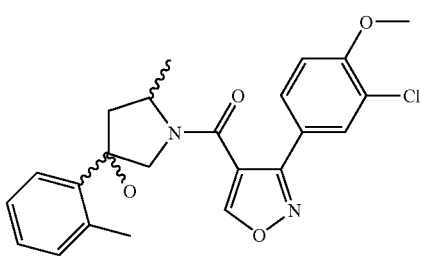

Example 234

1-{[3-(3-chloro-4-methoxyphenyl)isoxazol-4-yl]carbonyl}-5-methyl-3-(2-methylphenyl)pyrrolidin-3-ol A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 5-methyl-3-(2-methylphenyl)pyrrolidin-3-ol (8 mg, 0.04 mmol). After 1 h at rt the crude product was purified by RP-HPLC, evaporated and dried in vacuum to yield the title compound (5 mg). MS (ESI, pos. ion) m/z: calcd for $C_{23}H_{23}ClN_2O_4$: 426.1346, found 426.1350.

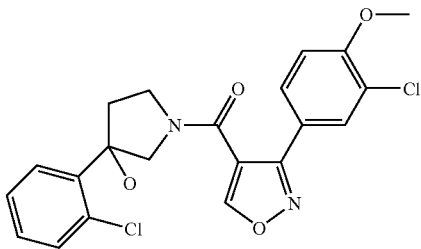

Example 235

1-{[3-(3-chloro-4-methoxyphenyl)isoxazol-4-yl]carbonyl}-3-(2-chlorophenyl)pyrrolidin-3-ol A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 3-(2-chlorophenyl)pyrrolidin-3-ol hydrochloride (9 mg, 0.04 mmol). After 1 h at rt the crude product was purified by RP-HPLC, evaporated and dried in vacuum to yield the title compound (6 mg). MS (ESI, pos. ion) m/z: calcd for $C_{21}H_{18}Cl_2N_2O_4$: 432.0644, found 432.0645.

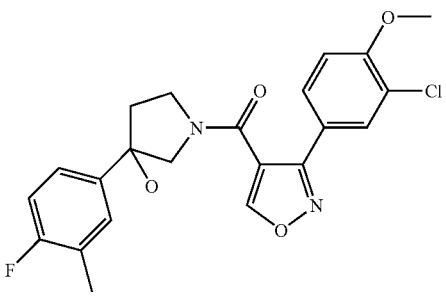

Example 236

1-{[3-(3-chloro-4-methoxyphenyl)isoxazol-4-yl]carbonyl}-3-(4-fluoro-3-methylphenyl)pyrrolidin-3-ol A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 3-(4-fluoro-3-methylphenyl)pyrrolidin-3-ol hydrochloride (9 mg, 0.04 mmol). After 1 h at rt the crude product was purified by RP-HPLC, evaporated and dried in vacuum to yield the title compound (7 mg). MS (ESI, pos. ion) m/z: calcd for $C_{22}H_{20}ClFN_2O_4$: 430.1096, found 430.1094.

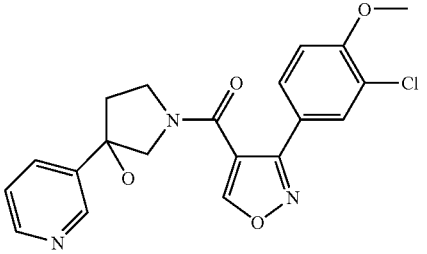

Example 237

1-{[3-(3-chloro-4-methoxyphenyl)isoxazol-4-yl]carbonyl}-3-pyridin-3-ylpyrrolidin-3-ol A solution of 3-(3-chloro-4-methoxyphenyl)-isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 3-pyridin-3-ylpyrrolidin-3-ol dihydrochloride (9 mg, 0.04 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (8 mg). MS (ESI, pos. ion) m/z: calcd for $C_{20}H_{18}ClN_3O_4$: 399.0986, found 399.0986.

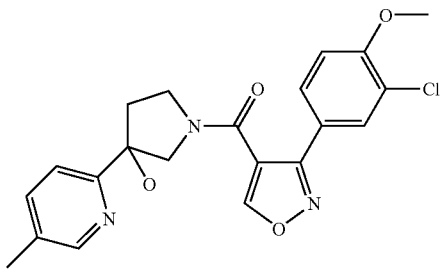

Example 238

1-{[3-(3-chloro-4-methoxyphenyl)isoxazol-4-yl]carbonyl}-3-(5-methylpyridin-2-yl)pyrrolidin-3-ol A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 3-(5-methylpyridin-2-yl)pyrrolidin-3-ol dihydrochloride (10 mg, 0.04 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (9 mg). MS (ESI, pos. ion) m/z: calcd for C$_{21}$H$_{20}$ClN$_3$O$_4$: 413.1142, found 413.1143.

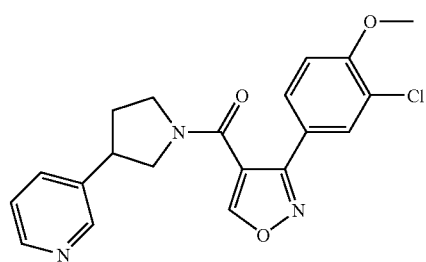

Example 239

3-(1-{[3-(3-chloro-4-methoxyphenyl)isoxazol-4-yl]carbonyl}pyrrolidin-3-yl)pyridine A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 3-pyrrolidin-3-ylpyridine (6 mg, 0.04 mmol). After 1 h at rt the crude product was purified by RP-HPLC. The pure fractions were basified (NaHCO$_3$) and extracted with ethyl acetate, dried (Na$_2$SO$_4$), evaporated and dried in vacuum to yield the title compound (10 mg). MS (ESI, pos. ion) m/z 384 (M+1); HRMS, calcd for C$_{20}$H$_{18}$ClN$_3$O$_3$: 383.1037, found 383.1033.

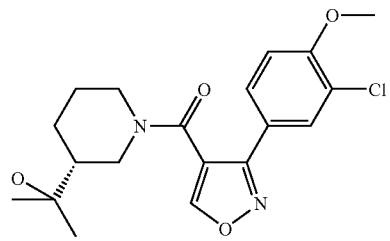

Example 240

2-((3R)-1-{[3-(3-chloro-4-methoxyphenyl)isoxazol-4-yl]carbonyl}piperidin-3-yl)propan-2-ol A solution of 3-(3-chloro-4-methoxyphenyl)isoxazole-4-carboxylic acid (10 mg, 0.04 mmol), N-ethyl-N-isopropyl-propan-2-amine (14 µL, 0.08 mmol, 2 equ.) and TBTU (15 mg, 0.046 mmol, 1.2 equ.) in DMF (0.3 mL) was added to 2-[(3R)-piperidin-3-yl]propan-2-ol hydrochloride (7 mg, 0.04 mmol). After 1 h at rt the crude product was purified by RP-HPLC, evaporated and dried in vacuum to yield the title compound (11 mg). MS (ESI, pos. ion) m/z 379 (M+1); HRMS, calcd for C$_{19}$H$_{23}$ClN$_2$O$_4$: 378.1346, found 378.1340.

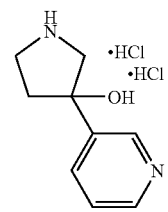

Example 241

3-pyridin-3-ylpyrrolidin-3-ol dihydrochloride

Isopropyl magnesium chloride (2.5 mL, 2 M in diethyl ether, 5 mmol) was added to a solution of 3-bromopyridine (0.79 g, 5 mmol) in THF (20 mL) at rt and the orange slurry was left stirring for 2 h. A solution of tert-butyl 3-oxopyrrolidine-1-carboxylate (0.93 g, 5 mmol) in THF (5 mL) was added dropwise during 5 minutes. The reaction was left stirring for 1 h and NH$_4$Cl solution (3 M, 10 mL) and diethyl ether was added. After stirring for 30 minutes the organic phase was separated, evaporated and purified on a silica gel column (CHCl$_3$:MeOH 98:2 to 90:10) to yield the Boc-protected product (135 mg, ca. 70% pure by HPLC). This material was dissolved in ethyl acetate (30 mL) and HCl was bubbled through in a gentle stream during 3 h. After 2 h a gray solid was filtered off. Yield: 100 mg. $^1$H NMR (400 MHz, methanol-D$_4$) δ ppm 2.38-2.50 (m, 1 H), 2.53-2.66 (m, 1 H), 3.59 (d, J=1.22 Hz, 2 H), 3.61-3.75 (m, 2 H), 8.15 (dd, J=8.18, 5.74 Hz, 1 H), 8.79-8.90 (m, 2 H), 9.08 (d, J=1.47 Hz, 1 H).

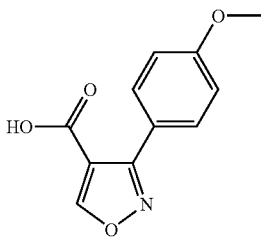

Example 242

3-(4-methoxyphenyl)isoxazole-4-carboxylic acid

A solution of pyrrolidine (0.63 mL, 7.5 mmol) in diethyl ether (6 mL) was added during 15 min to a solution of ethyl propiolate (0.76 mL, 7.5 mmol) in diethyl ether (6 mL) at 0° C. with stirring. The resulting solution was stirred for 30 min at rt, whereafter triethylamine (1.04 mL, 7.5 mmol) was added and the reaction was chilled to 0° C. again and a solution of N-hydroxy-4-methoxybenzenecarboximidoyl chloride (1.39 g, 7.5 mmol) in diethyl ether (10 mL) was added during 30 min. The temperature was allowed to go to rt and was washed with 1 M HCl and water, dried ($Na_2SO_4$) and evaporated. The crude intermediate was dissolved in acetic acid (3 mL) and conc. HCL (3 mL) and the mixture was refluxed for 2 h. The solvents were evaporated and the mixture was partioned between ethyl acetate and cold aqu. NaOH (0.5 M). The aqueous phase was acidified by conc. HCl and filtered. The crystals were purified by silica gel chromatography (DCM:MeOH 19:1 to 5:1) to give a white solid (45 mg), which was used in the next step without further analysis or purification (ca. 90% pure). MS 220 (M+1).

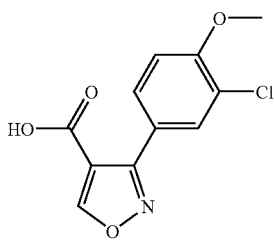

Example 243

3-(3-chloro-4-methoxyphenyl)isoxazole-4-carboxylic acid

A solution of pyrrolidine (0.33 mL, 4 mmol) in diethyl ether (4 mL) was added during 15 min to a solution of ethyl propiolate (0.40 mL, 4 mmol) in diethyl ether (4 mL) at 0° C. with stirring. The resulting solution was stirred for 30 min at rt, whereafter triethylamine (0.56 mL, 4 mmol) was added and the reaction was chilled to 0° C. again and a solution of N-hydroxy-4-methoxybenzenecarboximidoyl chloride (0.88 g, 4 mmol) in diethyl ether (5 mL) was added during 30 min and then allowed to go to rt. The mixture was filtered and the solid extensively washed with diethyl ether. The ether was washed with 1 M HCl. The water phase was back-extracted several times (6×50 mL) with ether, dried ($Na_2SO_4$) and evaporated to yield an off-white solid. Recrystallisation from MeOH gave the ethyl ester as white crystals (0.71 g). $^1$H NMR (400 MHz, chloroform-D) δ ppm 1.31 (t, J=7.08 Hz, 3 H), 3.94 (s, 3 H), 4.29 (d, J=7.16 Hz, 2 H), 6.99 (d, J=8.55 Hz, 1 H), 7.71 (dd, J=8.67, 2.08 Hz, 1 H), 7.86 (d, J=2.20 Hz, 1 H), 8.97 (s, 1 H).

The ester (0.56 g, 2 mmol) was dissolved in acetic acid (10 mL) and conc. HCL (10 mL) and refluxed for 3 h. After cooling to rt, filtering and washing with water gave the title compound as white crystals. $^1$H NMR (400 MHz, DMSO-$D_6$) δ ppm 3.92 (s, 3 H), 7.26 (d, J=8.79 Hz, 1 H), 7.72 (dd, J=8.55, 2.20 Hz, 1 H), 7.84 (d, J=1.95 Hz, 1 H), 9.61 (s, 1 H).

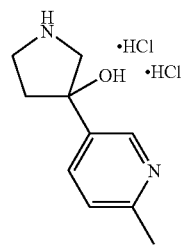

Example 244

3-(6-methylpyridin-3-yl)pyrrolidin-3-ol dihydrochloride

Isopropyl magnesium chloride (5 mL, 2 M in diethyl ether, 10 mmol, 2.5 equ.) was added to a solution of 5-bromo-2-methylpyridine (0.69 g, 4 mmol) in THF (20 mL) at rt and the orange slurry was left stirring for 2 h. A solution of tert-butyl 3-oxopyrrolidine-1-carboxylate (0.74 g, 4 mmol) in THF (5 mL) was added dropwise during 5 minutes. After stirring at rt overnight $NH_4Cl$ solution (3 M, 10 mL) and diethyl ether was added. After stirring for 30 minutes the organic phase was separated, evaporated and purified on a silica gel column (DCM:MeOH 98:2 to 90:10) and then a new column (ethyl acetate:petroleum ether 4:1) to yield the Boc-protected product (0.21 g). MS 279 (M+1).

The Boc-protected product was dissolved in ethyl acetate (30 mL) and HCl was bubbled through in a gentle stream during 30 minutes. Crystals were collected by decantation of the solvent and washings with new ethyl acetate. Yield: 60 mg. The material was used in the next step without further analysis or purification.

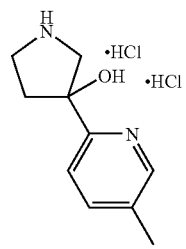

Example 245

3-(5-methylpyridin-2-yl)pyrrolidin-3-ol dihydrochloride

Isopropyl magnesium chloride (5 mL, 2 M in diethyl ether, 10 mmol, 2.5 equ.) was added to a solution of 2-bromo-5-methylpyridine (0.69 g, 4 mmol) in THF (10 mL) at rt and the reaction was left stirring for 2 h. More isopropyl magnesium chloride (2 mL, 2 M in diethyl ether, 4 mmol, 1 equ.) was added and the mixture was stirred for 1 h. A solution of tert-butyl 3-oxopyrrolidine-1-carboxylate (0.74 g, 4 mmol) in THF (5 mL) was added dropwise during 15 minutes. After stirring at rt 1 h a $NH_4Cl$ solution (3 M, 10 mL) and diethyl ether was added. After stirring for 30 minutes the organic phase was separated, evaporated and purified on a silica gel column (ethyl acetate:petroleum ether 2:1) to yield the Boc-protected product (0.15 g). MS 179 (M+1).

The Boc-protected product was dissolved in ethyl acetate (30 mL) and HCl was bubbled through in a gentle stream during 1 h. Crystals were collected by decantation of the solvent and washings with new ethyl acetate. Yield: 35 mg. The material was used in the next step without further analysis or purification. MS (M+1): 179.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it. Further, in any instance where necessary to satisfy the normal valence of a heteroatom (namely oxygen or nitrogen) in a depicted structure, it is understood that a hydrogen atom is attached to that heteroatom.

Pharmaceutical Compositions

Pharmaceutical compositions and single unit dosage forms comprising an azole aromatic heterocycle derivative, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The azole aromatic heterocycle derivatives can be administered to a mammal (human, mouse, rat, rabbit, dog, cat, bovine, pig, monkey etc.) as an 11β-HSD1 modulator, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by 11β-HSD1.

The azole aromatic heterocycle derivatives can be administered to a mammal concurrently with an additional therapeutic agent for the treatment of a disease, such as diabetes or obesity, with the aim of the prophylaxis or treatment of a disease. As such, the azole aromatic heterocycle derivatives of the present invention can be administered in combination with other therapeutic agents for the treatment or prevention of numerous diseases, including, but not limited to, diabetes and obesity.

Depending on the disease to be treated and the patient's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the case of a combined administration, the azole aromatic heterocycle derivatives may be administered simultaneously with other another therapeutic agent that is useful for the treatment or prevention of diabetes, obesity or other disease or may be administered at a time prior to or subsequent to another therapeutic agent. In the case of combined administration, a pharmaceutical composition containing the azole aromatic heterocycle derivative and an additional therapeutic agent can be administered. Alternatively, a pharmaceutical composition containing the azole aromatic heterocycle derivative and a pharmaceutical composition containing an additional therapeutic agent may be administered separately. The administration routes of respective pharmaceutical compositions may be the same or different.

In the case of a combined administration, the azole aromatic heterocycle derivatives may be administered at a dose of 50 mg to 800 mg per administration, which is given once to several times a day is contemplated (e.g., once-weekly). In addition, the compound may be administered at a smaller dose. The combined pharmaceutical agent can be administered at a dose generally employed for the prophylaxis or treatment of diabetes or obesity or at a smaller dose than that.

Like the amounts and types of excipients, the amounts and specific types of active ingredients in a dosage form may differ depending on factors such as, but not limited to, the route by which it is to be administered to patients. However, typical dosage forms of the invention comprise an azole aromatic heterocycle derivative, or a pharmaceutically acceptable salt, solvate, clathrate, hydrate, polymorph or prodrug thereof. In the treatment or prevention of diabetes, obesity, glaucoma, osteoporosis, cognitive disorders, immune disorders, depression or other conditions or disorders associated with the modulation of an hydroxysteroid dehydrogenase, an appropriate dosage level will generally be from about 0.001 to about 100 mg per kg patient body weight per day which can be administered in single or multiple doses. An exemplary dosage level will be from about 0.01 to about 25 mg/kg per day or about 0.05 to about 10 mg/kg per day. In other embodiments, a suitable dosage level may be from about 0.01 to about 25 mg/kg per day, about 0.05 to about 10 mg/kg per day, or about 0.1 to about 5 mg/kg per day. Within this range the dosage may be from about 0.005 to about 0.05, about 0.05 to about 0.5 or about 0.5 to about 5.0 mg/kg per day lie within the range of from about 0.1 mg to about 2000 mg per day, given as a single once-a-day dose in the morning but typically as divided doses throughout the day taken with food. In one embodiment, the daily dose is administered twice daily in equally divided doses. A daily dose range can be from about 5 mg to about 500 mg per day, or between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

For multidrug therapy, the weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, or about 200:1 to about 1:200. Combinations of a compound of the invention and other active ingredients will generally also be within the aforementioned range, but in each case, an effective dose of each active ingredient should be used.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the compositions can be provided in the form of tablets containing about 1 to about 1000 milligrams of the active ingredient. In other embodiments, the compositions are provided in provided in the form of tablets containing about 1.0, about 5.0, about 10.0, about 15.0. about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, or about 1000.0 milligrams of the active ingredient for the symptomatic adjustment of the dosage to the patient to be treated. The compounds may be administered on a regimen of 1 to 4 times per day, such as, for example, once or twice per day.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms can be sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are exemplary for the methods of preventing, treating or managing disease in a cancer patient.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants also can be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., International Publication No. WO 97/39745; Clark et al, International Publication No. WO 99/47196, which are herein incorporated by reference). For administration by inhalation, an azole aromatic heterocycle derivative can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver an azole aromatic heterocycle derivative directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer an azole aromatic heterocycle derivative to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as Astra-Zeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver an azole aromatic heterocycle derivative to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver an azole aromatic heterocycle derivative to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compounds, delivered by nebulizer devices, are currently under investigation as treatments for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In another embodiment, an electrohydrodynamic ("EHD") aerosol device is used to deliver an azole aromatic heterocycle derivative to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No. WO 94/12285; Coffee, International Publication No. WO 94/14543; Coffee, International Publication No. WO 95/26234, Coffee, International Publication No. WO 95/26235, Coffee, International Publication No. WO 95/32807, which are herein incorporated by reference). The electrochemical properties of the compound of the invention formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of an azole aromatic heterocycle derivative will be known to the skilled artisan and are within the scope of the invention.

Liquid drug formulations suitable for use with nebulizers and liquid spray devices and EHD aerosol devices will typically include an azole aromatic heterocycle derivative with a pharmaceutically acceptable carrier. In some embodiments, the pharmaceutically acceptable carrier is a liquid such as alcohol, water, polyethylene glycol or a perfluorocarbon. Optionally, another material may be added to alter the aerosol properties of the solution or suspension of an azole aromatic heterocycle derivative. This material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, an azole aromatic heterocycle derivative can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other Delivery Systems

Alternatively, other pharmaceutical delivery systems can be employed. Liposomes and emulsions are well known examples of delivery vehicles that can be used to deliver an azole aromatic heterocycle derivative. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Therapeutic Uses of the Azole Aromatic Heterocycle Derivatives

In one embodiment, the invention provides methods of treating or preventing a condition or disorder associated with the modulation of hydroxysteroid dehydrogenases by administering to a patient having such a condition or disorder a therapeutically effective amount of a compound or composition of the invention. In one group of embodiments, conditions and disorders, including chronic diseases of humans or other species, can be treated with modulators, stimulators, or inhibitors of hydroxysteroid dehydrogenases, such as 11β-HSD1.

Treatment or Prevention of Diabetes

Diabetes and diabetic conditions can be treated or prevented by administration of a therapeutically effective amount of an azole aromatic heterocycle derivative.

Types of diabetes that can be treated or prevented by administering a therapeutically effective amount of an azole aromatic heterocycle derivative include type I diabetes mellitus juvenile onset diabetes, insulin dependent-diabetes mellitus or IDDM), type II diabetes mellitus (non-insulin-dependent diabetes mellitus or NIDDM), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by β-cell toxins.

In some embodiments, the type of diabetes being treated is type II diabetes.

Treatment or Prevention of Obesity

Obesity can be treated or prevented by administration of a therapeutically effective amount of an azole aromatic heterocycle derivative.

Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

Complications due to obesity may also be treated or prevented by administering a therapeutically effective amount of an azole aromatic heterocycle derivative. Such complications include, but are not limited to, sleep apnea, Pickwickian syndrome, orthopedic disturbances of weight-bearing and non-weight-bearing joints, and skin disorders resulting from increased sweat or skin secretions.

Treatment or Prevention of Other Conditions

Other conditions that can be treated or prevented by administering a therapeutically effective amount of an azole aromatic heterocycle derivative include, but are not limited to any condition which is responsive to the modulation, such as inhibition, of hydroxysteroid dehydrogenases or specific isoforms thereof, and thereby benefit from administration of such a modulator. Representative conditions in this regard include, but are not limited to, metabolic disorders and related cardiovascular risk factors such as syndrome X, polycystic ovarian disease, eating disorders (e.g., anorexia and bulimia), craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia and Cushing's syndrome; diseases associated therewith such as hypertension, atherosclerosis, vascular restenosis, retinopathy and nephropathy; neurologic disorders such as neurodegenerative disease, neuropathy and musclewasting; cognitive disorders, such as age-related learning disorders, dementia, neurodegeneration, as well as for improvement of cognitive function in subjects ranging from the severely impaired (e.g., Parkinsons's or Alzheimer's associated dementia) to mildly impaired (e.g., age-associated memory impairment, drug-induced cognitive impairment) to unimpaired subjects (e.g., cognitive enhancers for the general population) (see, Sandeep, et al., PNAS, electronically available at www.pnas.org/cgi/doi/10.1073/pnas.0306996101); androgen and/or estrogen-related disorders such as prostate cancer, colon cancer, breast cancer, benign prostatic hyperplasia, ovarian cancer, uterine cancer, and male pseudohermaphrodism; endometriosis, dementia, depression, psoriasis, glaucoma, osteoporosis, viral infections, inflammatory disorders, and immune disorders.

Additional Therapeutic Agents

In one embodiment, the present methods for treating or preventing further comprise the administration of a therapeutically effective amount of another therapeutic agent useful for treating or preventing the diseases or disorders disclosed herein. In this embodiment, the time in which the therapeutic effect of the other therapeutic agent is exerted overlaps with the time in which the therapeutic effect of the azole aromatic heterocycle derivative is exerted.

The compounds of the invention can be combined or used in combination with other agents useful in the treatment, prevention, suppression or amelioration of the conditions or disorders for which compounds of the invention are useful, including diabetes, obesity, glaucoma, osteoporosis, cognitive disorders, immune disorders, depression and those pathologies noted above.

Such other agents, or drugs, may be administered, by a route and in an amount commonly used therefor, simultaneously or sequentially with an azole aromatic heterocycle derivative. In one embodiment, a pharmaceutical composition contains such other drugs in addition to the compound of the invention when an azole aromatic heterocycle derivative is used contemporaneously with one or more other drugs. Accordingly, the pharmaceutical compositions of the invention include those that also contain one or more other active ingredients or therapeutic agents, in addition to an azole aromatic heterocycle derivative.

In one embodiment, for the treatment or prevention of diabetes, an azole aromatic heterocycle derivative can be administered with another therapeutic agent, including, but not limited to, anti-diabetic agents such as insulin, inhaled insulin (Exubera®), insulin mimetics, insulin secretogues, sulfonylureas (e.g., glyburide, meglinatide, glimepiride, gliclazide, glipizide, gliquidone, chloropropresponsivemide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide), biguanides (e.g., metformin (Glucophage®)), α-glucosidase inhibitors (e.g., acarbose, voglibose and miglitol), thiazolidinone compounds (e.g., rosiglitazone (Avandia®), troglitazone (Rezulin®), ciglitazone, pioglitazone (Actos®) and englitazone), prandial glucose regulators (e.g., repaglinide and nateglinide) and glucagon receptor antagonists.

In another embodiment, for the treatment or prevention of obesity, an azole aromatic heterocycle derivative can be administered with another therapeutic agent, including, but not limited to, β3 adrenergic receptor agonists, leptin or derivatives thereof, neuropeptide Y (e.g., NPY5) antagonists, and mazindol.

Examples of other therapeutic agents that may be combined with an azole aromatic heterocycle derivative, either administered separately or in the same pharmaceutical compositions, include, but are not limited to: (i) cholesterol lowering agents such as HMG-CoA reductase inhibitors (e.g., lovastatin, simvastatin (Zocor®), pravastatin, fluvastatin, atorvastatin (Lipitor®) and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (ii) antithrombotic agents, such as thrombolytic agents (e.g., streptokinase, alteplase, anistreplase and reteplase), heparin, hirudin and warfarin derivatives, β-blockers (e.g., atenolol), β adrenergic agonists (e.g., isoproterenol), angiotensin II antagonists, ACE inhibitors and vasodilators (e.g., sodium nitroprusside, nicardipine hydrochloride, nitroglycerin and enaloprilat); (iii) PPAR agonists, e.g., PPARγ and PPAR$_δ$ agonists; (iv) DP antagonists; (v) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (vi) glaucoma therapies such as cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $α_2$-selective adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide; (vii) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (viii) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetylsalicylic acid and sulfasalazine) and the pyrazolones (e.g., apazone, bezpiperylon, feprazone, mofebutazone, oxyphenbutazone and phenylbutazone); (ix) cyclooxygenase-2 (COX-2) inhibitors such as celecoxib (Celebrex®) and rofecoxib (Vioxx®); (xi) inhibitors of phosphodiesterase type IV (PDE-IV); (xii) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (xiii) a hepatoprotective agent; and (xiv) other compounds such as 5-aminosalicylic acid and prodrugs thereof.

The weight ratio of the compound of the invention to the second active ingredient may be varied and will depend upon the effective dose of each ingredient. Generally, an effective dose of each will be used. Thus, for example, when an azole aromatic heterocycle derivative is combined with an NSAID, the weight ratio of the compound of the invention to the NSAID will generally range from about 1000:1 to about 1:1000, such as about 200:1 to about 1:200. Combinations of an azole aromatic heterocycle derivative and other active ingredients will generally also be within the aforementioned range, but in each case, an effective dose of each active ingredient should be used.

Kits

The invention encompasses kits that can simplify the administration of the azole aromatic heterocycle derivatives or composition of the invention to a patient.

A typical kit of the invention comprises a unit dosage of an azole aromatic heterocycle derivative. In one embodiment, the unit dosage form is in a container, which can be sterile, containing a therapeutically effective amount of an azole aromatic heterocycle derivative and a pharmaceutically acceptable vehicle. In another embodiment, the unit dosage form is in a container containing a therapeutically effective amount of an azole aromatic heterocycle derivative as a lyophilate or pharmaceutically acceptable salt. In this instance, the kit can further comprise another container that contains a solution useful for the reconstitution of the lyophilate or dissolution of the salt. The kit can also comprise a label or printed instructions for use of the azole aromatic heterocycle derivatives.

In a further embodiment, the kit comprises a unit dosage form of a composition of the invention.

Kits of the invention can further comprise one or more devices that are useful for administering the unit dosage forms of the azole aromatic heterocycle derivatives or a composition of the invention. Examples of such devices include, but are not limited to, a syringe, a drip bag, a patch or an enema, which optionally contain the unit dosage forms.

Biological Examples

Procedures Useful for the Biological Evaluation of the Substituted Azole Aromatic Heterocycles In addition to the extensive literature disclosing the role of HSDs in various diseases and disorders, described herein are assays useful for testing the compounds of the present invention.

Assays

Materials. [1,2(n)-$^3$H]-cortisone and [1,2,6,7-$^3$H]-hydrocortisone were purchased from Amersham. NADPH (tetrasodium salt) and NAD$^+$ (lithium salt, 10 mM stock in Tris buffer) were obtained from Sigma-Aldrich. 18β-glycyrrhetinic acid (GA) and carbenoxolone (disodium salt) were supplied by Sigma-Aldrich. Anti-cortisol monoclonal mouse antibody, clone 6D6.7 was obtained from Beckman Coulter (Marseille, France) and Ytrium Silicate (YSi) scintillation proximity assay (SPA) beads coated with monoclonal antimouse antibodies were purchased from Amersham. The human 11β-hydroxysteroid dehydrogenase type 1 (11β-HSD1) enzyme used was expressed in *Escherichia coli*. B. Elleby et al., High-level production and optimization of monodispersity of 11β-hydroxysteroid dehydrogenase type 1, *Biochim. Biophys. Acta* 1700 (2004) 199-207. The 3-fold serial dilutions of test compounds in assay buffer (30 mM Tris-HCl, pH 7.2 containing 1 mM EDTA) were performed on a Tecan Genesis RSP 150. The final concentration of the compounds spanned from 18 μM to 308 pM. Triplicates of the serial dilutions were performed on a Tomtec Quadra 96 instrument using 96 well microtiter plates (Perkin Elmer, white Optiplate-96). The amount of the product [$^3$H]-cortisol bound to the beads was determined in a Packard, Top Count NXT microplate liquid scintillation counter. Dilutions of stock solutions were made in assay buffer unless otherwise indicated.

The 11β-HSD2 enzyme was produced in HEK-293 cells transfected with a pcDNA3-derived plasmid.

Measurement of 11β-HSD1 Activity by Scintillation Proximity Assay (SPA):

Method A:

The 11β-HSD1 enzyme assay was carried out in the replica plates of the compounds in a total well volume of 110 μL. Each reaction replica contained 10 μL of diluted compound, 50 μL assay buffer, 25 μL substrate mixture [$^3$H]-Cortisone/NADPH (175 nM/200 μM). Reactions were initiated by the addition of 25 μL 11β-HSD1 of purified *Escherichia coli* derived enzyme (40 to 60 nM final concentration, depending on the batch). Following mixing, the plates were incubated on a shaker for about 60 minutes depending on the enzyme batch, at room temperature. The reactions were terminated with 10 μL stop solution (1 mM GA in ethanol). Monoclonal mouse antibody was then added (10 μL of 1.92 μM working solution) followed by 50 μL of YSi SPA beads (suspended according to the manufacturer's instructions). Appropriate controls were set up, i.e. determinations of non-specific binding (NSB) and of total activity (TOT) by adding or omitting 10 μL of 1 mM GA, respectively, before starting the reaction. As a reference, carbenoxolone was run in each plate. The plates were sealed with plastic film (Perkin Elmer, Top Seal-A) and incubated on a shaker for 30 minutes at room temperature before counting. The amount of the product, [$^3$H]-cortisol, captured on the beads was determined in a microplate liquid scintillation counter. Kinetic constants were calculated employing the Microsoft Excel integrated application XLfit (Version 5.3.0.19, ID Business Solutions Ltd) using the sigmoidal dose-response model 205 which is based on the non-linear curve fitting based on Levenberg-Marquardts algorithm.

Method B:

Enzyme assays were performed using purified, recombinant human 11β-HSD1. Assays were run in a total volume of 100 μl, including 40 μl purified enzyme, 10 μl compound dilutions, 10 μl [$^3$H]cortisone (100 nM final), 10 μl NADPH (200 μM final), and 30 μl assay buffer (50 mM Tris-HCl, 1 mM EDTA, pH 7.2). Assay was initiated by the addition of 40 μl of purified enzyme to achieve a final concentration of 20 nM. Assay plates were incubated on an orbital shaker for 1 hour at room temperature. The reaction was stopped by the addition of 10 μl of buffer containing 100 μM of 18β-glycyrrhetinic acid (GA). At the same time, 10 μl of a 1:50 diluted anti-cortisol antibody and 100 μl of 15 mg/ml anti-mouse SPA beads were added to the wells. Plates were incubated on an orbital shaker for 30 minutes at room temperature. Radiometric quantitation was determined on a TopCount NXT instrument (Perkin Elmer, Downers Grove, Ill.).

11β-HSD2 Enzyme Assay:

The assay was performed at room temperature in a 96 well microtiter plate (Costar 96 well V-bottom polypropylene, Cat. No. 3363) containing 160 μL substrate mixture [$^3$H]-cortisol/NAD$^+$ (200 nM/200 μM) in assay buffer, 20 μL of a 10 μM solution of inhibitors or control substance and 20 μL of 11β-HSD2 (crude extract from sonicated HEK-293 cells diluted 10-20 fold in assay buffer). When a dose response was desirable, the inhibitor was diluted in a 3-fold manner from 10 μM to 169 pM. Pure DMSO was diluted in parallel with inhibitors and used to assess the solvent effect on the enzyme. Following incubation for 10 min the reaction was terminated with perchloric acid (6 M, 50 μL). Samples were centrifuged for 5 min at 1800 g, and tritiated substrate and product were separated by HPLC (HP1100, Agilent Technologies). The injection volume was 15 μL and the flow rate was 0.8 mL/min on a $C_{18}$ 15 cm×4.6 mm, 5μ column (Hichrom Ltd), using acetonitrile/water (72/28) as the eluent. Detection was performed with a flow scintillation detector using an Ultima-Flo M (Packard) scintillator. Enzyme activity was quantified as area percentage of the product peak compared to the total area (substrate peak+product peak).

Primary Adipocyte Assay:

Compounds were dissolved in 100% DMSO to a final concentration of 10 mM and diluted in DMSO followed by a dilution in adipocyte medium. Cells were subjected to compounds serially diluted in eight steps (nine concentrations) ranging from 10 uM to 0.15 nM. The resulting compound solutions were added to cells in the presence of 100 nM cortisone. All samples were made and analyzed in triplicate. Human primary subcutaneous adipocytes from ZenBio (#SP-F-1) were propagated and differentiated according to the supplier's protocol. Induction with the diluted compounds was made for 5 hours and the cortisol level for each compound in the harvested media was determined with a Cortisol Immuno Assay Kit from Assay Designs (Correlate # ADI-901-071). Percent inhibition was calculated from absorbance ($A_{405}$) raw data of the samples relative to the positive control. Dose response curves were generated by plotting percent inhibition against compound concentrations and $IC_{50}$ values were calculated as the inflection point at 50% inhibition, using 4 Parameter Logistic Model in ExcelFit.

In Vitro Inhibition of 11β-HSD1 Activity:

The 11β-HSD1 inhibitory activity is examined by quantitative determination by an SPA (scintillation proximity assay) system of the suppressive action on the conversion from cortisone to cortisol using human 11β-HSD1 (hereinafter recombinant 11β-HSD1) expressed using a baculo-virus system as an enzyme source. For the reaction, a reagent is added to a 96 well plate (96 well Opti-plates™-96 (Packard)) to the following final concentration and a volume of 100 μl is reacted at room temperature for 90 min. The reaction solution used is 0.1 μg/ml recombinant 11β-HSD1, 500 μM NADPH, 16 nM $^3$H cortisone (Amersham Biosciences, 1.78 Tbq/mol) dissolved in 0.1% BSA (Sigma)-containing PBS and the test drug is 2 μl of a compound solution (dissolved in DMSO). After 90 min, the reaction is stopped by adding PBS (40 μl, containing 0.1% BSA (Sigma)) containing 0.08 μg of anti-cortisol mouse monoclonal antibody (East Coast Biologics), 365 μg SPA PVT mouse antibody-binding beads (Amersham Biosciences) and 175 μM carbenoxolone (Sigma) to the reaction solution. After the completion of the reaction, the plate is incubated overnight at room temperature and the radioactivity is measured by Topcount (Packard). For control, the value (0% inhibition) of the well containing 2 μl of DMSO instead of the test drug is used, and for positive control, the value (100% inhibition) of the well containing carbenoxolone instead of the test drug at the final concentration of 50 μM is used. The inhibition (%) of the test drug is calculated by ((value of control−value of test drug)/(value of control−value of positive control))×100 (%). The $IC_{50}$ value is analyzed using a computer-based curve fitting software.

Biochemical 11β-HSD1 Assay by SPA:

Recombinant human, mouse and rat 11β-HSD1 are expressed in baculovirus expression system, isolated by affinity purification and used as the enzyme sources for cortisone to cortisol conversion in vitro. $^3$H-Cortisone (Amersham Bioscience, 1.78 Tbq/mol. 49 Ci/mmol) is used as the substrate, and a monoclonal anti-cortisol antibody and the scintillation proximity assay (SPA) system are used to detect the product of the 11β-HSD1-catalyzed reaction, 3H-cortisol. Reactions take place at room temperature for 90 min. in 96-well Optiplates™-96 (Packard) in 100 μL volume with 2 μL test compounds or control in DMSO, 0.1 μg/mL 11β-HSD1 protein, 500 μM NADPH and 16 nM radioactive cortisone, in PBS buffer supplemented with 0.1% BSA (Sigma). Reaction is stopped with the addition of 40 μL buffer containing 0.08 μg anti-cortisol monoclonal antibody (East Coast Biologics), 365 μg SPA PVT antibody-binding beads (Amersham Biosciences) and 175 μM carbenoxolone (Sigma).

Plates are incubated at room temperature overnight before being read on a Topcount (Packard). The point of 50% inhibition of 11β-HSD1 enzyme activity ($IC_{50}$) is determined by computer-based curve fitting.

Cell-Based 11β-HSD1 Assay by SPA:

This cell-based assay measures the conversion of $^3$H-cortisone to $^3$H-cortisol in a HEK-293 cell line stably overexpressing human recombinant 11β-HSD1. HEK-293 cells are grown in DMEM/F12 supplemented with 10% fetal bovine serum, and plated onto poly-D-lysine-coated 96-well assay plates (Costar 3903), 100,000 cells per well in 50 μL assay media (phenol free DMEM/F12 (Invitrogen)+0.2% BSA+1% antibiotic-antimycotic solutions). The solution is incubated at 37° C. for 24 h, and the reaction is initiated by the addition of 25 μL of assay media containing compounds of desired concentration and 25 μL of assay media containing 40 nM of $^3$H-cortisone to each well. The reaction mixture is incubated at 37° C. for 90 min. and the reaction terminated by the addition of 25 μL of assay media containing 0.2 μg of anti-cortisol monoclonal antibody (East Coast Biologics), 500 μg SPA PVT antibody-binding beads (Amersham Biosciences) and 500 μM carbenoxolone (Sigma).

Plates are incubated at room temperature for at least 2 hour before being read on Topcount (Packard). The point of 50% inhibition of 11β-HSD1 enzyme activity ($IC_{50}$) is determined by computer-based curve fitting.

Scintillation Proximity Assay (SPA):

[1,2(n)-$^3$H]-cortisone may be purchased from Amersham Pharmacia Biotech. Anti-cortisol monoclonal mouse antibody, clone 6D6.7 may be obtained from Immunotech and Scintillation proximity assay (SPA) beads coated with monoclonal antimouse antibodies from Amersham Pharmacia Biotech. NADPH, tetrasodium salt may be obtained from Calbiochem and glucose-6-phosphate (G-6-P) from Sigma. The human 11-β-hydroxysteroid dehydrogenase type-1 enzyme (11-β-$HSD_1$) is expressed in *Pichia pastoris*. 18-β-glycyrrhetinic acid (GA) may be obtained from Sigma. The serial dilutions of the compounds are performed on a Tecan Genesis RSP 150. Compounds to be tested are dissolved in DMSO (1 mM) and diluted in 50 mM Tris-HCl, pH 7.2 containing 1 mM EDTA.

The multiplication of plates is done on a WallacQuadra. The amount of the product, [$^3$H]-cortisol, bound to the beads is determined in a Packard, Top Count microplate liquid scintillation counter.

The 11-β-$HSD_1$ enzyme assay is carried out in 96 well microtiter plates (Packard, Optiplate) in a total well volume of 220 μL and contains 30 mM Tris-HCl, pH 7.2 with 1 mM EDTA, a substrate mixture tritiated Cortisone/NADPH (175 nM/181 μM), G-6-P (1 mM) and inhibitors in serial dilutions (9 to 0.15 μM). Reactions are initiated by the addition of human 11-β-$HSD_1$, either as *Pichia pastoris* cell homogenate or microsomes prepared from *Pichia pastoris* (the final amount of enzyme used is varied between 0.057 to 0.11 mg/mL). Following mixing, the plates are shaken for 30 to 45 minutes at room temperature. The reactions are terminated with 10 μL 1 mM GA stop solution. Monoclonal mouse antibody is then added (10 μL of 4 μM) followed by 100 μL of SPA beads (suspended according to the manufacturers instructions). Appropriate controls are set up by omitting the 11-β-$HSD_1$ to obtain the non-specific binding (NSB) value.

The plates are covered with plastic film and incubated on a shaker for 30 minutes, at room temperature, before counting. The amount of [$^3$H]-cortisol bound to the beads is determined in a microplate liquid scintillation counter. The calculation of the $K_i$ values for the inhibitors is performed by use of Activity Base. The $K_i$ value is calculated from $IC_{50}$ and the $K_m$ value is calculated using the Cheng Prushoff equation (with reversible inhibition that follows the Michaelis-Menten equation): $K_i=IC_{50}(1+[S]/K_m)$ [Cheng, Y. C.; Prushoff, W. H. Biochem. Pharmacol. 1973, 22, 3099-3108]. The $IC_{50}$ is measured experimentally in an assay wherein the decrease of the turnover of cortisone to cortisol is dependent on the inhibition potential of each substance.

Cloning, Expression and Purification of 11β-HSD1:

The expression and purification of the murine enzyme is described by J. Zhang, et al. Biochemistry, 44, 2005, pp 6948-57. The expression and purification of the human enzyme is similar to that of the murine sequence.

Enzyme Assay:

The $IC_{50}$ and $K_i$ of the compounds were determined by the following method:

1. Prepare an Assay Buffer, (pH 7.2, 50 mM Tris-HCL, 1 mM EDTA) fresh each week.
2. Prepare the following solutions:
   NADPH (Sigma, 200 μM)
   $^3$H-Cortisone (Amersham Biosciences, 45 Ci/mmol, 100 nM)
   Enzyme Prep (20 nM for human, 10 nM for mouse)
   Cortisol Antibody (East Coast Biologicals, (1:50 dilution)
   Anti-mouse SPA beads (Amersham Biosciences, 15 mg/ml)
   18β-Glycyrrhetinic acid ("GA") (Aldrich, 1 μM)
   Compound Stock Solution (10 mM in DMSO), serially diluted in assay buffer. Each compound is tested at six different concentrations usually (10 μM to 0.1 nM). All of the solutions and dilutions are made in the Assay Buffer.
3. Assay is run using white/white, 96-well assay plates (Corning) in a total volume of 100 μL.
4. Into each well of a 96-well plate is added Assay Buffer (30 μL), compound (10 μL) NADPH (10 μL), and $^3$H-cortisone (10 μL).
5. Initiate reaction by adding 40 μL of HSD-1 enzyme prep to the wells.
6. The plate is covered with tape and incubated on an orbital shaker for 1 h at RT.
7. After 1 h, the tape is removed and anti-cortisol antibody (10 μL), GA solution (10 μL), and SPA bead preparation (100 μL) is added.

8. The plate is incubated (30 min) on an orbital shaker at RT.

9. The counts are read on a TopCount NXT reader.

10. A dose-response curve is plotted using the Graphpad Prism software, to generate the $IC_{50}$ values.

With this $IC_{50}$ value and the known $K_m$ value for the substrate and HSD1 enzyme, an estimated $K_i$ was calculated with the Chen and Prusoff equation $\{K_i=IC_{50}/[1+(\text{substrate}/K_m)]\}$. Compounds of Tables A to C were tested using this assay and the range of $IC_{50}$ values of the tested compounds was from 8 nM to 10 µM.

Measurement of 11β-HSD1 Activity in Whole Cells by ELISA:

Cell-based activity was measured by monitoring the conversion of cortisone to cortisol in a CHO cell line stably overexpressing human recombinant 11β-HSD1. Cells were maintained in DMEM supplemented with 10% dialyzed serum+penicillin/streptomycin/glutamine+non-essential amino acids+sodium-pyruvate. Assay plates were prepared one day prior to addition of compounds. Cells were seeded to a density of 30,000 cells/well in maintenance media in a total volume of 100 µl. Assay was initiated by removing media and rinsing cells 2× with GLC buffer (50 mM Hepes containing 120 mM NaCl, 1.85 mM $CaCl_2$, 1.3 mM $MgSO_4$, 4.8 mM KCl, pH 7.4), followed by the addition of 80 µl GLC buffer+ 0.1% DMSO. Compounds were added (10 µl) to a final concentration of 0.1 to 10000 nM. Plates were then incubated for 60 minutes at 37° C. After 60 minutes of incubation, 10 µl of 1 µM cortisone were added to each well. Plates were then incubated a further 40 minutes at 37° C. Cortisol formed from cortisone was quantitated using a cortisol ELISA kit supplied by Assay Designs Inc. (Cat. No. 901-071, Ann Arbor, Mich.).

We claim:

1. A compound according to formula I, or a stereoisomer, tautomer, or pharmaceutically acceptable salt thereof:

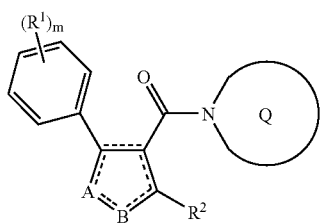

I wherein

A-B represents O—N, or N(H)—N;

each ═══ represents a single or double bond such that only two double bonds are simultaneously present in the ring containing A and B;

$R^1$ is selected from the group consisting of H, $C_{1-8}$-alkyl, $OC_{1-8}$-alkyl, $C_{1-3}$-haloalkyl, OH, CN, $NO_2$, F, Cl, Br, and I;

$R^2$ is selected from the group consisting of H, aryl, heteroaryl, $C_{1-8}$-alkyl, and $C_{1-6}$-haloalkyl;

ring Q, together with the nitrogen atom it contains, is a cyclic moiety according to formula IIa or IIb:

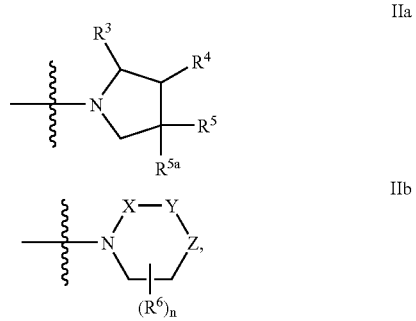

wherein $R^3$, $R^4$, and $R^5$ are independently selected from the group consisting of H, aryl, heteroaryl, $C_{1-8}$-alkyl, $C_{1-8}$-alkyl-aryl, $C_{1-8}$-alkyl-heteroaryl, $C_{1-8}$-alkyl-$C_{1-8}$-alkoxy, $C_3$-$C_{10}$-cycloalkyl, $C_3$-$C_{10}$-heterocycloalkyl, $N(R')_2$, —$C(O)N(R')_2$, —$N(R')C(O)OR'$;

$R^{5a}$ is H, OH, CN, or $CONH_2$;

$R^6$ is selected from the group consisting of H, aryl, heteroaryl, heteroaryloxy, —$N(R')_2$, —$C(O)N(R')_2$, OH, CN, $C_3$-$C_{10}$-cycloalkyl, —$C(O)R'$;

any two of $R^3$, $R^4$, $R^5$, and $R^6$, together with the atoms to which they are attached, optionally can combine to form a fused, and optionally further fused, saturated, partially saturated, or unsaturated polycycle containing from 5 to 20 atoms selected from C, N, O, and S;

X and Y are independently selected $CR'_2$;

Z is O or $CR'_2$; and wherein any cycloalkyl, heterocycloalkyl, aryl, heteroaryl, or fused polycycle is optionally substituted with from one to four members selected from the group consisting of oxo, halogen, —CN, —$NO_2$, $C_{1-8}$-alkyl, $C_{2-8}$-alkenyl, $C_{2-8}$-alkynyl, $C_{1-8}$-alkoxy, $C_{1-8}$-haloalkyl, $C_{2-8}$-hydroxyalkyl, aryloxy, heteroaryl, —$C(O)R'$, —$C(O)OR'$, —$NR'C(O)OR''$, —$OR'$, —$SR'$, —$OC(O)R'$, —$C(O)N(R')_2$, —$S(O)R''$, —$SO_2R''$, —$SO_2N(R')_2$, —$N(R')_2$ and —$NR'C(O)R'$;

each occurrence of R' is independently selected from the group consisting of H, $C_{1-8}$-alkyl, $C_{2-8}$-alkenyl, $C_{2-8}$-alkynyl, $C_{1-14}$-alkoxy, $C_{1-8}$-haloalkyl, $C_{1-8}$-hydroxyalkyl, $C_{1-8}$-hydroxy-diaryl-alkyl, $C_{3-8}$-cycloalkyl, $C_{3-8}$-heterocycloalkyl, heteroaryl, phenyl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl; and each occurrence of R'' is independently an unsubstituted member selected from the group consisting of $C_{1-8}$-alkyl, $C_{2-8}$-alkenyl, $C_{2-8}$-alkynyl, $C_{1-4}$-alkoxy, $C_{1-8}$-haloalkyl, $C_{1-8}$-hydroxyalkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl;

m and n are integers independently selected from 0, 1, 2, and 3;

provided that the compound is not:

4-[[3-methyl-5-(2,3,4,5-tetrafluoro-6-hydroxyphenyl)-4-isoxazolyl]carbonyl]-morpholine

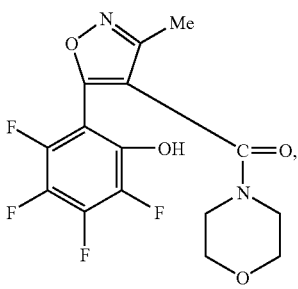

1-[(5-phenyl-4-isoxazolyl)carbonyl]-piperidine

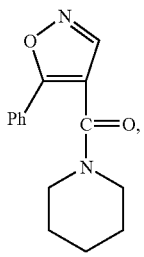

4-[(5-phenyl-4-isoxazolyl)carbonyl]-morpholine

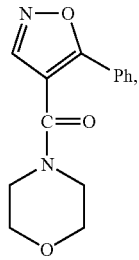

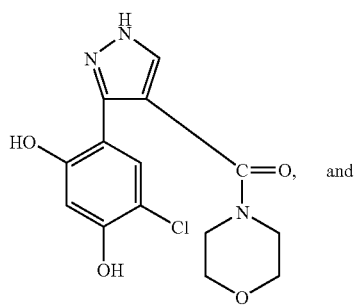

4-[[3-(5-chloro-2,4-dihydroxyphenyl)-1H-pyrazol-4-yl]carbonyl]-morpholine

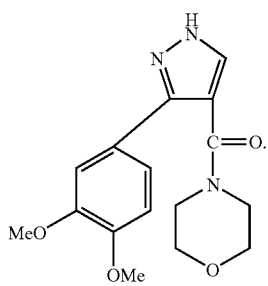

4-[[3-(3,4-dimethoxyphenyl)-1H-pyrazol-4-yl]carbonyl]-morpholine

2. The compound according to claim 1, or a stereoisomer, tautomer, solvate, or pharmaceutically acceptable salt thereof, wherein $R^2$ is selected from the group consisting of $C_{1-8}$-alkyl, $C_{1-6}$-haloalkyl, and aryl.

3. The compound according to claim 2, or a stereoisomer, tautomer, or pharmaceutically acceptable salt thereof, wherein $R^2$ is selected from the group consisting of $CH_3$, $CF_3$, and optionally substituted phenyl.

4. The compound according to claim 1, or a stereoisomer, tautomer, or pharmaceutically acceptable salt thereof, wherein ring Q is formula IIa:

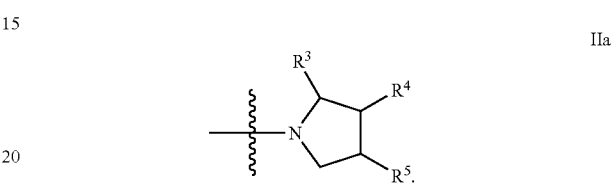

5. The compound according to claim 4, or a stereoisomer, tautomer, or pharmaceutically acceptable salt thereof, wherein:

$R^1$ is selected from the group consisting of H, F, Cl, Br, $NO_2$, and $CH_3$;

$R^3$ is H;

$R^4$ is aryl and heteroaryl;

$R^5$ is H; and m is 1.

6. The compound according to claim 5, or a stereoisomer, tautomer, or pharmaceutically acceptable salt thereof, wherein $R^4$ is selected from the group consisting of optionally substituted phenyl, 2-pyridyl, 3-pyridyl, and 4-pyridyl.

7. The compound according to claim 1, or a stereoisomer, tautomer, or pharmaceutically acceptable salt thereof, wherein the compound is of the formula I-IIb:

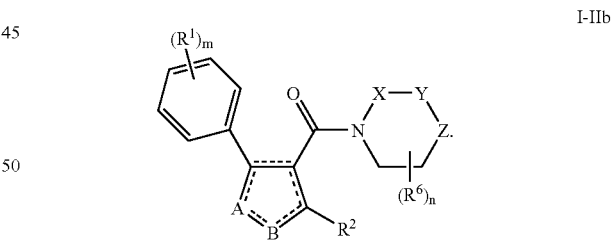

8. The compound according to claim 7, or a stereoisomer, tautomer, or pharmaceutically acceptable salt thereof, wherein:

n is 0, and $R^2$ is H.

9. The compound according to claim 1, wherein A-B represents N(H)—N.

10. A pharmaceutical composition comprising a therapeutically effective amount of a compound according to claim 1, or a stereoisomer, tautomer, or pharmaceutically acceptable salt thereof, and a pharmaceutically acceptable carrier.

11. A compound that is selected from the following table:
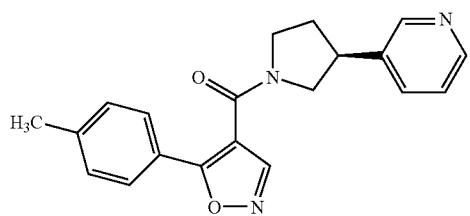
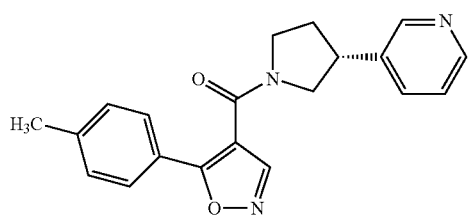
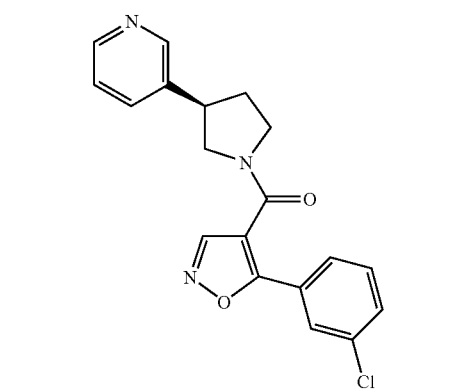
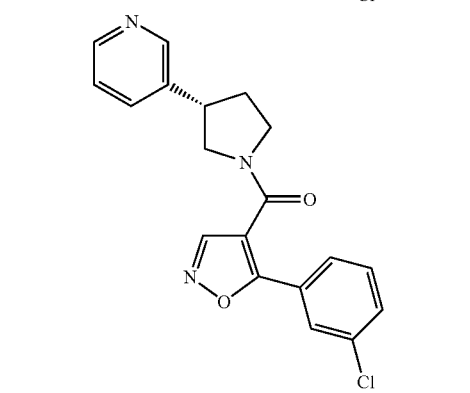
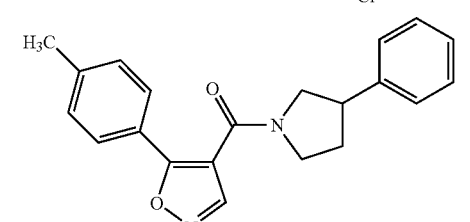
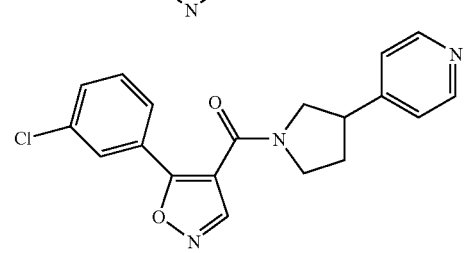
-continued
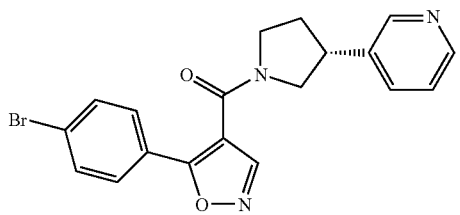
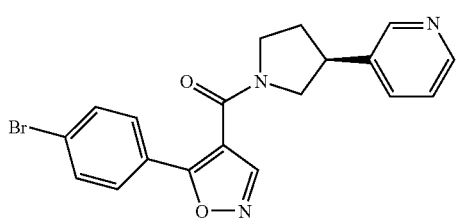
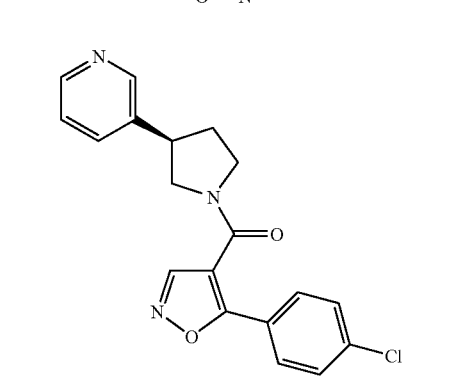
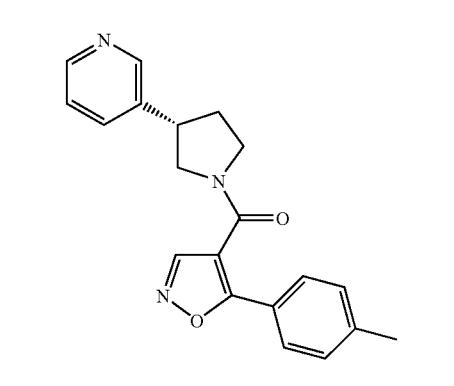
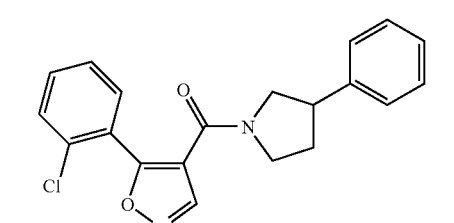
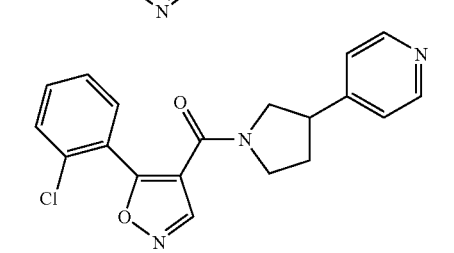

-continued
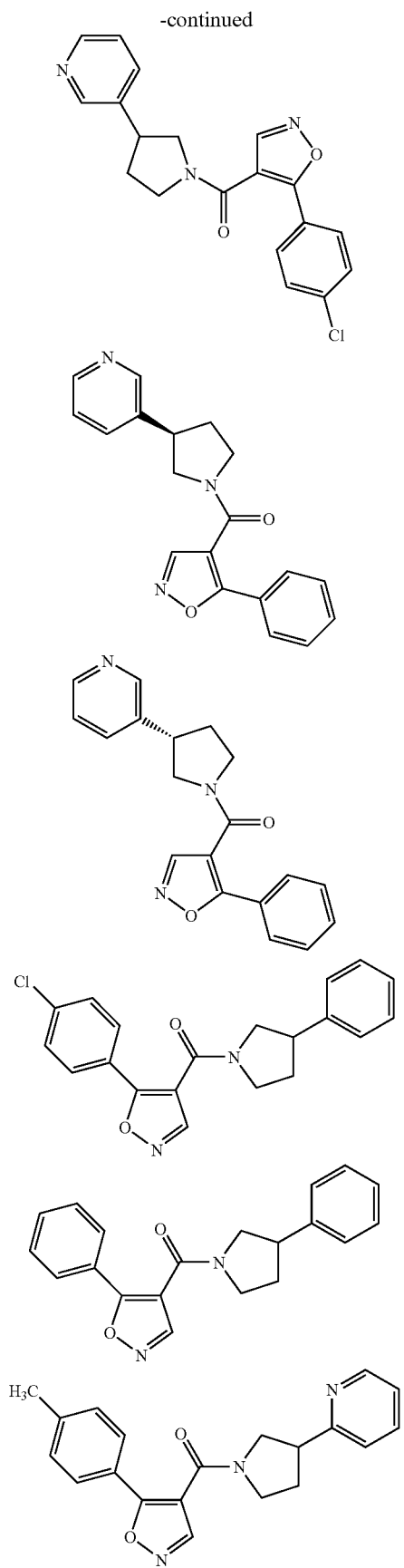
-continued
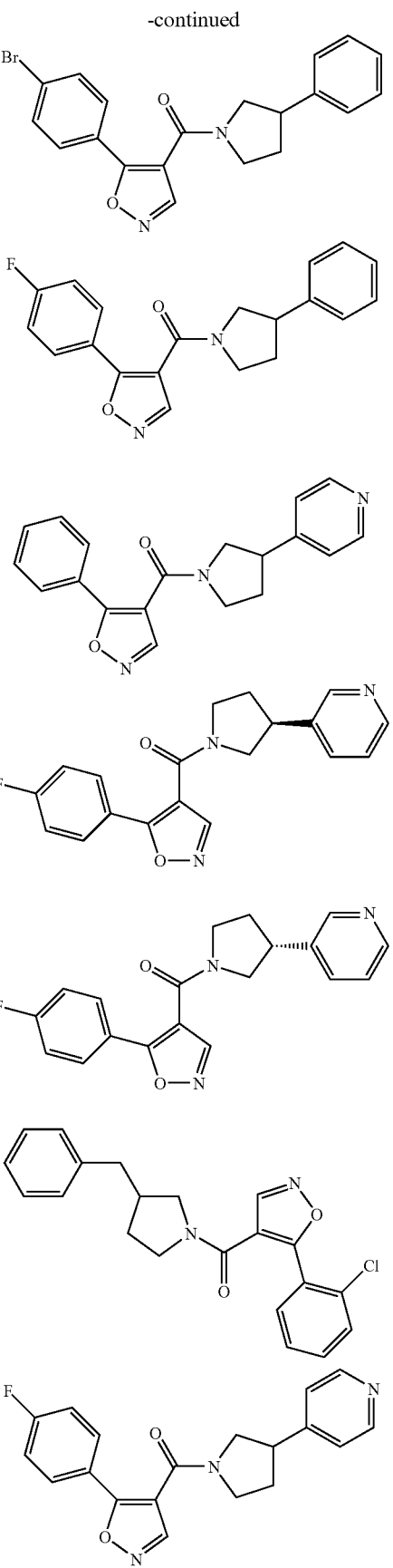

227
-continued
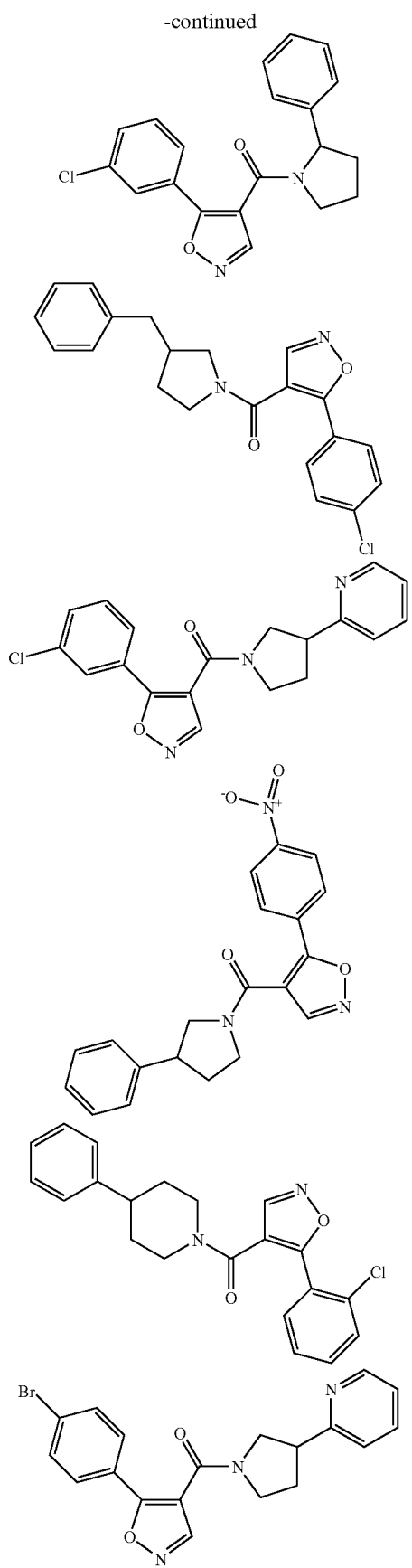
228
-continued
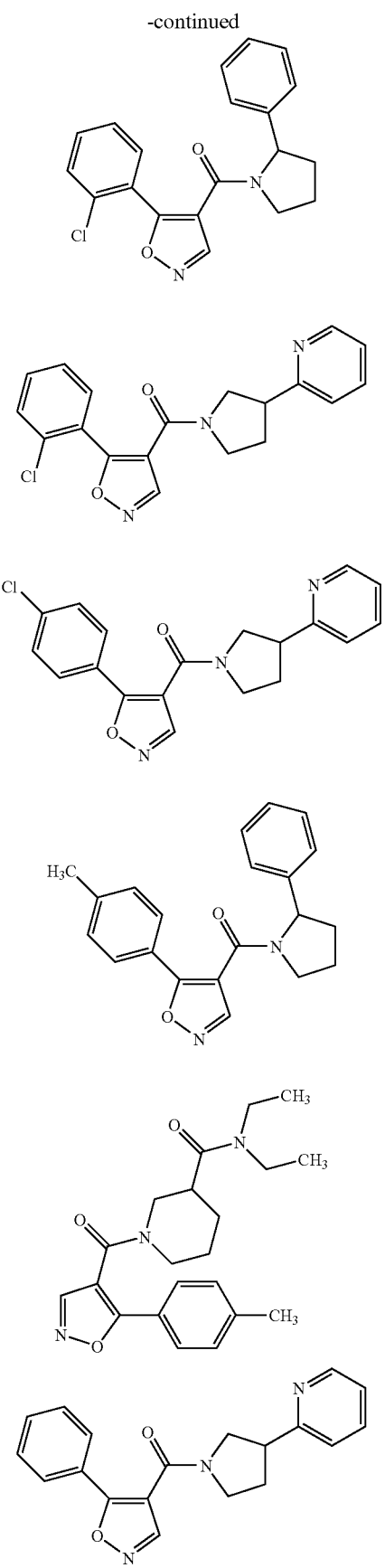

-continued
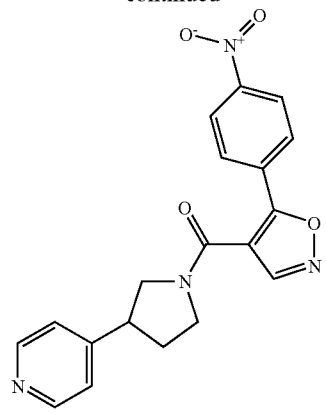
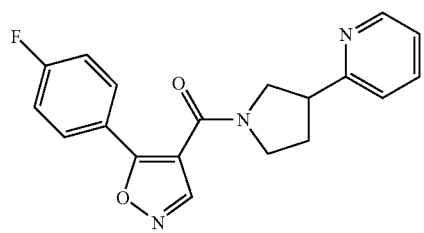
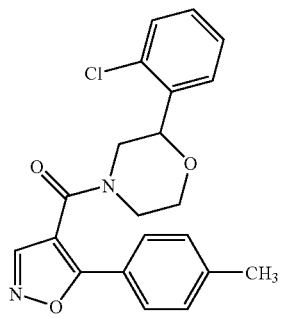
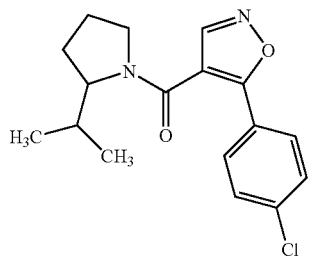
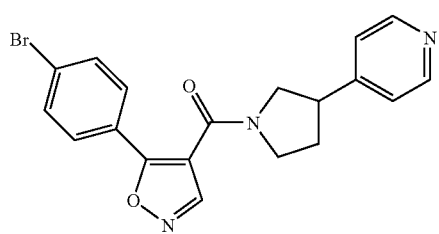
-continued
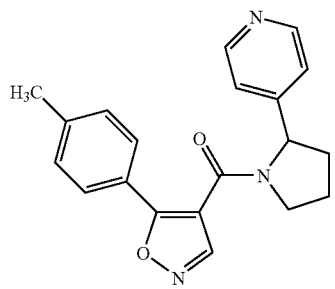
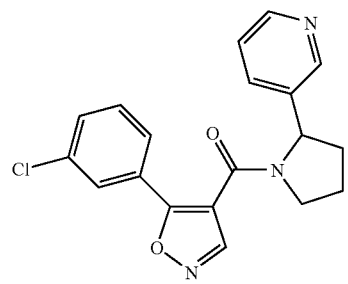
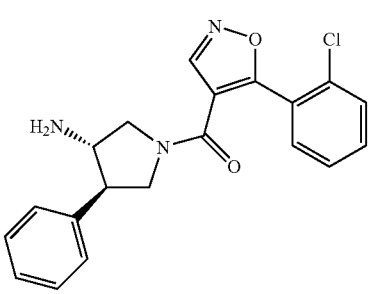
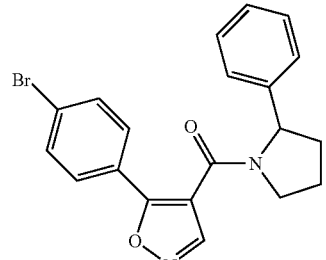
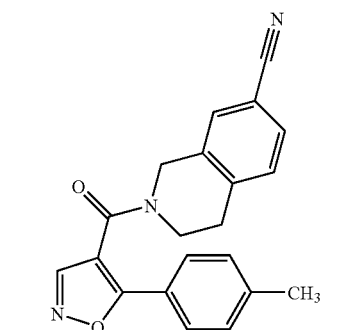
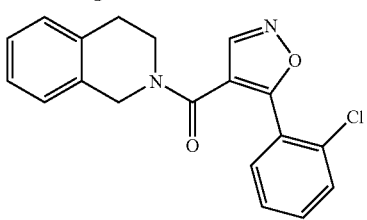

-continued
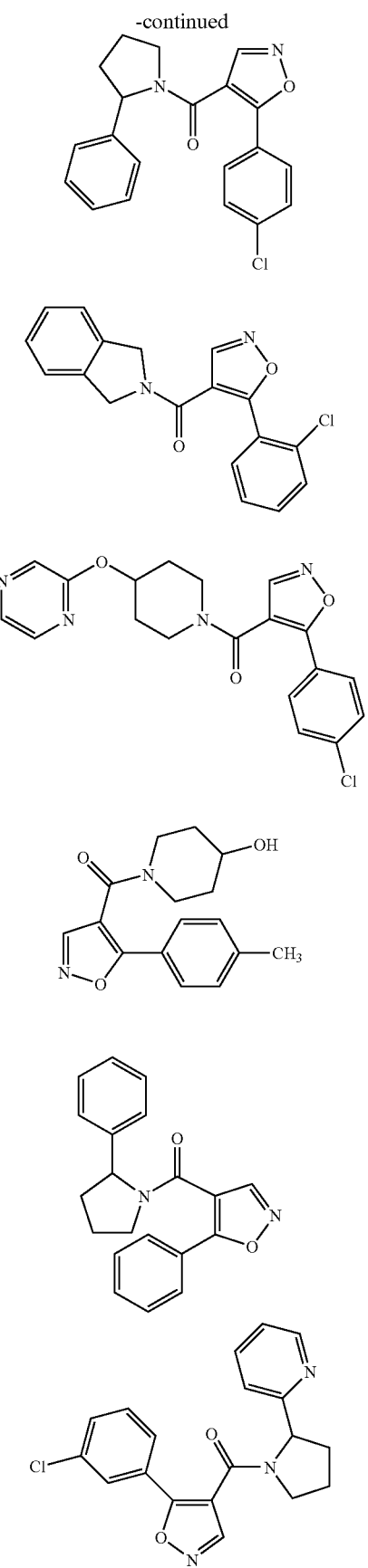
-continued
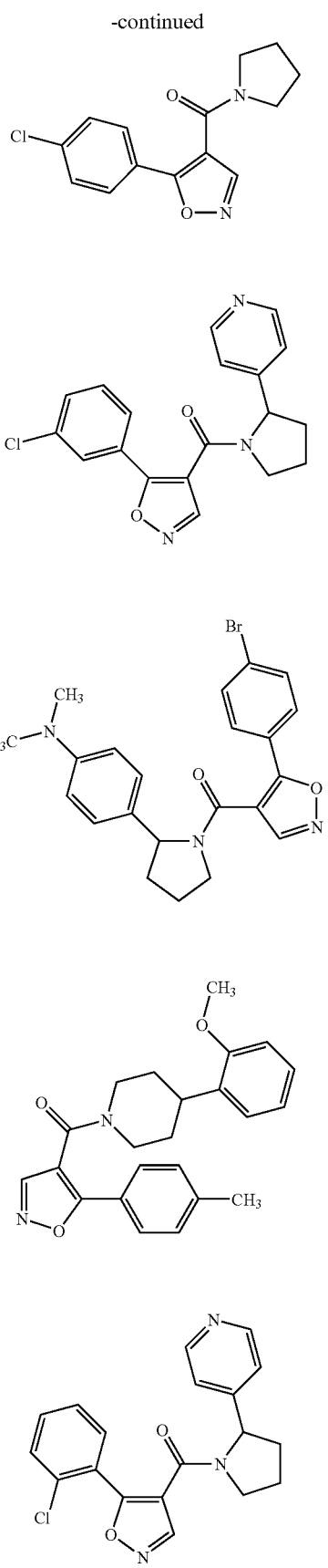

-continued
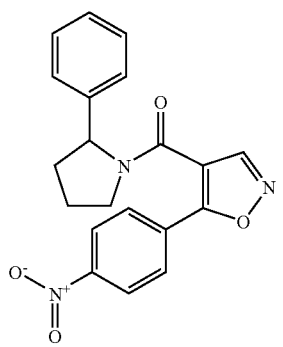
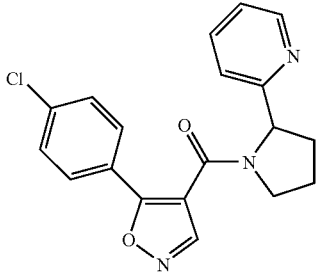
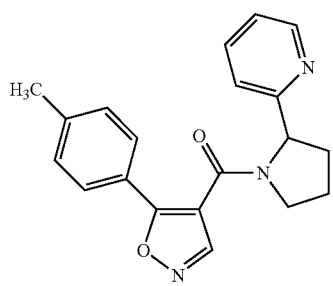
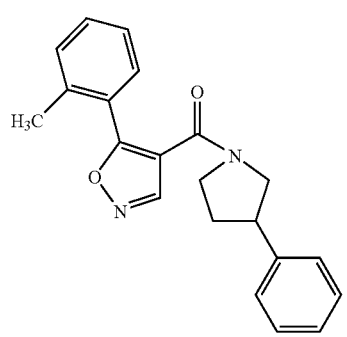
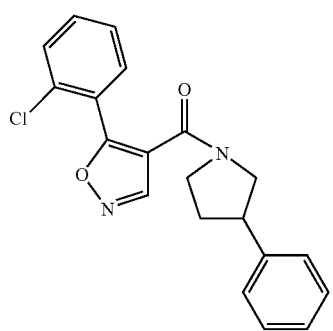
-continued
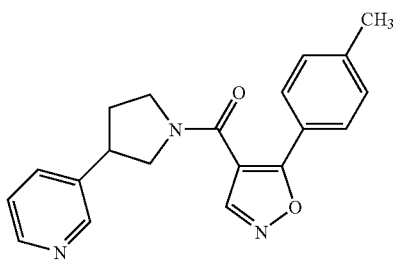
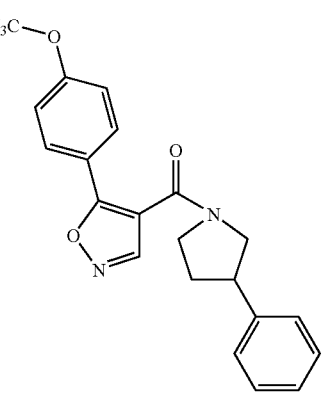
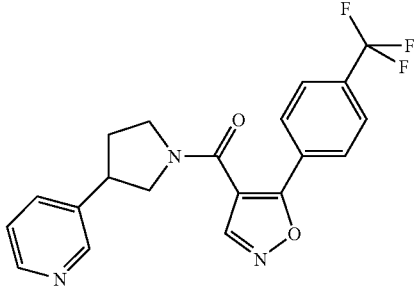
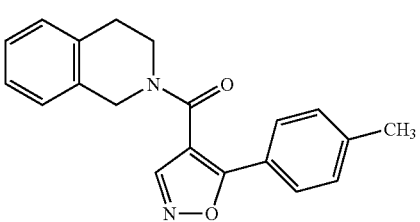
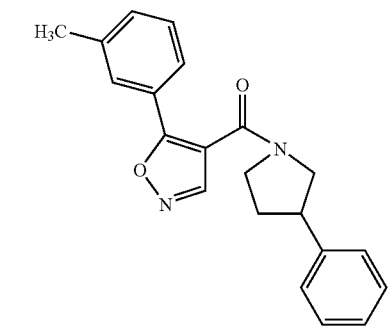

-continued
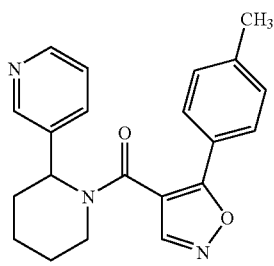
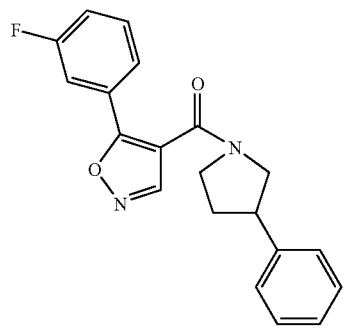
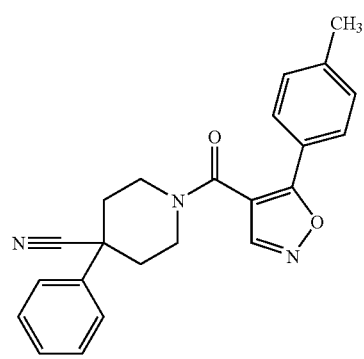
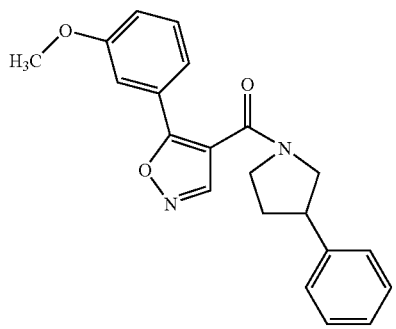
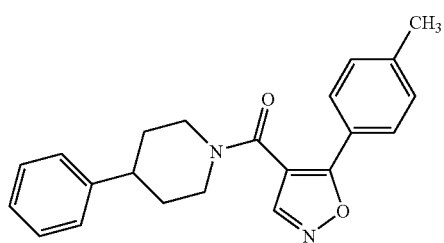
-continued
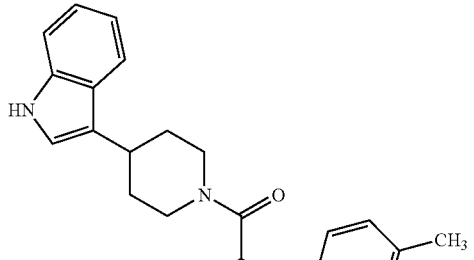
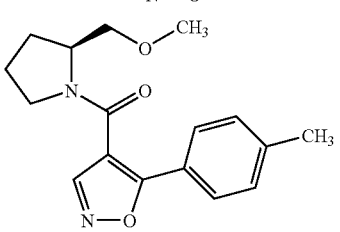
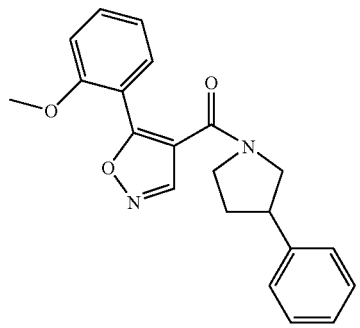
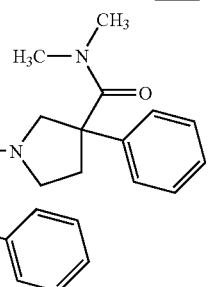
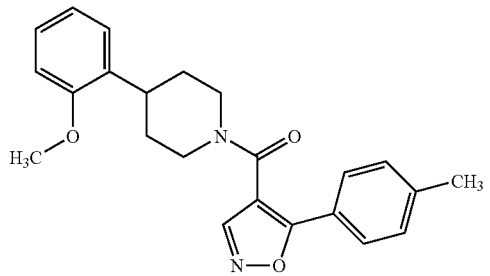
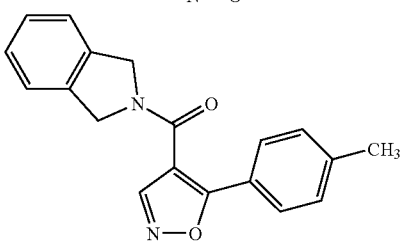

237
-continued
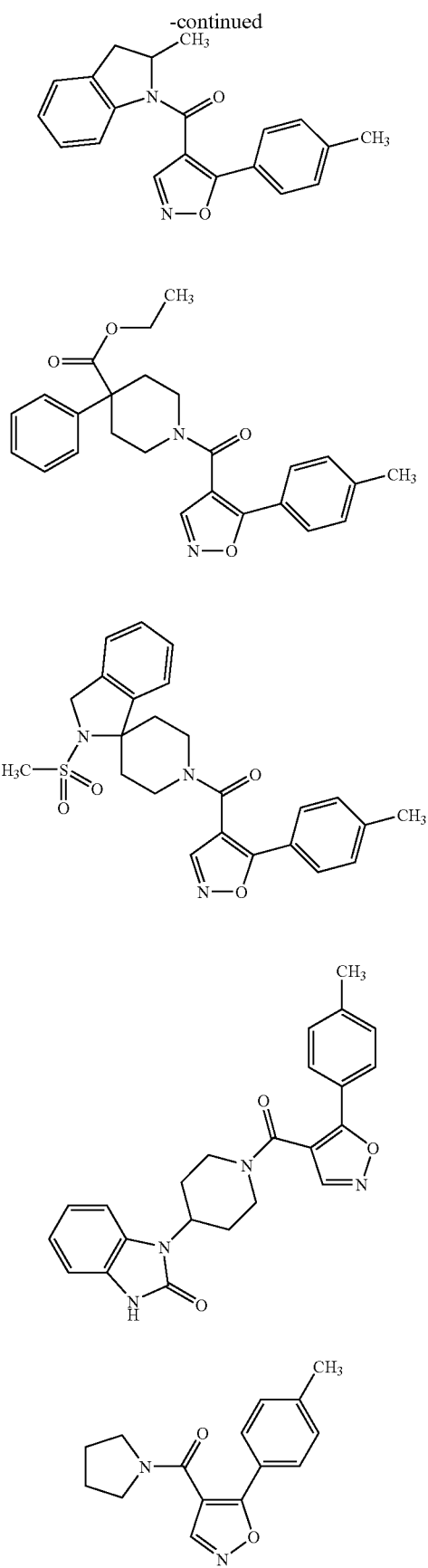
238
-continued
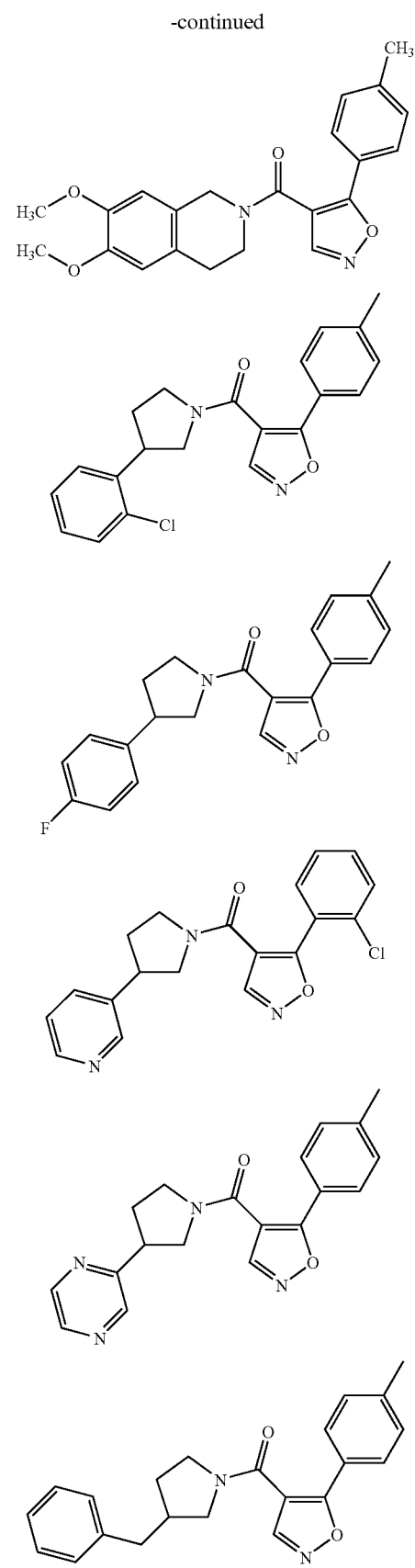

-continued
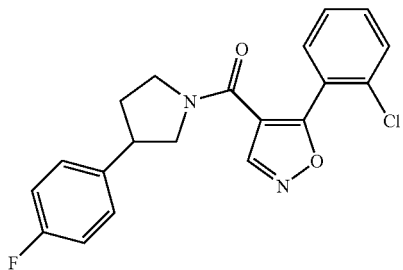
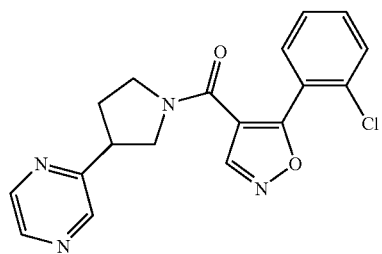
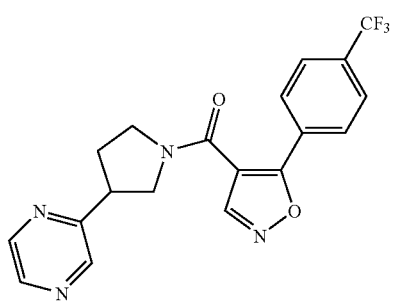
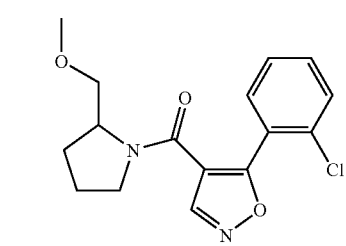
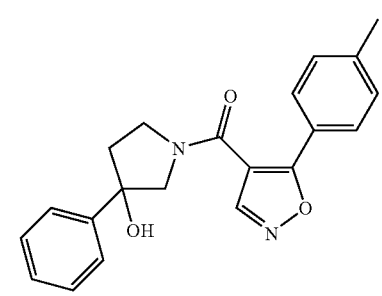
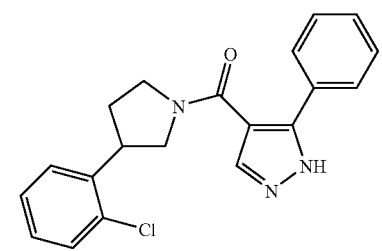
-continued
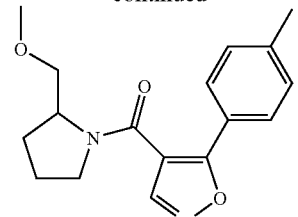
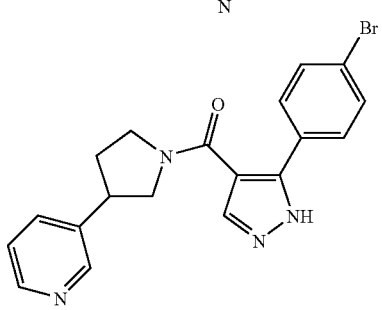
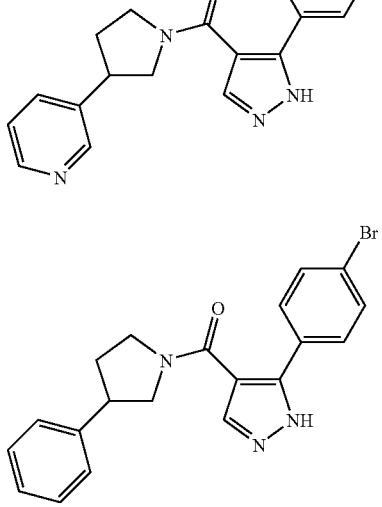
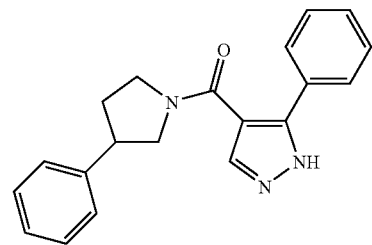
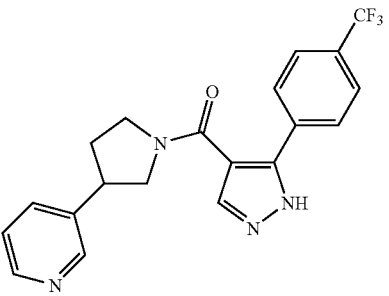
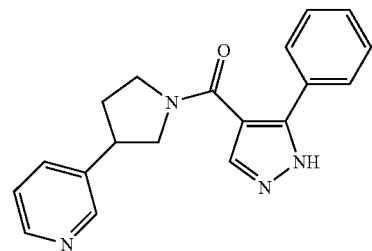

-continued
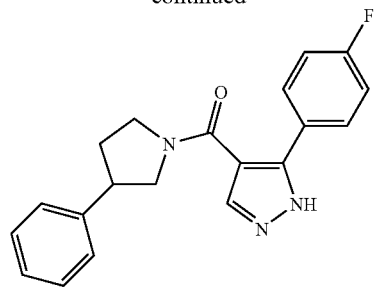
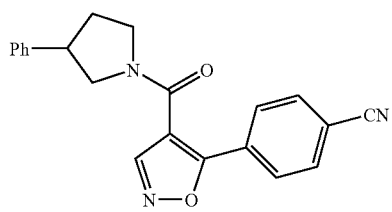
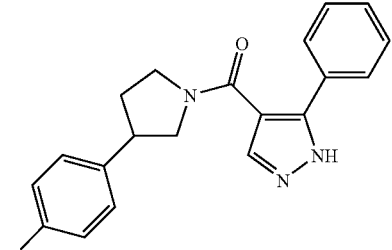
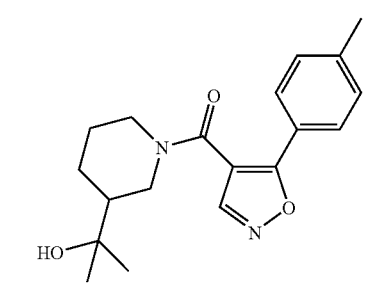
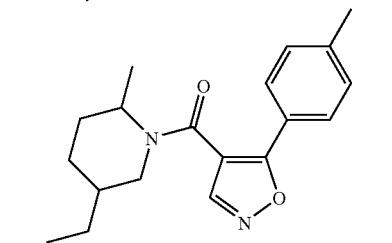
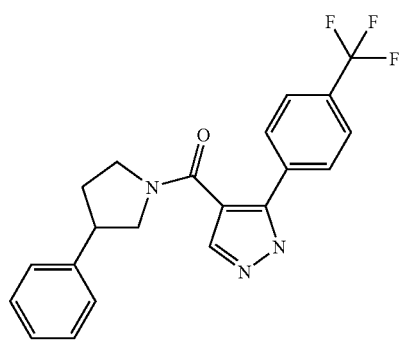
-continued
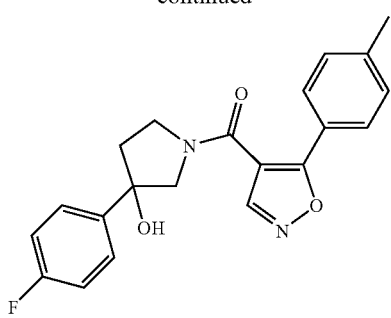
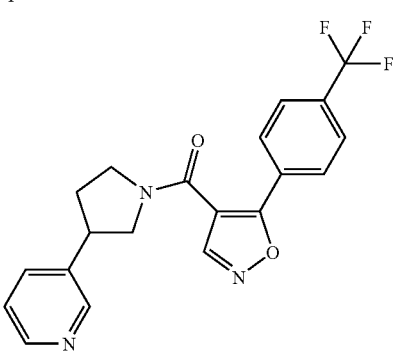
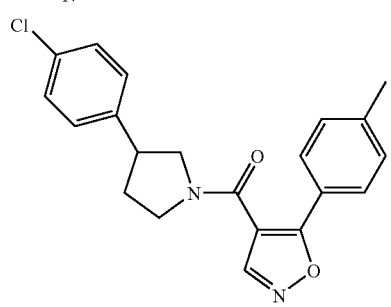
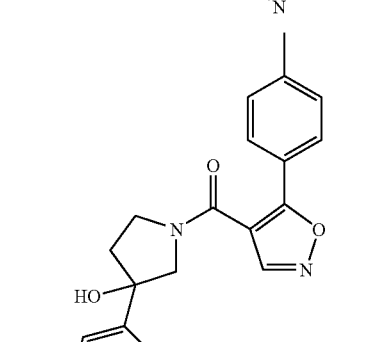
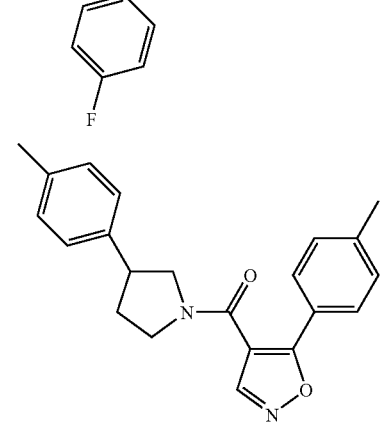

-continued
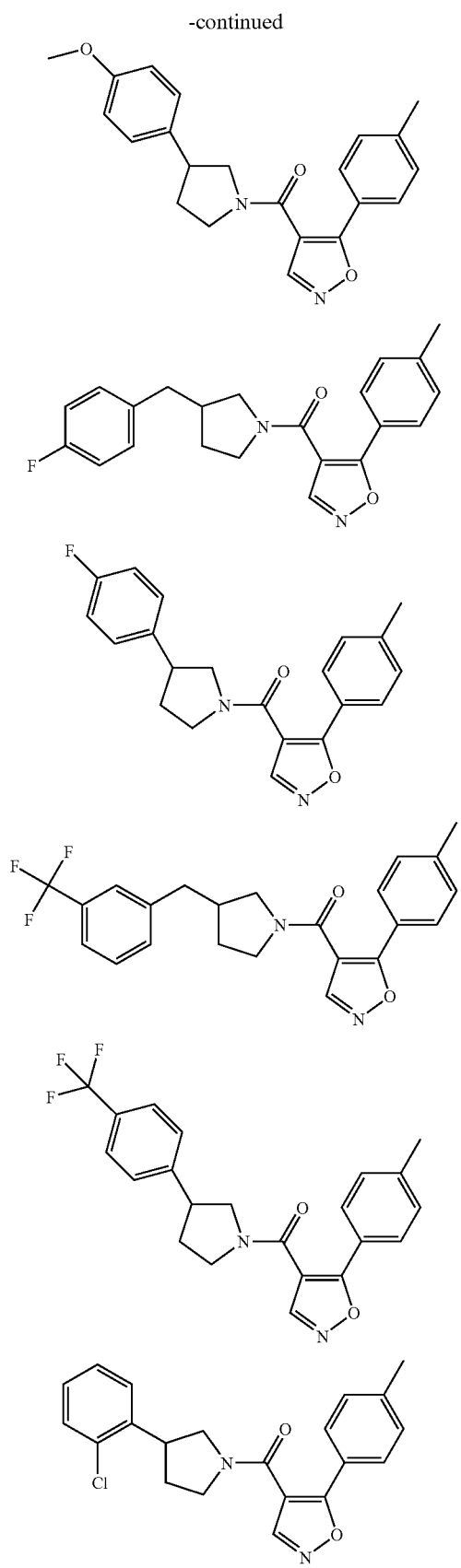
-continued
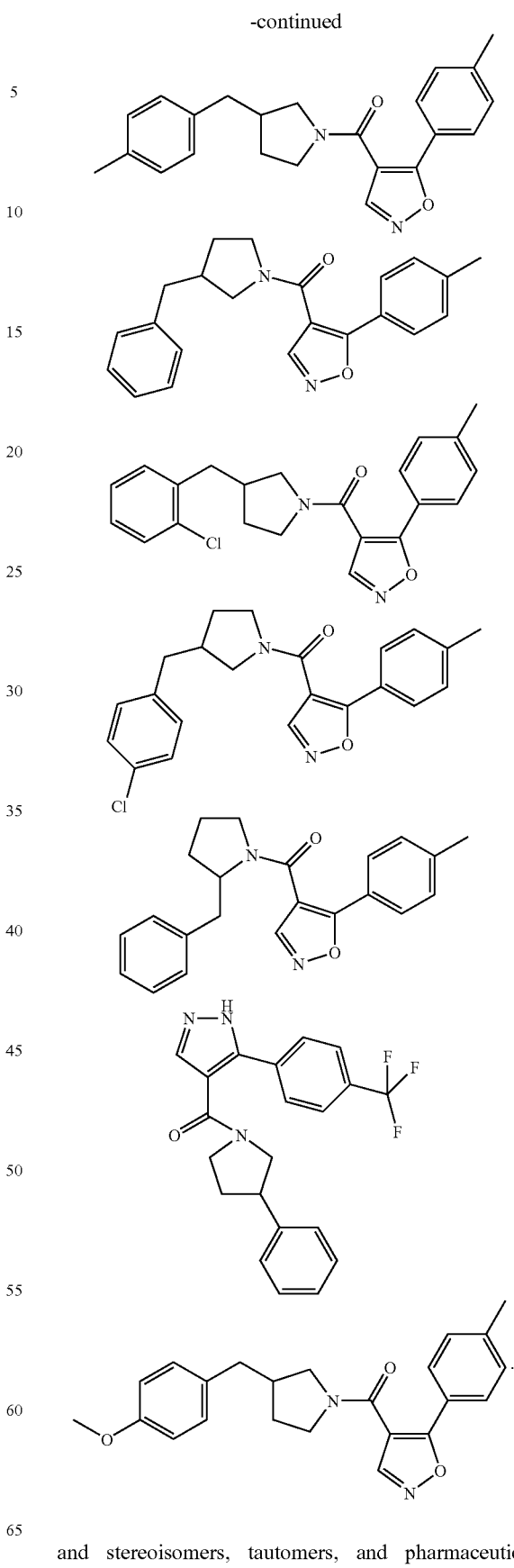
and stereoisomers, tautomers, and pharmaceutically acceptable salts thereof.

12. A compound that is selected from the following table:
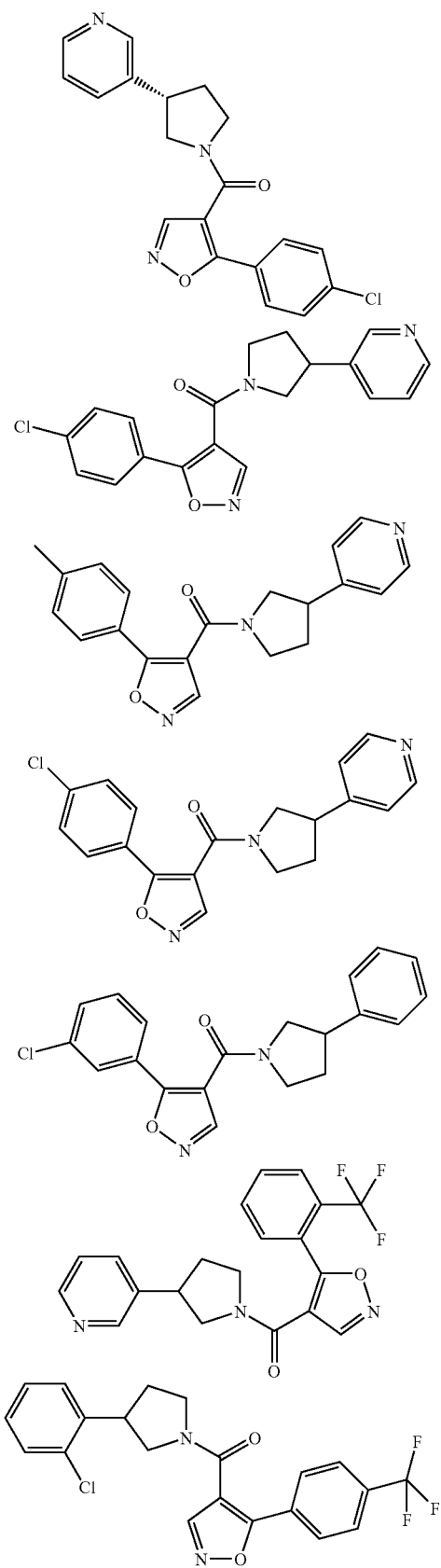
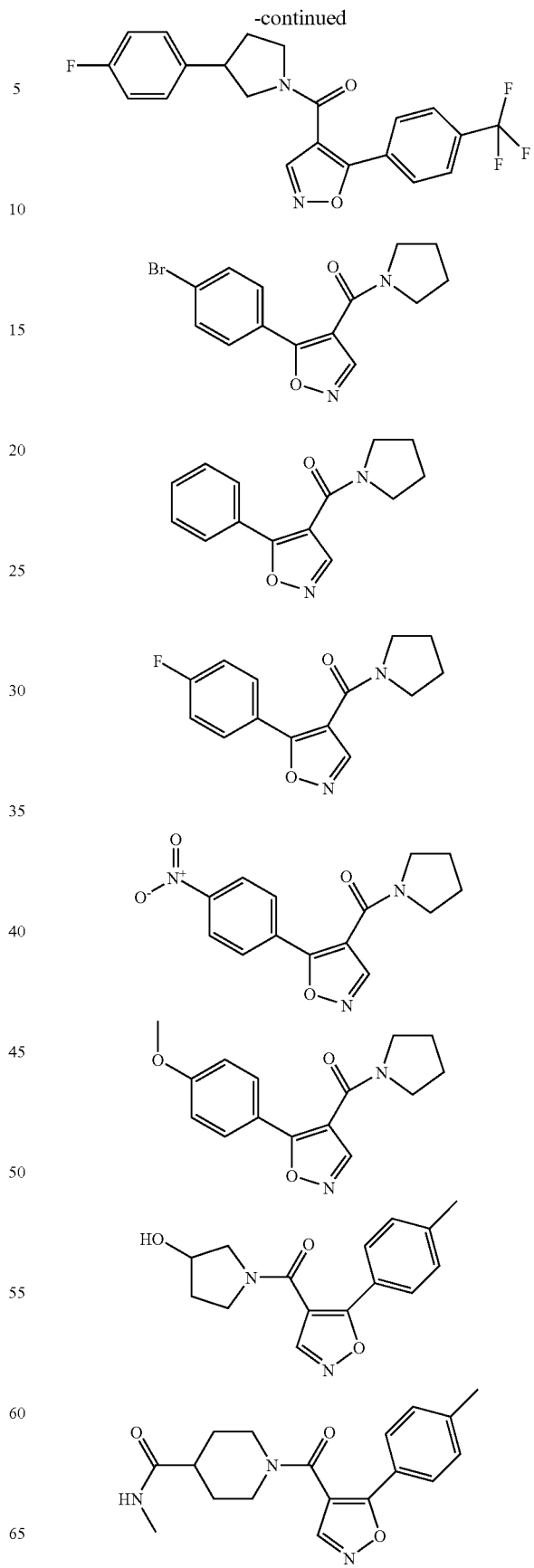

247
-continued
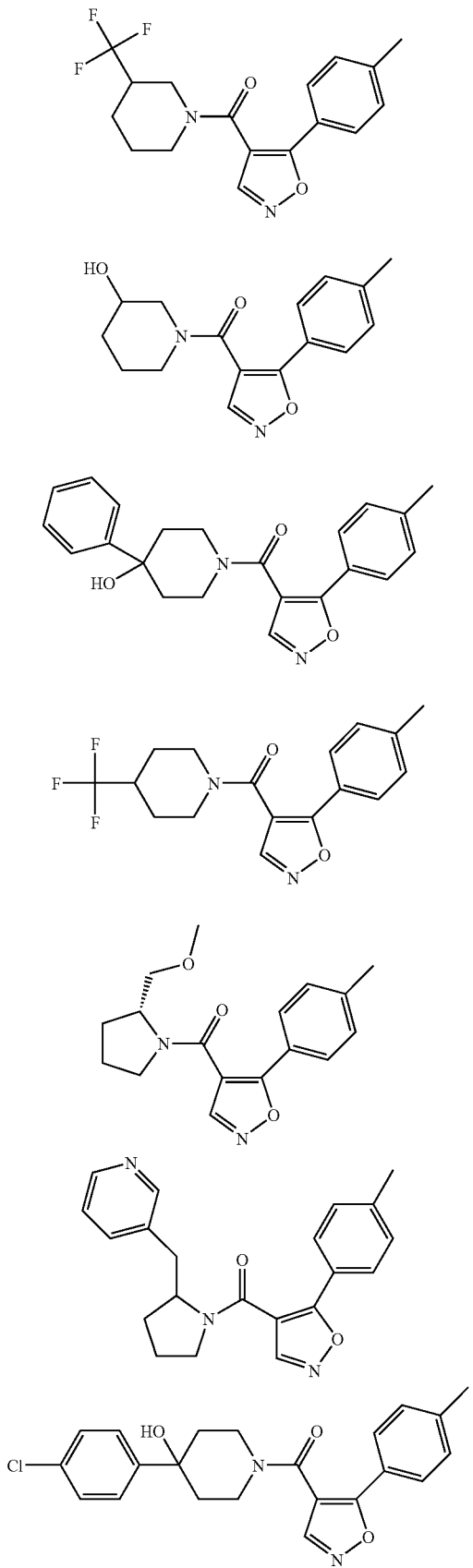
248
-continued
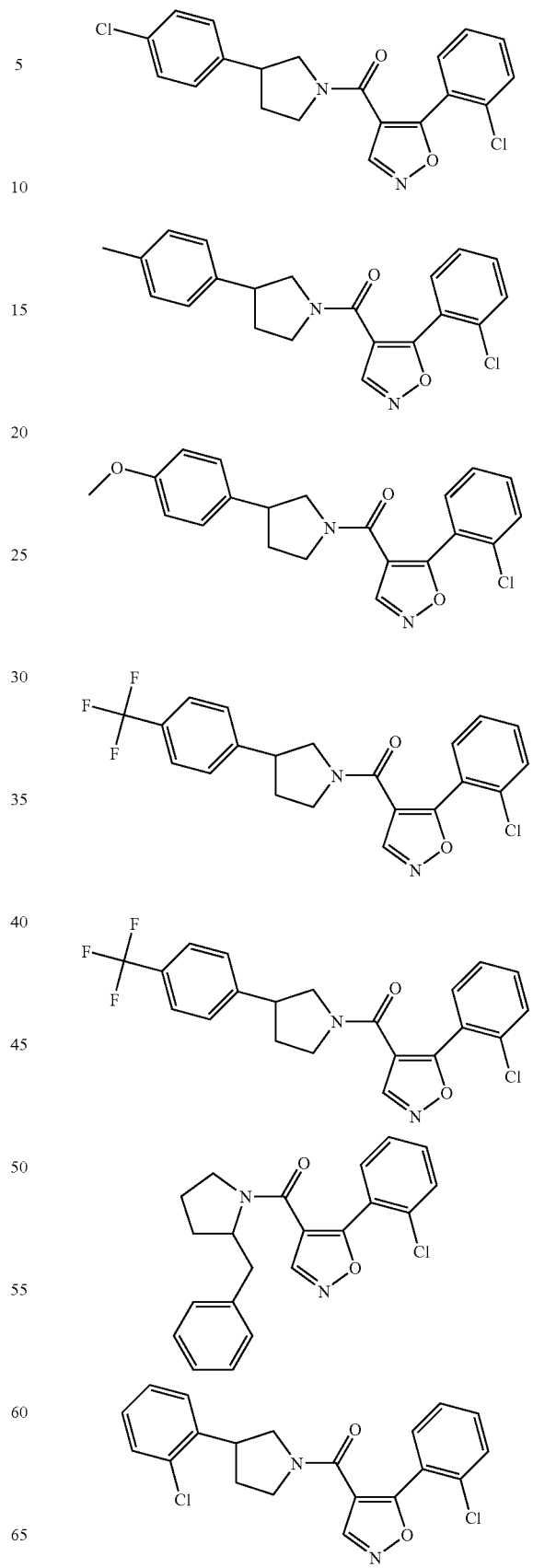

-continued
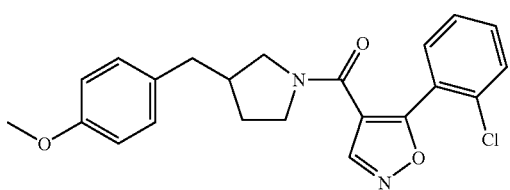
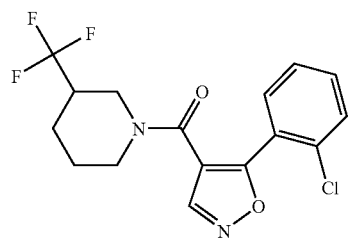
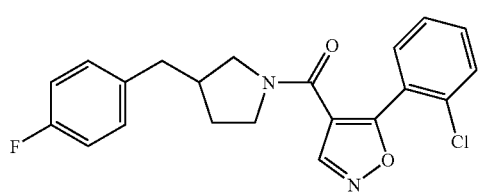
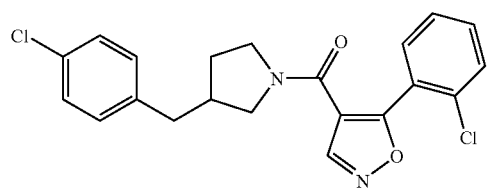
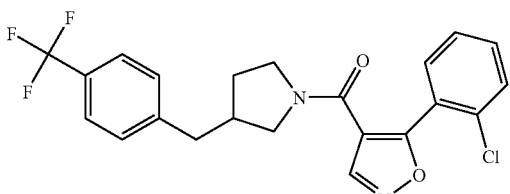
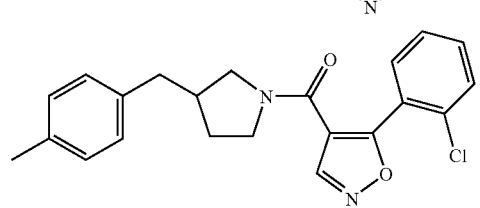
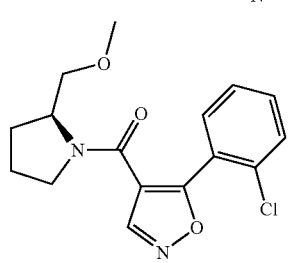
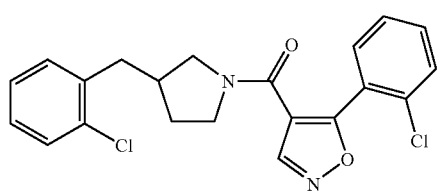
-continued
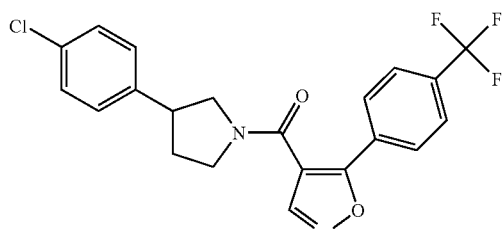
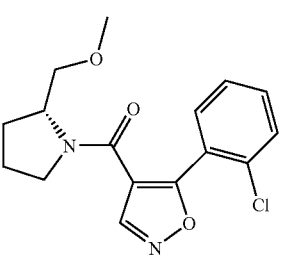
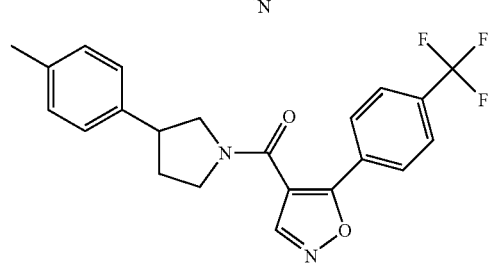
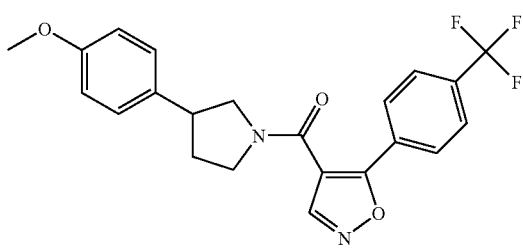
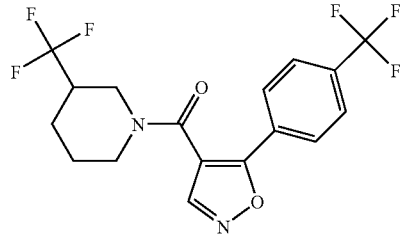
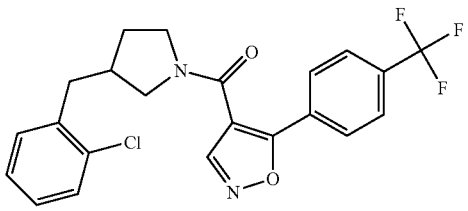
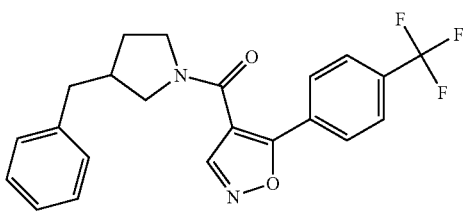

251
-continued
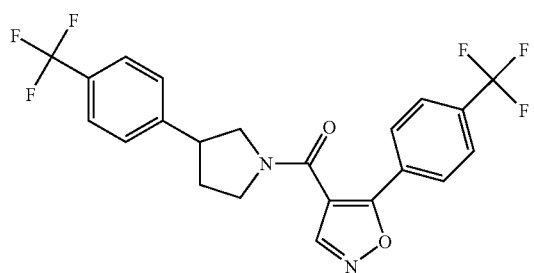
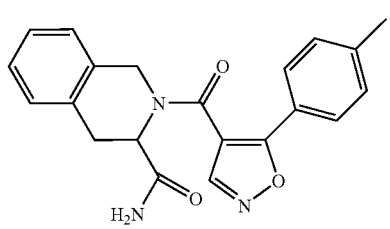
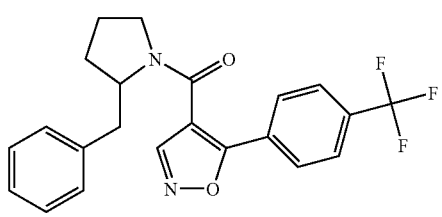
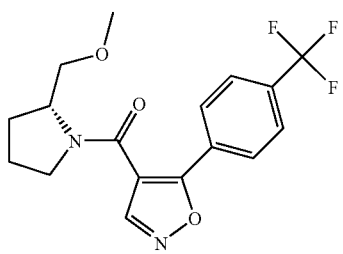
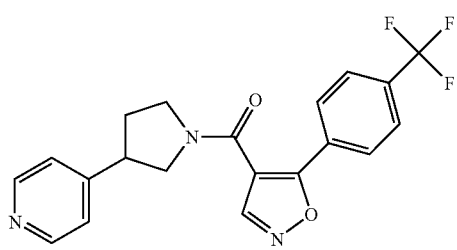
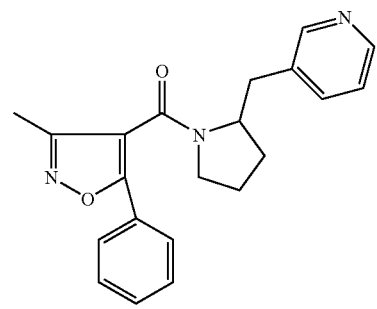
252
-continued
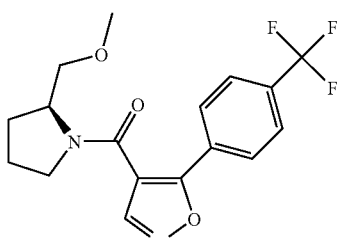
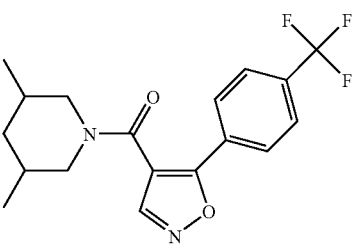
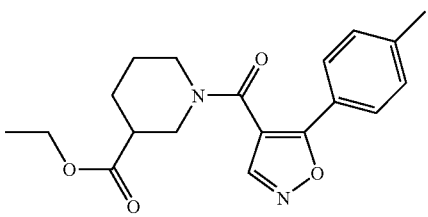
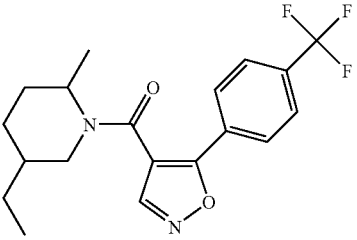
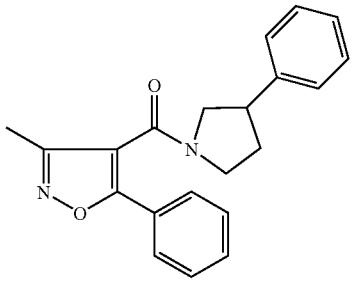
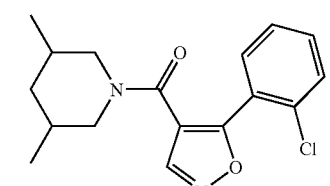
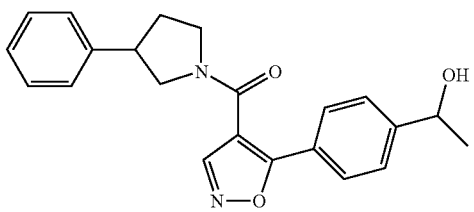

-continued
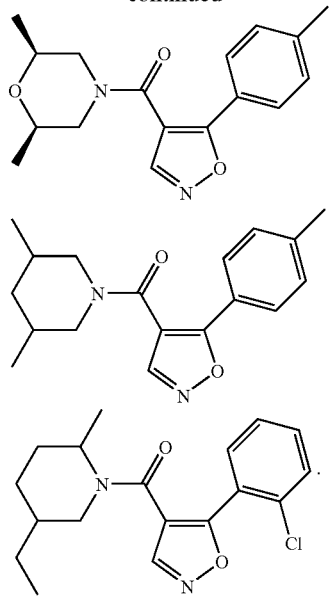
13. A compound that is selected from the following table:
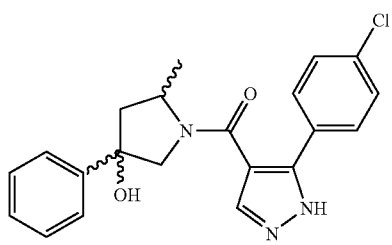
-continued
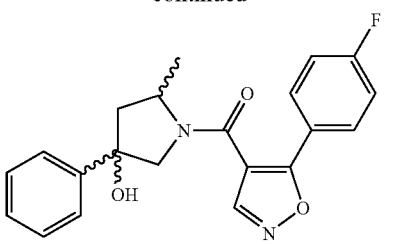
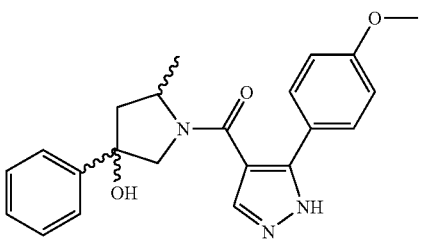
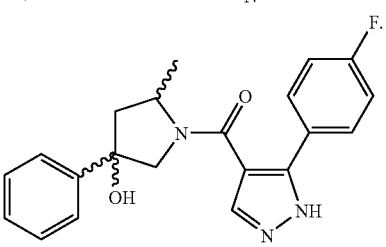
14. A pharmaceutical composition comprising a therapeutically effective amount of a compound according to claim 11, 12 or 13, or a stereoisomer, tautomer, or pharmaceutically acceptable salt thereof, and a pharmaceutically acceptable carrier.
* * * * *